US012644157B2

(12) United States Patent
Kozono et al.

(10) Patent No.: US 12,644,157 B2
(45) Date of Patent: Jun. 2, 2026

(54) COLORECTAL CANCER DETECTION KIT OR DEVICE, AND DETECTION METHOD

(71) Applicants: TORAY INDUSTRIES, INC., Tokyo (JP); NATIONAL CANCER CENTER, Tokyo (JP)

(72) Inventors: Satoko Kozono, Kamakura (JP); Hitoshi Nobumasa, Kamakura (JP); Satoshi Kondou, Kamakura (JP); Hiroko Sudo, Kamakura (JP); Junpei Kawauchi, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 264 days.

(21) Appl. No.: 18/606,093

(22) Filed: Mar. 15, 2024

(65) Prior Publication Data

US 2024/0263245 A1     Aug. 8, 2024

Related U.S. Application Data

(62) Division of application No. 17/945,243, filed on Sep. 15, 2022, now abandoned, which is a division of application No. 16/789,986, filed on Feb. 13, 2020, now Pat. No. 11,479,821, which is a division of application No. 15/318,312, filed as application No. PCT/JP2015/066970 on Jun. 12, 2015, now Pat. No. 10,604,810.

(30) Foreign Application Priority Data

Jun. 13, 2014   (JP) ................................. 2014-122686
Mar. 30, 2015   (JP) ................................. 2015-070182

(51) Int. Cl.
| | |
|---|---|
| *C12Q 1/68* | (2018.01) |
| *C12M 1/00* | (2006.01) |
| *C12N 15/09* | (2006.01) |
| *C12N 15/113* | (2010.01) |
| *C12P 19/34* | (2006.01) |
| *C12Q 1/6886* | (2018.01) |
| *G01N 33/53* | (2006.01) |
| *G01N 33/575* | (2026.01) |

(52) U.S. Cl.
CPC ............. *C12Q 1/6886* (2013.01); *C12M 1/00* (2013.01); *C12N 15/09* (2013.01); *C12N 15/113* (2013.01); *C12Q 1/68* (2013.01); *G01N 33/53* (2013.01); *G01N 33/575* (2026.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2001/0053519 | A1 | 12/2001 | Fodor et al. |
| 2008/0306006 | A1 | 12/2008 | Croce et al. |
| 2012/0088687 | A1 | 4/2012 | Goel et al. |
| 2012/0231970 | A1 | 9/2012 | Nakagama et al. |
| 2013/0102487 | A1 | 4/2013 | Gironella i Cos et al. |
| 2014/0147454 | A1 | 5/2014 | Chakraborty et al. |

FOREIGN PATENT DOCUMENTS

| | | | |
|---|---|---|---|
| CN | 102770560 | A | 11/2012 |
| CN | 103361408 | A | 10/2013 |
| JP | 2009-531019 | A | 9/2009 |
| WO | WO 2007/081204 | A2 | 7/2007 |
| WO | WO 2007/081740 | A2 | 7/2007 |
| WO | WO 2009/008720 | A2 | 1/2009 |
| WO | WO 2011/076142 | A1 | 6/2011 |
| WO | WO 2012/048236 | A1 | 4/2012 |
| WO | WO. 2013/026685 | A1 | 2/2013 |
| WO | WO 2013/095941 | A1 | 6/2013 |
| WO | WO 2013/109604 | A1 | 7/2013 |
| WO | WO 2014/048441 | A1 | 4/2014 |

OTHER PUBLICATIONS

F.E. Ahmed, et al. "Diagnostic MicroRNA Markers to Screen for Sporadic Human Colon Cancer in Blood" Cancer Genomics & Proteomics 9: 179-192 (2012) (Year: 2012).*
A.B. Vega, et al. "microRNA expression profile in stage III colorectal cancer: Circulating miR-18a and miR-29a as promising biomarkers" Oncology Reports 30: 320-326, 2013 (Year: 2013).*
Japanese Office Action for Japanese Application No. 2023-198041, dated Feb. 4, 2025.
Allison et al., "A comparison of fecal occult-blood tests for colorectal-cancer screening", The New England Journal of Medicine, vol. 334, No. 3, 1996, pp. 155-159.
American Cancer Society, "Colorectal Cancer", 2013, pp. 5-6, 17-28, 33, 45-54, and 67-71.
Cheung V.G. et al. Nature Genetics, pp. 422-425, vol. 33, March (Year: 2003).
Chinese Office Action and Search Report dated Aug. 11, 2023 for Application No. 202011464697.X.
Chinese Office Action for Chinese Application No. 201580031244. 9, dated Nov. 14, 2019.
Cobb, J. P. et al. Crit Care Med, pp. 2711-2721, vol. 30, No. 12 (Year: 2002).

(Continued)

*Primary Examiner* — Stephen T Kapushoc
(74) *Attorney, Agent, or Firm* — Birch, Stewart, Kolasch & Birch, LLP

(57)     ABSTRACT

It is intended to provide a kit or a device for the detection of colorectal cancer and a method for detecting colorectal cancer. The present invention provides a kit or a device for the detection of colorectal cancer, comprising a nucleic acid capable of specifically binding to a miRNA in a sample from a subject, and a method for detecting colorectal cancer, comprising measuring the miRNA in vitro.

6 Claims, 4 Drawing Sheets

Specification includes a Sequence Listing.

(56)            References Cited

OTHER PUBLICATIONS

Eto et al., "Prospect of microRNA toward laboratory medicine Gastrointestinal Cancer and microRNA", Clinical Chemistry, vol. 43, 2014, pp. 99-105.

GianpieroDi Leva, et al., "mi RNA profiling of cancer" Current Opinion in Genetics & Development, vol. 23, Issue 1, Feb. 2013, pp. 3-11 (Year: 2013).

Hao et al., "Progresses in research on miRNA as colorectal cancer biomarker", Anhui Medical and Pharmaceutical Journal, vol. 17, No. 2, Feb. 2013, pp. 183-185 with an English abstract.

Hoshikawa, Y. et al. Physiol Genomics 12: 209-219, (Year: 2003).

Huang et al., "Plasma microRNAs are promising novel biomarkers for early detection of colorectal cancer," Int. J. Cancer (2010), vol. 127, pp. 118-126.

International Search Report for PCT/JP2015/066970 (PCT/ISA/210) mailed on Sep. 8, 2015.

Japanese Office Action dated Mar. 31, 2020, for Japanese Patent Application No. 2016-527884.

Jing et al., "Advances in approaches for the quantitative detection of microRNAs", MicroRNA, Hereditas (Beijing), Jan. 2010, vol. 32, No. 1, pp. 31-40 with an English abstract.

Korean Office Action dated Jun. 18, 2023 for Application No. 10-2023-7008773.

Kozomara et al., "miRBase: annotating high confidence microRNAs using deep sequencing data", Nucleic Acids Research, vol. 42, 2014, Database issue, pp. D68-D73.

Ladewig et al., "Homo sapiens microRNA 6726 (MIR6726), microRNA", NCBI Reference Sequence: NR_106784.1, Apr. 3, 2014, https://www.ncbi.nlm.nih.gov/nuccore/563318489?sat=18&satkey=18644989.

Meng, Q.-L. et al. BMC Microbiology 2014, 14:37, Feb. 12, (Year: 2014).

MiScript™ miRNA PCR Array (384-well, 384HC) Human miRBase Profiler HC Plate 6, Qiagen, pp. 1-10 printed from https://b2b.qiagen.com/~/media/genetable/mi/hs/34/mihs-3406z. (Year: 2012).

Office Action issued Apr. 6, 2022, in Canadian Patent Application No. 2,951,127.

Office Action issued Sep. 24, 2021, in Korean Patent Application No. 10-2017-7000841.

Olsen et al., "p63 Attenuates Epithelial to Mesenchymal Potential in an Experimental Prostate Cell Model", PLOS ONE, vol. 8, No. 5, May 2013, pp. 1-12.

Palmqvist et al., "Prediagnostic levels of carcinoembryonic antigen and CA 242 in colorectal cancer: a matched case-control study", Diseases of colon and rectum, vol. 46, No. 11, 2003, pp. 1538-1544.

Partial European Search Report issued Feb. 8, 2022, in European Patent Application No. 21189691.5.

Partial Supplementary European Search Report, dated Dec. 15, 2017, for European Application No. 15806013.7.

Phua, L.E. et al., "Global fecal microRNA profiling in the identification of biomarkers for colorectal cancer screening among Asians" Oncology Reports, 32:97-104 Published online on: May 16, 2014 (Year: 2014).

Qiagen Product description sheet "mi Script™ miRNA PCR Array (384-well, 384HC) Human miRBase Profiler HC Plate 3" from https://b2b.qiagen.com/-/media/genetable/mi/hs/34/mihs-3403z, document No. 1073798, Aug., 2012. (Year: 2012).

Qu et al., "MiR-182 and miR-203 induce mesenchymal to epithelial transition and self-sufficiency of growth signals via repressing SNAI2 in prostate cells", International Journal of Cancer, vol. 133, Jan. 10, 2013, pp. 544-556.

Sheng, W. et al. Oncology Reports 36: 3387-3396, (Year: 2016).

Shivapurkar N, Weiner LM, Marshall JL, Madhavan S, Deslattes Mays A, et al. (Jan. 6, 2014) Recurrence of Early Stage Colon Cancer Predicted by Expression Pattern of Circulating microRNAs. PLoS ONE 9(1): e84686. doi: 10.1371/journal.pone.0084686 (Year: 2014).

Sobin, et al., "TNM Classification of Malignant Tumours", International Union Against Cancer, 7th edition, 2010, pp. 94-99.

Takizawa et al., "The difference of serum RNA profile: RNA extraction and detection method", Cancer Research, vol. 73, No. 8 (Suppl. 1), Abstract No. 5294, 2013, 1 page.

Takizawa et al. "Simultaneous Profiling of Multiple miRNAs in FFPE or Serum Samples Using DNA Chip 3D-Gene", BIO Clinica, vol. 28, No. 9, 2013, pp. 872 to 873.

Tian et al., "Serum microRNAs as promising novel biomarkers for hereditary nonpolyposis colorectal cancer," WCJD, vol. 21, Issue 11, Apr. 18, 2013, pp. 1040-1045, with abstract.

Wang et al., "Identification of Circulating MicroRNA Signature for Colorectal Cancer Detection," PLOS ONE (2014), vol. 9, Issue 4, e87451, pp. 1-9.

Written Opinion of the International Searching Authority for PCT/JP2015/066970 (PCT/ISA/237) mailed on Sep. 8, 2015.

Yang et al., "Advances in the Research of Colorectal Cancer-related MicroRNA", microRNA, vol. 35, No. 16, 2008, pp. 949-952 with an English abstract.

\* cited by examiner

Validation cohort

Training cohort

SEQUENCE LISTING

```
Sequence total quantity: 635
SEQ ID NO: 1          moltype = RNA   length = 21
FEATURE               Location/Qualifiers
source                1..21
                      mol_type = unassigned RNA
                      organism = Homo sapiens
SEQUENCE: 1
cgggagctgg ggtctgcagg t                                    21

SEQ ID NO: 2          moltype = RNA   length = 18
FEATURE               Location/Qualifiers
source                1..18
                      mol_type = unassigned RNA
                      organism = Homo sapiens
SEQUENCE: 2
ccagaggtgg ggactgag                                        18

SEQ ID NO: 3          moltype = RNA   length = 22
FEATURE               Location/Qualifiers
source                1..22
                      mol_type = unassigned RNA
```

-continued

```
                      organism = Homo sapiens
SEQUENCE: 3
tggcgggggt agagctggct gc                                         22

SEQ ID NO: 4          moltype = RNA   length = 23
FEATURE               Location/Qualifiers
source                1..23
                      mol_type = unassigned RNA
                      organism = Homo sapiens
SEQUENCE: 4
tggggaaggc ttggcaggga aga                                        23

SEQ ID NO: 5          moltype = RNA   length = 23
FEATURE               Location/Qualifiers
source                1..23
                      mol_type = unassigned RNA
                      organism = Homo sapiens
SEQUENCE: 5
tcgaggactg gtggaagggc ctt                                        23

SEQ ID NO: 6          moltype = RNA   length = 21
FEATURE               Location/Qualifiers
source                1..21
                      mol_type = unassigned RNA
                      organism = Homo sapiens
SEQUENCE: 6
gtgtggccgg caggcgggtg g                                          21

SEQ ID NO: 7          moltype = RNA   length = 22
FEATURE               Location/Qualifiers
source                1..22
                      mol_type = unassigned RNA
                      organism = Homo sapiens
SEQUENCE: 7
ctcctggggc ccgcactctc gc                                         22

SEQ ID NO: 8          moltype = RNA   length = 24
FEATURE               Location/Qualifiers
source                1..24
                      mol_type = unassigned RNA
                      organism = Homo sapiens
SEQUENCE: 8
ccccgggaac gtcgagactg gagc                                       24

SEQ ID NO: 9          moltype = RNA   length = 20
FEATURE               Location/Qualifiers
source                1..20
                      mol_type = unassigned RNA
                      organism = Homo sapiens
SEQUENCE: 9
cggggtgggt gaggtcgggc                                            20

SEQ ID NO: 10         moltype = RNA   length = 22
FEATURE               Location/Qualifiers
source                1..22
                      mol_type = unassigned RNA
                      organism = Homo sapiens
SEQUENCE: 10
tagggatggg aggccaggat ga                                         22

SEQ ID NO: 11         moltype = RNA   length = 23
FEATURE               Location/Qualifiers
source                1..23
                      mol_type = unassigned RNA
                      organism = Homo sapiens
SEQUENCE: 11
tgaggatatg gcagggaagg gga                                        23

SEQ ID NO: 12         moltype = RNA   length = 19
FEATURE               Location/Qualifiers
source                1..19
                      mol_type = unassigned RNA
                      organism = Homo sapiens
SEQUENCE: 12
ttgatctcgg aagctaagc                                             19

SEQ ID NO: 13         moltype = RNA   length = 22
FEATURE               Location/Qualifiers
source                1..22
```

-continued

```
                              mol_type = unassigned RNA
                              organism = Homo sapiens
SEQUENCE: 13
ccgggagaag gaggtggcct gg                                               22

SEQ ID NO: 14           moltype = RNA   length = 20
FEATURE                 Location/Qualifiers
source                  1..20
                        mol_type = unassigned RNA
                        organism = Homo sapiens
SEQUENCE: 14
ggcggcgggg aggtaggcag                                                  20

SEQ ID NO: 15           moltype = RNA   length = 22
FEATURE                 Location/Qualifiers
source                  1..22
                        mol_type = unassigned RNA
                        organism = Homo sapiens
SEQUENCE: 15
gtgggtgctg gtgggagccg tg                                               22

SEQ ID NO: 16           moltype = RNA   length = 21
FEATURE                 Location/Qualifiers
source                  1..21
                        mol_type = unassigned RNA
                        organism = Homo sapiens
SEQUENCE: 16
cggcggggac ggcgattggt c                                                21

SEQ ID NO: 17           moltype = RNA   length = 22
FEATURE                 Location/Qualifiers
source                  1..22
                        mol_type = unassigned RNA
                        organism = Homo sapiens
SEQUENCE: 17
ttggggattg ggtcaggcca gt                                               22

SEQ ID NO: 18           moltype = RNA   length = 21
FEATURE                 Location/Qualifiers
source                  1..21
                        mol_type = unassigned RNA
                        organism = Homo sapiens
SEQUENCE: 18
agcggtgctc ctgcgggccg a                                                21

SEQ ID NO: 19           moltype = RNA   length = 22
FEATURE                 Location/Qualifiers
source                  1..22
                        mol_type = unassigned RNA
                        organism = Homo sapiens
SEQUENCE: 19
tgcggggcta gggctaacag ca                                               22

SEQ ID NO: 20           moltype = RNA   length = 18
FEATURE                 Location/Qualifiers
source                  1..18
                        mol_type = unassigned RNA
                        organism = Homo sapiens
SEQUENCE: 20
cggtgagcgc tcgctggc                                                    18

SEQ ID NO: 21           moltype = RNA   length = 19
FEATURE                 Location/Qualifiers
source                  1..19
                        mol_type = unassigned RNA
                        organism = Homo sapiens
SEQUENCE: 21
aggcacggtg tcagcaggc                                                   19

SEQ ID NO: 22           moltype = RNA   length = 22
FEATURE                 Location/Qualifiers
source                  1..22
                        mol_type = unassigned RNA
                        organism = Homo sapiens
SEQUENCE: 22
cccctggggc tgggcaggcg ga                                               22

SEQ ID NO: 23           moltype = RNA   length = 22
FEATURE                 Location/Qualifiers
```

-continued

```
source                 1..22
                       mol_type = unassigned RNA
                       organism = Homo sapiens
SEQUENCE: 23
tggggaggtg tggagtcagc at                                                22

SEQ ID NO: 24          moltype = RNA   length = 23
FEATURE                Location/Qualifiers
source                 1..23
                       mol_type = unassigned RNA
                       organism = Homo sapiens
SEQUENCE: 24
tcaataggaa agaggtggga cct                                               23

SEQ ID NO: 25          moltype = RNA   length = 26
FEATURE                Location/Qualifiers
source                 1..26
                       mol_type = unassigned RNA
                       organism = Homo sapiens
SEQUENCE: 25
ctcggccgcg gcgcgtagcc cccgcc                                            26

SEQ ID NO: 26          moltype = RNA   length = 22
FEATURE                Location/Qualifiers
source                 1..22
                       mol_type = unassigned RNA
                       organism = Homo sapiens
SEQUENCE: 26
tggcggcggt agttatgggc tt                                                22

SEQ ID NO: 27          moltype = RNA   length = 23
FEATURE                Location/Qualifiers
source                 1..23
                       mol_type = unassigned RNA
                       organism = Homo sapiens
SEQUENCE: 27
agaggctttg tgcggatacg ggg                                               23

SEQ ID NO: 28          moltype = RNA   length = 20
FEATURE                Location/Qualifiers
source                 1..20
                       mol_type = unassigned RNA
                       organism = Homo sapiens
SEQUENCE: 28
gcggaaggcg gagcggcgga                                                   20

SEQ ID NO: 29          moltype = RNA   length = 23
FEATURE                Location/Qualifiers
source                 1..23
                       mol_type = unassigned RNA
                       organism = Homo sapiens
SEQUENCE: 29
agggtggggc tggaggtggg gct                                               23

SEQ ID NO: 30          moltype = RNA   length = 20
FEATURE                Location/Qualifiers
source                 1..20
                       mol_type = unassigned RNA
                       organism = Homo sapiens
SEQUENCE: 30
tcacacctgc ctcgcccccc                                                   20

SEQ ID NO: 31          moltype = RNA   length = 22
FEATURE                Location/Qualifiers
source                 1..22
                       mol_type = unassigned RNA
                       organism = Homo sapiens
SEQUENCE: 31
tcaaaatcag gagtcggggc tt                                                22

SEQ ID NO: 32          moltype = RNA   length = 23
FEATURE                Location/Qualifiers
source                 1..23
                       mol_type = unassigned RNA
                       organism = Homo sapiens
SEQUENCE: 32
ggatggttgg gggcggtcgg cgt                                               23

SEQ ID NO: 33          moltype = RNA   length = 21
```

-continued

```
FEATURE              Location/Qualifiers
source               1..21
                     mol_type = unassigned RNA
                     organism = Homo sapiens
SEQUENCE: 33
tgagggaccc aggacaggag a                                         21

SEQ ID NO: 34        moltype = RNA   length = 23
FEATURE              Location/Qualifiers
source               1..23
                     mol_type = unassigned RNA
                     organism = Homo sapiens
SEQUENCE: 34
agaagaaggc ggtcggtctg cgg                                       23

SEQ ID NO: 35        moltype = RNA   length = 21
FEATURE              Location/Qualifiers
source               1..21
                     mol_type = unassigned RNA
                     organism = Homo sapiens
SEQUENCE: 35
caggagtggg gggtgggacg t                                         21

SEQ ID NO: 36        moltype = RNA   length = 23
FEATURE              Location/Qualifiers
source               1..23
                     mol_type = unassigned RNA
                     organism = Homo sapiens
SEQUENCE: 36
tggggggaca gatggagagg aca                                       23

SEQ ID NO: 37        moltype = RNA   length = 23
FEATURE              Location/Qualifiers
source               1..23
                     mol_type = unassigned RNA
                     organism = Homo sapiens
SEQUENCE: 37
cggggccgta gcactgtctg aga                                       23

SEQ ID NO: 38        moltype = RNA   length = 23
FEATURE              Location/Qualifiers
source               1..23
                     mol_type = unassigned RNA
                     organism = Homo sapiens
SEQUENCE: 38
ctgggcccgc ggcgggcgtg ggg                                       23

SEQ ID NO: 39        moltype = RNA   length = 22
FEATURE              Location/Qualifiers
source               1..22
                     mol_type = unassigned RNA
                     organism = Homo sapiens
SEQUENCE: 39
ggaggggtcc cgcactggga gg                                        22

SEQ ID NO: 40        moltype = RNA   length = 22
FEATURE              Location/Qualifiers
source               1..22
                     mol_type = unassigned RNA
                     organism = Homo sapiens
SEQUENCE: 40
gtgggtacgg cccagtgggg gg                                        22

SEQ ID NO: 41        moltype = RNA   length = 18
FEATURE              Location/Qualifiers
source               1..18
                     mol_type = unassigned RNA
                     organism = Homo sapiens
SEQUENCE: 41
gaggctgaag gaagatgg                                             18

SEQ ID NO: 42        moltype = RNA   length = 21
FEATURE              Location/Qualifiers
source               1..21
                     mol_type = unassigned RNA
                     organism = Homo sapiens
SEQUENCE: 42
tgggggtgtg gggagagaga g                                         21
```

-continued

```
SEQ ID NO: 43        moltype = RNA   length = 22
FEATURE              Location/Qualifiers
source               1..22
                     mol_type = unassigned RNA
                     organism = Homo sapiens
SEQUENCE: 43
ggctacaaca caggacccgg gc                                              22

SEQ ID NO: 44        moltype = RNA   length = 24
FEATURE              Location/Qualifiers
source               1..24
                     mol_type = unassigned RNA
                     organism = Homo sapiens
SEQUENCE: 44
tgaggggcct cagaccgagc tttt                                           24

SEQ ID NO: 45        moltype = RNA   length = 21
FEATURE              Location/Qualifiers
source               1..21
                     mol_type = unassigned RNA
                     organism = Homo sapiens
SEQUENCE: 45
gctgggaagg caaagggacg t                                              21

SEQ ID NO: 46        moltype = RNA   length = 21
FEATURE              Location/Qualifiers
source               1..21
                     mol_type = unassigned RNA
                     organism = Homo sapiens
SEQUENCE: 46
gttggggtgc aggggtctgc t                                              21

SEQ ID NO: 47        moltype = RNA   length = 22
FEATURE              Location/Qualifiers
source               1..22
                     mol_type = unassigned RNA
                     organism = Homo sapiens
SEQUENCE: 47
tgggcgaggg cggctgagcg gc                                             22

SEQ ID NO: 48        moltype = RNA   length = 22
FEATURE              Location/Qualifiers
source               1..22
                     mol_type = unassigned RNA
                     organism = Homo sapiens
SEQUENCE: 48
gggggtcccc ggtgctcgga tc                                             22

SEQ ID NO: 49        moltype = RNA   length = 22
FEATURE              Location/Qualifiers
source               1..22
                     mol_type = unassigned RNA
                     organism = Homo sapiens
SEQUENCE: 49
tcgggcctgg ggttggggga gc                                             22

SEQ ID NO: 50        moltype = RNA   length = 20
FEATURE              Location/Qualifiers
source               1..20
                     mol_type = unassigned RNA
                     organism = Homo sapiens
SEQUENCE: 50
tctcttcatc tacccccag                                                 20

SEQ ID NO: 51        moltype = RNA   length = 23
FEATURE              Location/Qualifiers
source               1..23
                     mol_type = unassigned RNA
                     organism = Homo sapiens
SEQUENCE: 51
acaggcggct gtagcaatgg ggg                                            23

SEQ ID NO: 52        moltype = RNA   length = 22
FEATURE              Location/Qualifiers
source               1..22
                     mol_type = unassigned RNA
                     organism = Homo sapiens
SEQUENCE: 52
gcccaggact ttgtgcgggg tg                                             22
```

-continued

```
SEQ ID NO: 53              moltype = RNA   length = 21
FEATURE                    Location/Qualifiers
source                     1..21
                           mol_type = unassigned RNA
                           organism = Homo sapiens
SEQUENCE: 53
caggcaggtg tagggtggag c                                        21

SEQ ID NO: 54              moltype = RNA   length = 23
FEATURE                    Location/Qualifiers
source                     1..23
                           mol_type = unassigned RNA
                           organism = Homo sapiens
SEQUENCE: 54
tgggagggga gaggcagcaa gca                                      23

SEQ ID NO: 55              moltype = RNA   length = 22
FEATURE                    Location/Qualifiers
source                     1..22
                           mol_type = unassigned RNA
                           organism = Homo sapiens
SEQUENCE: 55
aggcgatgtg gggatgtaga ga                                       22

SEQ ID NO: 56              moltype = RNA   length = 23
FEATURE                    Location/Qualifiers
source                     1..23
                           mol_type = unassigned RNA
                           organism = Homo sapiens
SEQUENCE: 56
cctccctgcc cgcctctctg cag                                      23

SEQ ID NO: 57              moltype = RNA   length = 23
FEATURE                    Location/Qualifiers
source                     1..23
                           mol_type = unassigned RNA
                           organism = Homo sapiens
SEQUENCE: 57
ctgggggacg cgtgagcgcg agc                                      23

SEQ ID NO: 58              moltype = RNA   length = 22
FEATURE                    Location/Qualifiers
source                     1..22
                           mol_type = unassigned RNA
                           organism = Homo sapiens
SEQUENCE: 58
agacacattt ggagagggac cc                                       22

SEQ ID NO: 59              moltype = RNA   length = 21
FEATURE                    Location/Qualifiers
source                     1..21
                           mol_type = unassigned RNA
                           organism = Homo sapiens
SEQUENCE: 59
ctggggggag gagaccctgc t                                        21

SEQ ID NO: 60              moltype = RNA   length = 22
FEATURE                    Location/Qualifiers
source                     1..22
                           mol_type = unassigned RNA
                           organism = Homo sapiens
SEQUENCE: 60
tggggtggt ctctagccaa gg                                        22

SEQ ID NO: 61              moltype = RNA   length = 17
FEATURE                    Location/Qualifiers
source                     1..17
                           mol_type = unassigned RNA
                           organism = Homo sapiens
SEQUENCE: 61
gccggacaag agggagg                                             17

SEQ ID NO: 62              moltype = RNA   length = 21
FEATURE                    Location/Qualifiers
source                     1..21
                           mol_type = unassigned RNA
                           organism = Homo sapiens
SEQUENCE: 62
```

-continued

```
acaggagtgg gggtgggaca t                                                21

SEQ ID NO: 63            moltype = RNA   length = 23
FEATURE                  Location/Qualifiers
source                   1..23
                         mol_type = unassigned RNA
                         organism = Homo sapiens
SEQUENCE: 63
gccccggcgc gggcgggttc tgg                                              23

SEQ ID NO: 64            moltype = RNA   length = 18
FEATURE                  Location/Qualifiers
source                   1..18
                         mol_type = unassigned RNA
                         organism = Homo sapiens
SEQUENCE: 64
gtgaaggccc ggcggaga                                                    18

SEQ ID NO: 65            moltype = RNA   length = 22
FEATURE                  Location/Qualifiers
source                   1..22
                         mol_type = unassigned RNA
                         organism = Homo sapiens
SEQUENCE: 65
cgtcccgggg ctgcgcgagg ca                                               22

SEQ ID NO: 66            moltype = RNA   length = 25
FEATURE                  Location/Qualifiers
source                   1..25
                         mol_type = unassigned RNA
                         organism = Homo sapiens
SEQUENCE: 66
agcggggagg aagtgggcgc tgctt                                            25

SEQ ID NO: 67            moltype = RNA   length = 22
FEATURE                  Location/Qualifiers
source                   1..22
                         mol_type = unassigned RNA
                         organism = Homo sapiens
SEQUENCE: 67
tctgcccect ccgctgctgc ca                                               22

SEQ ID NO: 68            moltype = RNA   length = 23
FEATURE                  Location/Qualifiers
source                   1..23
                         mol_type = unassigned RNA
                         organism = Homo sapiens
SEQUENCE: 68
gacacgggcg acagctgcgg ccc                                              23

SEQ ID NO: 69            moltype = RNA   length = 24
FEATURE                  Location/Qualifiers
source                   1..24
                         mol_type = unassigned RNA
                         organism = Homo sapiens
SEQUENCE: 69
tggggagctg aggctctggg ggtg                                             24

SEQ ID NO: 70            moltype = RNA   length = 22
FEATURE                  Location/Qualifiers
source                   1..22
                         mol_type = unassigned RNA
                         organism = Homo sapiens
SEQUENCE: 70
caggaggcag tgggcgagca gg                                                22

SEQ ID NO: 71            moltype = RNA   length = 22
FEATURE                  Location/Qualifiers
source                   1..22
                         mol_type = unassigned RNA
                         organism = Homo sapiens
SEQUENCE: 71
gggacccagg gagagacgta ag                                                22

SEQ ID NO: 72            moltype = RNA   length = 21
FEATURE                  Location/Qualifiers
source                   1..21
                         mol_type = unassigned RNA
                         organism = Homo sapiens
```

-continued

```
SEQUENCE: 72
tggggcgggg caggtccctg c                                                 21

SEQ ID NO: 73          moltype = RNA   length = 23
FEATURE                Location/Qualifiers
source                 1..23
                       mol_type = unassigned RNA
                       organism = Homo sapiens
SEQUENCE: 73
gagggcagcg tgggtgtggc gga                                               23

SEQ ID NO: 74          moltype = RNA   length = 23
FEATURE                Location/Qualifiers
source                 1..23
                       mol_type = unassigned RNA
                       organism = Homo sapiens
SEQUENCE: 74
tgggcagggg cttattgtag gag                                               23

SEQ ID NO: 75          moltype = RNA   length = 21
FEATURE                Location/Qualifiers
source                 1..21
                       mol_type = unassigned RNA
                       organism = Homo sapiens
SEQUENCE: 75
cgtggaggac gaggaggagg c                                                 21

SEQ ID NO: 76          moltype = RNA   length = 19
FEATURE                Location/Qualifiers
source                 1..19
                       mol_type = unassigned RNA
                       organism = Homo sapiens
SEQUENCE: 76
agcagggctg gggattgca                                                    19

SEQ ID NO: 77          moltype = RNA   length = 22
FEATURE                Location/Qualifiers
source                 1..22
                       mol_type = unassigned RNA
                       organism = Homo sapiens
SEQUENCE: 77
gtgaacgggc gccatcccga gg                                                22

SEQ ID NO: 78          moltype = RNA   length = 22
FEATURE                Location/Qualifiers
source                 1..22
                       mol_type = unassigned RNA
                       organism = Homo sapiens
SEQUENCE: 78
cttccccca gtaatcttca tc                                                 22

SEQ ID NO: 79          moltype = RNA   length = 20
FEATURE                Location/Qualifiers
source                 1..20
                       mol_type = unassigned RNA
                       organism = Homo sapiens
SEQUENCE: 79
gccgggctt tgggtgaggg                                                    20

SEQ ID NO: 80          moltype = RNA   length = 22
FEATURE                Location/Qualifiers
source                 1..22
                       mol_type = unassigned RNA
                       organism = Homo sapiens
SEQUENCE: 80
acgcccttcc ccccttcttt ca                                                22

SEQ ID NO: 81          moltype = RNA   length = 20
FEATURE                Location/Qualifiers
source                 1..20
                       mol_type = unassigned RNA
                       organism = Homo sapiens
SEQUENCE: 81
gtgagtcagg gtggggctgg                                                   20

SEQ ID NO: 82          moltype = RNA   length = 21
FEATURE                Location/Qualifiers
source                 1..21
                       mol_type = unassigned RNA
```

-continued

```
                          organism = Homo sapiens
SEQUENCE: 82
atccagttct ctgaggggc t                                           21

SEQ ID NO: 83          moltype = RNA  length = 20
FEATURE                Location/Qualifiers
source                 1..20
                       mol_type = unassigned RNA
                       organism = Homo sapiens
SEQUENCE: 83
taggggtgg caggctggcc                                             20

SEQ ID NO: 84          moltype = RNA  length = 18
FEATURE                Location/Qualifiers
source                 1..18
                       mol_type = unassigned RNA
                       organism = Homo sapiens
SEQUENCE: 84
ggtgggcttc ccggaggg                                              18

SEQ ID NO: 85          moltype = RNA  length = 18
FEATURE                Location/Qualifiers
source                 1..18
                       mol_type = unassigned RNA
                       organism = Homo sapiens
SEQUENCE: 85
gggtcccggg gagggggg                                              18

SEQ ID NO: 86          moltype = RNA  length = 22
FEATURE                Location/Qualifiers
source                 1..22
                       mol_type = unassigned RNA
                       organism = Homo sapiens
SEQUENCE: 86
gctgcgggct gcggtcaggg cg                                         22

SEQ ID NO: 87          moltype = RNA  length = 22
FEATURE                Location/Qualifiers
source                 1..22
                       mol_type = unassigned RNA
                       organism = Homo sapiens
SEQUENCE: 87
tgattgtctt cccccaccct ca                                         22

SEQ ID NO: 88          moltype = RNA  length = 22
FEATURE                Location/Qualifiers
source                 1..22
                       mol_type = unassigned RNA
                       organism = Homo sapiens
SEQUENCE: 88
aggcggggcg ccgcgggacc gc                                         22

SEQ ID NO: 89          moltype = RNA  length = 22
FEATURE                Location/Qualifiers
source                 1..22
                       mol_type = unassigned RNA
                       organism = Homo sapiens
SEQUENCE: 89
agactgacgg ctggaggccc at                                         22

SEQ ID NO: 90          moltype = RNA  length = 21
FEATURE                Location/Qualifiers
source                 1..21
                       mol_type = unassigned RNA
                       organism = Homo sapiens
SEQUENCE: 90
cgggccggag gtcaagggcg t                                          21

SEQ ID NO: 91          moltype = RNA  length = 17
FEATURE                Location/Qualifiers
source                 1..17
                       mol_type = unassigned RNA
                       organism = Homo sapiens
SEQUENCE: 91
gtggggccag gcggtgg                                               17

SEQ ID NO: 92          moltype = RNA  length = 19
FEATURE                Location/Qualifiers
source                 1..19
```

-continued

```
                              mol_type = unassigned RNA
                              organism = Homo sapiens
SEQUENCE: 92
cggggccaga gcagagagc                                                  19

SEQ ID NO: 93           moltype = RNA   length = 23
FEATURE                 Location/Qualifiers
source                  1..23
                        mol_type = unassigned RNA
                        organism = Homo sapiens
SEQUENCE: 93
ccaggggggat gggcgagctt ggg                                            23

SEQ ID NO: 94           moltype = RNA   length = 22
FEATURE                 Location/Qualifiers
source                  1..22
                        mol_type = unassigned RNA
                        organism = Homo sapiens
SEQUENCE: 94
gtgggctggg ctgggctggg cc                                              22

SEQ ID NO: 95           moltype = RNA   length = 22
FEATURE                 Location/Qualifiers
source                  1..22
                        mol_type = unassigned RNA
                        organism = Homo sapiens
SEQUENCE: 95
accttgcctt gctgcccggg cc                                              22

SEQ ID NO: 96           moltype = RNA   length = 17
FEATURE                 Location/Qualifiers
source                  1..17
                        mol_type = unassigned RNA
                        organism = Homo sapiens
SEQUENCE: 96
gggagtctac agcaggg                                                    17

SEQ ID NO: 97           moltype = RNA   length = 22
FEATURE                 Location/Qualifiers
source                  1..22
                        mol_type = unassigned RNA
                        organism = Homo sapiens
SEQUENCE: 97
agacacattt ggagagggaa cc                                              22

SEQ ID NO: 98           moltype = RNA   length = 20
FEATURE                 Location/Qualifiers
source                  1..20
                        mol_type = unassigned RNA
                        organism = Homo sapiens
SEQUENCE: 98
actcaaactg tgggggcact                                                 20

SEQ ID NO: 99           moltype = RNA   length = 21
FEATURE                 Location/Qualifiers
source                  1..21
                        mol_type = unassigned RNA
                        organism = Homo sapiens
SEQUENCE: 99
aaggcagggc ccccgctccc c                                               21

SEQ ID NO: 100          moltype = RNA   length = 22
FEATURE                 Location/Qualifiers
source                  1..22
                        mol_type = unassigned RNA
                        organism = Homo sapiens
SEQUENCE: 100
tgggatttg gagaagtggt ga                                               22

SEQ ID NO: 101          moltype = RNA   length = 24
FEATURE                 Location/Qualifiers
source                  1..24
                        mol_type = unassigned RNA
                        organism = Homo sapiens
SEQUENCE: 101
tgggggagcc atgagataag agca                                            24

SEQ ID NO: 102          moltype = RNA   length = 22
FEATURE                 Location/Qualifiers
```

-continued

```
source                    1..22
                          mol_type = unassigned RNA
                          organism = Homo sapiens
SEQUENCE: 102
ctcggcgcgg ggcgcgggct cc                                              22

SEQ ID NO: 103            moltype = RNA   length = 22
FEATURE                   Location/Qualifiers
source                    1..22
                          mol_type = unassigned RNA
                          organism = Homo sapiens
SEQUENCE: 103
actgggtagg tggggctcca gg                                              22

SEQ ID NO: 104            moltype = RNA   length = 18
FEATURE                   Location/Qualifiers
source                    1..18
                          mol_type = unassigned RNA
                          organism = Homo sapiens
SEQUENCE: 104
atcctagtca cggcacca                                                   18

SEQ ID NO: 105            moltype = RNA   length = 22
FEATURE                   Location/Qualifiers
source                    1..22
                          mol_type = unassigned RNA
                          organism = Homo sapiens
SEQUENCE: 105
cagggcaggg aaggtgggag ag                                              22

SEQ ID NO: 106            moltype = RNA   length = 20
FEATURE                   Location/Qualifiers
source                    1..20
                          mol_type = unassigned RNA
                          organism = Homo sapiens
SEQUENCE: 106
ctaggtgggg ggcttgaagc                                                 20

SEQ ID NO: 107            moltype = RNA   length = 20
FEATURE                   Location/Qualifiers
source                    1..20
                          mol_type = unassigned RNA
                          organism = Homo sapiens
SEQUENCE: 107
cgggcgtggt ggtgggggtg                                                 20

SEQ ID NO: 108            moltype = RNA   length = 22
FEATURE                   Location/Qualifiers
source                    1..22
                          mol_type = unassigned RNA
                          organism = Homo sapiens
SEQUENCE: 108
ggtggcccgg ccgtgcctga gg                                              22

SEQ ID NO: 109            moltype = RNA   length = 22
FEATURE                   Location/Qualifiers
source                    1..22
                          mol_type = unassigned RNA
                          organism = Homo sapiens
SEQUENCE: 109
acaggtgagg ttcttgggag cc                                              22

SEQ ID NO: 110            moltype = RNA   length = 19
FEATURE                   Location/Qualifiers
source                    1..19
                          mol_type = unassigned RNA
                          organism = Homo sapiens
SEQUENCE: 110
ggggcctggc ggtgggcgg                                                  19

SEQ ID NO: 111            moltype = RNA   length = 20
FEATURE                   Location/Qualifiers
source                    1..20
                          mol_type = unassigned RNA
                          organism = Homo sapiens
SEQUENCE: 111
agagatgaag cggggggggcg                                                20

SEQ ID NO: 112            moltype = RNA   length = 23
```

-continued

```
FEATURE              Location/Qualifiers
source               1..23
                     mol_type = unassigned RNA
                     organism = Homo sapiens
SEQUENCE: 112
gtgagtggga gccggtgggg ctg                                        23

SEQ ID NO: 113       moltype = RNA   length = 22
FEATURE              Location/Qualifiers
source               1..22
                     mol_type = unassigned RNA
                     organism = Homo sapiens
SEQUENCE: 113
gagggttggg tggaggctct cc                                         22

SEQ ID NO: 114       moltype = RNA   length = 23
FEATURE              Location/Qualifiers
source               1..23
                     mol_type = unassigned RNA
                     organism = Homo sapiens
SEQUENCE: 114
cgaggggtag aagagcacag ggg                                        23

SEQ ID NO: 115       moltype = RNA   length = 23
FEATURE              Location/Qualifiers
source               1..23
                     mol_type = unassigned RNA
                     organism = Homo sapiens
SEQUENCE: 115
aggaagccct ggaggggctg gag                                        23

SEQ ID NO: 116       moltype = RNA   length = 20
FEATURE              Location/Qualifiers
source               1..20
                     mol_type = unassigned RNA
                     organism = Homo sapiens
SEQUENCE: 116
ggatccgagt cacggcacca                                            20

SEQ ID NO: 117       moltype = RNA   length = 17
FEATURE              Location/Qualifiers
source               1..17
                     mol_type = unassigned RNA
                     organism = Homo sapiens
SEQUENCE: 117
gggagaaggg tcgggc                                                17

SEQ ID NO: 118       moltype = RNA   length = 21
FEATURE              Location/Qualifiers
source               1..21
                     mol_type = unassigned RNA
                     organism = Homo sapiens
SEQUENCE: 118
aaggacagg gagggtcgtg g                                           21

SEQ ID NO: 119       moltype = RNA   length = 23
FEATURE              Location/Qualifiers
source               1..23
                     mol_type = unassigned RNA
                     organism = Homo sapiens
SEQUENCE: 119
cgggctgtcc ggaggggtcg gct                                        23

SEQ ID NO: 120       moltype = RNA   length = 22
FEATURE              Location/Qualifiers
source               1..22
                     mol_type = unassigned RNA
                     organism = Homo sapiens
SEQUENCE: 120
agggacggga cgcggtgcag tg                                          22

SEQ ID NO: 121       moltype = RNA   length = 24
FEATURE              Location/Qualifiers
source               1..24
                     mol_type = unassigned RNA
                     organism = Homo sapiens
SEQUENCE: 121
tggggggaca ggatgagagg ctgt                                       24
```

-continued

```
SEQ ID NO: 122        moltype = RNA   length = 23
FEATURE               Location/Qualifiers
source                1..23
                      mol_type = unassigned RNA
                      organism = Homo sapiens
SEQUENCE: 122
ttgctctgct cccccgcccc cag                                          23

SEQ ID NO: 123        moltype = RNA   length = 22
FEATURE               Location/Qualifiers
source                1..22
                      mol_type = unassigned RNA
                      organism = Homo sapiens
SEQUENCE: 123
tggggaaggc gtcagtgtcg gg                                           22

SEQ ID NO: 124        moltype = RNA   length = 25
FEATURE               Location/Qualifiers
source                1..25
                      mol_type = unassigned RNA
                      organism = Homo sapiens
SEQUENCE: 124
taggggtggg ggaattcagg ggtgt                                        25

SEQ ID NO: 125        moltype = RNA   length = 22
FEATURE               Location/Qualifiers
source                1..22
                      mol_type = unassigned RNA
                      organism = Homo sapiens
SEQUENCE: 125
taggggcagc agaggacctg gg                                           22

SEQ ID NO: 126        moltype = RNA   length = 22
FEATURE               Location/Qualifiers
source                1..22
                      mol_type = unassigned RNA
                      organism = Homo sapiens
SEQUENCE: 126
gtgcggaacg ctggccgggg cg                                           22

SEQ ID NO: 127        moltype = RNA   length = 23
FEATURE               Location/Qualifiers
source                1..23
                      mol_type = unassigned RNA
                      organism = Homo sapiens
SEQUENCE: 127
acggggagtc aggcagtggt gga                                          23

SEQ ID NO: 128        moltype = RNA   length = 22
FEATURE               Location/Qualifiers
source                1..22
                      mol_type = unassigned RNA
                      organism = Homo sapiens
SEQUENCE: 128
tgggagggcg tggatgatgg tg                                           22

SEQ ID NO: 129        moltype = RNA   length = 20
FEATURE               Location/Qualifiers
source                1..20
                      mol_type = unassigned RNA
                      organism = Homo sapiens
SEQUENCE: 129
tgggaggagg ggatcttggg                                              20

SEQ ID NO: 130        moltype = RNA   length = 23
FEATURE               Location/Qualifiers
source                1..23
                      mol_type = unassigned RNA
                      organism = Homo sapiens
SEQUENCE: 130
tgagcaccac acaggccggg cgc                                          23

SEQ ID NO: 131        moltype = RNA   length = 19
FEATURE               Location/Qualifiers
source                1..19
                      mol_type = unassigned RNA
                      organism = Homo sapiens
SEQUENCE: 131
ggctggtcag atgggagtg                                               19
```

-continued

```
SEQ ID NO: 132          moltype = RNA   length = 20
FEATURE                 Location/Qualifiers
source                  1..20
                        mol_type = unassigned RNA
                        organism = Homo sapiens
SEQUENCE: 132
ccccagggcg acgcggcggg                                           20

SEQ ID NO: 133          moltype = RNA   length = 17
FEATURE                 Location/Qualifiers
source                  1..17
                        mol_type = unassigned RNA
                        organism = Homo sapiens
SEQUENCE: 133
ccccggggag cccggcg                                              17

SEQ ID NO: 134          moltype = RNA   length = 19
FEATURE                 Location/Qualifiers
source                  1..19
                        mol_type = unassigned RNA
                        organism = Homo sapiens
SEQUENCE: 134
tgcggcagag ctggggtca                                            19

SEQ ID NO: 135          moltype = RNA   length = 22
FEATURE                 Location/Qualifiers
source                  1..22
                        mol_type = unassigned RNA
                        organism = Homo sapiens
SEQUENCE: 135
ttgaggagac atggtggggg cc                                        22

SEQ ID NO: 136          moltype = RNA   length = 21
FEATURE                 Location/Qualifiers
source                  1..21
                        mol_type = unassigned RNA
                        organism = Homo sapiens
SEQUENCE: 136
actcggctgc ggtggacaag t                                         21

SEQ ID NO: 137          moltype = RNA   length = 17
FEATURE                 Location/Qualifiers
source                  1..17
                        mol_type = unassigned RNA
                        organism = Homo sapiens
SEQUENCE: 137
ggcgggtgcg ggggtgg                                              17

SEQ ID NO: 138          moltype = RNA   length = 20
FEATURE                 Location/Qualifiers
source                  1..20
                        mol_type = unassigned RNA
                        organism = Homo sapiens
SEQUENCE: 138
cgcgggtcgg ggtctgcagg                                           20

SEQ ID NO: 139          moltype = RNA   length = 23
FEATURE                 Location/Qualifiers
source                  1..23
                        mol_type = unassigned RNA
                        organism = Homo sapiens
SEQUENCE: 139
tggtgggtgg ggaggagaag tgc                                       23

SEQ ID NO: 140          moltype = RNA   length = 21
FEATURE                 Location/Qualifiers
source                  1..21
                        mol_type = unassigned RNA
                        organism = Homo sapiens
SEQUENCE: 140
agggagggac gggggctgtg c                                         21

SEQ ID NO: 141          moltype = RNA   length = 21
FEATURE                 Location/Qualifiers
source                  1..21
                        mol_type = unassigned RNA
                        organism = Homo sapiens
SEQUENCE: 141
```

-continued atcacattgc cagggattac c                                            21

SEQ ID NO: 142          moltype = RNA   length = 22
FEATURE                 Location/Qualifiers
source                  1..22
                        mol_type = unassigned RNA
                        organism = Homo sapiens
SEQUENCE: 142
ggctggagcg agtgcagtgg tg                                           22

SEQ ID NO: 143          moltype = RNA   length = 23
FEATURE                 Location/Qualifiers
source                  1..23
                        mol_type = unassigned RNA
                        organism = Homo sapiens
SEQUENCE: 143
tgggggctgg gatgggccat ggt                                          23

SEQ ID NO: 144          moltype = RNA   length = 21
FEATURE                 Location/Qualifiers
source                  1..21
                        mol_type = unassigned RNA
                        organism = Homo sapiens
SEQUENCE: 144
aggtgggtat ggaggagccc t                                            21

SEQ ID NO: 145          moltype = RNA   length = 19
FEATURE                 Location/Qualifiers
source                  1..19
                        mol_type = unassigned RNA
                        organism = Homo sapiens
SEQUENCE: 145
ggcttgcatg ggggactgg                                               19

SEQ ID NO: 146          moltype = RNA   length = 21
FEATURE                 Location/Qualifiers
source                  1..21
                        mol_type = unassigned RNA
                        organism = Homo sapiens
SEQUENCE: 146
tcacctggct ggcccgccca g                                            21

SEQ ID NO: 147          moltype = RNA   length = 20
FEATURE                 Location/Qualifiers
source                  1..20
                        mol_type = unassigned RNA
                        organism = Homo sapiens
SEQUENCE: 147
tgggaatggg ggtaagggcc                                              20

SEQ ID NO: 148          moltype = RNA   length = 22
FEATURE                 Location/Qualifiers
source                  1..22
                        mol_type = unassigned RNA
                        organism = Homo sapiens
SEQUENCE: 148
agggccgaag ggtggaagct gc                                           22

SEQ ID NO: 149          moltype = RNA   length = 23
FEATURE                 Location/Qualifiers
source                  1..23
                        mol_type = unassigned RNA
                        organism = Homo sapiens
SEQUENCE: 149
ctcggggcag gcggctggga gcg                                          23

SEQ ID NO: 150          moltype = RNA   length = 17
FEATURE                 Location/Qualifiers
source                  1..17
                        mol_type = unassigned RNA
                        organism = Homo sapiens
SEQUENCE: 150
ggatggagga ggggtct                                                 17

SEQ ID NO: 151          moltype = RNA   length = 23
FEATURE                 Location/Qualifiers
source                  1..23
                        mol_type = unassigned RNA
                        organism = Homo sapiens

```
SEQUENCE: 151
gaacgcctgt tcttgccagg tgg                                              23

SEQ ID NO: 152          moltype = RNA  length = 21
FEATURE                 Location/Qualifiers
source                  1..21
                        mol_type = unassigned RNA
                        organism = Homo sapiens
SEQUENCE: 152
gtgccagctg cagtgggggga g                                               21

SEQ ID NO: 153          moltype = RNA  length = 19
FEATURE                 Location/Qualifiers
source                  1..19
                        mol_type = unassigned RNA
                        organism = Homo sapiens
SEQUENCE: 153
gagccagttg gacaggagc                                                   19

SEQ ID NO: 154          moltype = RNA  length = 19
FEATURE                 Location/Qualifiers
source                  1..19
                        mol_type = unassigned RNA
                        organism = Homo sapiens
SEQUENCE: 154
tggggggagat gggggttga                                                  19

SEQ ID NO: 155          moltype = RNA  length = 22
FEATURE                 Location/Qualifiers
source                  1..22
                        mol_type = unassigned RNA
                        organism = Homo sapiens
SEQUENCE: 155
tgcaggggtc gggtgggcca gg                                               22

SEQ ID NO: 156          moltype = RNA  length = 18
FEATURE                 Location/Qualifiers
source                  1..18
                        mol_type = unassigned RNA
                        organism = Homo sapiens
SEQUENCE: 156
ttcccagcca acgcacca                                                    18

SEQ ID NO: 157          moltype = RNA  length = 24
FEATURE                 Location/Qualifiers
source                  1..24
                        mol_type = unassigned RNA
                        organism = Homo sapiens
SEQUENCE: 157
tgggcgaggg gtgggctctc agag                                             24

SEQ ID NO: 158          moltype = RNA  length = 22
FEATURE                 Location/Qualifiers
source                  1..22
                        mol_type = unassigned RNA
                        organism = Homo sapiens
SEQUENCE: 158
ggggctgtga ttgaccagca gg                                               22

SEQ ID NO: 159          moltype = RNA  length = 21
FEATURE                 Location/Qualifiers
source                  1..21
                        mol_type = unassigned RNA
                        organism = Homo sapiens
SEQUENCE: 159
acggcccagg cggcattggt g                                                21

SEQ ID NO: 160          moltype = RNA  length = 21
FEATURE                 Location/Qualifiers
source                  1..21
                        mol_type = unassigned RNA
                        organism = Homo sapiens
SEQUENCE: 160
ctgggagggg ctgggtttgg c                                                21

SEQ ID NO: 161          moltype = RNA  length = 19
FEATURE                 Location/Qualifiers
source                  1..19
                        mol_type = unassigned RNA
```

-continued

```
                          organism = Homo sapiens
SEQUENCE: 161
gggggaagaa aaggtgggg                                                  19

SEQ ID NO: 162           moltype = RNA   length = 18
FEATURE                  Location/Qualifiers
source                   1..18
                         mol_type = unassigned RNA
                         organism = Homo sapiens
SEQUENCE: 162
cggggcggca ggggcctc                                                   18

SEQ ID NO: 163           moltype = RNA   length = 22
FEATURE                  Location/Qualifiers
source                   1..22
                         mol_type = unassigned RNA
                         organism = Homo sapiens
SEQUENCE: 163
ctgggggtgg ggggctgggc gt                                              22

SEQ ID NO: 164           moltype = RNA   length = 24
FEATURE                  Location/Qualifiers
source                   1..24
                         mol_type = unassigned RNA
                         organism = Homo sapiens
SEQUENCE: 164
gtaggggcgt cccgggcgcg cggg                                            24

SEQ ID NO: 165           moltype = RNA   length = 20
FEATURE                  Location/Qualifiers
source                   1..20
                         mol_type = unassigned RNA
                         organism = Homo sapiens
SEQUENCE: 165
tgtgggactg caaatgggag                                                 20

SEQ ID NO: 166           moltype = RNA   length = 17
FEATURE                  Location/Qualifiers
source                   1..17
                         mol_type = unassigned RNA
                         organism = Homo sapiens
SEQUENCE: 166
gcggggctgg gcgcgcg                                                    17

SEQ ID NO: 167           moltype = RNA   length = 22
FEATURE                  Location/Qualifiers
source                   1..22
                         mol_type = unassigned RNA
                         organism = Homo sapiens
SEQUENCE: 167
tgcggggaca ggccagggca tc                                              22

SEQ ID NO: 168           moltype = RNA   length = 18
FEATURE                  Location/Qualifiers
source                   1..18
                         mol_type = unassigned RNA
                         organism = Homo sapiens
SEQUENCE: 168
aggctgggct gggacgga                                                   18

SEQ ID NO: 169           moltype = RNA   length = 22
FEATURE                  Location/Qualifiers
source                   1..22
                         mol_type = unassigned RNA
                         organism = Homo sapiens
SEQUENCE: 169
tgggggagtg cagtgattgt gg                                              22

SEQ ID NO: 170           moltype = RNA   length = 20
FEATURE                  Location/Qualifiers
source                   1..20
                         mol_type = unassigned RNA
                         organism = Homo sapiens
SEQUENCE: 170
cctgagcccg ggccgcgcag                                                 20

SEQ ID NO: 171           moltype = RNA   length = 24
FEATURE                  Location/Qualifiers
source                   1..24
```

-continued

```
                           mol_type = unassigned RNA
                           organism = Homo sapiens
SEQUENCE: 171
aggcaggggc tggtgctggg cggg                                        24

SEQ ID NO: 172          moltype = RNA   length = 20
FEATURE                 Location/Qualifiers
source                  1..20
                        mol_type = unassigned RNA
                        organism = Homo sapiens
SEQUENCE: 172
gtgtctgggc ggacagctgc                                             20

SEQ ID NO: 173          moltype = RNA   length = 22
FEATURE                 Location/Qualifiers
source                  1..22
                        mol_type = unassigned RNA
                        organism = Homo sapiens
SEQUENCE: 173
agtgggaggc cagggcacgg ca                                          22

SEQ ID NO: 174          moltype = RNA   length = 22
FEATURE                 Location/Qualifiers
source                  1..22
                        mol_type = unassigned RNA
                        organism = Homo sapiens
SEQUENCE: 174
ctggtacagg cctgggggac ag                                          22

SEQ ID NO: 175          moltype = RNA   length = 22
FEATURE                 Location/Qualifiers
source                  1..22
                        mol_type = unassigned RNA
                        organism = Homo sapiens
SEQUENCE: 175
tgagcccctg tgccgccccc ag                                          22

SEQ ID NO: 176          moltype = RNA   length = 22
FEATURE                 Location/Qualifiers
source                  1..22
                        mol_type = unassigned RNA
                        organism = Homo sapiens
SEQUENCE: 176
gggtggggat ttgttgcatt ac                                          22

SEQ ID NO: 177          moltype = RNA   length = 23
FEATURE                 Location/Qualifiers
source                  1..23
                        mol_type = unassigned RNA
                        organism = Homo sapiens
SEQUENCE: 177
tgagggg cag agagcgagac ttt                                        23

SEQ ID NO: 178          moltype = RNA   length = 18
FEATURE                 Location/Qualifiers
source                  1..18
                        mol_type = unassigned RNA
                        organism = Homo sapiens
SEQUENCE: 178
cgggcgtggt ggtggggg                                               18

SEQ ID NO: 179          moltype = RNA   length = 23
FEATURE                 Location/Qualifiers
source                  1..23
                        mol_type = unassigned RNA
                        organism = Homo sapiens
SEQUENCE: 179
gggggccgat acactgtacg aga                                         23

SEQ ID NO: 180          moltype = RNA   length = 22
FEATURE                 Location/Qualifiers
source                  1..22
                        mol_type = unassigned RNA
                        organism = Homo sapiens
SEQUENCE: 180
tggctcagtt cagcaggaac ag                                          22

SEQ ID NO: 181          moltype = RNA   length = 22
FEATURE                 Location/Qualifiers
```

-continued

```
source                  1..22
                        mol_type = unassigned RNA
                        organism = Homo sapiens
SEQUENCE: 181
aggggcgca gtcactgacg tg                                        22

SEQ ID NO: 182          moltype = RNA   length = 23
FEATURE                 Location/Qualifiers
source                  1..23
                        mol_type = unassigned RNA
                        organism = Homo sapiens
SEQUENCE: 182
ggaggcgcag gctcggaaag gcg                                      23

SEQ ID NO: 183          moltype = RNA   length = 23
FEATURE                 Location/Qualifiers
source                  1..23
                        mol_type = unassigned RNA
                        organism = Homo sapiens
SEQUENCE: 183
tggtgcggag agggcccaca gtg                                      23

SEQ ID NO: 184          moltype = RNA   length = 17
FEATURE                 Location/Qualifiers
source                  1..17
                        mol_type = unassigned RNA
                        organism = Homo sapiens
SEQUENCE: 184
gctgggcgag gctggca                                             17

SEQ ID NO: 185          moltype = RNA   length = 22
FEATURE                 Location/Qualifiers
source                  1..22
                        mol_type = unassigned RNA
                        organism = Homo sapiens
SEQUENCE: 185
tcggcctggg gaggaggaag gg                                       22

SEQ ID NO: 186          moltype = RNA   length = 21
FEATURE                 Location/Qualifiers
source                  1..21
                        mol_type = unassigned RNA
                        organism = Homo sapiens
SEQUENCE: 186
atcacattgc cagggatttc c                                        21

SEQ ID NO: 187          moltype = RNA   length = 22
FEATURE                 Location/Qualifiers
source                  1..22
                        mol_type = unassigned RNA
                        organism = Homo sapiens
SEQUENCE: 187
actggggagc agaaggagaa cc                                       22

SEQ ID NO: 188          moltype = RNA   length = 22
FEATURE                 Location/Qualifiers
source                  1..22
                        mol_type = unassigned RNA
                        organism = Homo sapiens
SEQUENCE: 188
aaaccgttac cattactgag tt                                       22

SEQ ID NO: 189          moltype = RNA   length = 20
FEATURE                 Location/Qualifiers
source                  1..20
                        mol_type = unassigned RNA
                        organism = Homo sapiens
SEQUENCE: 189
gtgggttggg gcgggctctg                                          20

SEQ ID NO: 190          moltype = RNA   length = 22
FEATURE                 Location/Qualifiers
source                  1..22
                        mol_type = unassigned RNA
                        organism = Homo sapiens
SEQUENCE: 190
ggggaactgt agatgaaaag gc                                       22

SEQ ID NO: 191          moltype = RNA   length = 23
```

-continued

```
FEATURE              Location/Qualifiers
source               1..23
                     mol_type = unassigned RNA
                     organism = Homo sapiens
SEQUENCE: 191
caggggctgg ggtttcaggt tct                                                  23

SEQ ID NO: 192       moltype = RNA   length = 17
FEATURE              Location/Qualifiers
source               1..17
                     mol_type = unassigned RNA
                     organism = Homo sapiens
SEQUENCE: 192
ggggctgggc gcgcgcc                                                         17

SEQ ID NO: 193       moltype = RNA   length = 22
FEATURE              Location/Qualifiers
source               1..22
                     mol_type = unassigned RNA
                     organism = Homo sapiens
SEQUENCE: 193
caggaaggat ttagggacag gc                                                   22

SEQ ID NO: 194       moltype = RNA   length = 19
FEATURE              Location/Qualifiers
source               1..19
                     mol_type = unassigned RNA
                     organism = Homo sapiens
SEQUENCE: 194
ggggagcgag gggcggggc                                                       19

SEQ ID NO: 195       moltype = RNA   length = 61
FEATURE              Location/Qualifiers
source               1..61
                     mol_type = unassigned RNA
                     organism = Homo sapiens
SEQUENCE: 195
gggggcggga gctgggggtct gcaggttcgc actgatgcct gctcgccctg tctcccgcta  60
g                                                                          61

SEQ ID NO: 196       moltype = RNA   length = 86
FEATURE              Location/Qualifiers
source               1..86
                     mol_type = unassigned RNA
                     organism = Homo sapiens
SEQUENCE: 196
ggcttagaaa cagtccctag gtaggatttg gggaggagct aagaagcccc tacagggccc  60
agaggtgggg actgagcctt agttgg                                               86

SEQ ID NO: 197       moltype = RNA   length = 61
FEATURE              Location/Qualifiers
source               1..61
                     mol_type = unassigned RNA
                     organism = Homo sapiens
SEQUENCE: 197
tcggctggcg ggggtagagc tggctgcagg cccggcccct ctcagctgct gccctctcca  60
g                                                                          61

SEQ ID NO: 198       moltype = RNA   length = 79
FEATURE              Location/Qualifiers
source               1..79
                     mol_type = unassigned RNA
                     organism = Homo sapiens
SEQUENCE: 198
cagcctgggg aaggcttggc agggaagaca catgagcagt gcctccactt cacgcctctc  60
ccttgtctcc tttccctag                                                       79

SEQ ID NO: 199       moltype = RNA   length = 63
FEATURE              Location/Qualifiers
source               1..63
                     mol_type = unassigned RNA
                     organism = Homo sapiens
SEQUENCE: 199
gagtcgagga ctggtggaag ggcctttccc ctcagaccaa ggccctggcc ccagcttctt  60
ctc                                                                        63

SEQ ID NO: 200       moltype = RNA   length = 87
FEATURE              Location/Qualifiers
source               1..87
```

```
                          mol_type = unassigned RNA
                          organism = Homo sapiens
SEQUENCE: 200
gtgtggccgg caggcgggtg ggcgggggcg gccggtggga acccgcccc gccccgcgcc    60
cgcactcacc cgcccgtctc cccacag                                        87

SEQ ID NO: 201           moltype = RNA   length = 84
FEATURE                  Location/Qualifiers
source                   1..84
                          mol_type = unassigned RNA
                          organism = Homo sapiens
SEQUENCE: 201
gctggcgtcg gtgctgggga gcggcccccg ggtgggcctc tgctctggcc cctcctgggg    60
cccgcactct cgctctgggc ccgc                                           84

SEQ ID NO: 202           moltype = RNA   length = 136
FEATURE                  Location/Qualifiers
source                   1..136
                          mol_type = unassigned RNA
                          organism = Homo sapiens
SEQUENCE: 202
ccgcttgcct cgcccagcgc agccccggcc gctgggcgca cccgtcccgt tcgtccccgg    60
acgttgctct ctaccccggg aacgtcgaga ctggagcgcc cgaactgagc caccttcgcg   120
gaccccgaga gcggcg                                                   136

SEQ ID NO: 203           moltype = RNA   length = 73
FEATURE                  Location/Qualifiers
source                   1..73
                          mol_type = unassigned RNA
                          organism = Homo sapiens
SEQUENCE: 203
cggcgacggc ggggtgggtg aggtcgggcc ccaagactcg gggtttgccg ggcgcctcag    60
ttcaccgcgg ccg                                                       73

SEQ ID NO: 204           moltype = RNA   length = 69
FEATURE                  Location/Qualifiers
source                   1..69
                          mol_type = unassigned RNA
                          organism = Homo sapiens
SEQUENCE: 204
gggcttaggg atgggaggcc aggatgaaga ttaatcccta atcccaaca ctggccttgc     60
tatccccag                                                            69

SEQ ID NO: 205           moltype = RNA   length = 68
FEATURE                  Location/Qualifiers
source                   1..68
                          mol_type = unassigned RNA
                          organism = Homo sapiens
SEQUENCE: 205
cgtggtgagg atatggcagg gaaggggagt ttccctctat tcccttcccc ccagtaatct    60
tcatcatg                                                             68

SEQ ID NO: 206           moltype = RNA   length = 61
FEATURE                  Location/Qualifiers
source                   1..61
                          mol_type = unassigned RNA
                          organism = Homo sapiens
SEQUENCE: 206
tctcgtttga tctcggaagc taagcagggt tgggcctggt tagtacttgg atgggaaact    60
t                                                                    61

SEQ ID NO: 207           moltype = RNA   length = 53
FEATURE                  Location/Qualifiers
source                   1..53
                          mol_type = unassigned RNA
                          organism = Homo sapiens
SEQUENCE: 207
gtttgatctc ggaagctaag cagggtcggg cctggttagt acttggatgg gag            53

SEQ ID NO: 208           moltype = RNA   length = 63
FEATURE                  Location/Qualifiers
source                   1..63
                          mol_type = unassigned RNA
                          organism = Homo sapiens
SEQUENCE: 208
cttgcccggg agaaggaggt ggcctggaga gctgctgtct ccagccgccg cctgtctcca    60
cag                                                                  63

SEQ ID NO: 209           moltype = RNA   length = 80
```

-continued

```
FEATURE                  Location/Qualifiers
source                   1..80
                         mol_type = unassigned RNA
                         organism = Homo sapiens
SEQUENCE: 209
gcgtcaagat ggcggcgggg aggtaggcag agcaggacgc cgctgctgcc gccgccaccg   60
ccgcctccgc tccagtcgcc                                               80

SEQ ID NO: 210           moltype = RNA   length = 63
FEATURE                  Location/Qualifiers
source                   1..63
                         mol_type = unassigned RNA
                         organism = Homo sapiens
SEQUENCE: 210
aatgggtggg tgctggtggg agccgtgccc tggccactca ttcggctctc tccctcaccc   60
tag                                                                 63

SEQ ID NO: 211           moltype = RNA   length = 80
FEATURE                  Location/Qualifiers
source                   1..80
                         mol_type = unassigned RNA
                         organism = Homo sapiens
SEQUENCE: 211
cgggaatgcc gcggcgggga cggcgattgg tccgtatgtg tggtgccacc ggccgccggc   60
tccgccccgg cccccgcccc                                               80

SEQ ID NO: 212           moltype = RNA   length = 93
FEATURE                  Location/Qualifiers
source                   1..93
                         mol_type = unassigned RNA
                         organism = Homo sapiens
SEQUENCE: 212
gcttgttggg gattgggtca ggccagtgtt caagggcccc tcctctagta ctccctgttt   60
gtgttctgcc actgactgag cttctcccca cag                                93

SEQ ID NO: 213           moltype = RNA   length = 71
FEATURE                  Location/Qualifiers
source                   1..71
                         mol_type = unassigned RNA
                         organism = Homo sapiens
SEQUENCE: 213
gtgtctgtgc cggtcccagg agaacctgca gaggcatcgg gtcagcggtg ctcctgcggg   60
ccgacactca c                                                        71

SEQ ID NO: 214           moltype = RNA   length = 98
FEATURE                  Location/Qualifiers
source                   1..98
                         mol_type = unassigned RNA
                         organism = Homo sapiens
SEQUENCE: 214
ttgggcaagg tgcggggcta gggctaacag cagtcttact gaaggtttcc tggaaaccac   60
gcacatgctg ttgccactaa cctcaacctt actcggtc                           98

SEQ ID NO: 215           moltype = RNA   length = 74
FEATURE                  Location/Qualifiers
source                   1..74
                         mol_type = unassigned RNA
                         organism = Homo sapiens
SEQUENCE: 215
gcagcccggt gagcgctcgc tggcctggca gtgcgtcgga agaacagggc gggtggggcc   60
gcgcacatct ctgc                                                     74

SEQ ID NO: 216           moltype = RNA   length = 94
FEATURE                  Location/Qualifiers
source                   1..94
                         mol_type = unassigned RNA
                         organism = Homo sapiens
SEQUENCE: 216
cgggcagcgg gtgccaggca cggtgtcagc aggcaacatg gccgagaggc cggggcctcc   60
gggcggcgcc gtgtccgcga ccgcgtaccc tgac                               94

SEQ ID NO: 217           moltype = RNA   length = 67
FEATURE                  Location/Qualifiers
source                   1..67
                         mol_type = unassigned RNA
                         organism = Homo sapiens
SEQUENCE: 217
ccagacccct ggggctgggc aggcggaaag aggtctgaac tgcctctgcc tccttggtct   60
ccggcag                                                             67
```

-continued

```
SEQ ID NO: 218          moltype = RNA   length = 66
FEATURE                 Location/Qualifiers
source                  1..66
                        mol_type = unassigned RNA
                        organism = Homo sapiens
SEQUENCE: 218
gggcatgggg aggtgtggag tcagcatggg gctaggaggc cccgcgctga cccgccttct   60
ccgcag                                                              66

SEQ ID NO: 219          moltype = RNA   length = 98
FEATURE                 Location/Qualifiers
source                  1..98
                        mol_type = unassigned RNA
                        organism = Homo sapiens
SEQUENCE: 219
cttggtcaat aggaaagagg tgggacctcc tggcttttcc tctgcagcat ggctcggacc   60
tagtgcaatg tttaagctcc cctctctttc ctgttcag                           98

SEQ ID NO: 220          moltype = RNA   length = 79
FEATURE                 Location/Qualifiers
source                  1..79
                        mol_type = unassigned RNA
                        organism = Homo sapiens
SEQUENCE: 220
ctcgaggtgc tggggacgc gtgagcgcga gccgcttcct cacggctcgg ccgcggcgcg     60
tagccccgc cacatcggg                                                 79

SEQ ID NO: 221          moltype = RNA   length = 63
FEATURE                 Location/Qualifiers
source                  1..63
                        mol_type = unassigned RNA
                        organism = Homo sapiens
SEQUENCE: 221
tggtggcggc ggtagttatg ggcttctctt tctcaccagc agccctggg ccgccgcctc     60
cct                                                                 63

SEQ ID NO: 222          moltype = RNA   length = 85
FEATURE                 Location/Qualifiers
source                  1..85
                        mol_type = unassigned RNA
                        organism = Homo sapiens
SEQUENCE: 222
ggcgcctcct gctctgctgt gccgccaggg cctcccctag cgcgccttct ggagaggctt   60
tgtgcggata cggggctgga ggcct                                         85

SEQ ID NO: 223          moltype = RNA   length = 96
FEATURE                 Location/Qualifiers
source                  1..96
                        mol_type = unassigned RNA
                        organism = Homo sapiens
SEQUENCE: 223
gctctggggc gtgccgccgc cgtcgctgcc acctcccta ccgctagtgg aagaagatgg     60
cggaaggcgg agcggcggat ctggacaccc agcggt                             96

SEQ ID NO: 224          moltype = RNA   length = 63
FEATURE                 Location/Qualifiers
source                  1..63
                        mol_type = unassigned RNA
                        organism = Homo sapiens
SEQUENCE: 224
accctagggt ggggctggag gtggggctga ggctgagtct tcctccctt cctccctgcc     60
cag                                                                 63

SEQ ID NO: 225          moltype = RNA   length = 73
FEATURE                 Location/Qualifiers
source                  1..73
                        mol_type = unassigned RNA
                        organism = Homo sapiens
SEQUENCE: 225
gtgggcgggg gcaggtgtgt ggtgggtggt ggcctgcggt gagcagggcc ctcacacctg   60
cctcgccccc cag                                                      73

SEQ ID NO: 226          moltype = RNA   length = 81
FEATURE                 Location/Qualifiers
source                  1..81
                        mol_type = unassigned RNA
                        organism = Homo sapiens
SEQUENCE: 226
```

-continued

```
tagaggcagt ttcaacagat gtgtagactt ttgatatgag aaattggttt caaaatcagg   60
agtcggggct ttactgcttt t                                            81

SEQ ID NO: 227           moltype = RNA   length = 86
FEATURE                  Location/Qualifiers
source                   1..86
                         mol_type = unassigned RNA
                         organism = Homo sapiens
SEQUENCE: 227
cgcctgagcg tgcagcagga catcttcctg acctggtaat aattaggtga gaaggatggt   60
tgggggcggt cggcgtaact caggga                                       86

SEQ ID NO: 228           moltype = RNA   length = 72
FEATURE                  Location/Qualifiers
source                   1..72
                         mol_type = unassigned RNA
                         organism = Homo sapiens
SEQUENCE: 228
gagtctgagg gacccaggac aggagaaggc ctatggtgat ttgcattctt cctgccctgg   60
ctccatcctc ag                                                      72

SEQ ID NO: 229           moltype = RNA   length = 68
FEATURE                  Location/Qualifiers
source                   1..68
                         mol_type = unassigned RNA
                         organism = Homo sapiens
SEQUENCE: 229
gaatggaaga agaaggcggt cggtctgcgg gagccaggcc gcagagccat ccgccttctg   60
tccatgtc                                                           68

SEQ ID NO: 230           moltype = RNA   length = 102
FEATURE                  Location/Qualifiers
source                   1..102
                         mol_type = unassigned RNA
                         organism = Homo sapiens
SEQUENCE: 230
tgtgttccct atcctcctta tgtcccaccc ccactcctgt ttgaatattt caccagaaac   60
aggagtgggg ggtgggacgt aaggaggatg ggggaaagaa ca                    102

SEQ ID NO: 231           moltype = RNA   length = 65
FEATURE                  Location/Qualifiers
source                   1..65
                         mol_type = unassigned RNA
                         organism = Homo sapiens
SEQUENCE: 231
gagaatgggg ggacagatgg agaggacaca ggctggcact gaggtcccct ccactttcct   60
cctag                                                              65

SEQ ID NO: 232           moltype = RNA   length = 82
FEATURE                  Location/Qualifiers
source                   1..82
                         mol_type = unassigned RNA
                         organism = Homo sapiens
SEQUENCE: 232
tgagctgttg gattcggggc cgtagcactg tctgagaggt ttacatttct cacagtgaac   60
cggtctcttt ttcagctgct tc                                           82

SEQ ID NO: 233           moltype = RNA   length = 92
FEATURE                  Location/Qualifiers
source                   1..92
                         mol_type = unassigned RNA
                         organism = Homo sapiens
SEQUENCE: 233
cgctgcgctt ctgggcccgc ggcgggcgtg gggctgcccg ggccggtcga ccagcgcgcc   60
gtagctcccg aggcccgagc cgcgacccgc gg                                92

SEQ ID NO: 234           moltype = RNA   length = 80
FEATURE                  Location/Qualifiers
source                   1..80
                         mol_type = unassigned RNA
                         organism = Homo sapiens
SEQUENCE: 234
cgtgtgagcc cgccctgtgc ccggcccact tctgcttcct cttagcgcag gaggggtccc   60
gcactgggag gggccctcac                                              80

SEQ ID NO: 235           moltype = RNA   length = 90
FEATURE                  Location/Qualifiers
source                   1..90
                         mol_type = unassigned RNA
```

-continued

```
                           organism = Homo sapiens
SEQUENCE: 235
gtgggtacgg cccagtgggg gggagaggga cacgccctgg gctctgccca gggtgcagcc      60
ggactgactg agcccctgtg ccgcccccag                                       90

SEQ ID NO: 236            moltype = RNA   length = 68
FEATURE                   Location/Qualifiers
source                    1..68
                          mol_type = unassigned RNA
                          organism = Homo sapiens
SEQUENCE: 236
ctcaggctca gtggtgcatg cttatagtcc cagccactct ggaggctgaa ggaagatggc      60
ttgagcct                                                               68

SEQ ID NO: 237            moltype = RNA   length = 86
FEATURE                   Location/Qualifiers
source                    1..86
                          mol_type = unassigned RNA
                          organism = Homo sapiens
SEQUENCE: 237
ggggctgggg gtgtggggag agagagtgca cagccagctc aggattaaa gctctttctc       60
tctctctctc tcccacttcc ctgcag                                           86

SEQ ID NO: 238            moltype = RNA   length = 109
FEATURE                   Location/Qualifiers
source                    1..109
                          mol_type = unassigned RNA
                          organism = Homo sapiens
SEQUENCE: 238
ggtcgggctc accatgacac agtgtgagac ctcgggctac aacacaggac ccgggcgctg      60
ctctgacccc tcgtgtcttg tgttgcagcc ggagggacgc aggtccgca                  109

SEQ ID NO: 239            moltype = RNA   length = 75
FEATURE                   Location/Qualifiers
source                    1..75
                          mol_type = unassigned RNA
                          organism = Homo sapiens
SEQUENCE: 239
aagcaagact gagggggcctc agaccgagct tttggaaaat agaaaagtct cgctctctgc     60
ccctcagcct aactt                                                       75

SEQ ID NO: 240            moltype = RNA   length = 110
FEATURE                   Location/Qualifiers
source                    1..110
                          mol_type = unassigned RNA
                          organism = Homo sapiens
SEQUENCE: 240
ggctacagtc tttcttcatg tgactcgtgg acttccctt gtcatcctat gcctgagaat       60
atatgaagga ggctgggaag gcaaagggac gttcaattgt catcactggc                 110

SEQ ID NO: 241            moltype = RNA   length = 137
FEATURE                   Location/Qualifiers
source                    1..137
                          mol_type = unassigned RNA
                          organism = Homo sapiens
SEQUENCE: 241
agccagacaa gagggtcatg gggagtcact gtcaacccag agcaggcact gccctgcga       60
ccagcctggg gcatcggttg gggtgcaggg gtctgctggt gatgctttcc atctctttgc      120
tttgtcctga ttgtagc                                                     137

SEQ ID NO: 242            moltype = RNA   length = 65
FEATURE                   Location/Qualifiers
source                    1..65
                          mol_type = unassigned RNA
                          organism = Homo sapiens
SEQUENCE: 242
gagggtgggc gagggcggct gagcggctcc atccccggc ctgctcatcc ccctcgccct       60
ctcag                                                                  65

SEQ ID NO: 243            moltype = RNA   length = 96
FEATURE                   Location/Qualifiers
source                    1..96
                          mol_type = unassigned RNA
                          organism = Homo sapiens
SEQUENCE: 243
ctcgggaggg gcgggagggg ggtccccggt gctcggatct cgaggtgct tattgttcgg       60
tccgagcctg ggtctccctc ttccccccaa cccccc                                96

SEQ ID NO: 244            moltype = RNA   length = 69
```

-continued

```
FEATURE              Location/Qualifiers
source               1..69
                     mol_type = unassigned RNA
                     organism = Homo sapiens
SEQUENCE: 244
ggccctcggg cctggggttg ggggagctct gtcctgtctc actcattgct cctccctgc   60
ctggcccag                                                         69

SEQ ID NO: 245       moltype = RNA   length = 57
FEATURE              Location/Qualifiers
source               1..57
                     mol_type = unassigned RNA
                     organism = Homo sapiens
SEQUENCE: 245
cattggaggg tgtggaagac atctgggcca actctgatct cttcatctac cccccag      57

SEQ ID NO: 246       moltype = RNA   length = 106
FEATURE              Location/Qualifiers
source               1..106
                     mol_type = unassigned RNA
                     organism = Homo sapiens
SEQUENCE: 246
agaagaatgc ccaaccagcc ctcagttgct acagttccct gttgtttcag ctcgacaaca   60
acaggcggct gtagcaatgg ggggctggat gggcatctca atgtgc                106

SEQ ID NO: 247       moltype = RNA   length = 71
FEATURE              Location/Qualifiers
source               1..71
                     mol_type = unassigned RNA
                     organism = Homo sapiens
SEQUENCE: 247
tgaccacccc cgggcaaaga cctgcagatc ccctgttaga gacgggccca ggactttgtg   60
cggggtgccc a                                                       71

SEQ ID NO: 248       moltype = RNA   length = 69
FEATURE              Location/Qualifiers
source               1..69
                     mol_type = unassigned RNA
                     organism = Homo sapiens
SEQUENCE: 248
ccggcaggc aggtgtaggg tggagcccac tgtggctcct gactcagccc tgctgccttc     60
acctgccag                                                         69

SEQ ID NO: 249       moltype = RNA   length = 67
FEATURE              Location/Qualifiers
source               1..67
                     mol_type = unassigned RNA
                     organism = Homo sapiens
SEQUENCE: 249
gtgggagggg agaggcagca agcacacagg gcctgggact agcatgctga cctccctcct   60
gccccag                                                           67

SEQ ID NO: 250       moltype = RNA   length = 73
FEATURE              Location/Qualifiers
source               1..73
                     mol_type = unassigned RNA
                     organism = Homo sapiens
SEQUENCE: 250
ctggtgtttg aggcgatgtg gggatgtaga gacaacttcc cagtctcatt tcctcatcct   60
gccaggccac cat                                                     73

SEQ ID NO: 251       moltype = RNA   length = 59
FEATURE              Location/Qualifiers
source               1..59
                     mol_type = unassigned RNA
                     organism = Homo sapiens
SEQUENCE: 251
ctccagggag acagtgtgtg aggcctcttg ccatggcctc cctgcccgcc tctctgcag     59

SEQ ID NO: 252       moltype = RNA   length = 77
FEATURE              Location/Qualifiers
source               1..77
                     mol_type = unassigned RNA
                     organism = Homo sapiens
SEQUENCE: 252
gagttgggag gttccctctc caaatgtgtc ttgatccccc accccaagac acatttggag   60
agggaccctc ccaactc                                                77

SEQ ID NO: 253       moltype = RNA   length = 65
```

-continued

```
FEATURE                 Location/Qualifiers
source                  1..65
                        mol_type = unassigned RNA
                        organism = Homo sapiens
SEQUENCE: 253
gtctcctggg gggaggagac cctgctctcc ctggcagcaa gcctctcctg cccttccaga   60
ttagc                                                                65

SEQ ID NO: 254          moltype = RNA   length = 65
FEATURE                 Location/Qualifiers
source                  1..65
                        mol_type = unassigned RNA
                        organism = Homo sapiens
SEQUENCE: 254
agccctgggg gtggtctcta gccaaggctc tggggtctca cccttggctg gtctctgctc   60
cgcag                                                                65

SEQ ID NO: 255          moltype = RNA   length = 67
FEATURE                 Location/Qualifiers
source                  1..67
                        mol_type = unassigned RNA
                        organism = Homo sapiens
SEQUENCE: 255
gcgccctccc tctctccccg gtgtgcaaat gtgtgtgtgc ggtgttatgc cggacaagag   60
ggaggtg                                                              67

SEQ ID NO: 256          moltype = RNA   length = 81
FEATURE                 Location/Qualifiers
source                  1..81
                        mol_type = unassigned RNA
                        organism = Homo sapiens
SEQUENCE: 256
catcctcctt acgtcccacc ccccactcct gtttctggtg aaatattcaa acaggagtgg   60
gggtgggaca taaggaggat a                                              81

SEQ ID NO: 257          moltype = RNA   length = 80
FEATURE                 Location/Qualifiers
source                  1..80
                        mol_type = unassigned RNA
                        organism = Homo sapiens
SEQUENCE: 257
ggttccggag ccccggcgcg ggcgggttct ggggtgtaga cgctgctggc cagcccgccc   60
cagccgaggt tctcggcacc                                                80

SEQ ID NO: 258          moltype = RNA   length = 89
FEATURE                 Location/Qualifiers
source                  1..89
                        mol_type = unassigned RNA
                        organism = Homo sapiens
SEQUENCE: 258
agcctgtggg aaagagaaga gcagggcagg gtgaaggccc ggcggagaca ctctgcccac   60
cccacaccct gcctatgggc cacacagct                                      89

SEQ ID NO: 259          moltype = RNA   length = 66
FEATURE                 Location/Qualifiers
source                  1..66
                        mol_type = unassigned RNA
                        organism = Homo sapiens
SEQUENCE: 259
agcagccctc ggcggcccgg ggggcgggcg gcggtgcccg tcccggggct gcgcgaggca   60
caggcg                                                               66

SEQ ID NO: 260          moltype = RNA   length = 82
FEATURE                 Location/Qualifiers
source                  1..82
                        mol_type = unassigned RNA
                        organism = Homo sapiens
SEQUENCE: 260
gctacgggga gcggggagga agtgggcgct gcttctgcgt tatctggaag gagcagccca   60
ctcctgtcct gggctctgtg gt                                             82

SEQ ID NO: 261          moltype = RNA   length = 80
FEATURE                 Location/Qualifiers
source                  1..80
                        mol_type = unassigned RNA
                        organism = Homo sapiens
SEQUENCE: 261
acctctacct cccggcagag gaggctgcag aggctggctt tccaaaactc tgcccctcc    60
gctgctgcca agtggctggt                                                80
```

```
SEQ ID NO: 262            moltype = RNA   length = 98
FEATURE                   Location/Qualifiers
source                    1..98
                          mol_type = unassigned RNA
                          organism = Homo sapiens
SEQUENCE: 262
ttctcacccc cgcctgacac gggcgacagc tgcggcccgc tgtgttcact cgggccgagt    60
gcgtctcctg tcaggcaagg gagagcagag cccccctg                            98

SEQ ID NO: 263            moltype = RNA   length = 82
FEATURE                   Location/Qualifiers
source                    1..82
                          mol_type = unassigned RNA
                          organism = Homo sapiens
SEQUENCE: 263
tgtgggcagg ccctgggga gctgaggctc tgggggtggc cggggctgac cctgggcctc      60
tgctccccag tgtctgaccg cg                                             82

SEQ ID NO: 264            moltype = RNA   length = 74
FEATURE                   Location/Qualifiers
source                    1..74
                          mol_type = unassigned RNA
                          organism = Homo sapiens
SEQUENCE: 264
cctgcaggag gcagtgggcg agcaggcggg gcagcccaat gccatgggcc tgatctcacc     60
gctgcctcct tccc                                                      74

SEQ ID NO: 265            moltype = RNA   length = 76
FEATURE                   Location/Qualifiers
source                    1..76
                          mol_type = unassigned RNA
                          organism = Homo sapiens
SEQUENCE: 265
actgactttg agtctctcct cagggtgctg caggcaaagc tggggaccca gggagagacg     60
taagtgaggg gagatg                                                    76

SEQ ID NO: 266            moltype = RNA   length = 66
FEATURE                   Location/Qualifiers
source                    1..66
                          mol_type = unassigned RNA
                          organism = Homo sapiens
SEQUENCE: 266
ccgagtgggg cggggcaggt ccctgcaggg actgtgacac tgaaggacct gcaccttcgc     60
ccacag                                                               66

SEQ ID NO: 267            moltype = RNA   length = 61
FEATURE                   Location/Qualifiers
source                    1..61
                          mol_type = unassigned RNA
                          organism = Homo sapiens
SEQUENCE: 267
gagggcagcg tgggtgtggc ggaggcaggc gtgaccgttt gccgccctct cgctgctcta     60
g                                                                    61

SEQ ID NO: 268            moltype = RNA   length = 87
FEATURE                   Location/Qualifiers
source                    1..87
                          mol_type = unassigned RNA
                          organism = Homo sapiens
SEQUENCE: 268
ccctcatctc tgggcagggg cttattgtag gagtctctga agagagctgt ggactgacct     60
gctttaaccc ttccccaggt tcccatt                                        87

SEQ ID NO: 269            moltype = RNA   length = 103
FEATURE                   Location/Qualifiers
source                    1..103
                          mol_type = unassigned RNA
                          organism = Homo sapiens
SEQUENCE: 269
gtgtcggctg tggcgtgact gtccctctgt gtcccccact aggccactg ctcagtggag      60
cgtggaggac gaggaggagg ccgtccacga gcaatgccag cat                     103

SEQ ID NO: 270            moltype = RNA   length = 109
FEATURE                   Location/Qualifiers
source                    1..109
                          mol_type = unassigned RNA
                          organism = Homo sapiens
SEQUENCE: 270
```

```
tgctattgtc ttactgctac agcagggctg gggattgcag tatccgctgt tgctgctgct     60
cccagtcctg ccctgctgc tacctagtcc agcctcaccg catcccaga                   109

SEQ ID NO: 271          moltype = RNA   length = 79
FEATURE                 Location/Qualifiers
source                  1..79
                        mol_type = unassigned RNA
                        organism = Homo sapiens
SEQUENCE: 271
gtgcagatcc ttgggagccc tgttagactc tggattttac acttggagtg aacgggcgcc     60
atcccgaggc tttgcacag                                                   79

SEQ ID NO: 272          moltype = RNA   length = 67
FEATURE                 Location/Qualifiers
source                  1..67
                        mol_type = unassigned RNA
                        organism = Homo sapiens
SEQUENCE: 272
tacaggccgg ggctttgggt gagggacccc cggagtctgt cacggtctca ccccaactct     60
gccccag                                                                67

SEQ ID NO: 273          moltype = RNA   length = 66
FEATURE                 Location/Qualifiers
source                  1..66
                        mol_type = unassigned RNA
                        organism = Homo sapiens
SEQUENCE: 273
gggaggaggg aggagatggg ccaagttccc tctggctgga acgcccttcc cccccttctt     60
cacctg                                                                 66

SEQ ID NO: 274          moltype = RNA   length = 86
FEATURE                 Location/Qualifiers
source                  1..86
                        mol_type = unassigned RNA
                        organism = Homo sapiens
SEQUENCE: 274
agcactgccc ccggtgagtc agggtggggc tggccccctg cttcgtgccc atccgcgctc     60
tgactctctg cccacctgca ggagct                                           86

SEQ ID NO: 275          moltype = RNA   length = 115
FEATURE                 Location/Qualifiers
source                  1..115
                        mol_type = unassigned RNA
                        organism = Homo sapiens
SEQUENCE: 275
gagcaaaaac cagagaacaa catgggagcg ttcctaaccc ctaaggcaac tggatgggag     60
acctgaccca tccagttctc tgaggggct cttgtgtgtt ctacaaggtt gttca          115

SEQ ID NO: 276          moltype = RNA   length = 60
FEATURE                 Location/Qualifiers
source                  1..60
                        mol_type = unassigned RNA
                        organism = Homo sapiens
SEQUENCE: 276
aggcctaggg ggtggcaggc tggccatcag tgtgggctaa ccctgtcctc tccctcccag     60

SEQ ID NO: 277          moltype = RNA   length = 73
FEATURE                 Location/Qualifiers
source                  1..73
                        mol_type = unassigned RNA
                        organism = Homo sapiens
SEQUENCE: 277
gaaaacaacc aggtgggctt cccggagggc ggaacaccca gccccagcat ccagggctca     60
cctaccacgt ttg                                                         73

SEQ ID NO: 278          moltype = RNA   length = 62
FEATURE                 Location/Qualifiers
source                  1..62
                        mol_type = unassigned RNA
                        organism = Homo sapiens
SEQUENCE: 278
gctgggggtc ccccgacagt gtggagctgg ggccgggtcc cggggagggg ggttctgggc     60
ag                                                                     62

SEQ ID NO: 279          moltype = RNA   length = 70
FEATURE                 Location/Qualifiers
source                  1..70
                        mol_type = unassigned RNA
                        organism = Homo sapiens
```

-continued

```
SEQUENCE: 279
ctcgggcccg accgcgccgg cccgcacctc ccggcccgga gctgcgggct gcggtcaggg    60
cgatcccggg                                                           70

SEQ ID NO: 280          moltype = RNA   length = 72
FEATURE                 Location/Qualifiers
source                  1..72
                        mol_type = unassigned RNA
                        organism = Homo sapiens
SEQUENCE: 280
atgagcgggt gggagcagat cttattgaga gttccttctc ctgctcctga ttgtcttccc    60
ccaccctcac ag                                                        72

SEQ ID NO: 281          moltype = RNA   length = 93
FEATURE                 Location/Qualifiers
source                  1..93
                        mol_type = unassigned RNA
                        organism = Homo sapiens
SEQUENCE: 281
ccttccggcg tcccaggcgg ggcgccgcgg gaccgccctc gtgtctgtgg cggtgggatc    60
ccgcggccgt gttttcctgg tggcccggcc atg                                 93

SEQ ID NO: 282          moltype = RNA   length = 86
FEATURE                 Location/Qualifiers
source                  1..86
                        mol_type = unassigned RNA
                        organism = Homo sapiens
SEQUENCE: 282
attctaggtg gggagactga cggctggagg cccataagct gtctaaaact tcggccccca    60
gatttctggt ctccccactt cagaac                                         86

SEQ ID NO: 283          moltype = RNA   length = 64
FEATURE                 Location/Qualifiers
source                  1..64
                        mol_type = unassigned RNA
                        organism = Homo sapiens
SEQUENCE: 283
aaccccgggc cggaggtcaa gggcgtcgct tctccctaat gttgcctctt ttccacggcc    60
tcag                                                                 64

SEQ ID NO: 284          moltype = RNA   length = 88
FEATURE                 Location/Qualifiers
source                  1..88
                        mol_type = unassigned RNA
                        organism = Homo sapiens
SEQUENCE: 284
gtggggccag gcggtggtgg gcactgctgg ggtgggcaca gcagccatgc agagcgggca    60
tttgacccccg tgccaccctt ttccccag                                      88

SEQ ID NO: 285          moltype = RNA   length = 61
FEATURE                 Location/Qualifiers
source                  1..61
                        mol_type = unassigned RNA
                        organism = Homo sapiens
SEQUENCE: 285
aactgcgggg ccagagcaga gagcccttgc acaccaccag cctctcctcc ctgtgcccca    60
g                                                                    61

SEQ ID NO: 286          moltype = RNA   length = 67
FEATURE                 Location/Qualifiers
source                  1..67
                        mol_type = unassigned RNA
                        organism = Homo sapiens
SEQUENCE: 286
ggcagccagg gggatgggcg agcttgggcc cattcctttc cttaccctac cccccatccc    60
cctgtag                                                              67

SEQ ID NO: 287          moltype = RNA   length = 79
FEATURE                 Location/Qualifiers
source                  1..79
                        mol_type = unassigned RNA
                        organism = Homo sapiens
SEQUENCE: 287
gtgaggtggg ggccagcagg gagtgggctg ggctgggctg ggccaaggta caaggcctca    60
ccctgcatcc cgcacccag                                                 79

SEQ ID NO: 288          moltype = RNA   length = 80
FEATURE                 Location/Qualifiers
source                  1..80
```

-continued

```
                         mol_type = unassigned RNA
                         organism = Homo sapiens
SEQUENCE: 288
tgagaggccg caccttgcct tgctgcccgg gccgtgcacc cgtgggcccc agggcgacgc   60
ggcggggcg gccctagcga                                                80

SEQ ID NO: 289          moltype = RNA   length = 76
FEATURE                 Location/Qualifiers
source                  1..76
                        mol_type = unassigned RNA
                        organism = Homo sapiens
SEQUENCE: 289
ccgatgcctc gggagtctac agcagggcca tgtctgtgag ggcccaaggg tgcatgtgtc   60
tcccaggttt cggtgc                                                   76

SEQ ID NO: 290          moltype = RNA   length = 97
FEATURE                 Location/Qualifiers
source                  1..97
                        mol_type = unassigned RNA
                        organism = Homo sapiens
SEQUENCE: 290
atctgagttg ggagggtccc tctccaaatg tgtcttgggg tggggatca agacacattt     60
ggagagggaa cctcccaact cggcctctgc catcatt                            97

SEQ ID NO: 291          moltype = RNA   length = 67
FEATURE                 Location/Qualifiers
source                  1..67
                        mol_type = unassigned RNA
                        organism = Homo sapiens
SEQUENCE: 291
gtggcactca aactgtgggg gcactttctg ctctctggtg aaagtgccgc catcttttga   60
gtgttac                                                             67

SEQ ID NO: 292          moltype = RNA   length = 94
FEATURE                 Location/Qualifiers
source                  1..94
                        mol_type = unassigned RNA
                        organism = Homo sapiens
SEQUENCE: 292
gtgaggtgtg ggcccggccc caggagcggg gcctgggcag ccccgtgtgt tgaggaagga   60
aggcagggcc cccgctcccc gggcctgacc ccac                               94

SEQ ID NO: 293          moltype = RNA   length = 65
FEATURE                 Location/Qualifiers
source                  1..65
                        mol_type = unassigned RNA
                        organism = Homo sapiens
SEQUENCE: 293
tgtctgggga tttggagaag tggtgagcgc aggtctttgg caccatctcc cctggtccct   60
tggct                                                               65

SEQ ID NO: 294          moltype = RNA   length = 81
FEATURE                 Location/Qualifiers
source                  1..81
                        mol_type = unassigned RNA
                        organism = Homo sapiens
SEQUENCE: 294
agttggtggg ggagccatga gataagagca cctcctagag aatgttgaac taaaggtgcc   60
ctctctggct cctccccaaa g                                             81

SEQ ID NO: 295          moltype = RNA   length = 47
FEATURE                 Location/Qualifiers
source                  1..47
                        mol_type = unassigned RNA
                        organism = Homo sapiens
SEQUENCE: 295
ctcggcgcgg ggcgcgggct ccgggttggg gcgagccaac gccgggg                 47

SEQ ID NO: 296          moltype = RNA   length = 64
FEATURE                 Location/Qualifiers
source                  1..64
                        mol_type = unassigned RNA
                        organism = Homo sapiens
SEQUENCE: 296
gaggcactgg gtaggtgggg ctccagggct cctgacacct ggacctctcc tccccaggcc   60
caca                                                                64

SEQ ID NO: 297          moltype = RNA   length = 68
FEATURE                 Location/Qualifiers
```

```
source                    1..68
                          mol_type = unassigned RNA
                          organism = Homo sapiens
SEQUENCE: 297
gtgcaaagag caggaggaca ggggatttat ctcccaaggg aggtcccctg atcctagtca   60
cggcacca                                                            68

SEQ ID NO: 298            moltype = RNA   length = 66
FEATURE                   Location/Qualifiers
source                    1..66
                          mol_type = unassigned RNA
                          organism = Homo sapiens
SEQUENCE: 298
cagagcaggg cagggaaggt gggagagggg cccagctgac cctcctgtca cccgctcctt   60
gcccag                                                              66

SEQ ID NO: 299            moltype = RNA   length = 65
FEATURE                   Location/Qualifiers
source                    1..65
                          mol_type = unassigned RNA
                          organism = Homo sapiens
SEQUENCE: 299
gagggctagg tgggggctt gaagccccga gatgcctcac gtcttcaccc ctctcaccta    60
agcag                                                               65

SEQ ID NO: 300            moltype = RNA   length = 50
FEATURE                   Location/Qualifiers
source                    1..50
                          mol_type = unassigned RNA
                          organism = Homo sapiens
SEQUENCE: 300
acccgggcgt ggtggtgggg gtgggtgcct gtaattccag ctagttggga              50

SEQ ID NO: 301            moltype = RNA   length = 115
FEATURE                   Location/Qualifiers
source                    1..115
                          mol_type = unassigned RNA
                          organism = Homo sapiens
SEQUENCE: 301
ggtgccgagg gccgtccggc atcctaggcg ggtcgctgcg gtacctccct cctgtctgtg   60
gcggtgggat cccgtggccg tgttttcctg gtggcccggc cgtgcctgag gtttc        115

SEQ ID NO: 302            moltype = RNA   length = 86
FEATURE                   Location/Qualifiers
source                    1..86
                          mol_type = unassigned RNA
                          organism = Homo sapiens
SEQUENCE: 302
tgccagtctc taggtccctg agacccttta acctgtgagg acatccaggg tcacaggtga   60
ggttcttggg agcctggcgt ctggcc                                        86

SEQ ID NO: 303            moltype = RNA   length = 90
FEATURE                   Location/Qualifiers
source                    1..90
                          mol_type = unassigned RNA
                          organism = Homo sapiens
SEQUENCE: 303
ggcgcctctg cagctccggc tcccctggc ctctcgggaa ctacaagtcc caggggggcct  60
ggcggtgggc ggcgggcgga agaggcgggg                                    90

SEQ ID NO: 304            moltype = RNA   length = 51
FEATURE                   Location/Qualifiers
source                    1..51
                          mol_type = unassigned RNA
                          organism = Homo sapiens
SEQUENCE: 304
agagatgaag cggggggggcg gggtcttgct ctattgccta cgctgatctc a           51

SEQ ID NO: 305            moltype = RNA   length = 71
FEATURE                   Location/Qualifiers
source                    1..71
                          mol_type = unassigned RNA
                          organism = Homo sapiens
SEQUENCE: 305
ggtgagtggg agccggtggg gctggagtaa gggcacgccc ggggctgccc cacctgctga   60
ccaccctccc c                                                        71

SEQ ID NO: 306            moltype = RNA   length = 80
FEATURE                   Location/Qualifiers
```

-continued

```
source                  1..80
                        mol_type = unassigned RNA
                        organism = Homo sapiens
SEQUENCE: 306
aggacccttc cagagggccc cccctcaatc ctgttgtgcc taattcagag ggttgggtgg   60
aggctctcct gaagggctct                                              80

SEQ ID NO: 307          moltype = RNA   length = 64
FEATURE                 Location/Qualifiers
source                  1..64
                        mol_type = unassigned RNA
                        organism = Homo sapiens
SEQUENCE: 307
gaaggcgagg ggtagaagag cacagggggtt ctgataaacc cttctgcctg cattctactc   60
ccag                                                              64

SEQ ID NO: 308          moltype = RNA   length = 118
FEATURE                 Location/Qualifiers
source                  1..118
                        mol_type = unassigned RNA
                        organism = Homo sapiens
SEQUENCE: 308
gcaggtgaac tggcaggcca ggaagaggag gaagccctgg aggggctgga ggtgatggat   60
gttttcctcc ggttctcagg gctccacctc tttcgggccg tagagccagg gctggtgc   118

SEQ ID NO: 309          moltype = RNA   length = 55
FEATURE                 Location/Qualifiers
source                  1..55
                        mol_type = unassigned RNA
                        organism = Homo sapiens
SEQUENCE: 309
ccggatccga gtcacggcac caaatttcat gcgtgtccgt gtgaagagac cacca         55

SEQ ID NO: 310          moltype = RNA   length = 86
FEATURE                 Location/Qualifiers
source                  1..86
                        mol_type = unassigned RNA
                        organism = Homo sapiens
SEQUENCE: 310
agggagaagg gtcggggcag ggagggcagg gcaggctctg gggtggggggg tctgtgagtc   60
agccacggct ctgcccacgt ctcccc                                       86

SEQ ID NO: 311          moltype = RNA   length = 99
FEATURE                 Location/Qualifiers
source                  1..99
                        mol_type = unassigned RNA
                        organism = Homo sapiens
SEQUENCE: 311
gcaagggaca gggagggtcg tggcgacact cgcgccagct cccgggacgg ctgggctcgg   60
gctggtcgcc gacctccgac cctccactag atgcctggc                         99

SEQ ID NO: 312          moltype = RNA   length = 90
FEATURE                 Location/Qualifiers
source                  1..90
                        mol_type = unassigned RNA
                        organism = Homo sapiens
SEQUENCE: 312
cgggcggggc gggtccggcc gcctccgagc ccggccggca gcccccggcc ttaaagcgcg   60
ggctgtccgg aggggtcggc tttcccaccg                                   90

SEQ ID NO: 313          moltype = RNA   length = 96
FEATURE                 Location/Qualifiers
source                  1..96
                        mol_type = unassigned RNA
                        organism = Homo sapiens
SEQUENCE: 313
cgggccccgg gcgggcggga gggacgggac gcggtgcagt gttgtttttt cccccgccaa   60
tattgcactc gtcccggcct ccggcccccc cggccc                            96

SEQ ID NO: 314          moltype = RNA   length = 68
FEATURE                 Location/Qualifiers
source                  1..68
                        mol_type = unassigned RNA
                        organism = Homo sapiens
SEQUENCE: 314
agggttgggg ggacaggatg agaggctgtc ttcattccct cttgaccacc cctcgtttct   60
tcccccag                                                          68

SEQ ID NO: 315          moltype = RNA   length = 62
```

-continued

```
FEATURE                  Location/Qualifiers
source                   1..62
                         mol_type = unassigned RNA
                         organism = Homo sapiens
SEQUENCE: 315
tggcctaggg ggcggcttgt ggagtgtatg ggctgagcct tgctctgctc ccccgccccc    60
ag                                                                    62

SEQ ID NO: 316           moltype = RNA   length = 90
FEATURE                  Location/Qualifiers
source                   1..90
                         mol_type = unassigned RNA
                         organism = Homo sapiens
SEQUENCE: 316
gtgtctctct ggagaccctg cagccttccc acccaccagg gagctttcca tgggctgtgg    60
ggaaggcgtc agtgtcgggt gagggaacac                                     90

SEQ ID NO: 317           moltype = RNA   length = 69
FEATURE                  Location/Qualifiers
source                   1..69
                         mol_type = unassigned RNA
                         organism = Homo sapiens
SEQUENCE: 317
tggggtaggg gtgggggaat tcaggggtgt cgaactcatg gctgccacct ttgtgtcccc    60
atcctgcag                                                             69

SEQ ID NO: 318           moltype = RNA   length = 83
FEATURE                  Location/Qualifiers
source                   1..83
                         mol_type = unassigned RNA
                         organism = Homo sapiens
SEQUENCE: 318
gtctactccc agggtgccaa gctgtttcgt gttccctccc taggggatcc caggtagggg    60
cagcagagga cctgggcctg gac                                             83

SEQ ID NO: 319           moltype = RNA   length = 61
FEATURE                  Location/Qualifiers
source                   1..61
                         mol_type = unassigned RNA
                         organism = Homo sapiens
SEQUENCE: 319
gtgcggaacg ctggccgggg cgggagggga agggacgccc ggccggaacg ccgcactcac    60
g                                                                     61

SEQ ID NO: 320           moltype = RNA   length = 66
FEATURE                  Location/Qualifiers
source                   1..66
                         mol_type = unassigned RNA
                         organism = Homo sapiens
SEQUENCE: 320
tcaagacggg gagtcaggca gtggtggaga tggagagccc tgagcctcca ctctcctggc    60
ccccag                                                                66

SEQ ID NO: 321           moltype = RNA   length = 81
FEATURE                  Location/Qualifiers
source                   1..81
                         mol_type = unassigned RNA
                         organism = Homo sapiens
SEQUENCE: 321
ctccctggga gggcgtggat gatggtggga gaggagcccc actgtggaag tctgaccccc    60
acatcgcccc accttcccca g                                               81

SEQ ID NO: 322           moltype = RNA   length = 65
FEATURE                  Location/Qualifiers
source                   1..65
                         mol_type = unassigned RNA
                         organism = Homo sapiens
SEQUENCE: 322
gcttctggga ggaggggatc ttgggagtga tcccaacagc tgagctccct gaatccctgt    60
cccag                                                                 65

SEQ ID NO: 323           moltype = RNA   length = 97
FEATURE                  Location/Qualifiers
source                   1..97
                         mol_type = unassigned RNA
                         organism = Homo sapiens
SEQUENCE: 323
cccgggacct tggtccaggc gctggtctgc gtggtgctcg ggtggataag tctgatctga    60
gcaccacaca ggccgggcgc cgggaccaag ggggctc                              97
```

-continued

```
SEQ ID NO: 324            moltype = RNA   length = 109
FEATURE                   Location/Qualifiers
source                    1..109
                          mol_type = unassigned RNA
                          organism = Homo sapiens
SEQUENCE: 324
tcccgcattc cctctgcttt ggtcaggtgg tgccctcctt ccatgggtag agccagagat   60
ggtgggttct ggctggtcag atgggagtgg acagagaccc ggggtcctc               109

SEQ ID NO: 325            moltype = RNA   length = 51
FEATURE                   Location/Qualifiers
source                    1..51
                          mol_type = unassigned RNA
                          organism = Homo sapiens
SEQUENCE: 325
acagaccccg gggagcccgg cggtgaagct cctggtatcc tgggtgtctg a             51

SEQ ID NO: 326            moltype = RNA   length = 62
FEATURE                   Location/Qualifiers
source                    1..62
                          mol_type = unassigned RNA
                          organism = Homo sapiens
SEQUENCE: 326
ccttctgcgg cagagctggg gtcaccagcc ctcatgtact tgtgacttct cccctgccac   60
ag                                                                  62

SEQ ID NO: 327            moltype = RNA   length = 70
FEATURE                   Location/Qualifiers
source                    1..70
                          mol_type = unassigned RNA
                          organism = Homo sapiens
SEQUENCE: 327
ggtttctcct tgaggagaca tggtgggggc cggtcaggca gcccatgcca tgtgtcctca   60
tggagaggcc                                                          70

SEQ ID NO: 328            moltype = RNA   length = 68
FEATURE                   Location/Qualifiers
source                    1..68
                          mol_type = unassigned RNA
                          organism = Homo sapiens
SEQUENCE: 328
gactcggctg cggtggacaa gtccggctcc agaacctgga caccgctcag ccggccgcgg   60
caggggtc                                                            68

SEQ ID NO: 329            moltype = RNA   length = 69
FEATURE                   Location/Qualifiers
source                    1..69
                          mol_type = unassigned RNA
                          organism = Homo sapiens
SEQUENCE: 329
ctttcggcca gcgggacggc atccgaggtg ggctaggctc gggcccgtgg cgggtgcggg   60
ggtgggagg                                                           69

SEQ ID NO: 330            moltype = RNA   length = 85
FEATURE                   Location/Qualifiers
source                    1..85
                          mol_type = unassigned RNA
                          organism = Homo sapiens
SEQUENCE: 330
gtgagctgct ggggacgcgg gtcggggtct gcagggcggt gcggcagccg ccacctgacg   60
ccgcgccttt gtctgtgtcc cacag                                         85

SEQ ID NO: 331            moltype = RNA   length = 62
FEATURE                   Location/Qualifiers
source                    1..62
                          mol_type = unassigned RNA
                          organism = Homo sapiens
SEQUENCE: 331
cttcctggtg ggtggggagg agaagtgccg tcctcatgag cccctctctg tcccacccat   60
ag                                                                  62

SEQ ID NO: 332            moltype = RNA   length = 89
FEATURE                   Location/Qualifiers
source                    1..89
                          mol_type = unassigned RNA
                          organism = Homo sapiens
SEQUENCE: 332
gccggcgccc gagctctggc tccgtgtctt cactcccgtg cttgtccgag gagggaggga   60
```

-continued

```
gggacggggg ctgtgctggg gcagctgga                                      89

SEQ ID NO: 333           moltype = RNA   length = 97
FEATURE                  Location/Qualifiers
source                   1..97
                         mol_type = unassigned RNA
                         organism = Homo sapiens
SEQUENCE: 333
ctcaggtgct ctggctgctt gggttcctgg catgctgatt tgtgacttaa gattaaaatc   60
acattgccag ggattaccac gcaaccacga ccttggc                             97

SEQ ID NO: 334           moltype = RNA   length = 68
FEATURE                  Location/Qualifiers
source                   1..68
                         mol_type = unassigned RNA
                         organism = Homo sapiens
SEQUENCE: 334
tgcccaggct ggagcgagtg cagtggtgca gtcagtccta gctcactgca gcctcgaact   60
cctgggct                                                             68

SEQ ID NO: 335           moltype = RNA   length = 70
FEATURE                  Location/Qualifiers
source                   1..70
                         mol_type = unassigned RNA
                         organism = Homo sapiens
SEQUENCE: 335
gtccctgggg gctgggatgg gccatggtgt gctctgatcc ccctgtggtc tcttggcccc   60
caggaactcc                                                           70

SEQ ID NO: 336           moltype = RNA   length = 73
FEATURE                  Location/Qualifiers
source                   1..73
                         mol_type = unassigned RNA
                         organism = Homo sapiens
SEQUENCE: 336
aggccaggtg ggtatggagg agccctcata tggcagttgg cgagggccca gtgagcccct   60
ctctgctctc cag                                                       73

SEQ ID NO: 337           moltype = RNA   length = 85
FEATURE                  Location/Qualifiers
source                   1..85
                         mol_type = unassigned RNA
                         organism = Homo sapiens
SEQUENCE: 337
ggcctgggta ggcttgcatg ggggactggg aagagaccat gaacaggtta gtccagggag   60
ttctcatcaa gcctttactc agtag                                          85

SEQ ID NO: 338           moltype = RNA   length = 87
FEATURE                  Location/Qualifiers
source                   1..87
                         mol_type = unassigned RNA
                         organism = Homo sapiens
SEQUENCE: 338
gtgaggcggg gccaggaggg tgtgtggcgt gggtgctgcg gggccgtcag ggtgcctgcg   60
ggacgctcac ctggctggcc cgcccag                                        87

SEQ ID NO: 339           moltype = RNA   length = 80
FEATURE                  Location/Qualifiers
source                   1..80
                         mol_type = unassigned RNA
                         organism = Homo sapiens
SEQUENCE: 339
gagaggccaa gaccttggga atgggggtaa gggccttctg agcccaggtc cgaactctcc   60
attcctctgc agagcgctct                                                80

SEQ ID NO: 340           moltype = RNA   length = 64
FEATURE                  Location/Qualifiers
source                   1..64
                         mol_type = unassigned RNA
                         organism = Homo sapiens
SEQUENCE: 340
agttcagggc cgaagggtgg aagctgctgg tgctcatctc agcctctgcc cttggcctcc   60
ccag                                                                 64

SEQ ID NO: 341           moltype = RNA   length = 65
FEATURE                  Location/Qualifiers
source                   1..65
                         mol_type = unassigned RNA
                         organism = Homo sapiens
```

-continued

```
SEQUENCE: 341
gggtgctcgg ggcaggcggc tgggagcggc cctcacattg atggctcctg ccacctcctc   60
cgcag                                                              65

SEQ ID NO: 342          moltype = RNA   length = 60
FEATURE                 Location/Qualifiers
source                  1..60
                        mol_type = unassigned RNA
                        organism = Homo sapiens
SEQUENCE: 342
tgtgaatgac ccccttccag agccaaaatc accagggatg gaggaggggt cttgggtact   60

SEQ ID NO: 343          moltype = RNA   length = 90
FEATURE                 Location/Qualifiers
source                  1..90
                        mol_type = unassigned RNA
                        organism = Homo sapiens
SEQUENCE: 343
tctaagaaac gcagtggtct ctgaagcctg caggggcagg ccagccctgc actgaacgcc   60
tgttcttgcc aggtggcaga aggttgctgc                                   90

SEQ ID NO: 344          moltype = RNA   length = 83
FEATURE                 Location/Qualifiers
source                  1..83
                        mol_type = unassigned RNA
                        organism = Homo sapiens
SEQUENCE: 344
cctgctgcag aggtgccagc tgcagtgggg gaggcactgc cagggctgcc cactctgctt   60
agccagcagg tgccaagaac agg                                          83

SEQ ID NO: 345          moltype = RNA   length = 94
FEATURE                 Location/Qualifiers
source                  1..94
                        mol_type = unassigned RNA
                        organism = Homo sapiens
SEQUENCE: 345
aattcagccc tgccactggc ttatgtcatg accttgggct actcaggctg tctgcacaat   60
gagccagttg acaggagca gtgccactca actc                               94

SEQ ID NO: 346          moltype = RNA   length = 60
FEATURE                 Location/Qualifiers
source                  1..60
                        mol_type = unassigned RNA
                        organism = Homo sapiens
SEQUENCE: 346
caaggtgggg gagatggggg ttgaacttca tttctcatgc tcatccccat ctcctttcag   60

SEQ ID NO: 347          moltype = RNA   length = 78
FEATURE                 Location/Qualifiers
source                  1..78
                        mol_type = unassigned RNA
                        organism = Homo sapiens
SEQUENCE: 347
ggcctcaggc aggcgcaccc gaccacatgc atggctggtg gcggcgtgca ggggtcgggt   60
gggccaggct gtggggcg                                                78

SEQ ID NO: 348          moltype = RNA   length = 49
FEATURE                 Location/Qualifiers
source                  1..49
                        mol_type = unassigned RNA
                        organism = Homo sapiens
SEQUENCE: 348
ttccagccca acgcaccaaa aatgatatgg gtctgttgtc tggagaaac               49

SEQ ID NO: 349          moltype = RNA   length = 64
FEATURE                 Location/Qualifiers
source                  1..64
                        mol_type = unassigned RNA
                        organism = Homo sapiens
SEQUENCE: 349
tctgggcgag gggtgggctc tcagaggggc tggcagtact gctctgaggc ctgcctctcc   60
ccag                                                               64

SEQ ID NO: 350          moltype = RNA   length = 77
FEATURE                 Location/Qualifiers
source                  1..77
                        mol_type = unassigned RNA
                        organism = Homo sapiens
SEQUENCE: 350
```

```
catgagaaat cctgctggtc aaccatagcc ctggtcagac tctccggggc tgtgattgac   60
cagcaggact tctcatg                                                 77

SEQ ID NO: 351         moltype = RNA   length = 95
FEATURE                Location/Qualifiers
source                 1..95
                       mol_type = unassigned RNA
                       organism = Homo sapiens
SEQUENCE: 351
gacaccacat gctcctccag gcctgcctgc cctccaggtc atgttccagt gtcccacaga   60
tgcagcacca cggcccaggc ggcattggtg tcacc                             95

SEQ ID NO: 352         moltype = RNA   length = 64
FEATURE                Location/Qualifiers
source                 1..64
                       mol_type = unassigned RNA
                       organism = Homo sapiens
SEQUENCE: 352
gagctctggg aggggctggg tttggcagga cagtttccaa gccctgtctc ctcccatctt   60
ccag                                                               64

SEQ ID NO: 353         moltype = RNA   length = 67
FEATURE                Location/Qualifiers
source                 1..67
                       mol_type = unassigned RNA
                       organism = Homo sapiens
SEQUENCE: 353
aaatctctct ccatatcttt cctgcagccc ccaggtgggg gggaagaaaa ggtggggaat   60
tagattc                                                            67

SEQ ID NO: 354         moltype = RNA   length = 64
FEATURE                Location/Qualifiers
source                 1..64
                       mol_type = unassigned RNA
                       organism = Homo sapiens
SEQUENCE: 354
gggtgggggc ggggcggcag gggcctcccc cagtgccagg ccccattctg cttctctccc   60
agct                                                               64

SEQ ID NO: 355         moltype = RNA   length = 65
FEATURE                Location/Qualifiers
source                 1..65
                       mol_type = unassigned RNA
                       organism = Homo sapiens
SEQUENCE: 355
ctcctctggg ggtggggggc tgggcgtggt ggacagcgat gcatccctcg ccttctcacc   60
ctcag                                                              65

SEQ ID NO: 356         moltype = RNA   length = 98
FEATURE                Location/Qualifiers
source                 1..98
                       mol_type = unassigned RNA
                       organism = Homo sapiens
SEQUENCE: 356
cgaggtaggg gcgtcccggg cgcgcgggcg ggtcccaggc tgggcccctc ggaggccggg   60
tgctcactgc cccgtcccgg cgcccgtgtc tcctccag                          98

SEQ ID NO: 357         moltype = RNA   length = 72
FEATURE                Location/Qualifiers
source                 1..72
                       mol_type = unassigned RNA
                       organism = Homo sapiens
SEQUENCE: 357
tgtgggactg caaatgggag ctcagcacct gcctgccacc cacgcagacc agccctgct    60
ctgttcccac ag                                                      72

SEQ ID NO: 358         moltype = RNA   length = 70
FEATURE                Location/Qualifiers
source                 1..70
                       mol_type = unassigned RNA
                       organism = Homo sapiens
SEQUENCE: 358
aggacccagc ggggctgggc gcgcggagca gcgctgggtg cagcgcctgc gccggcagct   60
gcaagggccg                                                         70

SEQ ID NO: 359         moltype = RNA   length = 61
FEATURE                Location/Qualifiers
source                 1..61
                       mol_type = unassigned RNA
```

-continued

```
                             organism = Homo sapiens
SEQUENCE: 359
cctgcgggga caggccaggg catctaggct gtgcacagtg acgccctcc tgcccccaca    60
g                                                                    61

SEQ ID NO: 360          moltype = RNA   length = 73
FEATURE                 Location/Qualifiers
source                  1..73
                        mol_type = unassigned RNA
                        organism = Homo sapiens
SEQUENCE: 360
ggaggctggg ctgggacgga cacccggcct ccactttctg tggcaggtac ctcctccatg    60
tcggcccgcc ttg                                                       73

SEQ ID NO: 361          moltype = RNA   length = 72
FEATURE                 Location/Qualifiers
source                  1..72
                        mol_type = unassigned RNA
                        organism = Homo sapiens
SEQUENCE: 361
ctgtgcacct gggggagtgc agtgattgtg gaatgcaaag tcccacaatc actgtactcc    60
ccaggtgcac ag                                                        72

SEQ ID NO: 362          moltype = RNA   length = 119
FEATURE                 Location/Qualifiers
source                  1..119
                        mol_type = unassigned RNA
                        organism = Homo sapiens
SEQUENCE: 362
agcctgcgcc ggagccgggg cctgagcccg ggccgcgcag gccgtgaact cgtcgagctg    60
cgcgtgcggc cggtgctcaa cctgccgggt cctggccccg cgctcccgcg cgccctgga    119

SEQ ID NO: 363          moltype = RNA   length = 92
FEATURE                 Location/Qualifiers
source                  1..92
                        mol_type = unassigned RNA
                        organism = Homo sapiens
SEQUENCE: 363
cctgtccctc ctgccctgcg cctgcccagc cctcctgctc tggtgactga ggaccgccag    60
gcaggggctg gtgctgggcg gggggcggcg gg                                  92

SEQ ID NO: 364          moltype = RNA   length = 92
FEATURE                 Location/Qualifiers
source                  1..92
                        mol_type = unassigned RNA
                        organism = Homo sapiens
SEQUENCE: 364
gtcagtgtct gggcggacag ctgcaggaaa gggaagacca aggcttgctg tctgtccagt    60
ctgccaccct accctgtctg ttcttgccac ag                                  92

SEQ ID NO: 365          moltype = RNA   length = 82
FEATURE                 Location/Qualifiers
source                  1..82
                        mol_type = unassigned RNA
                        organism = Homo sapiens
SEQUENCE: 365
gtgagtggga ggccagggca cggcaggggg agctgcaggg ctatgggagg ggccccagcg    60
tctgagccct gtcctcccgc ag                                             82

SEQ ID NO: 366          moltype = RNA   length = 82
FEATURE                 Location/Qualifiers
source                  1..82
                        mol_type = unassigned RNA
                        organism = Homo sapiens
SEQUENCE: 366
gtgagtggga ggccagggca cggcaggggg agctgcaggg ctatgggagg ggccccagcg    60
tctgagccct gtcctcccgc ag                                             82

SEQ ID NO: 367          moltype = RNA   length = 84
FEATURE                 Location/Qualifiers
source                  1..84
                        mol_type = unassigned RNA
                        organism = Homo sapiens
SEQUENCE: 367
ctccccatgg ccctgtctcc caaccccttgt accagtgctg ggctcagacc ctggtacagg    60
cctgggggac agggacctgg ggac                                           84

SEQ ID NO: 368          moltype = RNA   length = 75
FEATURE                 Location/Qualifiers
```

-continued

```
source                 1..75
                       mol_type = unassigned RNA
                       organism = Homo sapiens
SEQUENCE: 368
tcatccctgg gtggggattt gttgcattac ttgtgttcta tataaagtat tgcacttgtc    60
ccggcctgtg gaaga                                                    75

SEQ ID NO: 369         moltype = RNA  length = 94
FEATURE                Location/Qualifiers
source                 1..94
                       mol_type = unassigned RNA
                       organism = Homo sapiens
SEQUENCE: 369
ataaaggaag ttaggctgag gggcagagag cgagactttt ctattttcca aaagctcggt    60
ctgaggcccc tcagtcttgc ttcctaaccc gcgc                               94

SEQ ID NO: 370         moltype = RNA  length = 52
FEATURE                Location/Qualifiers
source                 1..52
                       mol_type = unassigned RNA
                       organism = Homo sapiens
SEQUENCE: 370
tagccgggcg tggtggtggg ggcctgtggt cccagctact ttggaggctg ag            52

SEQ ID NO: 371         moltype = RNA  length = 84
FEATURE                Location/Qualifiers
source                 1..84
                       mol_type = unassigned RNA
                       organism = Homo sapiens
SEQUENCE: 371
tgtgcagtgg gaagggggc cgatacactg tacgagagtg agtagcaggt ctcacagtga     60
accggtctct ttccctactg tgtc                                          84

SEQ ID NO: 372         moltype = RNA  length = 68
FEATURE                Location/Qualifiers
source                 1..68
                       mol_type = unassigned RNA
                       organism = Homo sapiens
SEQUENCE: 372
ctccggtgcc tactgagctg atatcagttc tcattttaca cactggctca gttcagcagg    60
aacaggag                                                            68

SEQ ID NO: 373         moltype = RNA  length = 73
FEATURE                Location/Qualifiers
source                 1..73
                       mol_type = unassigned RNA
                       organism = Homo sapiens
SEQUENCE: 373
ctctgcctcc cgtgcctact gagctgaaac acagttggtt tgtgtacact ggctcagttc    60
agcaggaaca ggg                                                      73

SEQ ID NO: 374         moltype = RNA  length = 78
FEATURE                Location/Qualifiers
source                 1..78
                       mol_type = unassigned RNA
                       organism = Homo sapiens
SEQUENCE: 374
gggcccagaa gggggcgcag tcactgacgt gaagggacca catcccgctt catgtcagtg    60
actcctgccc cttggtct                                                 78

SEQ ID NO: 375         moltype = RNA  length = 73
FEATURE                Location/Qualifiers
source                 1..73
                       mol_type = unassigned RNA
                       organism = Homo sapiens
SEQUENCE: 375
ggcgagggga ggcgcaggct cggaaaggcg cgcgaggctc caggctcctt cccgatccac    60
cgctctcctc gct                                                      73

SEQ ID NO: 376         moltype = RNA  length = 73
FEATURE                Location/Qualifiers
source                 1..73
                       mol_type = unassigned RNA
                       organism = Homo sapiens
SEQUENCE: 376
cccaggggtct ggtgcggaga gggcccacag tggacttggt gacgctgtat gccctcaccg   60
ctcagccct ggg                                                       73

SEQ ID NO: 377         moltype = RNA  length = 63
```

-continued

```
FEATURE                 Location/Qualifiers
source                  1..63
                        mol_type = unassigned RNA
                        organism = Homo sapiens
SEQUENCE: 377
gcatgctggg cgaggctggc atctagcaca ggcggtagat gcttgctctt gccattgcaa   60
tga                                                                 63

SEQ ID NO: 378          moltype = RNA   length = 80
FEATURE                 Location/Qualifiers
source                  1..80
                        mol_type = unassigned RNA
                        organism = Homo sapiens
SEQUENCE: 378
tgccgtcggc ctggggagga ggaagggcaa gtccaaaggt atacagttgg tctgttcatt   60
ctctcttttt ggcctacaag                                               80

SEQ ID NO: 379          moltype = RNA   length = 73
FEATURE                 Location/Qualifiers
source                  1..73
                        mol_type = unassigned RNA
                        organism = Homo sapiens
SEQUENCE: 379
ggccggctgg ggttcctggg gatgggattt gcttcctgtc acaaatcaca ttgccaggga   60
tttccaaccg acc                                                      73

SEQ ID NO: 380          moltype = RNA   length = 66
FEATURE                 Location/Qualifiers
source                  1..66
                        mol_type = unassigned RNA
                        organism = Homo sapiens
SEQUENCE: 380
tgactgggga gcagaaggag aacccaagaa aagctgactt ggaggtccct ccttctgtcc   60
ccacag                                                              66

SEQ ID NO: 381          moltype = RNA   length = 72
FEATURE                 Location/Qualifiers
source                  1..72
                        mol_type = unassigned RNA
                        organism = Homo sapiens
SEQUENCE: 381
cttgggaatg gcaaggaaac cgttaccatt actgagttta gtaatggtaa tggttctctt   60
gctataccca ga                                                       72

SEQ ID NO: 382          moltype = RNA   length = 102
FEATURE                 Location/Qualifiers
source                  1..102
                        mol_type = unassigned RNA
                        organism = Homo sapiens
SEQUENCE: 382
gcttatcgag gaaaagatcg aggtgggttg gggcgggctc tggggatttg gtctcacagc   60
ccggatccca gcccacttac cttggttact ctccttcctt ct                     102

SEQ ID NO: 383          moltype = RNA   length = 81
FEATURE                 Location/Qualifiers
source                  1..81
                        mol_type = unassigned RNA
                        organism = Homo sapiens
SEQUENCE: 383
tacaggtgca ggggaactgt agatgaaaag gcttggcact tgagggaaag cctcagttca   60
ttctcatttt gctcacctgt t                                             81

SEQ ID NO: 384          moltype = RNA   length = 56
FEATURE                 Location/Qualifiers
source                  1..56
                        mol_type = unassigned RNA
                        organism = Homo sapiens
SEQUENCE: 384
gtaggcaggg gctggggttt caggttctca gtcagaacct ggcccctct ccccag        56

SEQ ID NO: 385          moltype = RNA   length = 80
FEATURE                 Location/Qualifiers
source                  1..80
                        mol_type = unassigned RNA
                        organism = Homo sapiens
SEQUENCE: 385
ctgcagcgtg cttctccagg ccccgcgcgc ggacagacac acggacaagt cccgccaggg   60
gctgggcgcg cgccagccgg                                               80
```

-continued

```
SEQ ID NO: 386          moltype = RNA  length = 70
FEATURE                 Location/Qualifiers
source                  1..70
                        mol_type = unassigned RNA
                        organism = Homo sapiens
SEQUENCE: 386
aaaagcctgt ccctaagtcc ctcccagcct tccagagttg gtgccaggaa ggatttaggg  60
acaggctttg                                                          70

SEQ ID NO: 387          moltype = RNA  length = 60
FEATURE                 Location/Qualifiers
source                  1..60
                        mol_type = unassigned RNA
                        organism = Homo sapiens
SEQUENCE: 387
cgctgggtcc gcgcgccctg ggccgggcga tgtccgcttg ggggagcgag gggcggggcg  60

SEQ ID NO: 388          moltype = RNA  length = 24
FEATURE                 Location/Qualifiers
source                  1..24
                        mol_type = unassigned RNA
                        organism = Homo sapiens
SEQUENCE: 388
tcgaggactg gtggaagggc cttt                                          24

SEQ ID NO: 389          moltype = RNA  length = 16
FEATURE                 Location/Qualifiers
source                  1..16
                        mol_type = unassigned RNA
                        organism = Homo sapiens
SEQUENCE: 389
tcgaggactg gtggaa                                                   16

SEQ ID NO: 390          moltype = RNA  length = 23
FEATURE                 Location/Qualifiers
source                  1..23
                        mol_type = unassigned RNA
                        organism = Homo sapiens
SEQUENCE: 390
ctcctggggc ccgcactctc gct                                           23

SEQ ID NO: 391          moltype = RNA  length = 18
FEATURE                 Location/Qualifiers
source                  1..18
                        mol_type = unassigned RNA
                        organism = Homo sapiens
SEQUENCE: 391
ctcctggggc ccgcactc                                                 18

SEQ ID NO: 392          moltype = RNA  length = 22
FEATURE                 Location/Qualifiers
source                  1..22
                        mol_type = unassigned RNA
                        organism = Homo sapiens
SEQUENCE: 392
ccgggaacgt cgagactgga gc                                            22

SEQ ID NO: 393          moltype = RNA  length = 15
FEATURE                 Location/Qualifiers
source                  1..15
                        mol_type = unassigned RNA
                        organism = Homo sapiens
SEQUENCE: 393
cgggaacgtc gagac                                                    15

SEQ ID NO: 394          moltype = RNA  length = 23
FEATURE                 Location/Qualifiers
source                  1..23
                        mol_type = unassigned RNA
                        organism = Homo sapiens
SEQUENCE: 394
ggtgggtgag gtcgggcccc aag                                           23

SEQ ID NO: 395          moltype = RNA  length = 20
FEATURE                 Location/Qualifiers
source                  1..20
                        mol_type = unassigned RNA
                        organism = Homo sapiens
SEQUENCE: 395
```

-continued

```
cggggtgggt gaggtcgggc                                              20

SEQ ID NO: 396           moltype = RNA   length = 23
FEATURE                  Location/Qualifiers
source                   1..23
                         mol_type = unassigned RNA
                         organism = Homo sapiens
SEQUENCE: 396
tgaggatatg gcagggaagg gga                                          23

SEQ ID NO: 397           moltype = RNA   length = 19
FEATURE                  Location/Qualifiers
source                   1..19
                         mol_type = unassigned RNA
                         organism = Homo sapiens
SEQUENCE: 397
tgaggatatg gcagggaag                                               19

SEQ ID NO: 398           moltype = RNA   length = 22
FEATURE                  Location/Qualifiers
source                   1..22
                         mol_type = unassigned RNA
                         organism = Homo sapiens
SEQUENCE: 398
cgcggcgggg acggcgattg gt                                           22

SEQ ID NO: 399           moltype = RNA   length = 17
FEATURE                  Location/Qualifiers
source                   1..17
                         mol_type = unassigned RNA
                         organism = Homo sapiens
SEQUENCE: 399
cggcggggac ggcgatt                                                 17

SEQ ID NO: 400           moltype = RNA   length = 25
FEATURE                  Location/Qualifiers
source                   1..25
                         mol_type = unassigned RNA
                         organism = Homo sapiens
SEQUENCE: 400
tgcgggctta gggctaacag cagtc                                        25

SEQ ID NO: 401           moltype = RNA   length = 15
FEATURE                  Location/Qualifiers
source                   1..15
                         mol_type = unassigned RNA
                         organism = Homo sapiens
SEQUENCE: 401
tgcgggctta gggct                                                   15

SEQ ID NO: 402           moltype = RNA   length = 17
FEATURE                  Location/Qualifiers
source                   1..17
                         mol_type = unassigned RNA
                         organism = Homo sapiens
SEQUENCE: 402
ggtgagcgct cgctggc                                                 17

SEQ ID NO: 403           moltype = RNA   length = 15
FEATURE                  Location/Qualifiers
source                   1..15
                         mol_type = unassigned RNA
                         organism = Homo sapiens
SEQUENCE: 403
cggtgagcgc tcgct                                                   15

SEQ ID NO: 404           moltype = RNA   length = 18
FEATURE                  Location/Qualifiers
source                   1..18
                         mol_type = unassigned RNA
                         organism = Homo sapiens
SEQUENCE: 404
ctccgggcgg cgccgtgt                                                18

SEQ ID NO: 405           moltype = RNA   length = 18
FEATURE                  Location/Qualifiers
source                   1..18
                         mol_type = unassigned RNA
                         organism = Homo sapiens
```

-continued

```
SEQUENCE: 405
ctccgggcgg cgccgtgt                                                    18

SEQ ID NO: 406        moltype = RNA   length = 25
FEATURE               Location/Qualifiers
source                1..25
                      mol_type = unassigned RNA
                      organism = Homo sapiens
SEQUENCE: 406
tggcggcggt agttatgggc ttctc                                            25

SEQ ID NO: 407        moltype = RNA   length = 25
FEATURE               Location/Qualifiers
source                1..25
                      mol_type = unassigned RNA
                      organism = Homo sapiens
SEQUENCE: 407
tggcggcggt agttatgggc ttctc                                            25

SEQ ID NO: 408        moltype = RNA   length = 26
FEATURE               Location/Qualifiers
source                1..26
                      mol_type = unassigned RNA
                      organism = Homo sapiens
SEQUENCE: 408
ccttctggag aggctttgtg cggata                                           26

SEQ ID NO: 409        moltype = RNA   length = 15
FEATURE               Location/Qualifiers
source                1..15
                      mol_type = unassigned RNA
                      organism = Homo sapiens
SEQUENCE: 409
ccttctggag aggct                                                       15

SEQ ID NO: 410        moltype = RNA   length = 23
FEATURE               Location/Qualifiers
source                1..23
                      mol_type = unassigned RNA
                      organism = Homo sapiens
SEQUENCE: 410
ctagtggaag aagatggcgg aag                                              23

SEQ ID NO: 411        moltype = RNA   length = 15
FEATURE               Location/Qualifiers
source                1..15
                      mol_type = unassigned RNA
                      organism = Homo sapiens
SEQUENCE: 411
tagtggaaga agatg                                                       15

SEQ ID NO: 412        moltype = RNA   length = 22
FEATURE               Location/Qualifiers
source                1..22
                      mol_type = unassigned RNA
                      organism = Homo sapiens
SEQUENCE: 412
cctcacacct gcctcgcccc cc                                               22

SEQ ID NO: 413        moltype = RNA   length = 15
FEATURE               Location/Qualifiers
source                1..15
                      mol_type = unassigned RNA
                      organism = Homo sapiens
SEQUENCE: 413
tcacacctgc ctcgc                                                       15

SEQ ID NO: 414        moltype = RNA   length = 23
FEATURE               Location/Qualifiers
source                1..23
                      mol_type = unassigned RNA
                      organism = Homo sapiens
SEQUENCE: 414
agaagaaggc ggtcggtctg cgg                                              23

SEQ ID NO: 415        moltype = RNA   length = 21
FEATURE               Location/Qualifiers
source                1..21
                      mol_type = unassigned RNA
```

-continued

```
                           organism = Homo sapiens
SEQUENCE: 415
aagaaggcgg tcggtctgcg g                                                        21

SEQ ID NO: 416            moltype = RNA   length = 23
FEATURE                   Location/Qualifiers
source                    1..23
                          mol_type = unassigned RNA
                          organism = Homo sapiens
SEQUENCE: 416
cggggccgta gcactgtctg aga                                                      23

SEQ ID NO: 417            moltype = RNA   length = 20
FEATURE                   Location/Qualifiers
source                    1..20
                          mol_type = unassigned RNA
                          organism = Homo sapiens
SEQUENCE: 417
cggggccgta gcactgtctg                                                          20

SEQ ID NO: 418            moltype = RNA   length = 25
FEATURE                   Location/Qualifiers
source                    1..25
                          mol_type = unassigned RNA
                          organism = Homo sapiens
SEQUENCE: 418
ttctgggccc gcggcgggcg tgggg                                                    25

SEQ ID NO: 419            moltype = RNA   length = 15
FEATURE                   Location/Qualifiers
source                    1..15
                          mol_type = unassigned RNA
                          organism = Homo sapiens
SEQUENCE: 419
cgcggcgggc gtggg                                                               15

SEQ ID NO: 420            moltype = RNA   length = 23
FEATURE                   Location/Qualifiers
source                    1..23
                          mol_type = unassigned RNA
                          organism = Homo sapiens
SEQUENCE: 420
aggaggggtc ccgcactggg agg                                                      23

SEQ ID NO: 421            moltype = RNA   length = 15
FEATURE                   Location/Qualifiers
source                    1..15
                          mol_type = unassigned RNA
                          organism = Homo sapiens
SEQUENCE: 421
tgggaggggc cctca                                                               15

SEQ ID NO: 422            moltype = RNA   length = 18
FEATURE                   Location/Qualifiers
source                    1..18
                          mol_type = unassigned RNA
                          organism = Homo sapiens
SEQUENCE: 422
gaggctgaag gaagatgg                                                            18

SEQ ID NO: 423            moltype = RNA   length = 15
FEATURE                   Location/Qualifiers
source                    1..15
                          mol_type = unassigned RNA
                          organism = Homo sapiens
SEQUENCE: 423
gaggctgaag gaaga                                                               15

SEQ ID NO: 424            moltype = RNA   length = 23
FEATURE                   Location/Qualifiers
source                    1..23
                          mol_type = unassigned RNA
                          organism = Homo sapiens
SEQUENCE: 424
ggctacaaca caggacccgg gcg                                                      23

SEQ ID NO: 425            moltype = RNA   length = 21
FEATURE                   Location/Qualifiers
source                    1..21
```

-continued

```
                              mol_type = unassigned RNA
                              organism = Homo sapiens
SEQUENCE: 425
ggctacaaca caggacccgg g                                    21

SEQ ID NO: 426         moltype = RNA   length = 24
FEATURE                Location/Qualifiers
source                 1..24
                       mol_type = unassigned RNA
                       organism = Homo sapiens
SEQUENCE: 426
gaggctggga aggcaaaggg acgt                                 24

SEQ ID NO: 427         moltype = RNA   length = 15
FEATURE                Location/Qualifiers
source                 1..15
                       mol_type = unassigned RNA
                       organism = Homo sapiens
SEQUENCE: 427
gaaggaggct gggaa                                           15

SEQ ID NO: 428         moltype = RNA   length = 16
FEATURE                Location/Qualifiers
source                 1..16
                       mol_type = unassigned RNA
                       organism = Homo sapiens
SEQUENCE: 428
tgctggtgat gctttc                                          16

SEQ ID NO: 429         moltype = RNA   length = 16
FEATURE                Location/Qualifiers
source                 1..16
                       mol_type = unassigned RNA
                       organism = Homo sapiens
SEQUENCE: 429
tgctggtgat gctttc                                          16

SEQ ID NO: 430         moltype = RNA   length = 23
FEATURE                Location/Qualifiers
source                 1..23
                       mol_type = unassigned RNA
                       organism = Homo sapiens
SEQUENCE: 430
gggggtcccc ggtgctcgga tct                                  23

SEQ ID NO: 431         moltype = RNA   length = 16
FEATURE                Location/Qualifiers
source                 1..16
                       mol_type = unassigned RNA
                       organism = Homo sapiens
SEQUENCE: 431
tcgggagggg cgggag                                          16

SEQ ID NO: 432         moltype = RNA   length = 21
FEATURE                Location/Qualifiers
source                 1..21
                       mol_type = unassigned RNA
                       organism = Homo sapiens
SEQUENCE: 432
caactctgat ctcttcatct a                                    21

SEQ ID NO: 433         moltype = RNA   length = 20
FEATURE                Location/Qualifiers
source                 1..20
                       mol_type = unassigned RNA
                       organism = Homo sapiens
SEQUENCE: 433
tctcttcatc tacccccccag                                     20

SEQ ID NO: 434         moltype = RNA   length = 22
FEATURE                Location/Qualifiers
source                 1..22
                       mol_type = unassigned RNA
                       organism = Homo sapiens
SEQUENCE: 434
tgggagggga gaggcagcaa gc                                   22

SEQ ID NO: 435         moltype = RNA   length = 22
FEATURE                Location/Qualifiers
```

-continued

```
source                  1..22
                        mol_type = unassigned RNA
                        organism = Homo sapiens
SEQUENCE: 435
tgggaggggga gaggcagcaa gc                                               22

SEQ ID NO: 436          moltype = RNA  length = 21
FEATURE                 Location/Qualifiers
source                  1..21
                        mol_type = unassigned RNA
                        organism = Homo sapiens
SEQUENCE: 436
gaggcgatgt ggggatgtag a                                                 21

SEQ ID NO: 437          moltype = RNA  length = 20
FEATURE                 Location/Qualifiers
source                  1..20
                        mol_type = unassigned RNA
                        organism = Homo sapiens
SEQUENCE: 437
cccagtctca tttcctcatc                                                   20

SEQ ID NO: 438          moltype = RNA  length = 23
FEATURE                 Location/Qualifiers
source                  1..23
                        mol_type = unassigned RNA
                        organism = Homo sapiens
SEQUENCE: 438
ctgggggacg cgtgagcgcg agc                                               23

SEQ ID NO: 439          moltype = RNA  length = 21
FEATURE                 Location/Qualifiers
source                  1..21
                        mol_type = unassigned RNA
                        organism = Homo sapiens
SEQUENCE: 439
ctgggggacg cgtgagcgcg a                                                 21

SEQ ID NO: 440          moltype = RNA  length = 20
FEATURE                 Location/Qualifiers
source                  1..20
                        mol_type = unassigned RNA
                        organism = Homo sapiens
SEQUENCE: 440
aagacacatt tggagaggga                                                   20

SEQ ID NO: 441          moltype = RNA  length = 16
FEATURE                 Location/Qualifiers
source                  1..16
                        mol_type = unassigned RNA
                        organism = Homo sapiens
SEQUENCE: 441
agacacattt ggagag                                                       16

SEQ ID NO: 442          moltype = RNA  length = 20
FEATURE                 Location/Qualifiers
source                  1..20
                        mol_type = unassigned RNA
                        organism = Homo sapiens
SEQUENCE: 442
ctccccggtg tgcaaatgtg                                                   20

SEQ ID NO: 443          moltype = RNA  length = 15
FEATURE                 Location/Qualifiers
source                  1..15
                        mol_type = unassigned RNA
                        organism = Homo sapiens
SEQUENCE: 443
gtgtgcggtg ttatg                                                        15

SEQ ID NO: 444          moltype = RNA  length = 23
FEATURE                 Location/Qualifiers
source                  1..23
                        mol_type = unassigned RNA
                        organism = Homo sapiens
SEQUENCE: 444
acaggagtgg gggtgggaca taa                                               23

SEQ ID NO: 445          moltype = RNA  length = 20
```

-continued

```
FEATURE            Location/Qualifiers
source             1..20
                   mol_type = unassigned RNA
                   organism = Homo sapiens
SEQUENCE: 445
acaggagtgg gggtgggaca                                            20

SEQ ID NO: 446     moltype = RNA   length = 23
FEATURE            Location/Qualifiers
source             1..23
                   mol_type = unassigned RNA
                   organism = Homo sapiens
SEQUENCE: 446
gccccggcgc gggcgggttc tgg                                        23

SEQ ID NO: 447     moltype = RNA   length = 16
FEATURE            Location/Qualifiers
source             1..16
                   mol_type = unassigned RNA
                   organism = Homo sapiens
SEQUENCE: 447
ggagccccgg cgcggg                                                16

SEQ ID NO: 448     moltype = RNA   length = 16
FEATURE            Location/Qualifiers
source             1..16
                   mol_type = unassigned RNA
                   organism = Homo sapiens
SEQUENCE: 448
gtgaaggccc ggcgga                                                16

SEQ ID NO: 449     moltype = RNA   length = 15
FEATURE            Location/Qualifiers
source             1..15
                   mol_type = unassigned RNA
                   organism = Homo sapiens
SEQUENCE: 449
gtgaaggccc ggcgg                                                 15

SEQ ID NO: 450     moltype = RNA   length = 26
FEATURE            Location/Qualifiers
source             1..26
                   mol_type = unassigned RNA
                   organism = Homo sapiens
SEQUENCE: 450
gtcccggggc tgcgcgaggc acaggc                                     26

SEQ ID NO: 451     moltype = RNA   length = 15
FEATURE            Location/Qualifiers
source             1..15
                   mol_type = unassigned RNA
                   organism = Homo sapiens
SEQUENCE: 451
ggcccggggg gcggg                                                 15

SEQ ID NO: 452     moltype = RNA   length = 25
FEATURE            Location/Qualifiers
source             1..25
                   mol_type = unassigned RNA
                   organism = Homo sapiens
SEQUENCE: 452
agcggggagg aagtgggcgc tgctt                                      25

SEQ ID NO: 453     moltype = RNA   length = 21
FEATURE            Location/Qualifiers
source             1..21
                   mol_type = unassigned RNA
                   organism = Homo sapiens
SEQUENCE: 453
agcggggagg aagtgggcgc t                                          21

SEQ ID NO: 454     moltype = RNA   length = 22
FEATURE            Location/Qualifiers
source             1..22
                   mol_type = unassigned RNA
                   organism = Homo sapiens
SEQUENCE: 454
ccggcagagg aggctgcaga gg                                         22
```

-continued

```
SEQ ID NO: 455          moltype = RNA   length = 19
FEATURE                 Location/Qualifiers
source                  1..19
                        mol_type = unassigned RNA
                        organism = Homo sapiens
SEQUENCE: 455
ccggcagagg aggctgcag                                                  19

SEQ ID NO: 456          moltype = RNA   length = 24
FEATURE                 Location/Qualifiers
source                  1..24
                        mol_type = unassigned RNA
                        organism = Homo sapiens
SEQUENCE: 456
tggggagctg aggctctggg ggtg                                            24

SEQ ID NO: 457          moltype = RNA   length = 15
FEATURE                 Location/Qualifiers
source                  1..15
                        mol_type = unassigned RNA
                        organism = Homo sapiens
SEQUENCE: 457
ggccctgggg agctg                                                      15

SEQ ID NO: 458          moltype = RNA   length = 21
FEATURE                 Location/Qualifiers
source                  1..21
                        mol_type = unassigned RNA
                        organism = Homo sapiens
SEQUENCE: 458
aggaggcagt gggcgagcag g                                               21

SEQ ID NO: 459          moltype = RNA   length = 21
FEATURE                 Location/Qualifiers
source                  1..21
                        mol_type = unassigned RNA
                        organism = Homo sapiens
SEQUENCE: 459
aggaggcagt gggcgagcag g                                               21

SEQ ID NO: 460          moltype = RNA   length = 16
FEATURE                 Location/Qualifiers
source                  1..16
                        mol_type = unassigned RNA
                        organism = Homo sapiens
SEQUENCE: 460
ggacccaggg agagac                                                     16

SEQ ID NO: 461          moltype = RNA   length = 16
FEATURE                 Location/Qualifiers
source                  1..16
                        mol_type = unassigned RNA
                        organism = Homo sapiens
SEQUENCE: 461
ggacccaggg agagac                                                     16

SEQ ID NO: 462          moltype = RNA   length = 21
FEATURE                 Location/Qualifiers
source                  1..21
                        mol_type = unassigned RNA
                        organism = Homo sapiens
SEQUENCE: 462
gagggcagcg tgggtgtggc g                                               21

SEQ ID NO: 463          moltype = RNA   length = 21
FEATURE                 Location/Qualifiers
source                  1..21
                        mol_type = unassigned RNA
                        organism = Homo sapiens
SEQUENCE: 463
gagggcagcg tgggtgtggc g                                               21

SEQ ID NO: 464          moltype = RNA   length = 25
FEATURE                 Location/Qualifiers
source                  1..25
                        mol_type = unassigned RNA
                        organism = Homo sapiens
SEQUENCE: 464
tgggcagggg cttattgtag gagtc                                           25
```

-continued

```
SEQ ID NO: 465          moltype = RNA   length = 19
FEATURE                 Location/Qualifiers
source                  1..19
                        mol_type = unassigned RNA
                        organism = Homo sapiens
SEQUENCE: 465
tgggcagggg cttattgta                                              19

SEQ ID NO: 466          moltype = RNA   length = 23
FEATURE                 Location/Qualifiers
source                  1..23
                        mol_type = unassigned RNA
                        organism = Homo sapiens
SEQUENCE: 466
acagcagggc tggggattgc agt                                         23

SEQ ID NO: 467          moltype = RNA   length = 19
FEATURE                 Location/Qualifiers
source                  1..19
                        mol_type = unassigned RNA
                        organism = Homo sapiens
SEQUENCE: 467
tgctgctccc agtcctgcc                                              19

SEQ ID NO: 468          moltype = RNA   length = 27
FEATURE                 Location/Qualifiers
source                  1..27
                        mol_type = unassigned RNA
                        organism = Homo sapiens
SEQUENCE: 468
gtgaacgggc gccatcccga ggctttg                                     27

SEQ ID NO: 469          moltype = RNA   length = 16
FEATURE                 Location/Qualifiers
source                  1..16
                        mol_type = unassigned RNA
                        organism = Homo sapiens
SEQUENCE: 469
gtgaacgggc gccatc                                                 16

SEQ ID NO: 470          moltype = RNA   length = 21
FEATURE                 Location/Qualifiers
source                  1..21
                        mol_type = unassigned RNA
                        organism = Homo sapiens
SEQUENCE: 470
cttcccccca gtaatcttca t                                           21

SEQ ID NO: 471          moltype = RNA   length = 21
FEATURE                 Location/Qualifiers
source                  1..21
                        mol_type = unassigned RNA
                        organism = Homo sapiens
SEQUENCE: 471
cttcccccca gtaatcttca t                                           21

SEQ ID NO: 472          moltype = RNA   length = 26
FEATURE                 Location/Qualifiers
source                  1..26
                        mol_type = unassigned RNA
                        organism = Homo sapiens
SEQUENCE: 472
aggagggagg agatgggcca agttcc                                      26

SEQ ID NO: 473          moltype = RNA   length = 15
FEATURE                 Location/Qualifiers
source                  1..15
                        mol_type = unassigned RNA
                        organism = Homo sapiens
SEQUENCE: 473
gggaggaggg aggag                                                  15

SEQ ID NO: 474          moltype = RNA   length = 21
FEATURE                 Location/Qualifiers
source                  1..21
                        mol_type = unassigned RNA
                        organism = Homo sapiens
SEQUENCE: 474
```

-continued

```
gtgagtcagg gtggggctgg c                                          21

SEQ ID NO: 475          moltype = RNA   length = 21
FEATURE                 Location/Qualifiers
source                  1..21
                        mol_type = unassigned RNA
                        organism = Homo sapiens
SEQUENCE: 475
gtgagtcagg gtggggctgg c                                          21

SEQ ID NO: 476          moltype = RNA   length = 21
FEATURE                 Location/Qualifiers
source                  1..21
                        mol_type = unassigned RNA
                        organism = Homo sapiens
SEQUENCE: 476
atccagttct ctgagggggc t                                          21

SEQ ID NO: 477          moltype = RNA   length = 21
FEATURE                 Location/Qualifiers
source                  1..21
                        mol_type = unassigned RNA
                        organism = Homo sapiens
SEQUENCE: 477
atccagttct ctgagggggc t                                          21

SEQ ID NO: 478          moltype = RNA   length = 18
FEATURE                 Location/Qualifiers
source                  1..18
                        mol_type = unassigned RNA
                        organism = Homo sapiens
SEQUENCE: 478
ggtgggcttc ccggaggg                                              18

SEQ ID NO: 479          moltype = RNA   length = 15
FEATURE                 Location/Qualifiers
source                  1..15
                        mol_type = unassigned RNA
                        organism = Homo sapiens
SEQUENCE: 479
ggtgggcttc ccgga                                                 15

SEQ ID NO: 480          moltype = RNA   length = 16
FEATURE                 Location/Qualifiers
source                  1..16
                        mol_type = unassigned RNA
                        organism = Homo sapiens
SEQUENCE: 480
ctgggggtcc cccgac                                                16

SEQ ID NO: 481          moltype = RNA   length = 15
FEATURE                 Location/Qualifiers
source                  1..15
                        mol_type = unassigned RNA
                        organism = Homo sapiens
SEQUENCE: 481
gtgtggagct ggggc                                                 15

SEQ ID NO: 482          moltype = RNA   length = 24
FEATURE                 Location/Qualifiers
source                  1..24
                        mol_type = unassigned RNA
                        organism = Homo sapiens
SEQUENCE: 482
gctgcgggct gcggtcaggg cgat                                       24

SEQ ID NO: 483          moltype = RNA   length = 20
FEATURE                 Location/Qualifiers
source                  1..20
                        mol_type = unassigned RNA
                        organism = Homo sapiens
SEQUENCE: 483
gctgcgggct gcggtcaggg                                            20

SEQ ID NO: 484          moltype = RNA   length = 26
FEATURE                 Location/Qualifiers
source                  1..26
                        mol_type = unassigned RNA
                        organism = Homo sapiens
```

-continued

```
SEQUENCE: 484
cggtgggatc ccgcggccgt gttttc                                            26

SEQ ID NO: 485          moltype = RNA   length = 15
FEATURE                 Location/Qualifiers
source                  1..15
                        mol_type = unassigned RNA
                        organism = Homo sapiens
SEQUENCE: 485
ggggcgccgc gggac                                                        15

SEQ ID NO: 486          moltype = RNA   length = 18
FEATURE                 Location/Qualifiers
source                  1..18
                        mol_type = unassigned RNA
                        organism = Homo sapiens
SEQUENCE: 486
tctaggtggg gagactga                                                     18

SEQ ID NO: 487          moltype = RNA   length = 16
FEATURE                 Location/Qualifiers
source                  1..16
                        mol_type = unassigned RNA
                        organism = Homo sapiens
SEQUENCE: 487
gtggggagac tgacgg                                                       16

SEQ ID NO: 488          moltype = RNA   length = 23
FEATURE                 Location/Qualifiers
source                  1..23
                        mol_type = unassigned RNA
                        organism = Homo sapiens
SEQUENCE: 488
gtgggctggg ctgggctggg cca                                               23

SEQ ID NO: 489          moltype = RNA   length = 15
FEATURE                 Location/Qualifiers
source                  1..15
                        mol_type = unassigned RNA
                        organism = Homo sapiens
SEQUENCE: 489
gggctgggct gggct                                                        15

SEQ ID NO: 490          moltype = RNA   length = 23
FEATURE                 Location/Qualifiers
source                  1..23
                        mol_type = unassigned RNA
                        organism = Homo sapiens
SEQUENCE: 490
caccttgcct tgctgcccgg gcc                                               23

SEQ ID NO: 491          moltype = RNA   length = 22
FEATURE                 Location/Qualifiers
source                  1..22
                        mol_type = unassigned RNA
                        organism = Homo sapiens
SEQUENCE: 491
caccttgcct tgctgcccgg gc                                                22

SEQ ID NO: 492          moltype = RNA   length = 24
FEATURE                 Location/Qualifiers
source                  1..24
                        mol_type = unassigned RNA
                        organism = Homo sapiens
SEQUENCE: 492
agacacattt ggagagggaa cctc                                              24

SEQ ID NO: 493          moltype = RNA   length = 16
FEATURE                 Location/Qualifiers
source                  1..16
                        mol_type = unassigned RNA
                        organism = Homo sapiens
SEQUENCE: 493
agacacattt ggagag                                                       16

SEQ ID NO: 494          moltype = RNA   length = 22
FEATURE                 Location/Qualifiers
source                  1..22
                        mol_type = unassigned RNA
```

-continued

```
                         organism = Homo sapiens
SEQUENCE: 494
actcaaactg tggggcact tt                                          22

SEQ ID NO: 495          moltype = RNA   length = 19
FEATURE                 Location/Qualifiers
source                  1..19
                        mol_type = unassigned RNA
                        organism = Homo sapiens
SEQUENCE: 495
actcaaactg tggggcac                                              19

SEQ ID NO: 496          moltype = RNA   length = 25
FEATURE                 Location/Qualifiers
source                  1..25
                        mol_type = unassigned RNA
                        organism = Homo sapiens
SEQUENCE: 496
aaggcagggc ccccgctccc cgggc                                      25

SEQ ID NO: 497          moltype = RNA   length = 15
FEATURE                 Location/Qualifiers
source                  1..15
                        mol_type = unassigned RNA
                        organism = Homo sapiens
SEQUENCE: 497
gtgtgttgag gaagg                                                 15

SEQ ID NO: 498          moltype = RNA   length = 22
FEATURE                 Location/Qualifiers
source                  1..22
                        mol_type = unassigned RNA
                        organism = Homo sapiens
SEQUENCE: 498
tggggatttg gagaagtggt ga                                         22

SEQ ID NO: 499          moltype = RNA   length = 22
FEATURE                 Location/Qualifiers
source                  1..22
                        mol_type = unassigned RNA
                        organism = Homo sapiens
SEQUENCE: 499
tggggatttg gagaagtggt ga                                         22

SEQ ID NO: 500          moltype = RNA   length = 25
FEATURE                 Location/Qualifiers
source                  1..25
                        mol_type = unassigned RNA
                        organism = Homo sapiens
SEQUENCE: 500
gggggagcca tgagataaga gcacc                                      25

SEQ ID NO: 501          moltype = RNA   length = 20
FEATURE                 Location/Qualifiers
source                  1..20
                        mol_type = unassigned RNA
                        organism = Homo sapiens
SEQUENCE: 501
tgggggagcc atgagataag                                            20

SEQ ID NO: 502          moltype = RNA   length = 17
FEATURE                 Location/Qualifiers
source                  1..17
                        mol_type = unassigned RNA
                        organism = Homo sapiens
SEQUENCE: 502
tcctagtcac ggcacca                                               17

SEQ ID NO: 503          moltype = RNA   length = 17
FEATURE                 Location/Qualifiers
source                  1..17
                        mol_type = unassigned RNA
                        organism = Homo sapiens
SEQUENCE: 503
tcctagtcac ggcacca                                               17

SEQ ID NO: 504          moltype = RNA   length = 24
FEATURE                 Location/Qualifiers
source                  1..24
```

```
                            mol_type = unassigned RNA
                            organism = Homo sapiens
SEQUENCE: 504
cgggcgtggt ggtgggggtg ggtg                                                24

SEQ ID NO: 505         moltype = RNA   length = 15
FEATURE                Location/Qualifiers
source                 1..15
                       mol_type = unassigned RNA
                       organism = Homo sapiens
SEQUENCE: 505
cgggcgtggt ggtgg                                                          15

SEQ ID NO: 506         moltype = RNA   length = 23
FEATURE                Location/Qualifiers
source                 1..23
                       mol_type = unassigned RNA
                       organism = Homo sapiens
SEQUENCE: 506
ggcccggccg tgcctgaggt ttc                                                 23

SEQ ID NO: 507         moltype = RNA   length = 15
FEATURE                Location/Qualifiers
source                 1..15
                       mol_type = unassigned RNA
                       organism = Homo sapiens
SEQUENCE: 507
ggcggtggga tcccg                                                          15

SEQ ID NO: 508         moltype = RNA   length = 23
FEATURE                Location/Qualifiers
source                 1..23
                       mol_type = unassigned RNA
                       organism = Homo sapiens
SEQUENCE: 508
cacaggtgag gttcttggga gcc                                                 23

SEQ ID NO: 509         moltype = RNA   length = 15
FEATURE                Location/Qualifiers
source                 1..15
                       mol_type = unassigned RNA
                       organism = Homo sapiens
SEQUENCE: 509
acaggtgagg ttctt                                                          15

SEQ ID NO: 510         moltype = RNA   length = 16
FEATURE                Location/Qualifiers
source                 1..16
                       mol_type = unassigned RNA
                       organism = Homo sapiens
SEQUENCE: 510
ggcggtgggc ggcggg                                                         16

SEQ ID NO: 511         moltype = RNA   length = 15
FEATURE                Location/Qualifiers
source                 1..15
                       mol_type = unassigned RNA
                       organism = Homo sapiens
SEQUENCE: 511
ggcctctcgg gaact                                                          15

SEQ ID NO: 512         moltype = RNA   length = 15
FEATURE                Location/Qualifiers
source                 1..15
                       mol_type = unassigned RNA
                       organism = Homo sapiens
SEQUENCE: 512
tgaagcgggg gggcg                                                          15

SEQ ID NO: 513         moltype = RNA   length = 15
FEATURE                Location/Qualifiers
source                 1..15
                       mol_type = unassigned RNA
                       organism = Homo sapiens
SEQUENCE: 513
tgaagcgggg gggcg                                                          15

SEQ ID NO: 514         moltype = RNA   length = 24
FEATURE                Location/Qualifiers
```

-continued

```
source                    1..24
                          mol_type = unassigned RNA
                          organism = Homo sapiens
SEQUENCE: 514
gtgagtggga gccggtgggg ctgg                                          24

SEQ ID NO: 515           moltype = RNA   length = 15
FEATURE                  Location/Qualifiers
source                    1..15
                          mol_type = unassigned RNA
                          organism = Homo sapiens
SEQUENCE: 515
ggggctggag taagg                                                    15

SEQ ID NO: 516           moltype = RNA   length = 22
FEATURE                  Location/Qualifiers
source                    1..22
                          mol_type = unassigned RNA
                          organism = Homo sapiens
SEQUENCE: 516
gagggttggg tggaggctct cc                                            22

SEQ ID NO: 517           moltype = RNA   length = 15
FEATURE                  Location/Qualifiers
source                    1..15
                          mol_type = unassigned RNA
                          organism = Homo sapiens
SEQUENCE: 517
gagggttggg tggag                                                    15

SEQ ID NO: 518           moltype = RNA   length = 25
FEATURE                  Location/Qualifiers
source                    1..25
                          mol_type = unassigned RNA
                          organism = Homo sapiens
SEQUENCE: 518
aggaagccct ggaggggctg gaggt                                         25

SEQ ID NO: 519           moltype = RNA   length = 15
FEATURE                  Location/Qualifiers
source                    1..15
                          mol_type = unassigned RNA
                          organism = Homo sapiens
SEQUENCE: 519
aggaagagga ggaag                                                    15

SEQ ID NO: 520           moltype = RNA   length = 21
FEATURE                  Location/Qualifiers
source                    1..21
                          mol_type = unassigned RNA
                          organism = Homo sapiens
SEQUENCE: 520
cggatccgag tcacggcacc a                                             21

SEQ ID NO: 521           moltype = RNA   length = 15
FEATURE                  Location/Qualifiers
source                    1..15
                          mol_type = unassigned RNA
                          organism = Homo sapiens
SEQUENCE: 521
ggatccgagt cacgg                                                    15

SEQ ID NO: 522           moltype = RNA   length = 23
FEATURE                  Location/Qualifiers
source                    1..23
                          mol_type = unassigned RNA
                          organism = Homo sapiens
SEQUENCE: 522
agggtcgggg cagggagggc agg                                           23

SEQ ID NO: 523           moltype = RNA   length = 15
FEATURE                  Location/Qualifiers
source                    1..15
                          mol_type = unassigned RNA
                          organism = Homo sapiens
SEQUENCE: 523
gggagaaggg tcggg                                                    15

SEQ ID NO: 524           moltype = RNA   length = 26
```

-continued

```
FEATURE              Location/Qualifiers
source               1..26
                     mol_type = unassigned RNA
                     organism = Homo sapiens
SEQUENCE: 524
gcgggctgtc cggaggggtc ggcttt                                     26

SEQ ID NO: 525       moltype = RNA   length = 16
FEATURE              Location/Qualifiers
source               1..16
                     mol_type = unassigned RNA
                     organism = Homo sapiens
SEQUENCE: 525
gctgtccgga ggggtc                                                16

SEQ ID NO: 526       moltype = RNA   length = 26
FEATURE              Location/Qualifiers
source               1..26
                     mol_type = unassigned RNA
                     organism = Homo sapiens
SEQUENCE: 526
agggacggga cgcggtgcag tgttgt                                     26

SEQ ID NO: 527       moltype = RNA   length = 15
FEATURE              Location/Qualifiers
source               1..15
                     mol_type = unassigned RNA
                     organism = Homo sapiens
SEQUENCE: 527
ggcgggcggg aggga                                                 15

SEQ ID NO: 528       moltype = RNA   length = 23
FEATURE              Location/Qualifiers
source               1..23
                     mol_type = unassigned RNA
                     organism = Homo sapiens
SEQUENCE: 528
tgggggaaggc gtcagtgtcg ggt                                       23

SEQ ID NO: 529       moltype = RNA   length = 16
FEATURE              Location/Qualifiers
source               1..16
                     mol_type = unassigned RNA
                     organism = Homo sapiens
SEQUENCE: 529
tgggggaaggc gtcagt                                               16

SEQ ID NO: 530       moltype = RNA   length = 23
FEATURE              Location/Qualifiers
source               1..23
                     mol_type = unassigned RNA
                     organism = Homo sapiens
SEQUENCE: 530
tagggggcagc agaggacctg ggc                                       23

SEQ ID NO: 531       moltype = RNA   length = 20
FEATURE              Location/Qualifiers
source               1..20
                     mol_type = unassigned RNA
                     organism = Homo sapiens
SEQUENCE: 531
tagggggcagc agaggacctg                                           20

SEQ ID NO: 532       moltype = RNA   length = 20
FEATURE              Location/Qualifiers
source               1..20
                     mol_type = unassigned RNA
                     organism = Homo sapiens
SEQUENCE: 532
ggctggtcag atgggagtgg                                            20

SEQ ID NO: 533       moltype = RNA   length = 20
FEATURE              Location/Qualifiers
source               1..20
                     mol_type = unassigned RNA
                     organism = Homo sapiens
SEQUENCE: 533
ggctggtcag atgggagtgg                                            20
```

-continued

```
SEQ ID NO: 534          moltype = RNA   length = 20
FEATURE                 Location/Qualifiers
source                  1..20
                        mol_type = unassigned RNA
                        organism = Homo sapiens
SEQUENCE: 534
ccccagggcg acgcggcggg                                              20

SEQ ID NO: 535          moltype = RNA   length = 15
FEATURE                 Location/Qualifiers
source                  1..15
                        mol_type = unassigned RNA
                        organism = Homo sapiens
SEQUENCE: 535
cgcggcgggg gcggc                                                   15

SEQ ID NO: 536          moltype = RNA   length = 20
FEATURE                 Location/Qualifiers
source                  1..20
                        mol_type = unassigned RNA
                        organism = Homo sapiens
SEQUENCE: 536
ccccggggag cccggcggtg                                              20

SEQ ID NO: 537          moltype = RNA   length = 15
FEATURE                 Location/Qualifiers
source                  1..15
                        mol_type = unassigned RNA
                        organism = Homo sapiens
SEQUENCE: 537
accccgggga gcccg                                                   15

SEQ ID NO: 538          moltype = RNA   length = 21
FEATURE                 Location/Qualifiers
source                  1..21
                        mol_type = unassigned RNA
                        organism = Homo sapiens
SEQUENCE: 538
ttgaggagac atggtggggg c                                            21

SEQ ID NO: 539          moltype = RNA   length = 15
FEATURE                 Location/Qualifiers
source                  1..15
                        mol_type = unassigned RNA
                        organism = Homo sapiens
SEQUENCE: 539
ttgaggagac atggt                                                   15

SEQ ID NO: 540          moltype = RNA   length = 22
FEATURE                 Location/Qualifiers
source                  1..22
                        mol_type = unassigned RNA
                        organism = Homo sapiens
SEQUENCE: 540
actcggctgc ggtggacaag tc                                           22

SEQ ID NO: 541          moltype = RNA   length = 20
FEATURE                 Location/Qualifiers
source                  1..20
                        mol_type = unassigned RNA
                        organism = Homo sapiens
SEQUENCE: 541
actcggctgc ggtggacaag                                              20

SEQ ID NO: 542          moltype = RNA   length = 19
FEATURE                 Location/Qualifiers
source                  1..19
                        mol_type = unassigned RNA
                        organism = Homo sapiens
SEQUENCE: 542
tggcgggtgc gggggtggg                                               19

SEQ ID NO: 543          moltype = RNA   length = 15
FEATURE                 Location/Qualifiers
source                  1..15
                        mol_type = unassigned RNA
                        organism = Homo sapiens
SEQUENCE: 543
tggcgggtgc ggggg                                                   15
```

-continued

```
SEQ ID NO: 544             moltype = RNA   length = 23
FEATURE                    Location/Qualifiers
source                     1..23
                           mol_type = unassigned RNA
                           organism = Homo sapiens
SEQUENCE: 544
gagggaggga cggggctgt gct                                            23

SEQ ID NO: 545             moltype = RNA   length = 15
FEATURE                    Location/Qualifiers
source                     1..15
                           mol_type = unassigned RNA
                           organism = Homo sapiens
SEQUENCE: 545
gaggagggag ggagg                                                    15

SEQ ID NO: 546             moltype = RNA   length = 26
FEATURE                    Location/Qualifiers
source                     1..26
                           mol_type = unassigned RNA
                           organism = Homo sapiens
SEQUENCE: 546
aaaatcacat tgccagggat taccac                                        26

SEQ ID NO: 547             moltype = RNA   length = 15
FEATURE                    Location/Qualifiers
source                     1..15
                           mol_type = unassigned RNA
                           organism = Homo sapiens
SEQUENCE: 547
aatcacattg ccagg                                                    15

SEQ ID NO: 548             moltype = RNA   length = 21
FEATURE                    Location/Qualifiers
source                     1..21
                           mol_type = unassigned RNA
                           organism = Homo sapiens
SEQUENCE: 548
cccaggctgg agcgagtgca g                                             21

SEQ ID NO: 549             moltype = RNA   length = 15
FEATURE                    Location/Qualifiers
source                     1..15
                           mol_type = unassigned RNA
                           organism = Homo sapiens
SEQUENCE: 549
agctcactgc agcct                                                    15

SEQ ID NO: 550             moltype = RNA   length = 21
FEATURE                    Location/Qualifiers
source                     1..21
                           mol_type = unassigned RNA
                           organism = Homo sapiens
SEQUENCE: 550
tgggaatggg ggtaagggcc t                                             21

SEQ ID NO: 551             moltype = RNA   length = 15
FEATURE                    Location/Qualifiers
source                     1..15
                           mol_type = unassigned RNA
                           organism = Homo sapiens
SEQUENCE: 551
cttctgagcc caggt                                                    15

SEQ ID NO: 552             moltype = RNA   length = 17
FEATURE                    Location/Qualifiers
source                     1..17
                           mol_type = unassigned RNA
                           organism = Homo sapiens
SEQUENCE: 552
tgcaggggca ggccagc                                                  17

SEQ ID NO: 553             moltype = RNA   length = 17
FEATURE                    Location/Qualifiers
source                     1..17
                           mol_type = unassigned RNA
                           organism = Homo sapiens
SEQUENCE: 553
```

-continued

```
tgcaggggca ggccagc                                                   17

SEQ ID NO: 554        moltype = RNA   length = 16
FEATURE               Location/Qualifiers
source                1..16
                      mol_type = unassigned RNA
                      organism = Homo sapiens SEQUENCE: 554
agctgcagtg ggggag                                                    16

SEQ ID NO: 555        moltype = RNA   length = 15
FEATURE               Location/Qualifiers
source                1..15
                      mol_type = unassigned RNA
                      organism = Homo sapiens SEQUENCE: 555
gctgcagtgg gggag                                                     15

SEQ ID NO: 556        moltype = RNA   length = 15
FEATURE               Location/Qualifiers
source                1..15
                      mol_type = unassigned RNA
                      organism = Homo sapiens SEQUENCE: 556
tctgggcgag gggtg                                                     15

SEQ ID NO: 557        moltype = RNA   length = 15
FEATURE               Location/Qualifiers
source                1..15
                      mol_type = unassigned RNA
                      organism = Homo sapiens SEQUENCE: 557
tctgggcgag gggtg                                                     15

SEQ ID NO: 558        moltype = RNA   length = 16
FEATURE               Location/Qualifiers
source                1..16
                      mol_type = unassigned RNA
                      organism = Homo sapiens SEQUENCE: 558
tgggggggaa gaaaag                                                    16

SEQ ID NO: 559        moltype = RNA   length = 16
FEATURE               Location/Qualifiers
source                1..16
                      mol_type = unassigned RNA
                      organism = Homo sapiens SEQUENCE: 559
tgggggggaa gaaaag                                                    16

SEQ ID NO: 560        moltype = RNA   length = 17
FEATURE               Location/Qualifiers
source                1..17
                      mol_type = unassigned RNA
                      organism = Homo sapiens SEQUENCE: 560
gcggggcggc aggggcc                                                   17

SEQ ID NO: 561        moltype = RNA   length = 15
FEATURE               Location/Qualifiers
source                1..15
                      mol_type = unassigned RNA
                      organism = Homo sapiens SEQUENCE: 561
ggggcgggg cggca                                                      15

SEQ ID NO: 562        moltype = RNA   length = 22
FEATURE               Location/Qualifiers
source                1..22
                      mol_type = unassigned RNA
                      organism = Homo sapiens SEQUENCE: 562
tgtgggactg caaatgggag ct                                             22

SEQ ID NO: 563        moltype = RNA   length = 22
FEATURE               Location/Qualifiers
source                1..22
                      mol_type = unassigned RNA
                      organism = Homo sapiens
```

-continued

```
SEQUENCE: 563
tgtgggactg caaatgggag ct                                            22

SEQ ID NO: 564          moltype = RNA  length = 18
FEATURE                 Location/Qualifiers
source                  1..18
                        mol_type = unassigned RNA
                        organism = Homo sapiens
SEQUENCE: 564
cagcggggct gggcgcgc                                                 18

SEQ ID NO: 565          moltype = RNA  length = 15
FEATURE                 Location/Qualifiers
source                  1..15
                        mol_type = unassigned RNA
                        organism = Homo sapiens
SEQUENCE: 565
cagcggggct gggcg                                                    15

SEQ ID NO: 566          moltype = RNA  length = 24
FEATURE                 Location/Qualifiers
source                  1..24
                        mol_type = unassigned RNA
                        organism = Homo sapiens
SEQUENCE: 566
ctgcggggac aggccagggc atct                                          24

SEQ ID NO: 567          moltype = RNA  length = 20
FEATURE                 Location/Qualifiers
source                  1..20
                        mol_type = unassigned RNA
                        organism = Homo sapiens
SEQUENCE: 567
ctgcggggac aggccagggc                                               20

SEQ ID NO: 568          moltype = RNA  length = 30
FEATURE                 Location/Qualifiers
source                  1..30
                        mol_type = unassigned RNA
                        organism = Homo sapiens
SEQUENCE: 568
gctgggctgg gacggacacc cggcctccac                                    30

SEQ ID NO: 569          moltype = RNA  length = 19
FEATURE                 Location/Qualifiers
source                  1..19
                        mol_type = unassigned RNA
                        organism = Homo sapiens
SEQUENCE: 569
gaggctgggc tgggacgga                                                19

SEQ ID NO: 570          moltype = RNA  length = 24
FEATURE                 Location/Qualifiers
source                  1..24
                        mol_type = unassigned RNA
                        organism = Homo sapiens
SEQUENCE: 570
tgggggagtg cagtgattgt ggaa                                          24

SEQ ID NO: 571          moltype = RNA  length = 19
FEATURE                 Location/Qualifiers
source                  1..19
                        mol_type = unassigned RNA
                        organism = Homo sapiens
SEQUENCE: 571
tgggggagtg cagtgattg                                                19

SEQ ID NO: 572          moltype = RNA  length = 24
FEATURE                 Location/Qualifiers
source                  1..24
                        mol_type = unassigned RNA
                        organism = Homo sapiens
SEQUENCE: 572
aggcaggggc tggtgctggg cggg                                          24

SEQ ID NO: 573          moltype = RNA  length = 15
FEATURE                 Location/Qualifiers
source                  1..15
                        mol_type = unassigned RNA
```

-continued

```
                            organism = Homo sapiens
SEQUENCE: 573
gggcggggg cggcg                                                      15

SEQ ID NO: 574          moltype = RNA   length = 19
FEATURE                 Location/Qualifiers
source                  1..19
                        mol_type = unassigned RNA
                        organism = Homo sapiens
SEQUENCE: 574
agtgggaggc cagggcacg                                                 19

SEQ ID NO: 575          moltype = RNA   length = 15
FEATURE                 Location/Qualifiers
source                  1..15
                        mol_type = unassigned RNA
                        organism = Homo sapiens
SEQUENCE: 575
aggggagct gcagg                                                      15

SEQ ID NO: 576          moltype = RNA   length = 24
FEATURE                 Location/Qualifiers
source                  1..24
                        mol_type = unassigned RNA
                        organism = Homo sapiens
SEQUENCE: 576
ctggtacagg cctgggggac aggg                                           24

SEQ ID NO: 577          moltype = RNA   length = 18
FEATURE                 Location/Qualifiers
source                  1..18
                        mol_type = unassigned RNA
                        organism = Homo sapiens
SEQUENCE: 577
ctggtacagg cctggggg                                                  18

SEQ ID NO: 578          moltype = RNA   length = 25
FEATURE                 Location/Qualifiers
source                  1..25
                        mol_type = unassigned RNA
                        organism = Homo sapiens
SEQUENCE: 578
gggtggggat ttgttgcatt acttg                                          25

SEQ ID NO: 579          moltype = RNA   length = 20
FEATURE                 Location/Qualifiers
source                  1..20
                        mol_type = unassigned RNA
                        organism = Homo sapiens
SEQUENCE: 579
gggtggggat ttgttgcatt                                                20

SEQ ID NO: 580          moltype = RNA   length = 30
FEATURE                 Location/Qualifiers
source                  1..30
                        mol_type = unassigned RNA
                        organism = Homo sapiens
SEQUENCE: 580
tgaggggcag agagcgagac ttttctattt                                     30

SEQ ID NO: 581          moltype = RNA   length = 15
FEATURE                 Location/Qualifiers
source                  1..15
                        mol_type = unassigned RNA
                        organism = Homo sapiens
SEQUENCE: 581
tgaggggcag agagc                                                     15

SEQ ID NO: 582          moltype = RNA   length = 21
FEATURE                 Location/Qualifiers
source                  1..21
                        mol_type = unassigned RNA
                        organism = Homo sapiens
SEQUENCE: 582
gccgggcgtg gtggtggggg c                                              21

SEQ ID NO: 583          moltype = RNA   length = 15
FEATURE                 Location/Qualifiers
source                  1..15
```

-continued

```
                              mol_type = unassigned RNA
                              organism = Homo sapiens
SEQUENCE: 583
tagccgggcg tggtg                                            15

SEQ ID NO: 584         moltype = RNA   length = 23
FEATURE                Location/Qualifiers
source                 1..23
                       mol_type = unassigned RNA
                       organism = Homo sapiens
SEQUENCE: 584
gggggccgat acactgtacg aga                                   23

SEQ ID NO: 585         moltype = RNA   length = 20
FEATURE                Location/Qualifiers
source                 1..20
                       mol_type = unassigned RNA
                       organism = Homo sapiens
SEQUENCE: 585
gggggccgat acactgtacg                                       20

SEQ ID NO: 586         moltype = RNA   length = 24
FEATURE                Location/Qualifiers
source                 1..24
                       mol_type = unassigned RNA
                       organism = Homo sapiens
SEQUENCE: 586
actggctcag ttcagcagga acag                                  24

SEQ ID NO: 587         moltype = RNA   length = 15
FEATURE                Location/Qualifiers
source                 1..15
                       mol_type = unassigned RNA
                       organism = Homo sapiens
SEQUENCE: 587
tggctcagtt cagca                                            15

SEQ ID NO: 588         moltype = RNA   length = 23
FEATURE                Location/Qualifiers
source                 1..23
                       mol_type = unassigned RNA
                       organism = Homo sapiens
SEQUENCE: 588
ggaggcgcag gctcggaaag gcg                                   23

SEQ ID NO: 589         moltype = RNA   length = 15
FEATURE                Location/Qualifiers
source                 1..15
                       mol_type = unassigned RNA
                       organism = Homo sapiens
SEQUENCE: 589
gcaggctcgg aaagg                                            15

SEQ ID NO: 590         moltype = RNA   length = 23
FEATURE                Location/Qualifiers
source                 1..23
                       mol_type = unassigned RNA
                       organism = Homo sapiens
SEQUENCE: 590
tggtgcggag agggcccaca gtg                                   23

SEQ ID NO: 591         moltype = RNA   length = 15
FEATURE                Location/Qualifiers
source                 1..15
                       mol_type = unassigned RNA
                       organism = Homo sapiens
SEQUENCE: 591
gggtctggtg cggag                                            15

SEQ ID NO: 592         moltype = RNA   length = 19
FEATURE                Location/Qualifiers
source                 1..19
                       mol_type = unassigned RNA
                       organism = Homo sapiens
SEQUENCE: 592
gctgggcgag gctggcatc                                        19

SEQ ID NO: 593         moltype = RNA   length = 17
FEATURE                Location/Qualifiers
```

-continued

```
source                  1..17
                        mol_type = unassigned RNA
                        organism = Homo sapiens
SEQUENCE: 593
gctgggcgag gctggca                                                      17

SEQ ID NO: 594         moltype = RNA  length = 27
FEATURE                Location/Qualifiers
source                  1..27
                        mol_type = unassigned RNA
                        organism = Homo sapiens
SEQUENCE: 594
atcacattgc cagggatttc caaccga                                           27

SEQ ID NO: 595         moltype = RNA  length = 15
FEATURE                Location/Qualifiers
source                  1..15
                        mol_type = unassigned RNA
                        organism = Homo sapiens
SEQUENCE: 595
aatcacattg ccagg                                                        15

SEQ ID NO: 596         moltype = RNA  length = 24
FEATURE                Location/Qualifiers
source                  1..24
                        mol_type = unassigned RNA
                        organism = Homo sapiens
SEQUENCE: 596
tgactgggga gcagaaggag aacc                                              24

SEQ ID NO: 597         moltype = RNA  length = 15
FEATURE                Location/Qualifiers
source                  1..15
                        mol_type = unassigned RNA
                        organism = Homo sapiens
SEQUENCE: 597
gactggggag cagaa                                                        15

SEQ ID NO: 598         moltype = RNA  length = 27
FEATURE                Location/Qualifiers
source                  1..27
                        mol_type = unassigned RNA
                        organism = Homo sapiens
SEQUENCE: 598
aaaccgttac cattactgag tttagta                                           27

SEQ ID NO: 599         moltype = RNA  length = 15
FEATURE                Location/Qualifiers
source                  1..15
                        mol_type = unassigned RNA
                        organism = Homo sapiens
SEQUENCE: 599
gaaaccgtta ccatt                                                        15

SEQ ID NO: 600         moltype = RNA  length = 19
FEATURE                Location/Qualifiers
source                  1..19
                        mol_type = unassigned RNA
                        organism = Homo sapiens
SEQUENCE: 600
gtgggttggg gcgggctct                                                    19

SEQ ID NO: 601         moltype = RNA  length = 19
FEATURE                Location/Qualifiers
source                  1..19
                        mol_type = unassigned RNA
                        organism = Homo sapiens
SEQUENCE: 601
gtgggttggg gcgggctct                                                    19

SEQ ID NO: 602         moltype = RNA  length = 17
FEATURE                Location/Qualifiers
source                  1..17
                        mol_type = unassigned RNA
                        organism = Homo sapiens
SEQUENCE: 602
aggggctggg cgcgcgc                                                      17

SEQ ID NO: 603         moltype = RNA  length = 15
```

-continued

```
FEATURE                Location/Qualifiers
source                 1..15
                       mol_type = unassigned RNA
                       organism = Homo sapiens
SEQUENCE: 603
caggggctgg gcgcg                                                       15

SEQ ID NO: 604         moltype = RNA   length = 25
FEATURE                Location/Qualifiers
source                 1..25
                       mol_type = unassigned RNA
                       organism = Homo sapiens
SEQUENCE: 604
caggaaggat ttagggacag gcttt                                            25

SEQ ID NO: 605         moltype = RNA   length = 19
FEATURE                Location/Qualifiers
source                 1..19
                       mol_type = unassigned RNA
                       organism = Homo sapiens
SEQUENCE: 605
caggaaggat ttagggaca                                                   19

SEQ ID NO: 606         moltype = RNA   length = 21
FEATURE                Location/Qualifiers
source                 1..21
                       mol_type = unassigned RNA
                       organism = Homo sapiens
SEQUENCE: 606
atgcctcccc cggccccgca g                                                21

SEQ ID NO: 607         moltype = RNA   length = 17
FEATURE                Location/Qualifiers
source                 1..17
                       mol_type = unassigned RNA
                       organism = Homo sapiens
SEQUENCE: 607
cgcgccgggc ccgggtt                                                     17

SEQ ID NO: 608         moltype = RNA   length = 21
FEATURE                Location/Qualifiers
source                 1..21
                       mol_type = unassigned RNA
                       organism = Homo sapiens
SEQUENCE: 608
cttccgcccc gccgggcgtc g                                                21

SEQ ID NO: 609         moltype = RNA   length = 17
FEATURE                Location/Qualifiers
source                 1..17
                       mol_type = unassigned RNA
                       organism = Homo sapiens
SEQUENCE: 609
ggggcgcggc cggatcg                                                     17

SEQ ID NO: 610         moltype = RNA   length = 25
FEATURE                Location/Qualifiers
source                 1..25
                       mol_type = unassigned RNA
                       organism = Homo sapiens
SEQUENCE: 610
agggatcgcg ggcgggtggc ggcct                                            25

SEQ ID NO: 611         moltype = RNA   length = 17
FEATURE                Location/Qualifiers
source                 1..17
                       mol_type = unassigned RNA
                       organism = Homo sapiens
SEQUENCE: 611
ctccgggacg gctgggc                                                     17

SEQ ID NO: 612         moltype = RNA   length = 19
FEATURE                Location/Qualifiers
source                 1..19
                       mol_type = unassigned RNA
                       organism = Homo sapiens
SEQUENCE: 612
aaggggctgg gggagcaca                                                   19
```

```
SEQ ID NO: 613           moltype = RNA   length = 22
FEATURE                  Location/Qualifiers
source                   1..22
                         mol_type = unassigned RNA
                         organism = Homo sapiens
SEQUENCE: 613
ggggggtgtg gagccagggg gc                                                  22

SEQ ID NO: 614           moltype = RNA   length = 22
FEATURE                  Location/Qualifiers
source                   1..22
                         mol_type = unassigned RNA
                         organism = Homo sapiens
SEQUENCE: 614
tatagggatt ggagccgtgg cg                                                  22

SEQ ID NO: 615           moltype = RNA   length = 63
FEATURE                  Location/Qualifiers
source                   1..63
                         mol_type = unassigned RNA
                         organism = Homo sapiens
SEQUENCE: 615
ggctccgcag ggccctggcg caggcatcca dacagcgggc gaatgcctcc cccggccccg         60
cag                                                                       63

SEQ ID NO: 616           moltype = RNA   length = 84
FEATURE                  Location/Qualifiers
source                   1..84
                         mol_type = unassigned RNA
                         organism = Homo sapiens
SEQUENCE: 616
ccgcagccgc cgcgccgggc ccgggttggc cgctgacccc cgcggggccc ccggcggccg         60
gggcgggggc gggggctgcc ccgg                                                84

SEQ ID NO: 617           moltype = RNA   length = 70
FEATURE                  Location/Qualifiers
source                   1..70
                         mol_type = unassigned RNA
                         organism = Homo sapiens
SEQUENCE: 617
ggccgcggcg cgcaagatgg cggcgggccc gggcaccgcc ccttccgccc cgccgggcgt         60
cgcacgaggc                                                                70

SEQ ID NO: 618           moltype = RNA   length = 84
FEATURE                  Location/Qualifiers
source                   1..84
                         mol_type = unassigned RNA
                         organism = Homo sapiens
SEQUENCE: 618
gaggctgggc ggggcgcggc cggatcggtc gagagcgtcc tggctgatga cggtctcccg         60
tgcccacgcc ccaaacgcag tctc                                                84

SEQ ID NO: 619           moltype = RNA   length = 100
FEATURE                  Location/Qualifiers
source                   1..100
                         mol_type = unassigned RNA
                         organism = Homo sapiens
SEQUENCE: 619
gtgagcgggc gcggcaggga tcgcgggcgg gtggcggcct agggcgcgga gggcggaccg         60
ggaatggcgc gccgtgcgcc gccggcgtaa ctgcggcgct                              100

SEQ ID NO: 620           moltype = RNA   length = 89
FEATURE                  Location/Qualifiers
source                   1..89
                         mol_type = unassigned RNA
                         organism = Homo sapiens
SEQUENCE: 620
acctccggga cggctgggcg ccggcggccg ggagatccgc gcttcctgaa tcccggccgg         60
cccgcccggc gccgtccgc ccgcgggtc                                            89

SEQ ID NO: 621           moltype = RNA   length = 110
FEATURE                  Location/Qualifiers
source                   1..110
                         mol_type = unassigned RNA
                         organism = Homo sapiens
SEQUENCE: 621
gtctaccagg tgtgggccca gctttacata gttcatgctg aggccgggat ttcatgcaga         60
aaactggttg caaaaggtgc tgaaggggct gggggagcac aagggagaag                   110
```

-continued

```
SEQ ID NO: 622          moltype = RNA   length = 71
FEATURE                 Location/Qualifiers
source                  1..71
                        mol_type = unassigned RNA
                        organism = Homo sapiens
SEQUENCE: 622
atggaggggg gtgtggagcc aggggggccca ggtctacagc ttctccccgc tccctgcccc    60
catactccca g                                                          71

SEQ ID NO: 623          moltype = RNA   length = 90
FEATURE                 Location/Qualifiers
source                  1..90
                        mol_type = unassigned RNA
                        organism = Homo sapiens
SEQUENCE: 623
aggcctcgct gttctctatg gcttttttatt cctatgtgat tctactgctc actcatatag    60
ggattggagc cgtggcgcac ggcggggaca                                      90

SEQ ID NO: 624          moltype = RNA   length = 17
FEATURE                 Location/Qualifiers
source                  1..17
                        mol_type = unassigned RNA
                        organism = Homo sapiens
SEQUENCE: 624
ggggcggggg cggggggc                                                   17

SEQ ID NO: 625          moltype = RNA   length = 15
FEATURE                 Location/Qualifiers
source                  1..15
                        mol_type = unassigned RNA
                        organism = Homo sapiens
SEQUENCE: 625
cgcgccgggc ccggg                                                      15

SEQ ID NO: 626          moltype = RNA   length = 15
FEATURE                 Location/Qualifiers
source                  1..15
                        mol_type = unassigned RNA
                        organism = Homo sapiens
SEQUENCE: 626
ggcggcgggc ccggg                                                      15

SEQ ID NO: 627          moltype = RNA   length = 15
FEATURE                 Location/Qualifiers
source                  1..15
                        mol_type = unassigned RNA
                        organism = Homo sapiens
SEQUENCE: 627
ggcggcgggc ccggg                                                      15

SEQ ID NO: 628          moltype = RNA   length = 24
FEATURE                 Location/Qualifiers
source                  1..24
                        mol_type = unassigned RNA
                        organism = Homo sapiens
SEQUENCE: 628
gatcggtcga gagcgtcctg gctg                                            24

SEQ ID NO: 629          moltype = RNA   length = 15
FEATURE                 Location/Qualifiers
source                  1..15
                        mol_type = unassigned RNA
                        organism = Homo sapiens
SEQUENCE: 629
gctgggcggg gcgcg                                                      15

SEQ ID NO: 630          moltype = RNA   length = 16
FEATURE                 Location/Qualifiers
source                  1..16
                        mol_type = unassigned RNA
                        organism = Homo sapiens
SEQUENCE: 630
ggcgcggagg gcggac                                                     16

SEQ ID NO: 631          moltype = RNA   length = 15
FEATURE                 Location/Qualifiers
source                  1..15
                        mol_type = unassigned RNA
                        organism = Homo sapiens
```

-continued

```
SEQUENCE: 631
ggcgcggagg gcgga                                                          15

SEQ ID NO: 632        moltype = RNA  length = 17
FEATURE               Location/Qualifiers
source                1..17
                      mol_type = unassigned RNA
                      organism = Homo sapiens
SEQUENCE: 632
cctccgggac ggctggg                                                        17

SEQ ID NO: 633        moltype = RNA  length = 15
FEATURE               Location/Qualifiers
source                1..15
                      mol_type = unassigned RNA
                      organism = Homo sapiens
SEQUENCE: 633
ctccgggacg gctgg                                                          15

SEQ ID NO: 634        moltype = RNA  length = 22
FEATURE               Location/Qualifiers
source                1..22
                      mol_type = unassigned RNA
                      organism = Homo sapiens
SEQUENCE: 634
atatagggat tggagccgtg gc                                                  22

SEQ ID NO: 635        moltype = RNA  length = 20
FEATURE               Location/Qualifiers
source                1..20
                      mol_type = unassigned RNA
                      organism = Homo sapiens
SEQUENCE: 635
atatagggat tggagccgtg                                                     20
```

COLORECTAL CANCER DETECTION KIT OR DEVICE, AND DETECTION METHOD

CROSS-REFERENCE TO RELATED APPLICATIONS

This application is a Divisional of U.S. application Ser. No. 17/945,243 filed Sep. 15, 2022, which is a Divisional of U.S. application Ser. No. 16/789,986 filed Feb. 13, 2020 (now U.S. Pat. No. 11,479,821), which is a Divisional of application Ser. No. 15/318,312, filed on Dec. 12, 2016 (now U.S. Pat. No. 10,604,810), which is the National Phase under 35 U.S.C. § 371 of International Application No. PCT/JP2015/066970, filed on Jun. 12, 2015, which claims the benefit under 35 U.S.C. § 119(a) to Patent Application No. 2014-122686, filed in Japan on Jun. 13, 2014, and to Patent Application No. 2015-070182, filed in Japan on Mar. 30, 2015, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said. XML copy, created on Sep. 12, 2022, is named "PH-6235-PCT-US-DIV1-DIV1 Sequence Listing ST26" and is 571,313 bytes in size. The sequence listing contained in this .XML file is part of the specification and is hereby incorporated by reference herein in its entirety.

TECHNICAL FIELD

The present invention relates to a kit or a device for the detection of colorectal cancer, comprising a nucleic acid capable of specifically binding to a particular miRNA, which is used for examining the presence or absence of colorectal cancer in a subject, and a method for detecting colorectal cancer, comprising measuring an expression level of the miRNA using the nucleic acid.

BACKGROUND ART

The large intestine is an organ that stores residual bowel contents after digestion and absorption, and produces feces while absorbing water. The large intestine begins with the cecum, which is then connected to the ascending colon, the transverse colon, the descending colon, the sigmoid colon, the rectum, and the anal canal. According to the 2011 type-specific cancer statistics in Japan disclosed by the Center for Cancer Control and Information Services, National Cancer Center, the number of individuals affected by colorectal cancer was 112,772 people. Namely, it is estimated that one in approximately 14 Japanese people experience colorectal cancer. The number of incidences of this cancer takes the 2nd place by cancer site. The number of colorectal cancer deaths in men and women together climbs to 45,744 people and takes the 3rd place by cancer site. It is estimated that one in approximately 20 Americans develop colorectal cancer. The estimated number of American individuals affected by colorectal cancer climbed to 96,830 people in 2014, among which approximately 40,000 people reportedly died (Non Patent Literature 1).

The progression stages of colorectal cancer are specified in Non Patent Literature 2 and classified into stage 0 (Tis/N0/M0), stage I (T1 to T2/N0/M0), stage II (T3 to T4/N0/M0), stage IIA (T3/N0/M0), stage IIB (T4a/N0/M0), stage IIC (T4b/N0/M0), stage III (N1 to N2/M0), stage IIIA (T1 to T2/N1/M0 and T1/N2a/M0), stage IIIB (T3 to T4a/N1/M0 and T2 to T3/N2a/M0 and T1 to T2/N2b/M0), stage IIIC (T4a/N2a/M0 and T3 to T4a/N2b/M0 and T4b/N1 to N2/M0), stage IVA (M1a), and stage IVB (M1b) according to the degrees of tumor spread (Tis and T1 to T4), lymph node metastasis (N0, N1a to N1c, and N2a to N2b), and distant metastasis (M0 and M1a to M1b).

The survival rate of colorectal cancer differs depending on the stages of progression. Non Patent Literature 1 has reported the following respective statistic values of colon cancer and rectal cancer. The 5-year relative survival rate of colon cancer is reportedly 74% for stage I, 67% for stage IIA, 59% for stage IIB, 37% for stage IIC, 73% for stage IIIA, 46% for stage IIIB, 28% for stage IIIC, and 6% for stage IV. Also, the 5-year relative survival rate of rectal cancer is reportedly 74% for stage I, 65% for stage IIA, 52% for stage IIB, 32% for stage IIC, 74% for stage IIIA, 45% for stage IIIB, 33% for stage IIIC, and 6% for stage IV. Evidently, colorectal cancer at an early stage of progression leads to a high survival rate. Thus, the early detection and treatment of colorectal cancer makes a significant contribution to improvement in survival rate.

The treatment of colorectal cancer is mainly laparotomy or laparoscopic surgery, which is often used in combination with postoperative anticancer drug treatment or radiotherapy (Non Patent Literature 1). Particularly, early colorectal cancer may be adaptable to endoscopic surgery which permits treatment without abdominal resection.

As described in Non Patent Literature 1, fecal occult blood test and endoscopy are widely prevalent as tests of colorectal cancer. Particularly, the fecal occult blood test is inexpensive and noninvasive and is also carried out at home. Therefore, the American Cancer Society recommends taking the fecal occult blood test every year. In order to further examine a tumor site and spread of the cancer, an imaging test such as barium enema, CT, or MRI is also carried out in addition to the colonoscopy. Alternatively, tests on blood tumor markers such as CEA and CA19-9 may be carried out for the purpose of observing the prognosis or the therapeutic effects on patients already diagnosed with colorectal cancer (Non Patent Literature 1).

As shown in Patent Literatures 1 to 4, there are reports, albeit at a research stage, on the detection of colorectal cancer using the expression levels of microRNAs (miRNAs) or combinations of the expression levels of miRNAs and the expression levels of additional protein markers in biological samples including blood.

Patent Literature 1 discloses a method for detecting colorectal cancer or other cancers using hsa-miR-92a-2-5p, hsa-miR-128-2-5p, and hsa-miR-24-3p in colorectal cancer tissues. Patent Literature 2 discloses a method for detecting colorectal cancer using hsa-miR-1233-5p and hsa-miR-1225-3p in plasma.

Patent Literature 3 discloses a method for detecting colorectal cancer using multiple miRNAs such as hsa-miR-1231, hsa-miR-423-5p, and hsa-miR-1268a in large intestine tissues or feces.

Patent Literature 4 discloses a method for detecting colorectal cancer using hsa-miR-150-3p, miR-92a-2-5p, and the like in tissues.

CITATION LIST

Patent Literature

Patent Literature 1: International Publication No. WO 2007/081740

US 12,644,157 B2

3

Patent Literature 2: U.S. Patent Application Publication No. 2013/102487

Patent Literature 3: U.S. Patent Application Publication No. 2012/088687

Patent Literature 4: JP Patent Publication (Kohyo) No. 2009-531019 A (2009)

Non Patent Literature

Non Patent Literature 1: American Cancer Society, "Colorectal Cancer", 2013, p. 5 to 6, 17 to 28, 33 to, 45 to 54, and 67 to 71

Non Patent Literature 2: Sobin, L. et al., "TNM Classification of Malignant Tumours, the 7th edition", 2010, p. 94-99

Non Patent Literature 3: Allison, J E. et al., 1996, The New England Journal of Medicine, Vol. 334 (3), p. 155-9

Non Patent Literature 4: Palmqvist, R. et al., 2007, Diseases of colon and rectum, Vol. 46 (11), p. 1538-44

SUMMARY OF INVENTION

Technical Problem

An object of the present invention is to find a novel tumor marker for colorectal cancer and to provide a method that can effectively detect colorectal cancer using a nucleic acid capable of specifically binding to the marker. The fecal occult blood test, which is widely used at present as a first test of colorectal cancer, produces positive results even for non-cancerous reasons such as hemorrhoid, whereas this test fails to detect early colorectal cancer without bleeding and overlooks 90% or more of abnormalities in the large intestine (including cancer) according to the report (Non Patent Literature 1). The specific sensitivity of the fecal occult blood test differs largely from 37% to 79.4% depending on a testing kit used, and its specificity is reportedly 86.7% to 97.7% (Non Patent Literature 3). Although the colonoscopy is known to have high examination accuracy, this examination is difficult to apply as a primary screening because of the necessity of pretreatment or sedatives on patients, relatively high cost, etc. (Non Patent Literature 1). The tumor markers such as CEA and CA19-9 in blood may elevate in cancers other than colorectal cancer and therefore allegedly fail to determine the presence or absence of colorectal cancer. The false diagnosis of other cancers as colorectal cancer wastes appropriate therapeutic opportunity or places unnecessary economical and physical burdens on patients due to the application of wrong medicine. Therefore, use of CEA or CA19-9 is often limited to the observation of the prognosis and of therapeutic effects on patients already diagnosed with colorectal cancer (Non Patent Literature 1). The report states that the CEA test has specificity of 99%, but sensitivity of only 12%, suggesting that the significance of tumor marker measurement as a colorectal cancer screening test is poor (Non Patent Literature 4).

As described below, there are reports, albeit at a research stage, on the determination of colorectal cancer using the expression levels of microRNAs (miRNAs) in biological samples including blood, none of which, however, have yet been brought into practical use.

Patent Literature 1 discloses a method for detecting colorectal cancer or other cancers using hsa-miR-92a-2-5p, hsa-miR-128-2-5p, and hsa-miR-24-3p in colorectal cancer tissues. This detection method, however, requires obtaining colorectal cancer tissue samples by surgical operation, and this step places a heavy physical burden on patients. Therefore, this method is not favorable as an examination method. In addition, this detection method does not describe specific colorectal cancer detection performance such as accuracy, sensitivity, or specificity and is thus industrially less practical.

Patent Literature 3 discloses a method for detecting colorectal cancer using multiple miRNAs such as hsa-miR-1231, hsa-miR-423-5p, and hsa-miR-1268a in large intestine tissues or feces. Since surgical operation for obtaining colorectal cancer tissues places a heavy physical burden on patients, this method is not favorable as an examination method. In addition, although the collection of fecal samples is noninvasive, test substances may exist unevenly in feces. This tends to cause unfavorable variations in testing results.

Patent Literature 4 discloses a method for detecting colorectal cancer using hsa-miR-150-3p, miR-92a-2-5p, and the like in tissues. This literature, however, neither describes detection performance such as accuracy, sensitivity, or specificity nor describes a specific method for determining colorectal cancer using blood. Therefore, this method is industrially less practical. In addition, these miRNA markers were not validated in an independent sample group and are thus less reliable.

As mentioned above, the existing tumor markers exhibit low performance in the detection of colorectal cancer, or neither performance nor detection methods are specifically shown as to the markers at a research stage. Therefore, use of these markers might lead to imposing needless extra examination due to the false detection of healthy subjects as being colorectal cancer patients, or might waste therapeutic opportunity because of overlooking colorectal cancer patients. In addition, the measurement of several dozens to several hundreds of miRNAs increases examination cost and is therefore difficult to use in large-scale screening such as medical checkup. Furthermore, the collection of colorectal tissues for measuring the tumor markers is highly invasive to patients and is not favorable. Hence, there is a demand for a highly accurate colorectal cancer marker that is detectable from blood, which can be collected in a less invasive manner, and is capable of correctly determining a colorectal cancer patient as a colorectal cancer patient and a healthy subject as a healthy subject. The early detection and treatment of colorectal cancer can drastically improve survival rates. Furthermore, the early detection of colorectal cancer leads to the applicability of endoscopic surgery which permits treatment without abdominal resection. Therefore, a highly sensitive colorectal cancer marker that can detect colorectal cancer even at an early stage of progression is desired.

Solution to Problem

The present inventors have conducted diligent studies to attain the object and consequently completed the present invention by finding multiple genes usable as markers for the detection of colorectal cancer from blood, which can be collected with limited invasiveness, and finding that colorectal cancer can be significantly detected by using a nucleic acid capable of specifically binding to any of these markers.

SUMMARY OF INVENTION

Specifically, the Present Invention has the Following Features:

(1) A kit for the detection of colorectal cancer, comprising a nucleic acid capable of specifically binding to at least one or more polynucleotide(s) selected from the group consisting of colorectal cancer markers miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p.

(2) The kit according to (1), wherein miR-6726-5p is hsa-miR-6726-5p, miR-4257 is hsa-miR-4257, miR-6787-5p is hsa-miR-6787-5p, miR-6780b-5p is hsa-miR-6780b-5p, miR-3131 is hsa-miR-3131, miR-7108-5p is hsa-miR-7108-5p, miR-1343-3p is hsa-miR-1343-3p, miR-1247-3p is hsa-miR-1247-3p, miR-4651 is hsa-miR-4651, miR-6757-5p is hsa-miR-6757-5p, miR-3679-5p is hsa-miR-3679-5p, miR-7641 is hsa-miR-7641, miR-6746-5p is hsa-miR-6746-5p, miR-8072 is hsa-miR-8072, miR-6741-5p is hsa-miR-6741-5p, miR-1908-5p is hsa-miR-1908-5p, miR-6857-5p is hsa-miR-6857-5p, miR-4746-3p is hsa-miR-4746-3p, miR-744-5p is hsa-miR-744-5p, miR-4792 is hsa-miR-4792, miR-564 is hsa-miR-564, miR-6791-5p is hsa-miR-6791-5p, miR-6825-5p is hsa-miR-6825-5p, miR-6826-5p is hsa-miR-6826-5p, miR-4665-3p is hsa-miR-4665-3p, miR-4467 is hsa-miR-4467, miR-3188 is hsa-miR-3188, miR-6125 is hsa-miR-6125, miR-6756-5p is hsa-miR-6756-5p, miR- 1228-3p is hsa-miR-1228-3p, miR-8063 is hsa-miR-8063, miR-8069 is hsa-miR-8069, miR-6875-5p is hsa-miR-6875-5p, miR-3185 is hsa-miR-3185, miR-4433b-3p is hsa-miR-4433b-3p, miR-6887-5p is hsa-miR-6887-5p, miR-128-1-5p is hsa-miR-128-1-5p, miR-6724-5p is hsa-miR-6724-5p, miR-1914-3p is hsa-miR-1914-3p, miR-1225-5p is hsa-miR-1225-5p, miR-4419b is hsa-miR-4419b, miR-7110-5p is hsa-miR-7110-5p, miR-187-5p is hsa-miR-187-5p, miR-3184-5p is hsa-miR-3184-5p, miR-204-3p is hsa-miR-204-3p, miR-5572 is hsa-miR-5572, miR-6729-5p is hsa-miR-6729-5p, miR-615-5p is hsa-miR-615-5p, miR-6749-5p is hsa-miR-6749-5p, miR-6515-3p is hsa-miR-6515-3p, miR-3937 is hsa-miR-3937, miR-6840-3p is hsa-miR-6840-3p, miR-6893-5p is hsa-miR-6893-5p, miR-4728-5p is hsa-miR-4728-5p, miR-6717-5p is hsa-miR-6717-5p, miR-7113-3p is hsa-miR-7113-3p, miR-4665-5p is hsa-miR-4665-5p, miR-642b-3p is hsa-miR-642b-3p, miR-7109-5p is hsa-miR-7109-5p, miR-6842-5p is hsa-miR-6842-5p, miR-4442 is hsa-miR-4442, miR-4433-3p is hsa-miR-4433-3p, miR-4707-5p is hsa-miR-4707-5p, miR-6126 is hsa-miR-6126, miR-4449 is hsa-miR-4449, miR-4706 is hsa-miR-4706, miR-1913 is hsa-miR-1913, miR-602 is hsa-miR-602, miR-939-5p is hsa-miR-939-5p, miR-4695-5p is hsa-miR-4695-5p, miR-711 is hsa-miR-711, miR-6816-5p is hsa-miR-6816-5p, miR-4632-5p is hsa-miR-4632-5p, miR-6721-5p is hsa-miR-6721-5p, miR-7847-3p is hsa-miR-7847-3p, miR-6132 is hsa-miR-6132, miR-887-3p is hsa-miR-887-3p, miR-3679-3p is hsa-miR-3679-3p, miR-6784-5p is hsa-miR-6784-5p, miR-1249 is hsa-miR-1249, miR-937-5p is hsa-miR-937-5p, miR-5195-3p is hsa-miR-5195-3p, miR-6732-5p is hsa-miR-6732-5p, miR-4417 is hsa-miR-4417, miR-4281 is hsa-miR-4281, miR-4734 is hsa-miR-4734, miR-6766-3p is hsa-miR-6766-3p, miR-663a is hsa-miR-663a, miR-4513 is hsa-miR-4513, miR-6781-5p is hsa-miR-6781-5p, miR-1227-5p is hsa-miR-1227-5p, miR-6845-5p is hsa-miR-6845-5p, miR-6798-5p is hsa-miR-6798-5p, miR-3620-5p is hsa-miR-3620-5p, miR-1915-5p is hsa-miR-1915-5p, miR-4294 is hsa-miR-4294, miR-642a-3p is hsa-miR-642a-3p, miR-371a-5p is hsa-miR-371a-5p, miR-940 is hsa-miR-940, miR-4450 is hsa-miR-4450, miR-4723-5p is hsa-miR-4723-5p, miR-1469 is hsa-miR-1469, miR-6861-5p is hsa-miR-6861-5p, miR-7975 is hsa-miR-7975, miR-6879-5p is hsa-miR-6879-5p, miR-6802-5p is hsa-miR-6802-5p, miR-1268b is hsa-miR-1268b, miR-663b is hsa-miR-663b, miR-125a-3p is hsa-miR-125a-3p, miR-2861 is hsa-miR-2861, miR-6088 is hsa-miR-6088, miR-4758-5p is hsa-miR-4758-5p, miR-296-3p is hsa-miR-296-3p, miR-6738-5p is hsa-miR-6738-5p, miR-671-5p is hsa-miR-671-5p, miR-4454 is hsa-miR-4454, miR-4516 is hsa-miR-4516, miR-7845-5p is hsa-miR-7845-5p, miR-4741 is hsa-miR-4741, miR-92b-5p is hsa-miR-92b-5p, miR-6795-5p is hsa-miR-6795-5p, miR-6805-3p is hsa-miR-6805-3p, miR-4725-3p is hsa-miR-4725-3p, miR-6782-5p is hsa-miR-6782-5p, miR-4688 is hsa-miR-4688, miR-6850-5p is hsa-miR-6850-5p, miR-6777-5p is hsa-miR-6777-5p, miR-6785-5p is hsa-miR-6785-5p, miR-7106-5p is hsa-miR-7106-5p, miR-3663-3p is hsa-miR-3663-3p, miR-6131 is hsa-miR-6131, miR-1915-3p is hsa-miR-1915-3p, miR-4532 is hsa-miR-4532, miR-6820-5p is hsa-miR-6820-5p, miR-4689 is hsa-miR-4689, miR-4638-5p is hsa-miR-4638-5p, miR-3656 is hsa-miR-3656, miR-3621 is hsa-miR-3621, miR-6769b-5p is hsa-miR-6769b-5p, miR-149-3p is hsa-miR-149-3p, miR-23b-3p is hsa-miR-23b-3p, miR-3135b is hsa-miR-3135b, miR-6848-5p is hsa-miR-6848-5p, miR-6769a-5p is hsa-miR-6769a-5p, miR-4327 is hsa-miR-4327, miR-6765-3p is hsa-miR-6765-3p, miR-6716-5p is hsa-miR-6716-5p, miR-6877-5p is hsa-miR-6877-5p, miR-6727-5p is hsa-miR-6727-5p, miR-4534 is hsa-miR-4534, miR-614 is hsa-miR-614, miR-1202 is hsa-miR-1202, miR-575 is hsa-miR-575, miR-6870-5p is hsa-miR-6870-5p, miR-6722-3p is hsa-miR-6722-3p, miR-7977 is hsa-miR-7977, miR-4649-5p is hsa-miR-4649-5p, miR-4675 is hsa-miR-4675, miR-6075 is hsa-miR-6075, miR-6779-5p is hsa-miR-6779-5p, miR-4271 is hsa-miR-4271, miR-3196 is hsa-miR-3196, miR-6803-5p is hsa-miR-6803-5p, miR-6789-5p is hsa-miR-6789-5p, miR-4648 is hsa-miR-4648, miR-4508 is hsa-miR-4508, miR-4749-5p is hsa-miR-4749-5p, miR-4505 is hsa-miR-4505, miR-5698 is hsa-miR-5698, miR-1199-5p is hsa-miR-1199-5p, miR-4763-3p is hsa-miR-4763-3p, miR-6836-3p is hsa-miR-6836-3p, miR-3195 is hsa-miR-3195, miR-718 is hsa-miR-718, miR-3178 is hsa-miR-3178, miR-638 is hsa-miR-638, miR-4497 is hsa-miR-4497, miR-6085 is hsa-miR-6085, miR-6752-5p is hsa-miR-6752-5p, and miR-135a-3p is hsa-miR-135a-3p.

(3) The kit according to (1) or (2), wherein the nucleic acid is a polynucleotide selected from the group consisting of the following polynucleotides (a) to (e):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

(4) The kit according to any of (1) to (3), wherein the kit further comprises a nucleic acid capable of specifically binding to at least one or more polynucleotide(s) selected from the group consisting of other colorectal cancer markers miR-1231-5p, miR-1233-5p, miR-150-3p, miR-1225-3p, miR-92a-2-5p, miR-423-5p, miR-1268a, miR-128-2-5p and miR-24-3p.

(5) The kit according to (4), wherein miR-1231 is hsa-miR-1231, miR-1233-5p is hsa-miR-1233-5p, miR-150-3p is hsa-miR-150-3p, miR-1225-3p is hsa-miR-1225-3p, miR-92a-2-5p is hsa-miR-92a-2-5p, miR-423-5p is hsa-miR-423-5p, miR-1268a is hsa-miR-1268a, miR-128-2-5p is hsa-miR-128-2-5p, and miR-24-3p is hsa-miR-24-3p.

(6) The kit according to (4) or (5), wherein the nucleic acid is a polynucleotide selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180,

(h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

(7) The kit according to any of (1) to (6), wherein the kit further comprises a nucleic acid capable of specifically binding to at least one or more polynucleotide(s) selected from the group consisting of other colorectal cancer markers miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476 and miR-6090.

(8) The kit according to (7), wherein miR-4697-5p is hsa-miR-4697-5p, miR-3197 is hsa-miR-3197, miR-675-5p is hsa-miR-675-5p, miR-4486 is hsa-miR-4486, miR-7107-5p is hsa-miR-7107-5p, miR-23a-3p is hsa-miR-23a-3p, miR-4667-5p is hsa-miR-4667-5p, miR-451a is hsa-miR-451a, miR-3940-5p is hsa-miR-3940-5p, miR-8059 is hsa-miR-8059, miR-6813-5p is hsa-miR-6813-5p, miR-4492 is hsa-miR-4492, miR-4476 is hsa-miR-4476, and miR-6090 is hsa-miR-6090.

(9) The kit according to (7) or (8), wherein the nucleic acid is a polynucleotide selected from the group consisting of the following polynucleotides (k) to (o):

(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 181 to 194, (m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 181 to 194 or a nucleotide sequence derived from the nucleotide sequence by the replacement of u with t, and (o) a polynucleotide hybridizing under stringent conditions to any of the polynucleotides (k) to (n).

(10) The kit according to any one of (1) to (9), wherein the kit comprises at least two or more nucleic acids capable of specifically binding to at least two or more polynucleotides, respectively, selected from the group consisting of all of the colorectal cancer markers according to (1) or (2).

(11) A device for the detection of colorectal cancer, comprising a nucleic acid capable of specifically binding to at least one or more polynucleotide(s) selected from the group consisting of colorectal cancer markers miR-6726-5p, miR-4257, miR-6787-5p, miR-6780b-5p, miR-3131, miR-7108-5p, miR-1343-3p, miR-1247-3p, miR-4651, miR- 6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p.

(12) The device according to (11), wherein miR-6726-5p is hsa-miR-6726-5p, miR-4257 is hsa-miR-4257, miR-6787-5p is hsa-miR-6787-5p, miR-6780b-5p is hsa-miR-6780b-5p, miR-3131 is hsa-miR-3131, miR-7108-5p is hsa-miR-7108-5p, miR-1343-3p is hsa-miR-1343-3p, miR-1247-3p is hsa-miR-1247-3p, miR-4651 is hsa-miR-4651, miR-6757-5p is hsa-miR-6757-5p, miR-3679-5p is hsa-miR-3679-5p, miR-7641 is hsa-miR-7641, miR-6746-5p is hsa-miR-6746-5p, miR-8072 is hsa-miR-8072, miR-6741-5p is hsa-miR-6741-5p, miR-1908-5p is hsa-miR-1908-5p, miR-6857-5p is hsa-miR-6857-5p, miR-4746-3p is hsa-miR-4746-3p, miR-744-5p is hsa-miR-744-5p, miR-4792 is hsa-miR-4792, miR-564 is hsa-miR-564, miR-6791-5p is hsa-miR-6791-5p, miR-6825-5p is hsa-miR-6825-5p, miR-6826-5p is hsa-miR-6826-5p, miR-4665-3p is hsa-miR-4665-3p, miR-4467 is hsa-miR-4467, miR-3188 is hsa-miR-3188, miR-6125 is hsa-miR-6125, miR-6756-5p is hsa-miR-6756-5p, miR-1228-3p is hsa-miR-1228-3p, miR-8063 is hsa-miR-8063, miR-8069 is hsa-miR-8069, miR-6875-5p is hsa-miR-6875-5p, miR-3185 is hsa-miR-3185, miR-4433b-3p is hsa-miR-4433b-3p, miR-6887-5p is hsa-miR-6887-5p, miR-128-1-5p is hsa-miR-128-1-5p, miR-6724-5p is hsa-miR-6724-5p, miR-1914-3p is hsa-miR-1914-3p, miR-1225-5p is hsa-miR-1225-5p, miR-4419b is hsa-miR-4419b, miR-7110-5p is hsa-miR-7110-5p, miR-187-5p is hsa-miR-187-5p, miR-3184-5p is hsa-miR-3184-5p, miR-204-3p is hsa-miR-204-3p, miR-5572 is hsa-miR-5572, miR-6729-5p is hsa-miR-6729-5p, miR-615-5p is hsa-miR-615-5p, miR-6749-5p is hsa-miR-6749-5p, miR-6515-3p is hsa-miR-6515-3p, miR-3937 is hsa-miR-3937, miR-6840-3p is hsa-miR-6840-3p, miR-6893-5p is hsa-miR-6893-5p, miR-4728-5p is hsa-miR-4728-5p, miR-6717-5p is hsa-miR-6717-5p, miR-7113-3p is hsa-miR-7113-3p, miR-4665-5p is hsa-miR-4665-5p, miR-642b-3p is hsa-miR-642b-3p, miR-7109-5p is hsa-miR-7109-5p, miR-6842-5p is hsa-miR-6842-5p, miR-4442 is hsa-miR-4442, miR-4433-3p is hsa-miR-4433-3p, miR-4707-5p is hsa-miR-4707-5p, miR-6126 is hsa-miR-6126, miR-4449 is hsa-miR-4449, miR-4706 is hsa-miR-4706, miR-1913 is hsa-miR-1913, miR-602 is hsa-miR-602, miR-939-5p is hsa-miR-939-5p, miR-4695-5p is hsa-miR-4695-5p, miR-711 is hsa-miR-711, miR-6816-5p is hsa-miR-6816-5p, miR-4632-5p is hsa-miR-4632-5p, miR-6721-5p is hsa-miR-6721-5p, miR-7847-3p is hsa-miR-7847-3p, miR-6132 is hsa-miR-6132, miR-887-3p is hsa-miR-887-3p, miR-3679-3p is hsa-miR-3679-3p, miR-6784-5p is hsa-miR-6784-5p, miR-1249 is hsa-miR-1249, miR-937-5p is hsa-miR-937-5p, miR-5195-3p is hsa-miR-5195-3p, miR-6732-5p is hsa-miR-6732-5p, miR-4417 is hsa-miR-4417, miR-4281 is hsa-miR-4281, miR-4734 is hsa-miR-4734, miR-6766-3p is hsa-miR-6766-3p, miR-663a is hsa-miR-663a, miR-4513 is hsa-miR-4513, miR-6781-5p is hsa-miR-6781-5p, miR-1227-5p is hsa-miR-1227-5p, miR-6845-5p is hsa-miR-6845-5p, miR-6798-5p is hsa-miR-6798-5p, miR-3620-5p is hsa-miR-3620-5p, miR-1915-5p is hsa-miR-1915-5p, miR-4294 is hsa-miR-4294, miR-642a-3p is hsa-miR-642a-3p, miR-371a-5p is hsa-miR-371a-5p, miR-940 is hsa-miR-940, miR-4450 is hsa-miR-4450, miR-4723-5p is hsa-miR-4723-5p, miR-1469 is hsa-miR-1469, miR-6861-5p is hsa-miR-6861-5p, miR-7975 is hsa-miR-7975, miR-6879-5p is hsa-miR-6879-5p, miR-6802-5p is hsa-miR-6802-5p, miR-1268b is hsa-miR-1268b, miR-663b is hsa-miR-663b, miR-125a-3p is hsa-miR-125a-3p, miR-2861 is hsa-miR-2861, miR-6088 is hsa-miR-6088, miR-4758-5p is hsa-miR-4758-5p, miR-296-3p is hsa-miR-296-3p, miR-6738-5p is hsa-miR-6738-5p, miR-671-5p is hsa-miR-671-5p, miR-4454 is hsa-miR-4454, miR-4516 is hsa-miR-4516, miR-7845-5p is hsa-miR-7845-5p, miR-4741 is hsa-miR-4741, miR-92b-5p is hsa-miR-92b-5p, miR-6795-5p is hsa-miR-6795-5p, miR-6805-3p is hsa-miR-6805-3p, miR-4725-3p is hsa-miR-4725-3p, miR-6782-5p is hsa-miR-6782-5p, miR-4688 is hsa-miR-4688, miR-6850-5p is hsa-miR-6850-5p, miR-6777-5p is hsa-miR-6777-5p, miR-6785-5p is hsa-miR-6785-5p, miR-7106-5p is hsa-miR-7106-5p, miR-3663-3p is hsa-miR-3663-3p, miR-6131 is hsa-miR-6131, miR-1915-3p is hsa-miR-1915-3p, miR-4532 is hsa-miR-4532, miR-6820-5p is hsa-miR-6820-5p, miR-4689 is hsa-miR-4689, miR-4638-5p is hsa-miR-4638-5p, miR-3656 is hsa-miR-3656, miR-3621 is hsa-miR-3621, miR-6769b-5p is hsa-miR-6769b-5p, miR-149-3p is hsa-miR-149-3p, miR-23b-3p is hsa-miR-23b-3p, miR-3135b is hsa-miR-3135b, miR-6848-5p is hsa-miR-6848-5p, miR-6769a-5p is hsa-miR-6769a-5p, miR-4327 is hsa-miR-4327, miR-6765-3p is hsa-miR-6765-3p, miR-6716-5p is hsa-miR-6716-5p, miR-6877-5p is hsa-miR-6877-5p, miR-6727-5p is hsa-miR-6727-5p, miR-4534 is hsa-miR-4534, miR-614 is hsa-miR-614, miR-1202 is hsa-miR-1202, miR-575 is hsa-miR-575, miR-6870-5p is hsa-miR-6870-5p, miR-6722-3p is hsa-miR-6722-3p, miR-7977 is hsa-miR-7977, miR-4649-5p is hsa-miR-4649-5p, miR-4675 is hsa-miR-4675, miR-6075 is hsa-miR-6075, miR-6779-5p is hsa-miR-6779-5p, miR-4271 is hsa-miR-4271, miR-3196 is hsa-miR-3196, miR-6803-5p is hsa-miR-6803-5p, miR-6789-5p is hsa-miR-6789-5p, miR-4648 is hsa-miR-4648, miR-4508 is hsa-miR-4508, miR-4749-5p is hsa-miR-4749-

5p, miR-4505 is hsa-miR-4505, miR-5698 is hsa-miR-5698, miR-1199-5p is hsa-miR-1199-5p, miR-4763-3p is hsa-miR-4763-3p, miR-6836-3p is hsa-miR-6836-3p, miR-3195 is hsa-miR-3195, miR-718 is hsa-miR-718, miR-3178 is hsa-miR-3178, miR-638 is hsa-miR-638, miR-4497 is hsa-miR-4497, miR-6085 is hsa-miR-6085, miR-6752-5p is hsa-miR-6752-5p, and miR-135a-3p is hsa-miR-135a-3p.

(13) The device according to (11) or (12), wherein the nucleic acid is a polynucleotide selected from the group consisting of the following polynucleotides (a) to (c):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

(14) The device according to any of (11) to (13), wherein the device further comprises a nucleic acid capable of specifically binding to at least one or more polynucleotide(s) selected from the group consisting of other colorectal cancer markers miR-1231, miR-1233-5p, miR-150-3p, miR-1225-3p, miR-92a-2-5p, miR-423-5p, miR-1268a, miR-128-2-5p and miR-24-3p.

(15) The device according to (14), wherein miR-1231 is hsa-miR-1231, miR-1233-5p is hsa-miR-1233-5p, miR-150-3p is hsa-miR-150-3p, miR-1225-3p is hsa-miR-1225-3p, miR-92a-2-5p is hsa-miR-92a-2-5p, miR-423-5p is hsa-miR-423-5p, miR-1268a is hsa-miR-1268a, miR-128-2-5p is hsa-miR-128-2-5p, and miR-24-3p is hsa-miR-24-3p.

(16) The device according to (14) or (15), wherein the nucleic acid is a polynucleotide selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180, (h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

(17) The device according to any of (11) to (16), wherein the device further comprises a nucleic acid capable of specifically binding to at least one or more polynucleotide(s) selected from the group consisting of other colorectal cancer markers miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090.

(18) The device according to (17), wherein miR-4697-5p is hsa-miR-4697-5p, miR-3197 is hsa-miR-3197, miR-675-5p is hsa-miR-675-5p, miR-4486 is hsa-miR-4486, miR-7107-5p is hsa-miR-7107-5p, miR-23a-3p is hsa-miR-23a-3p, miR-4667-5p is hsa-miR-4667-5p, miR-451a is hsa-miR-451a, miR-3940-5p is hsa-miR-3940-5p, miR-8059 is hsa-miR-8059, miR-6813-5p is hsa-miR-6813-5p, miR-4492 is hsa-miR-4492, miR-4476 is hsa-miR-4476, and miR-6090 is hsa-miR-6090.

(19) The device according to (17) or (18), wherein the nucleic acid is a polynucleotide selected from the group consisting of the following polynucleotides (k) to (0):

(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 181 to 194, (m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 181 to 194 or a nucleotide sequence derived from the nucleotide sequence by the replacement of u with t, and (o) a polynucleotide hybridizing under stringent conditions to any of the polynucleotides (k) to (n).

(20) The device according to any one of (11) to (19), wherein the device is a device for measurement by a hybridization technique.

(21) The device according to (20), wherein the hybridization technique is a nucleic acid array technique.

(22) The device according to any one of (11) to (21), wherein the device comprises at least two or more nucleic acids capable of specifically binding to at least two or more polynucleotides, respectively, selected from all of the colorectal cancer markers according to (11) or (12).

(23) A method for detecting colorectal cancer, comprising measuring an expression level of a target nucleic acid in a sample from a subject using a kit according to any one of (1) to (10) or a device according to any one of (11) to (22), and evaluating in vitro whether or not the subject has colorectal cancer using both of the measured expression level and a control expression level in a sample from a healthy subject measured in the same way.

(24) The method according to (23), wherein the subject is a human.

(25) The method according to (23) or (24), wherein the sample is blood, serum, or plasma.

Definition of Term

The terms used herein are defined as follows.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein is used for a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here, the "synthetic DNA" and the "synthetic RNA" refer to DNA and RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotide(s) (i.e., a variant sequence) and a sequence comprising one or more modified nucleotide(s) (i.e., a modified sequence), which are different from the natural sequence. Here, the term "polynucleotide" is used interchangeably with the term "nucleic acid".

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but each single-stranded DNA such as a plus strand (or a sense strand) or a complementary strand (or an antisense strand) that constitutes a duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand) including cDNA, microRNA (miRNA), and their fragments, and transcripts, unless otherwise specified. The "gene" includes not only a "gene" represented by a particular nucleotide sequence (or SEQ ID N0) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 635 or a nucleotide sequence derived from the nucleotide sequence by the replacement of u with t. The "gene" is not particularly limited by its functional region and can contain, for example, an expression control region, a coding region, an exon, or an intron. The "gene" may be contained in a cell or may exist alone after being released into the outside of a cell. Alternatively, the "gene" may be in a state enclosed in a vesicle called exosome.

The term "exosome" used herein is a vesicle that is encapsulated by a lipid bilayer and secreted from a cell. The exosome is derived from a multivesicular endosome and may incorporate a biomaterial such as a "gene" (e.g., RNA or DNA) or a protein when released into an extracellular environment. The exosome is known to be contained in a body fluid such as blood, serum, plasma, or lymph.

The term "transcript" used herein refers to RNA synthesized with the DNA sequence of a gene as a template. RNA polymerase binds to a site called promoter which is located upstream of the gene and adds ribonucleotides complementary to the nucleotide sequence of the DNA to the 3' end to synthesize RNA. This RNA contains not only the gene itself but the whole sequence from a transcription initiation site to the end of a polyA sequence, including an expression regulatory region, a coding region, an exon, or an intron.

The term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and is involved in the suppression of translation of mRNA, unless otherwise specified. The term "miRNA" used herein includes not only a "miRNA" represented by a particular nucleotide sequence (or SEQ ID N0) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 635. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting RNA resulting from the expression of a gene or a polynucleotide derived from the RNA, and/or a polynucleotide complementary thereto.

The term "primer" used herein includes a polynucleotide that specifically recognizes and amplifies RNA resulting from the expression of a gene or a polynucleotide derived from the RNA, and/or a polynucleotide complementary thereto.

In this context, the complementary polynucleotide (complementary strand or reverse strand) means a polynucleotide in a complementary base relationship of A:T (U) and G:C base pairs with the full-length sequence of a polynucleotide consisting of a nucleotide sequence defined by any of SEQ ID NOs: 1 to 635 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a larger extent (e.g., a measurement value equal to or larger than a mean of background measurement values+a standard deviation of the background measurement values×2) than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant that contains the deletion, substitution, addition, or insertion of 1 or 2 or more nucleotides in a nucleotide sequence represented by any of SEQ ID NOs: 1 to 194 and 606 to 614 or a nucleotide sequence derived from the nucleotide sequence by the replacement of u with t, or a partial sequence thereof; a variant that exhibits % identity of approximately 90% or higher, approximately 95% or higher, approximately 97% or higher, approximately 98% or higher, approximately 99% or higher to each of these nucleotide sequences or the partial sequence thereof; or a nucleic acid hybridizing under the stringent conditions defined above to a polynucleotide or an oligonucleotide comprising each of these nucleotide sequences or the partial sequence thereof.

The term "several" used herein means an integer of approximately 10, 9, 8, 7, 6, 5, 4, 3, or 2.

The variant used herein can be prepared by use of a well-known technique such as site-directed mutagenesis or PCR-based mutagenesis.

The term "percent (%) identity" used herein can be determined with or without an introduced gap, using a protein or gene search system based on BLAST or FASTA described above (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include a modified nucleic acid, for example, a derivative that is labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404) without any limitation.

As used herein, the "nucleic acid" capable of specifically binding to a polynucleotide selected from the colorectal cancer marker miRNAs described above is a synthesized or prepared nucleic acid and specifically includes a "nucleic acid probe" or a "primer". The "nucleic acid" is utilized directly or indirectly for detecting the presence or absence of colorectal cancer in a subject, for diagnosing the presence or absence of colorectal cancer, for diagnosing the severity of colorectal cancer, the presence or absence of amelioration or the degree of amelioration of colorectal cancer, or the sensitivity to treatment for colorectal cancer, or for screening for a candidate substance useful in the prevention, amelioration, or treatment of colorectal cancer. The "nucleic acid" includes a nucleotide, an oligonucleotide, and a polynucleotide capable of specifically recognizing and binding to a transcript represented by any of SEQ ID NOs: 1 to 635 or a synthetic cDNA nucleic acid thereof in vivo, particularly, in a sample such as a body fluid (e.g., blood or urine), in relation to the development of colorectal cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "capable of specifically binding" used herein means that the nucleic acid probe or the primer used in the present invention binds to a particular target nucleic acid and cannot substantially bind to other nucleic acids.

The term "detection" used herein is interchangeable with the term "examination", "measurement", "detection", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, and a rodent including a mouse and a rat. The term "healthy subject" also means such a mammal without the cancer to be detected.

The term "P" or "P value" used herein refers to a probability at which a more extreme statistic than that is actually calculated from data under null hypothesis is observed in a statistical test. Thus, smaller "P" or "P value" means more significant difference between subjects to be compared.

The term "sensitivity" used herein means a value of (the number of true positives)/(the number of true positives+the number of false negatives). High sensitivity allows colorectal cancer to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being colorectal cancer patients, leading to reduction in burden on patients and reduction in medical expense.

The term "accuracy" used herein means a value of (the number of true positives+the number of true negatives)/(the total number of cases). The accuracy indicates the ratio of samples that correctly identified in discriminant results to all samples, and serves as a primary index for evaluating detection performance.

As used herein, the "sample" that is subject to determination, detection, or diagnosis refers to a tissue and a biological material in which the expression of the gene of the present invention varies as colorectal cancer develops, colorectal cancer progresses, and therapeutic effects on colorectal cancer are exerted. Specifically, the "sample" refers to a large intestine tissue, a vascular channel around the large intestine, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6726-5p gene" or "hsa-miR-6726-5p" used herein includes the hsa-miR-6726-5p gene (miRBase Accession No. MIMAT0027353) described in SEQ ID NO: 1, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 195) having a hairpin-like structure is known as a precursor of "hsa-miR-6726-5p".

The term "hsa-miR-4257 gene" or "hsa-miR-4257" used herein includes the hsa-miR-4257 gene (miRBase Accession No. MIMAT0016878) described in SEQ ID NO: 2, a homolog or an ortholog of a different organism species, and the like. The hsa-miR-4257 gene can be obtained by a method described in Goff L A et al., 2009, PLOS One, Vol. 4, e7192. Also, "hsa-mir-4257" (miRBase Accession No. MI0015856, SEQ ID NO: 196) having a hairpin-like structure is known as a precursor of "hsa-miR-4257".

The term "hsa-miR-6787-5p gene" or "hsa-miR-6787-5p" used herein includes the hsa-miR-6787-5p gene (miRBase Accession No. MIMAT0027474) described in SEQ ID NO: 3, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 197) having a hairpin-like structure is known as a precursor of "hsa-miR-6787-5p".

The term "hsa-miR-6780b-5p gene" or "hsa-miR-6780b-5p" used herein includes the hsa-miR-6780b-5p gene (miRBase Accession No. MIMAT0027572) described in SEQ ID NO: 4, a homolog or an ortholog of a different organism species, and the like. The hsa-miR-6780b-5p gene can be obtained by a method described in Ladewig E at al., 2012, Genome Res, Vol. 22, p. 1634-1645. Also, "hsa-mir-6780b" (miRBase Accession No. MI0022681, SEQ ID NO: 198) having a hairpin-like structure is known as a precursor of "hsa-miR-6780b-5p".

The term "hsa-miR-3131 gene" or "hsa-miR-3131" used herein includes the hsa-miR-3131 gene (miRBase Accession No. MIMAT0014996) described in SEQ ID NO: 5, a homolog or an ortholog of a different organism species, and the like. The hsa-miR-3131 gene can be obtained by a method described in Stark M S et al., 2010, PLOS One, Vol. 5, e9685. Also, "hsa-mir-3131" (miRBase Accession No. MI0014151, SEQ ID NO: 199) having a hairpin-like structure is known as a precursor of "hsa-miR-3131".

The term "hsa-miR-7108-5p gene" or "hsa-miR-7108-5p" used herein includes the hsa-miR-7108-5p gene (miRBase Accession No. MIMAT0028113) described in SEQ ID NO: 6, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 200) having a hairpin-like structure is known as a precursor of "hsa-miR-7108-5p".

The term "hsa-miR-1343-3p gene" or "hsa-miR-1343-3p" used herein includes the hsa-miR-1343-3p gene (miRBase Accession No. MIMAT0019776) described in SEQ ID NO: 7, a homolog or an ortholog of a different organism species, and the like. The hsa-miR-1343-3p gene can be obtained by a method described in Persson H et al., 2011, Cancer Res, Vol. 71, p. 78-86. Also, "hsa-mir-1343" (miRBase Accession No. MI0017320, SEQ ID NO: 201) having a hairpin-like structure is known as a precursor of "hsa-miR-1343-3p".

The term "hsa-miR-1247-3p gene" or "hsa-miR-1247-3p" used herein includes the hsa-miR-1247-3p gene (miRBase Accession No. MIMAT0022721) described in SEQ ID NO: 8, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 202) having a hairpin-like structure is known as a precursor of "hsa-miR-1247-3p".

The term "hsa-miR-4651 gene" or "hsa-miR-4651" used herein includes the hsa-miR-4651 gene (miRBase Accession No. MIMAT0019715) described in SEQ ID NO: 9, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 203) having a hairpin-like structure is known as a precursor of "hsa-miR-4651".

The term "hsa-miR-6757-5p gene" or "hsa-miR-6757-5p" used herein includes the hsa-miR-6757-5p gene (miRBase Accession No. MIMAT0027414) described in SEQ ID NO: 10, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 204) having a hairpin-like structure is known as a precursor of "hsa-miR-6757-5p".

The term "hsa-miR-3679-5p gene" or "hsa-miR-3679-5p" used herein includes the hsa-miR-3679-5p gene (miRBase Accession No. MIMAT0018104) described in SEQ ID NO: 11, a homolog or an ortholog of a different organism species, and the like. The hsa-miR-3679-5p gene can be obtained by a method described in Creighton C J et al., 2010, PLOS One, Vol. 5, e9637. Also, "hsa-mir-3679" (miRBase Accession No. MI0016080, SEQ ID NO: 205) having a hairpin-like structure is known as a precursor of "hsa-miR-3679-5p".

The term "hsa-miR-7641 gene" or "hsa-miR-7641" used herein includes the hsa-miR-7641 gene (miRBase Accession No. MIMAT0029782) described in SEQ ID NO: 12, a homolog or an ortholog of a different organism species, and the like. The hsa-miR-7641 gene can be obtained by a method described in Yoo J K et al., 2013, Arch Pharm Res, Vol. 36, p. 353-358. Also, "hsa-mir-7641-1" and "hsa-mir-7641-2" (miRBase Accession Nos. MI0024975 and MI0024976, SEQ ID NOs: 206 and 207) having a hairpin-like structure are known as precursors of "hsa-miR-7641".

The term "hsa-miR-6746-5p gene" or "hsa-miR-6746-5p" used herein includes the hsa-miR-6746-5p gene (miRBase Accession No. MIMAT0027392) described in SEQ ID NO: 13, a homolog or an ortholog of a different organism species, and the like. The hsa-miR-6746-5p gene can be obtained by a method described in Ladewig E et al., 2012, Genome Res, Vol. 22, p. 1634-1645. Also, "hsa-mir-6746" (miRBase Accession No. MI0022591, SEQ ID NO: 208) having a hairpin-like structure is known as a precursor of "hsa-miR-6746-5p".

The term "hsa-miR-8072 gene" or "hsa-miR-8072" used herein includes the hsa-miR-8072 gene (miRBase Accession No. MIMAT0030999) described in SEQ ID NO: 14, a homolog or an ortholog of a different organism species, and the like. The hsa-miR-8072 gene can be obtained by a method described in Wang H J et al., 2013, Shock, Vol. 39, p. 480-487. Also, "hsa-mir-8072" (miRBase Accession No. MI0025908, SEQ ID NO: 209) having a hairpin-like structure is known as a precursor of "hsa-miR-8072".

The term "hsa-miR-6741-5p gene" or "hsa-miR-6741-5p" used herein includes the hsa-miR-6741-5p gene (miRBase Accession No. MIMAT0027383) described in SEQ ID NO: 15, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 210) having a hairpin-like structure is known as a precursor of "hsa-miR-6741-5p".

The term "hsa-miR-1908-5p gene" or "hsa-miR-1908-5p" used herein includes the hsa-miR-1908-5p gene (miRBase Accession No. MIMAT0007881) described in SEQ ID NO: 16, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI0008329, SEQ ID NO: 211) having a hairpin-like structure is known as a precursor of "hsa-miR-1908-5p".

The term "hsa-miR-6857-5p gene" or "hsa-miR-6857-5p" used herein includes the hsa-miR-6857-5p gene (miRBase Accession No. MIMAT0027614) described in SEQ ID NO: 17, a homolog or an ortholog of a different organism species, and the like. The hsa-miR-6857-5p gene can be obtained by a method described in Ladewig E et al., 2012, Genome Res, Vol. 22, p. 1634-1645. Also, "hsa-mir-6857" (miRBase Accession No. MI0022703, SEQ ID NO: 212) having a hairpin-like structure is known as a precursor of "hsa-miR-6857-5p".

The term "hsa-miR-4746-3p gene" or "hsa-miR-4746-3p" used herein includes the hsa-miR-4746-3p gene (miRBase Accession No. MIMAT0019881) described in SEQ ID NO: 18, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 213) having a hairpin-like structure is known as a precursor of "hsa-miR-4746-3p".

The term "hsa-miR-744-5p gene" or "hsa-miR-744-5p" used herein includes the hsa-miR-744-5p gene (miRBase Accession No. MIMAT0004945) described in SEQ ID NO: 19, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 214) having a hairpin-like structure is known as a precursor of "hsa-miR-744-5p".

The term "hsa-miR-4792 gene" or "hsa-miR-4792" used herein includes the hsa-miR-4792 gene (miRBase Accession No. MIMAT0019964) described in SEQ ID NO: 20, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 215) having a hairpin-like structure is known as a precursor of "hsa-miR-4792".

The term "hsa-miR-564 gene" or "hsa-miR-564" used herein includes the hsa-miR-564 gene (miRBase Accession No. MIMAT0003228) described in SEQ ID NO: 21, a homolog or an ortholog of a different organism species, and the like. The hsa-miR-564 gene can be obtained by a method described in Cummins J M et al., 2006, Proc Natl Acad Sci USA, Vol. 103, p. 3687-3692. Also, "hsa-mir-564" (miRBase Accession No. MI0003570, SEQ ID NO: 216) having a hairpin-like structure is known as a precursor of "hsa-miR-564".

The term "hsa-miR-6791-5p gene" or "hsa-miR-6791-5p" used herein includes the hsa-miR-6791-5p gene (miRBase Accession No. MIMAT0027482) described in SEQ ID NO:

22, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 217) having a hairpin-like structure is known as a precursor of "hsa-miR-6791-5p".

The term "hsa-miR-6825-5p gene" or "hsa-miR-6825-5p" used herein includes the hsa-miR-6825-5p gene (miRBase Accession No. MIMAT0027550) described in SEQ ID NO: 23, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 218) having a hairpin-like structure is known as a precursor of "hsa-miR-6825-5p".

The term "hsa-miR-6826-5p gene" or "hsa-miR-6826-5p" used herein includes the hsa-miR-6826-5p gene (miRBase Accession No. MIMAT0027552) described in SEQ ID NO: 24, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 219) having a hairpin-like structure is known as a precursor of "hsa-miR-6826-5p".

The term "hsa-miR-4665-3p gene" or "hsa-miR-4665-3p" used herein includes the hsa-miR-4665-3p gene (miRBase Accession No. MIMAT0019740) described in SEQ ID NO: 25, a homolog or an ortholog of a different organism species, and the like. The hsa-miR-4665-3p gene can be obtained by a method described in Persson H et al., 2011, Cancer Res, Vol. 71, p. 78-86. Also, "hsa-mir-4665" (miRBase Accession No. MI0017295, SEQ ID NO: 220) having a hairpin-like structure is known as a precursor of "hsa-miR-4665-3p".

The term "hsa-miR-4467 gene" or "hsa-miR-4467" used herein includes the hsa-miR-4467 gene (miRBase Accession No. MIMAT0018994) described in SEQ ID NO: 26, a homolog or an ortholog of a different organism species, and the like. The hsa-miR-4467 gene can be obtained by a method described in Jima D D et al., 2010, Blood, Vol. 116, e118-e127. Also, "hsa-mir-4467" (miRBase Accession No. MI0016818, SEQ ID NO: 221) having a hairpin-like structure is known as a precursor of "hsa-miR-4467".

The term "hsa-miR-3188 gene" or "hsa-miR-3188" used herein includes the hsa-miR-3188 gene (miRBase Accession No. MIMAT0015070) described in SEQ ID NO: 27, a homolog or an ortholog of a different organism species, and the like. The hsa-miR-3188 gene can be obtained by a method described in Stark M S et al., 2010, PLOS One, Vol. 5, e9685. Also, "hsa-mir-3188" (miRBase Accession No. MI0014232, SEQ ID NO: 222) having a hairpin-like structure is known as a precursor of "hsa-miR-3188".

The term "hsa-miR-6125 gene" or "hsa-miR-6125" used herein includes the hsa-miR-6125 gene (miRBase Accession No. MIMAT0024598) described in SEQ ID NO: 28, a homolog or an ortholog of a different organism species, and the like. The hsa-miR-6125 gene can be can be obtained by a method described in Smith J L et al., 2012, J Virol, Vol. 86, p. 5278-5287. Also "hsa-mir-6125" (miRBase Accession No. MI0021259, SEQ ID NO: 223) having a hairpin-like structure is known as a precursor of "hsa-miR-6125".

The term "hsa-miR-6756-5p gene" or "hsa-miR-6756-5p" used herein includes the hsa-miR-6756-5p gene (miRBase Accession No. MIMAT0027412) described in SEQ ID NO: 29, a homolog or an ortholog of a different organism species, and the like. The hsa-miR-6756-5p gene can be obtained by a method described in Ladewig E et al., 2012, Genome Res, Vol. 22, p. 1634-1645. Also, "hsa-mir-6756" (miRBase Accession No. MI0022601, SEQ ID NO: 224) having a hairpin-like structure is known as a precursor of "hsa-miR-6756-5p".

The term "hsa-miR-1228-3p gene" or "hsa-miR-1228-3p" used herein includes the hsa-miR-1228-3p gene (miRBase Accession No. MIMAT0005583) described in SEQ ID NO: 30, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 225) having a hairpin-like structure is known as a precursor of "hsa-miR-1228-3p".

The term "hsa-miR-8063 gene" or "hsa-miR-8063" used herein includes the hsa-miR-8063 gene (miRBase Accession No. MIMAT0030990) described in SEQ ID NO: 31, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 226) having a hairpin-like structure is known as a precursor of "hsa-miR-8063".

The term "hsa-miR-8069 gene" or "hsa-miR-8069" used herein includes the hsa-miR-8069 gene (miRBase Accession No. MIMAT0030996) described in SEQ ID NO: 32, a homolog or an ortholog of a different organism species, and the like. The hsa-miR-8069 gene can be obtained by a method described in Wang H J et al., 2013, Shock, Vol. 39, p. 480-487. Also, "hsa-mir-8069" (miRBase Accession No. MI0025905, SEQ ID NO: 227) having a hairpin-like structure is known as a precursor of "hsa-miR-8069".

The term "hsa-miR-6875-5p gene" or "hsa-miR-6875-5p" used herein includes the hsa-miR-6875-5p gene (miRBase Accession No. MIMAT0027650) described in SEQ ID NO: 33, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875" (miRBase Accession No. MI0022722, SEQ ID NO: 228) having a hairpin-like structure is known as a precursor of "hsa-miR-6875-5p".

The term "hsa-miR-3185 gene" or "hsa-miR-3185" used herein includes the hsa-miR-3185 gene (miRBase Accession No. MIMAT0015065) described in SEQ ID NO: 34, a homolog or an ortholog of a different organism species, and the like. The hsa-miR-3185 gene can be obtained by a method described in Stark M S et al., 2010, PLOS One, Vol. 5, e9685. Also, "hsa-mir-3185" (miRBase Accession No. MI0014227, SEQ ID NO: 229) having a hairpin-like structure is known as a precursor of "hsa-miR-3185".

The term "hsa-miR-4433b-3p gene" or "hsa-miR-4433b-3p" used herein includes the hsa-miR-4433b-3p gene (miRBase Accession No. MIMAT0030414) described in SEQ ID NO: 35, a homolog or an ortholog of a different organism species, and the like. The hsa-miR-4433b-3p gene can be obtained by a method described in Ple H et al., 2012, PLOS One, Vol. 7, e50746. Also, "hsa-mir-4433b" (miRBase Accession No. MI0025511, SEQ ID NO: 230) having a hairpin-like structure is known as a precursor of "hsa-miR-4433b-3p".

The term "hsa-miR-6887-5p gene" or "hsa-miR-6887-5p" used herein includes the hsa-miR-6887-5p gene (miRBase Accession No. MIMAT0027674) described in SEQ ID NO: 36, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 231) having a hairpin-like structure is known as a precursor of "hsa-miR-6887-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 37, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 232) having a hairpin-like structure is known as a precursor of "hsa-miR-128-1-5p".

The term "hsa-miR-6724-5p gene" or "hsa-miR-6724-5p" used herein includes the hsa-miR-6724-5p gene (miRBase Accession No. MIMAT0025856) described in SEQ ID NO: 38, a homolog or an ortholog of a different organism species, and the like. The hsa-miR-6724-5p gene can be obtained by a method described in Li Y et al., 2012, Gene, Vol. 497, p. 330-335. Also, "hsa-mir-6724" (miRBase Accession No. MI0022559, SEQ ID NO: 233) having a hairpin-like structure is known as a precursor of "hsa-miR-6724-5p".

The term "hsa-miR-1914-3p gene" or "hsa-miR-1914-3p" used herein includes the hsa-miR-1914-3p gene (miRBase Accession No. MIMAT0007890) described in SEQ ID NO: 39, a homolog or an ortholog of a different organism species, and the like. The hsa-miR-1914-3p gene can be obtained by a method described in Bar M et al., 2008, Stem Cells, Vol. 26, p. 2496-2505. Also, "hsa-mir-1914" (miRBase Accession No. MI0008335, SEQ ID NO: 234) having a hairpin-like structure is known as a precursor of "hsa-miR-1914-3p".

The term "hsa-miR-1225-5p gene" or "hsa-miR-1225-5p" used herein includes the hsa-miR-1225-5p gene (miRBase Accession No. MIMAT0005572) described in SEQ ID NO: 40, a homolog or an ortholog of a different organism species, and the like. The hsa-miR-1225-5p gene can be obtained by a method described in Berezikov E et al., 2007, Mol Cell, Vol. 28, p. 328-336. Also, "hsa-mir-1225" (miRBase Accession No. MI0006311, SEQ ID NO: 235) having a hairpin-like structure is known as a precursor of "hsa-miR-1225-5p".

The term "hsa-miR-4419b gene" or "hsa-miR-4419b" used herein includes the hsa-miR-4419b gene (miRBase Accession No. MIMAT0019034) described in SEQ ID NO: 41, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 236) having a hairpin-like structure is known as a precursor of "hsa-miR-4419b".

The term "hsa-miR-7110-5p gene" or "hsa-miR-7110-5p" used herein includes the hsa-miR-7110-5p gene (miRBase Accession No. MIMAT0028117) described in SEQ ID NO: 42, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 237) having a hairpin-like structure is known as a precursor of "hsa-miR-7110-5p".

The term "hsa-miR-187-5p gene" or "hsa-miR-187-5p" used herein includes the hsa-miR-187-5p gene (miRBase Accession No. MIMAT0004561) described in SEQ ID NO:

43, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 238) having a hairpin-like structure is known as a precursor of "hsa-miR-187-5p".

The term "hsa-miR-3184-5p gene" or "hsa-miR-3184-5p" used herein includes the hsa-miR-3184-5p gene (miRBase Accession No. MIMAT0015064) described in SEQ ID NO: 44, a homolog or an ortholog of a different organism species, and the like. The hsa-miR-3184-5p gene can be obtained by a method described in Stark M S et al., 2010, PLOS One, Vol. 5, e9685. Also, "hsa-mir-3184" (miRBase Accession No. MI0014226, SEQ ID NO: 239) having a hairpin-like structure is known as a precursor of "hsa-miR-3184-5p".

The term "hsa-miR-204-3p gene" or "hsa-miR-204-3p" used herein includes the hsa-miR-204-3p gene (miRBase Accession No. MIMAT0022693) described in SEQ ID NO: 45, a homolog or an ortholog of a different organism species, and the like. The hsa-miR-204-3p gene can be obtained by a method described in Lim L P et al., 2003, Science, Vol. 299, p. 1540. Also, "hsa-mir-204" (miRBase Accession No. MI0000284, SEQ ID NO: 240) having a hairpin-like structure is known as a precursor of "hsa-miR-204-3p".

The term "hsa-miR-5572 gene" or "hsa-miR-5572" used herein includes the hsa-miR-5572 gene (miRBase Accession No. MIMAT0022260) described in SEQ ID NO: 46, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 241) having a hairpin-like structure is known as a precursor of "hsa-miR-5572".

The term "hsa-miR-6729-5p gene" or "hsa-miR-6729-5p" used herein includes the hsa-miR-6729-5p gene (miRBase Accession No. MIMAT0027359) described in SEQ ID NO: 47, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 242) having a hairpin-like structure is known as a precursor of "hsa-miR-6729-5p".

The term "hsa-miR-615-5p gene" or "hsa-miR-615-5p" used herein includes the hsa-miR-615-5p gene (miRBase Accession No. MIMAT0004804) described in SEQ ID NO: 48, a homolog or an ortholog of a different organism species, and the like. The hsa-miR-615-5p gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 243) having a hairpin-like structure is known as a precursor of "hsa-miR-615-5p".

The term "hsa-miR-6749-5p gene" or "hsa-miR-6749-5p" used herein includes the hsa-miR-6749-5p gene (miRBase Accession No. MIMAT0027398) described in SEQ ID NO: 49, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 244) having a hairpin-like structure is known as a precursor of "hsa-miR-6749-5p".

The term "hsa-miR-6515-3p gene" or "hsa-miR-6515-3p" used herein includes the hsa-miR-6515-3p gene (miRBase Accession No. MIMAT0025487) described in SEQ ID NO: 50, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 245) having a hairpin-like structure is known as a precursor of "hsa-miR-6515-3p".

The term "hsa-miR-3937 gene" or "hsa-miR-3937" used herein includes the hsa-miR-3937 gene (miRBase Accession No. MIMAT0018352) described in SEQ ID NO: 51, a homolog or an ortholog of a different organism species, and the like. The hsa-miR-3937 gene can be obtained by a method described in Liao J Y et al., 2010, PLOS One, Vol. 5, e10563. Also, "hsa-mir-3937" (miRBase Accession No. MI0016593, SEQ ID NO: 246) having a hairpin-like structure is known as a precursor of "hsa-miR-3937".

The term "hsa-miR-6840-3p gene" or "hsa-miR-6840-3p" used herein includes the hsa-miR-6840-3p gene (miRBase Accession No. MIMAT0027583) described in SEQ ID NO: 52, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 247) having a hairpin-like structure is known as a precursor of "hsa-miR-6840-3p".

The term "hsa-miR-6893-5p gene" or "hsa-miR-6893-5p" used herein includes the hsa-miR-6893-5p gene (miRBase Accession No. MIMAT0027686) described in SEQ ID NO: 53, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 248) having a hairpin-like structure is known as a precursor of "hsa-miR-6893-5p".

The term "hsa-miR-4728-5p gene" or "hsa-miR-4728-5p" used herein includes the hsa-miR-4728-5p gene (miRBase Accession No. MIMAT0019849) described in SEQ ID NO: 54, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI0017365, SEQ ID NO: 249) having a hairpin-like structure is known as a precursor of "hsa-miR-4728-5p".

The term "hsa-miR-6717-5p gene" or "hsa-miR-6717-5p" used herein includes the hsa-miR-6717-5p gene (miRBase Accession No. MIMAT0025846) described in SEQ ID NO: 55, a homolog or an ortholog of a different organism species, and the like. The hsa-miR-6717-5p gene can be obtained by a method described in Li Y et al., 2012, Gene, Vol. 497, p. 330-335. Also, "hsa-mir-6717" (miRBase Accession No. MI0022551, SEQ ID NO: 250) having a hairpin-like structure is known as a precursor of "hsa-miR-6717-5p".

The term "hsa-miR-7113-3p gene" or "hsa-miR-7113-3p" used herein includes the hsa-miR-7113-3p gene (miRBase Accession No. MIMAT0028124) described in SEQ ID NO: 56, a homolog or an ortholog of a different organism species, and the like. The hsa-miR-7113-3p gene 1645. Also, "hsa-mir-7113" (miRBase Accession No. MI0022964, SEQ ID NO: 251) having a hairpin-like structure is known as a precursor of "hsa-miR-7113-3p".

The term "hsa-miR-4665-5p gene" or "hsa-miR-4665-5p" used herein includes the hsa-miR-4665-5p gene (miRBase Accession No. MIMAT0019739) described in SEQ ID NO: 57, a homolog or an ortholog of a different organism species, and the like. The hsa-miR-4665-5p gene can be obtained by a method described in Persson H et al., 2011, Cancer Res, Vol. 71, p. 78-86. Also, "hsa-mir-4665" (miRBase Accession No. MI0017295, SEQ ID NO: 220) having a hairpin-like structure is known as a precursor of "hsa-miR-4665-5p".

The term "hsa-miR-642b-3p gene" or "hsa-miR-642b-3p" used herein includes the hsa-miR-642b-3p gene (miRBase Accession No. MIMAT0018444) described in SEQ ID NO: 58, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 252) having a hairpin-like structure is known as a precursor of "hsa-miR-642b-3p".

The term "hsa-miR-7109-5p gene" or "hsa-miR-7109-5p" used herein includes the hsa-miR-7109-5p gene (miRBase Accession No. MIMAT0028115) described in SEQ ID NO: 59, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 253) having a hairpin-like structure is known as a precursor of "hsa-miR-7109-5p".

The term "hsa-miR-6842-5p gene" or "hsa-miR-6842-5p" used herein includes the hsa-miR-6842-5p gene (miRBase Accession No. MIMAT0027586) described in SEQ ID NO: 60, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 254) having a hairpin-like structure is known as a precursor of "hsa-miR-6842-5p".

The term "hsa-miR-4442 gene" or "hsa-miR-4442" used herein includes the hsa-miR-4442 gene (miRBase Accession No. MIMAT0018960) described in SEQ ID NO: 61, a homolog or an ortholog of a different organism species, and the like. The hsa-miR-4442 gene can be obtained by a method described in Jima D D et al., 2010, Blood, Vol. 116, e118-e127. Also, "hsa-mir-4442" (miRBase Accession No. MI0016785, SEQ ID NO: 255) having a hairpin-like structure is known as a precursor of "hsa-miR-4442".

The term "hsa-miR-4433-3p gene" or "hsa-miR-4433-3p" used herein includes the hsa-miR-4433-3p gene (miRBase Accession No. MIMAT0018949) described in SEQ ID NO: 62, a homolog or an ortholog of a different organism species, and the like. The hsa-miR-4433-3p gene can be obtained by a method described in Jima D D et al., 2010, Blood, Vol. 116, e118-e127. Also, "hsa-mir-4433" (miRBase Accession No. MI0016773, SEQ ID NO: 256) having a hairpin-like structure is known as a precursor of "hsa-miR-4433-3p".

The term "hsa-miR-4707-5p gene" or "hsa-miR-4707-5p" used herein includes the hsa-miR-4707-5p gene (miRBase Accession No. MIMAT0019807) described in SEQ ID NO: 63, a homolog or an ortholog of a different organism species, and the like. The hsa-miR-4707-5p gene can be obtained by a method described in Persson H et al., 2011, Cancer Res, Vol. 71, p. 78-86. Also, "hsa-mir-4707" (miRBase Accession No. MI0017340, SEQ ID NO: 257) having a hairpin-like structure is known as a precursor of "hsa-miR-4707-5p".

The term "hsa-miR-6126 gene" or "hsa-miR-6126" used herein includes the hsa-miR-6126 gene (miRBase Accession No. MIMAT0024599) described in SEQ ID NO: 64, a homolog or an ortholog of a different organism species, and the like. The hsa-miR-6126 gene can be can be obtained by a method described in Smith J L et al., 2012, J Virol, Vol. 86, p. 5278-5287. Also, "hsa-mir-6126" (miRBase Accession No. MI0021260, SEQ ID NO: 258) having a hairpin-like structure is known as a precursor of "hsa-miR-6126".

The term "hsa-miR-4449 gene" or "hsa-miR-4449" used herein includes the hsa-miR-4449 gene (miRBase Accession No. MIMAT0018968) described in SEQ ID NO: 65, a homolog or an ortholog of a different organism species, and the like. The hsa-miR-4449 gene can be obtained by a method described in Jima D D et al., 2010, Blood, Vol. 116, e118-e127. Also, "hsa-mir-4449" (miRBase Accession No. MI0016792, SEQ ID NO: 259) having a hairpin-like structure is known as a precursor of "hsa-miR-4449".

The term "hsa-miR-4706 gene" or "hsa-miR-4706" used herein includes the hsa-miR-4706 gene (miRBase Accession No. MIMAT0019806) described in SEQ ID NO: 66, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 260) having a hairpin-like structure is known as a precursor of "hsa-miR-4706".

The term "hsa-miR-1913 gene" or "hsa-miR-1913" used herein includes the hsa-miR-1913 gene (miRBase Accession No. MIMAT0007888) described in SEQ ID NO: 67, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 261) having a hairpin-like structure is known as a precursor of "hsa-miR-1913".

The term "hsa-miR-602 gene" or "hsa-miR-602" used herein includes the hsa-miR-602 gene (miRBase Accession No. MIMAT0003270) described in SEQ ID NO: 68, a homolog or an ortholog of a different organism species, and the like. The hsa-miR-602 gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 262) having a hairpin-like structure is known as a precursor of "hsa-miR-602".

The term "hsa-miR-939-5p gene" or "hsa-miR-939-5p" used herein includes the hsa-miR-939-5p gene (miRBase Accession No. MIMAT0004982) described in SEQ ID NO: 69, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 263) having a hairpin-like structure is known as a precursor of "hsa-miR-939-5p".

The term "hsa-miR-4695-5p gene" or "hsa-miR-4695-5p" used herein includes the hsa-miR-4695-5p gene (miRBase Accession No. MIMAT0019788) described in SEQ ID NO: 70, a homolog or an ortholog of a different organism species, and the like. The hsa-miR-4695-5p gene can be obtained by a method described in Persson H et al., 2011, Cancer Res, Vol. 71, p. 78-86. Also, "hsa-mir-4695" (miRBase Accession No. MI0017328, SEQ ID NO: 264) having a hairpin-like structure is known as a precursor of "hsa-miR-4695-5p".

The term "hsa-miR-711 gene" or "hsa-miR-711" used herein includes the hsa-miR-711 gene (miRBase Accession No. MIMAT0012734) described in SEQ ID NO: 71, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 265) having a hairpin-like structure is known as a precursor of "hsa-miR-711".

The term "hsa-miR-6816-5p gene" or "hsa-miR-6816-5p" used herein includes the hsa-miR-6816-5p gene (miRBase Accession No. MIMAT0027532) described in SEQ ID NO: 72, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 266) having a hairpin-like structure is known as a precursor of "hsa-miR-6816-5p".

The term "hsa-miR-4632-5p gene" or "hsa-miR-4632-5p" used herein includes the hsa-miR-4632-5p gene (miRBase Accession No. MIMAT0022977) described in SEQ ID NO: 73, a homolog or an ortholog of a different organism species, and the like. The hsa-miR-4632-5p gene can be obtained by a method described in Persson H et al., 2011, Cancer Res, Vol. 71, p. 78-86. Also, "hsa-mir-4632" (miRBase Accession No. MI0017259, SEQ ID NO: 267) having a hairpin-like structure is known as a precursor of "hsa-miR-4632-5p".

The term "hsa-miR-6721-5p gene" or "hsa-miR-6721-5p" used herein includes the hsa-miR-6721-5p gene (miRBase Accession No. MIMAT0025852) described in SEQ ID NO: 74, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 268) having a hairpin-like structure is known as a precursor of "hsa-miR-6721-5p".

The term "hsa-miR-7847-3p gene" or "hsa-miR-7847-3p" used herein includes the hsa-miR-7847-3p gene (miRBase Accession No. MIMAT0030422) described in SEQ ID NO: 75, a homolog or an ortholog of a different organism species, and the like. The hsa-miR-7847-3p gene can be obtained by a method described in Ple H et al., 2012, PLOS One, Vol. 7, e50746. Also, "hsa-mir-7847" (miRBase Accession No. MI0025517, SEQ ID NO: 269) having a hairpin-like structure is known as a precursor of "hsa-miR-7847-3p".

The term "hsa-miR-6132 gene" or "hsa-miR-6132" used herein includes the hsa-miR-6132 gene (miRBase Accession No. MIMAT0024616) described in SEQ ID NO: 76, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 270) having a hairpin-like structure is known as a precursor of "hsa-miR-6132".

The term "hsa-miR-887-3p gene" or "hsa-miR-887-3p" used herein includes the hsa-miR-887-3p gene (miRBase Accession No. MIMAT0004951) described in SEQ ID NO: 77, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 271) having a hairpin-like structure is known as a precursor of "hsa-miR-887-3p".

The term "hsa-miR-3679-3p gene" or "hsa-miR-3679-3p" used herein includes the hsa-miR-3679-3p gene (miRBase Accession No. MIMAT0018105) described in SEQ ID NO: 78, a homolog or an ortholog of a different organism species, and the like. The hsa-miR-3679-3p gene can be obtained by a method described in Creighton C J et al., 2010, PLOS One, Vol. 5, e9637. Also, "hsa-mir-3679" (miRBase Accession No. MI0016080, SEQ ID NO: 205) having a hairpin-like structure is known as a precursor of "hsa-miR-3679-3p".

The term "hsa-miR-6784-5p gene" or "hsa-miR-6784-5p" used herein includes the hsa-miR-6784-5p gene (miRBase Accession No. MIMAT0027468) described in SEQ ID NO: 79, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 272) having a hairpin-like structure is known as a precursor of "hsa-miR-6784-5p".

The term "hsa-miR-1249 gene" or "hsa-miR-1249" used herein includes the hsa-miR-1249 gene (miRBase Accession No. MIMAT0005901) described in SEQ ID NO: 80, a homolog or an ortholog of a different organism species, and the like. The hsa-miR-1249 gene can be obtained by a method described in Morin R D et al., 2008, Genome Res, Vol. 18, p. 610-621. Also, "hsa-mir-1249" (miRBase Accession No. MI0006384, SEQ ID NO: 273) having a hairpin-like structure is known as a precursor of "hsa-miR-1249".

The term "hsa-miR-937-5p gene" or "hsa-miR-937-5p" used herein includes the hsa-miR-937-5p gene (miRBase Accession No. MIMAT0022938) described in SEQ ID NO: 81, a homolog or an ortholog of a different organism species, and the like. The hsa-miR-937-5p gene can be obtained by a method described in Lui W O et al., 2007, Cancer Res, Vol. 67, p. 6031-6043. Also, "hsa-mir-937" (miRBase Accession No. MI0005759, SEQ ID NO: 274) having a hairpin-like structure is known as a precursor of "hsa-miR-937-5p".

The term "hsa-miR-5195-3p gene" or "hsa-miR-5195-3p" used herein includes the hsa-miR-5195-3p gene (miRBase Accession No. MIMAT0021127) described in SEQ ID NO: 82, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 275) having a hairpin-like structure is known as a precursor of "hsa-miR-5195-3p".

The term "hsa-miR-6732-5p gene" or "hsa-miR-6732-5p" used herein includes the hsa-miR-6732-5p gene (miRBase Accession No. MIMAT0027365) described in SEQ ID NO: 83, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 276) having a hairpin-like structure is known as a precursor of "hsa-miR-6732-5p".

The term "hsa-miR-4417 gene" or "hsa-miR-4417" used herein includes the hsa-miR-4417 gene (miRBase Accession No. MIMAT0018929) described in SEQ ID NO: 84, a homolog or an ortholog of a different organism species, and the like. The hsa-miR-4417 gene can be can be obtained by a method described in Jima D D et al., 2010, Blood, Vol. 116, e118-e127. Also, "hsa mir-4417" (miRBase Accession No. MI0016753, SEQ ID NO: 277) having a hairpin-like structure is known as a precursor of "hsa-miR-4417".

The term "hsa-miR-4281 gene" or "hsa-miR-4281" used herein includes the hsa-miR-4281 gene (miRBase Accession No. MIMAT0016907) described in SEQ ID NO: 85, a homolog or an ortholog of a different organism species, and the like. The hsa-miR-4281 gene can be obtained by a method described in Goff L A et al., 2009, PLOS One, Vol. 4, e7192. Also, "hsa-mir-4281" (miRBase Accession No. MI0015885, SEQ ID NO: 278) having a hairpin-like structure is known as a precursor of "hsa-miR-4281".

The term "hsa-miR-4734 gene" or "hsa-miR-4734" used herein includes the hsa-miR-4734 gene (miRBase Accession No. MIMAT0019859) described in SEQ ID NO: 86, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 279) having a hairpin-like structure is known as a precursor of "hsa-miR-4734".

The term "hsa-miR-6766-3p gene" or "hsa-miR-6766-3p" used herein includes the hsa-miR-6766-3p gene (miRBase Accession No. MIMAT0027433) described in SEQ ID NO: 87, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 280) having a hairpin-like structure is known as a precursor of "hsa-miR-6766-3p".

The term "hsa-miR-663a gene" or "hsa-miR-663a" used herein includes the hsa-miR-663a gene (miRBase Accession No. MIMAT0003326) described in SEQ ID NO: 88, a homolog or an ortholog of a different organism species, and the like. The hsa-miR-663a gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 281) having a hairpin-like structure is known as a precursor of "hsa-miR-663a".

The term "hsa-miR-4513 gene" or "hsa-miR-4513" used herein includes the hsa-miR-4513 gene (miRBase Accession No. MIMAT0019050) described in SEQ ID NO: 89, a homolog or an ortholog of a different organism species, and the like. The hsa-miR-4513 gene can be obtained by a method described in Jima D D et al., 2010, Blood, Vol. 116, e118-e127. Also, "hsa-mir-4513" (miRBase Accession No. MI0016879, SEQ ID NO: 282) having a hairpin-like structure is known as a precursor of "hsa-miR-4513".

The term "hsa-miR-6781-5p gene" or "hsa-miR-6781-5p" used herein includes the hsa-miR-6781-5p gene (miRBase Accession No. MIMAT0027462) described in SEQ ID NO: 90, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 283) having a hairpin-like structure is known as a precursor of "hsa-miR-6781-5p".

The term "hsa-miR-1227-5p gene" or "hsa-miR-1227-5p" used herein includes the hsa-miR-1227-5p gene (miRBase Accession No. MIMAT0022941) described in SEQ ID NO: 91, a homolog or an ortholog of a different organism species, and the like. The hsa-miR-1227-5p gene can be obtained by a method described in Berezikov E et al., 2007, Mol Cell, Vol. 28, p. 328-336. Also, "hsa-mir-1227" (miRBase Accession No. MI0006316, SEQ ID NO: 284) having a hairpin-like structure is known as a precursor of "hsa-miR-1227-5p".

The term "hsa-miR-6845-5p gene" or "hsa-miR-6845-5p" used herein includes the hsa-miR-6845-5p gene (miRBase Accession No. MIMAT0027590) described in SEQ ID NO: 92, a homolog or an ortholog of a different organism species, and the like. The hsa-miR-6845-5p gene can be obtained by a method described in Ladewig E et al., 2012, Genome Res, Vol. 22, p. 1634-1645. Also, "hsa-mir-6845" (miRBase Accession No. MI0022691, SEQ ID NO: 285) having a hairpin-like structure is known as a precursor of "hsa-miR-6845-5p".

The term "hsa-miR-6798-5p gene" or "hsa-miR-6798-5p" used herein includes the hsa-miR-6798-5p gene (miRBase Accession No. MIMAT0027496) described in SEQ ID NO: 93, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 286) having a hairpin-like structure is known as a precursor of "hsa-miR-6798-5p".

The term "hsa-miR-3620-5p gene" or "hsa-miR-3620-5p" used herein includes the hsa-miR-3620-5p gene (miRBase Accession No. MIMAT0022967) described in SEQ ID NO: 94, a homolog or an ortholog of a different organism species, and the like. The hsa-miR-3620-5p gene can be obtained by a method described in Witten D et al., 2010, BMC Biol, Vol. 8, p. 58. Also, "hsa-mir-3620" (miRBase Accession No. MI0016011, SEQ ID NO: 287) having a hairpin-like structure is known as a precursor of "hsa-miR-3620-5p".

The term "hsa-miR-1915-5p gene" or "hsa-miR-1915-5p" used herein includes the hsa-miR-1915-5p gene (miRBase Accession No. MIMAT0007891) described in SEQ ID NO: 95, a homolog or an ortholog of a different organism species, and the like. The hsa-miR-1915-5p gene can be obtained by a method described in Bar M et al., 2008, Stem Cells, Vol. 26, p. 2496-2505. Also, "hsa-mir-1915" (miRBase Accession No. MI0008336, SEQ ID NO: 288) having a hairpin-like structure is known as a precursor of "hsa-miR-1915-5p".

The term "hsa-miR-4294 gene" or "hsa-miR-4294" used herein includes the hsa-miR-4294 gene (miRBase Accession No. MIMAT0016849) described in SEQ ID NO: 96, a homolog or an ortholog of a different organism species, and the like. The hsa-miR-4294 gene can be obtained by a method described in Goff L A et al., 2009, PLOS One, Vol. 4, e7192. Also, "hsa-mir-4294" (miRBase Accession No. MI0015827, SEQ ID NO: 289) having a hairpin-like structure is known as a precursor of "hsa-miR-4294".

The term "hsa-miR-642a-3p gene" or "hsa-miR-642a-3p" used herein includes the hsa-miR-642a-3p gene (miRBase Accession No. MIMAT0020924) described in SEQ ID NO: 97, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 290) having a hairpin-like structure is known as a precursor of "hsa-miR-642a-3p".

The term "hsa-miR-371a-5p gene" or "hsa-miR-371a-5p" used herein includes the hsa-miR-371a-5p gene (miRBase Accession No. MIMAT0004687) described in SEQ ID NO: 98, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 291) having a hairpin-like structure is known as a precursor of "hsa-miR-371a-5p".

The term "hsa-miR-940 gene" or "hsa-miR-940" used herein includes the hsa-miR-940 gene (miRBase Accession No. MIMAT0004983) described in SEQ ID NO: 99, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No.

MI0005762, SEQ ID NO: 292) having a hairpin-like structure is known as a precursor of "hsa-miR-940".

The term "hsa-miR-4450 gene" or "hsa-miR-4450" used herein includes the hsa-miR-4450 gene (miRBase Accession No. MIMAT0018971) described in SEQ ID NO: 100, a homolog or an ortholog of a different organism species, and the like. The hsa-miR-4450 gene can be can be obtained by a method described in Jima D D et al., 2010, Blood, Vol. 116, e118-e127. Also, "hsa-mir-4450" (miRBase Accession No. MI0016795, SEQ ID NO: 293) having a hairpin-like structure is known as a precursor of "hsa-miR-4450".

The term "hsa-miR-4723-5p gene" or "hsa-miR-4723-5p" used herein includes the hsa-miR-4723-5p gene (miRBase Accession No. MIMAT0019838) described in SEQ ID NO: 101, a homolog or an ortholog of a different organism species, and the like. The hsa-miR-4723-5p gene can be obtained by a method described in Persson H et al., 2011, Cancer Res, Vol. 71, p. 78-86. Also, "hsa-mir-4723" (miRBase Accession No. MI0017359, SEQ ID NO: 294) having a hairpin-like structure is known as a precursor of "hsa-miR-4723-5p".

The term "hsa-miR-1469 gene" or "hsa-miR-1469" used herein includes the hsa-miR-1469 gene (miRBase Accession No. MIMAT0007347) described in SEQ ID NO: 102, a homolog or an ortholog of a different organism species, and the like. The hsa-miR-1469 gene can be obtained by a method described in Kawaji H et al., 2008, BMC Genomics, Vol. 9, p. 157. Also, "hsa-mir-1469" (miRBase Accession No. MI0007074, SEQ ID NO: 295) having a hairpin-like structure is known as a precursor of "hsa-miR-1469".

The term "hsa-miR-6861-5p gene" or "hsa-miR-6861-5p" used herein includes the hsa-miR-6861-5p gene (miRBase Accession No. MIMAT0027623) described in SEQ ID NO: 103, a homolog or an ortholog of a different organism species, and the like. The hsa-miR-6861-5p gene can be obtained by a method described in Ladewig E et al., 2012, Genome Res, Vol. 22, p. 1634-1645. Also, "hsa-mir-6861" (miRBase Accession No. MI0022708, SEQ ID NO: 296) having a hairpin-like structure is known as a precursor of "hsa-miR-6861-5p".

The term "hsa-miR-7975 gene" or "hsa-miR-7975" used herein includes the hsa-miR-7975 gene (miRBase Accession No. MIMAT0031178) described in SEQ ID NO: 104, a homolog or an ortholog of a different organism species, and the like. The hsa-miR-7975 gene can be obtained by a method described in Velthut-Meikas A et al., 2013, Mol Endocrinol, online. Also, "hsa-mir-7975" (miRBase Accession No. MI0025751, SEQ ID NO: 297) having a hairpin-like structure is known as a precursor of "hsa-miR-7975".

The term "hsa-miR-6879-5p gene" or "hsa-miR-6879-5p" used herein includes the hsa-miR-6879-5p gene (miRBase Accession No. MIMAT0027658) described in SEQ ID NO: 105, a homolog or an ortholog of a different organism species, and the like. The hsa-miR-6879-5p gene can be obtained by a method described in Ladewig E et al., 2012, Genome Res, Vol. 22, p. 1634-1645. Also, "hsa-mir-6879" (miRBase Accession No. MI0022726, SEQ ID NO: 298) having a hairpin-like structure is known as a precursor of "hsa-miR-6879-5p".

The term "hsa-miR-6802-5p gene" or "hsa-miR-6802-5p" used herein includes the hsa-miR-6802-5p gene (miRBase Accession No. MIMAT0027504) described in SEQ ID NO: 106, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802"

(miRBase Accession No. MI0022647, SEQ ID NO: 299) having a hairpin-like structure is known as a precursor of "hsa-miR-6802-5p".

The term "hsa-miR-1268b gene" or "hsa-miR-1268b" used herein includes the hsa-miR-1268b gene (miRBase Accession No. MIMAT0018925) described in SEQ ID NO: 107, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 300) having a hairpin-like structure is known as a precursor of "hsa-miR-1268b".

The term "hsa-miR-663b gene" or "hsa-miR-663b" used herein includes the hsa-miR-663b gene (miRBase Accession No. MIMAT0005867) described in SEQ ID NO: 108, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 301) having a hairpin-like structure is known as a precursor of "hsa-miR-663b".

The term "hsa-miR-125a-3p gene" or "hsa-miR-125a-3p" used herein includes the hsa-miR-125a-3p gene (miRBase Accession No. MIMAT0004602) described in SEQ ID NO: 109, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 302) having a hairpin-like structure is known as a precursor of "hsa-miR-125a-3p".

The term "hsa-miR-2861 gene" or "hsa-miR-2861" used herein includes the hsa-miR-2861 gene (miRBase Accession No. MIMAT0013802) described in SEQ ID NO: 110, a homolog or an ortholog of a different organism species, and the like. The hsa-miR-2861 gene can be obtained by a method described in Li H et al., 2009, J Clin Invest, Vol. 119, p. 3666-3677. Also, "hsa-mir-2861" (miRBase Accession No. MI0013006, SEQ ID NO: 303) having a hairpin-like structure is known as a precursor of "hsa-miR-2861".

The term "hsa-miR-6088 gene" or "hsa-miR-6088" used herein includes the hsa-miR-6088 gene (miRBase Accession No. MIMAT0023713) described in SEQ ID NO: 111, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 304) having a hairpin-like structure is known as a precursor of "hsa-miR-6088".

The term "hsa-miR-4758-5p gene" or "hsa-miR-4758-5p" used herein includes the hsa-miR-4758-5p gene (miRBase Accession No. MIMAT0019903) described in SEQ ID NO: 112, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 305) having a hairpin-like structure is known as a precursor of "hsa-miR-4758-5p".

The term "hsa-miR-296-3p gene" or "hsa-miR-296-3p" used herein includes the hsa-miR-296-3p gene (miRBase Accession No. MIMAT0004679) described in SEQ ID NO: 113, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 306) having a hairpin-like structure is known as a precursor of "hsa-miR-296-3p".

The term "hsa-miR-6738-5p gene" or "hsa-miR-6738-5p" used herein includes the hsa-miR-6738-5p gene (miRBase Accession No. MIMAT0027377) described in SEQ ID NO: 114, a homolog or an ortholog of a different organism species, and the like. The hsa-miR-6738-5p gene can be obtained by a method described in Ladewig E et al., 2012, Genome Res, Vol. 22, p. 1634-1645. Also, "hsa-mir-6738" (miRBase Accession No. MI0022583, SEQ ID NO: 307) having a hairpin-like structure is known as a precursor of "hsa-miR-6738-5p".

The term "hsa-miR-671-5p gene" or "hsa-miR-671-5p" used herein includes the hsa-miR-671-5p gene (miRBase Accession No. MIMAT0003880) described in SEQ ID NO: 115, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 308) having a hairpin-like structure is known as a precursor of "hsa-miR-671-5p".

The term "hsa-miR-4454 gene" or "hsa-miR-4454" used herein includes the hsa-miR-4454 gene (miRBase Accession No. MIMAT0018976) described in SEQ ID NO: 116, a homolog or an ortholog of a different organism species, and the like. The hsa-miR-4454 gene can be can be obtained by a method described in Jima D D et al., 2010, Blood, Vol. 116, e118-e127. Also, "hsa-mir-4454" (miRBase Accession No. MI0016800, SEQ ID NO: 309) having a hairpin-like structure is known as a precursor of "hsa-miR-4454".

The term "hsa-miR-4516 gene" or "hsa-miR-4516" used herein includes the hsa-miR-4516 gene (miRBase Accession No. MIMAT0019053) described in SEQ ID NO: 117, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 310) having a hairpin-like structure is known as a precursor of "hsa-miR-4516".

The term "hsa-miR-7845-5p gene" or "hsa-miR-7845-5p" used herein includes the hsa-miR-7845-5p gene (miRBase Accession No. MIMAT0030420) described in SEQ ID NO: 118, a homolog or an ortholog of a different organism species, and the like. The hsa-miR-7845-5p gene can be obtained by a method described in Ple H et al., 2012, PLOS One, Vol. 7, e50746. Also, "hsa-mir-7845" (miRBase Accession No. MI0025515, SEQ ID NO: 311) having a hairpin-like structure is known as a precursor of "hsa-miR-7845-5p".

The term "hsa-miR-4741 gene" or "hsa-miR-4741" used herein includes the hsa-miR-4741 gene (miRBase Accession No. MIMAT0019871) described in SEQ ID NO: 119, a homolog or an ortholog of a different organism species, and the like. The hsa-miR-4741 gene can be obtained by a method described in Persson H et al., 2011, Cancer Res, Vol. 71, p. 78-86. Also, "hsa-mir-4741" (miRBase Accession No. MI0017379, SEQ ID NO: 312) having a hairpin-like structure is known as a precursor of "hsa-miR-4741".

The term "hsa-miR-92b-5p gene" or "hsa-miR-92b-5p" used herein includes the hsa-miR-92b-5p gene (miRBase Accession No. MIMAT0004792) described in SEQ ID NO: 120, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 313) having a hairpin-like structure is known as a precursor of "hsa-miR-92b-5p".

The term "hsa-miR-6795-5p gene" or "hsa-miR-6795-5p" used herein includes the hsa-miR-6795-5p gene (miRBase Accession No. MIMAT0027490) described in SEQ ID NO: 121, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795" (miRBase Accession No. MI0022640, SEQ ID NO: 314) having a hairpin-like structure is known as a precursor of "hsa-miR-6795-5p".

The term "hsa-miR-6805-3p gene" or "hsa-miR-6805-3p" used herein includes the hsa-miR-6805-3p gene (miRBase Accession No. MIMAT0027511) described in SEQ ID NO: 122, a homolog or an ortholog of a different organism species, and the like. The hsa-miR-6805-3p gene can be obtained by a method described in Ladewig E et al., 2012, Genome Res, Vol. 22, p. 1634-1645. Also, "hsa-mir-6805" (miRBase Accession No. MI0022650, SEQ ID NO: 315) having a hairpin-like structure is known as a precursor of "hsa-miR-6805-3p".

The term "hsa-miR-4725-3p gene" or "hsa-miR-4725-3p" used herein includes the hsa-miR-4725-3p gene (miRBase Accession No. MIMAT0019844) described in SEQ ID NO: 123, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 316) having a hairpin-like structure is known as a precursor of "hsa-miR-4725-3p".

The term "hsa-miR-6782-5p gene" or "hsa-miR-6782-5p" used herein includes the hsa-miR-6782-5p gene (miRBase Accession No. MIMAT0027464) described in SEQ ID NO: 124, a homolog or an ortholog of a different organism species, and the like. The hsa-miR-6782-5p gene can be obtained by a method described in Ladewig E et al., 2012, Genome Res, Vol. 22, p. 1634-1634-1645. Also, "hsa-mir-6782" (miRBase Accession No. MI0022627, SEQ ID NO: 317) having a hairpin-like structure is known as a precursor of "hsa-miR-6782-5p".

The term "hsa-miR-4688 gene" or "hsa-miR-4688" used herein includes the hsa-miR-4688 gene (miRBase Accession No. MIMAT0019777) described in SEQ ID NO: 125, a homolog or an ortholog of a different organism species, and the like. The hsa-miR-4688 gene can be obtained by a method described in Persson H et al., 2011, Cancer Res, Vol. 71, p. 78-86. Also, "hsa-mir-4688" (miRBase Accession No. MI0017321, SEQ ID NO: 318) having a hairpin-like structure is known as a precursor of "hsa-miR-4688".

The term "hsa-miR-6850-5p gene" or "hsa-miR-6850-5p" used herein includes the hsa-miR-6850-5p gene (miRBase Accession No. MIMAT0027600) described in SEQ ID NO: 126, a homolog or an ortholog of a different organism species, and the like. The hsa-miR-6850-5p gene can be obtained by a method described in Ladewig E et al., 2012, Genome Res, Vol. 22, p. 1634-1645. Also, "hsa-mir-6850" (miRBase Accession No. MI0022696, SEQ ID NO: 319) having a hairpin-like structure is known as a precursor of "hsa-miR-6850-5p".

The term "hsa-miR-6777-5p gene" or "hsa-miR-6777-5p" used herein includes the hsa-miR-6777-5p gene (miRBase Accession No. MIMAT0027454) described in SEQ ID NO: 127, a homolog or an ortholog of a different organism species, and the like. The hsa-miR-6777-5p gene can be obtained by a method described in Ladewig E et al., 2012, Genome Res, Vol. 22, p. 1634-1645. Also, "hsa-mir-6777" (miRBase Accession No. MI0022622, SEQ ID NO: 320) having a hairpin-like structure is known as a precursor of "hsa-miR-6777-5p".

The term "hsa-miR-6785-5p gene" or "hsa-miR-6785-5p" used herein includes the hsa-miR-6785-5p gene (miRBase Accession No. MIMAT0027470) described in SEQ ID NO: 128, a homolog or an ortholog of a different organism species, and the like. The hsa-miR-6785-5p gene can be obtained by a method described in Ladewig E et al., 2012, Genome Res, Vol. 22, p. 1634-1634-1645. Also, "hsa-mir-6785" (miRBase Accession No. MI0022630, SEQ ID NO: 321) having a hairpin-like structure is known as a precursor of "hsa-miR-6785-5p".

The term "hsa-miR-7106-5p gene" or "hsa-miR-7106-5p" used herein includes the hsa-miR-7106-5p gene (miRBase Accession No. MIMAT0028109) described in SEQ ID NO: 129, a homolog or an ortholog of a different organism species, and the like. The hsa-miR-7106-5p gene can be obtained by a method described in Ladewig E et al., 2012, Genome Res, Vol. 22, p. 1634-1645. Also, "hsa-mir-7106" (miRBase Accession No. MI0022957, SEQ ID NO: 322) having a hairpin-like structure is known as a precursor of "hsa-miR-7106-5p".

The term "hsa-miR-3663-3p gene" or "hsa-miR-3663-3p" used herein includes the hsa-miR-3663-3p gene (miRBase Accession No. MIMAT0018085) described in SEQ ID NO: 130, a homolog or an ortholog of a different organism species, and the like. The hsa-miR-3663-3p gene can be obtained by a method described in Liao J Y et al., 2010, PLOS One, Vol. 5, e10563. Also, "hsa-mir-3663" (miRBase Accession No. MI0016064, SEQ ID NO: 323) having a hairpin-like structure is known as a precursor of "hsa-miR-3663-3p".

The term "hsa-miR-6131 gene" or "hsa-miR-6131" used herein includes the hsa-miR-6131 gene (miRBase Accession No. MIMAT0024615) described in SEQ ID NO: 131, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 324) having a hairpin-like structure is known as a precursor of "hsa-miR-6131".

The term "hsa-miR-1915-3p gene" or "hsa-miR-1915-3p" used herein includes the hsa-miR-1915-3p gene (miRBase Accession No. MIMAT0007892) described in SEQ ID NO: 132, a homolog or an ortholog of a different organism species, and the like. The hsa-miR-1915-3p gene can be obtained by a method described in Bar M et al., 2008, Stem Cells, Vol. 26, p. 2496-2505. Also, "hsa-mir-1915" (miRBase Accession No. MI0008336, SEQ ID NO: 288) having a hairpin-like structure is known as a precursor of "hsa-miR-1915-3p".

The term "hsa-miR-4532 gene" or "hsa-miR-4532" used herein includes the hsa-miR-4532 gene (miRBase Accession No. MIMAT0019071) described in SEQ ID NO: 133, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 325) having a hairpin-like structure is known as a precursor of "hsa-miR-4532".

The term "hsa-miR-6820-5p gene" or "hsa-miR-6820-5p" used herein includes the hsa-miR-6820-5p gene (miRBase Accession No. MIMAT0027540) described in SEQ ID NO: 134, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 326) having a hairpin-like structure is known as a precursor of "hsa-miR-6820-5p".

The term "hsa-miR-4689 gene" or "hsa-miR-4689" used herein includes the hsa-miR-4689 gene (miRBase Accession No. MIMAT0019778) described in SEQ ID NO: 135, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 327) having a hairpin-like structure is known as a precursor of "hsa-miR-4689".

The term "hsa-miR-4638-5p gene" or "hsa-miR-4638-5p" used herein includes the hsa-miR-4638-5p gene (miRBase Accession No. MIMAT0019695) described in SEQ ID NO: 136, a homolog or an ortholog of a different organism species, and the like. The hsa-miR-4638-5p gene can be obtained by a method described in Persson H et al., 2011, Cancer Res, Vol. 71, p. 78-86. Also, "hsa-mir-4638" (miRBase Accession No. MI0017265, SEQ ID NO: 328) having a hairpin-like structure is known as a precursor of "hsa-miR-4638-5p".

The term "hsa-miR-3656 gene" or "hsa-miR-3656" used herein includes the hsa-miR-3656 gene (miRBase Accession No. MIMAT0018076) described in SEQ ID NO: 137, a homolog or an ortholog of a different organism species, and the like. The hsa-miR-3656 gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 329) having a hairpin-like structure is known as a precursor of "hsa-miR-3656".

The term "hsa-miR-3621 gene" or "hsa-miR-3621" used herein includes the hsa-miR-3621 gene (miRBase Accession No. MIMAT0018002) described in SEQ ID NO: 138, a homolog or an ortholog of a different organism species, and the like. The hsa-miR-3621 gene can be obtained by a method described in Witten D et al., 2010, BMC Biol, Vol. 8, p. 58. Also, "hsa-mir-3621" (miRBase Accession No. MI0016012, SEQ ID NO: 330) having a hairpin-like structure is known as a precursor of "hsa-miR-3621".

The term "hsa-miR-6769b-5p gene" or "hsa-miR-6769b-5p" used herein includes the hsa-miR-6769b-5p gene (miRBase Accession No. MIMAT0027620) described in SEQ ID NO: 139, a homolog or an ortholog of a different organism species, and the like. The hsa-miR-6769b-5p gene can be obtained by a method described in Ladewig E et al., 2012, Genome Res, Vol. 22, p. 1634-1645. Also, "hsa-mir-6769b" (miRBase Accession No. MI0022706, SEQ ID NO: 331) having a hairpin-like structure is known as a precursor of "hsa-miR-6769b-5p".

The term "hsa-miR-149-3p gene" or "hsa-miR-149-3p" used herein includes the hsa-miR-149-3p gene (miRBase Accession No. MIMAT0004609) described in SEQ ID NO: 140, a homolog or an ortholog of a different organism species, and the like. The hsa-miR-149-3p gene can be obtained by a method described in Lagos-Quintana M et al., 2002, Curr Biol, Vol. 12, p. 735-739. Also, "hsa-mir-149" (miRBase Accession No. MI0000478, SEQ ID NO: 332) having a hairpin-like structure is known as a precursor of "hsa-miR-149-3p".

The term "hsa-miR-23b-3p gene" or "hsa-miR-23b-3p" used herein includes the hsa-miR-23b-3p gene (miRBase Accession No. MIMAT0000418) described in SEQ ID NO: 141, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 333) having a hairpin-like structure is known as a precursor of "hsa-miR-23b-3p".

The term "hsa-miR-3135b gene" or "hsa-miR-3135b" used herein includes the hsa-miR-3135b gene (miRBase Accession No. MIMAT0018985) described in SEQ ID NO: 142, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 334) having a hairpin-like structure is known as a precursor of "hsa-miR-3135b".

The term "hsa-miR-6848-5p gene" or "hsa-miR-6848-5p" used herein includes the hsa-miR-6848-5p gene (miRBase Accession No. MIMAT0027596) described in SEQ ID NO: 143, a homolog or an ortholog of a different organism species, and the like. The hsa-miR-6848-5p gene can be obtained by a method described in Ladewig E et al., 2012, Genome Res, Vol. 22, p. 1634-1645. Also, "hsa-mir-6848" (miRBase Accession No. MI0022694, SEQ ID NO: 335) having a hairpin-like structure is known as a precursor of "hsa-miR-6848-5p".

The term "hsa-miR-6769a-5p gene" or "hsa-miR-6769a-5p" used herein includes the hsa-miR-6769a-5p gene (miRBase Accession No. MIMAT0027438) described in SEQ ID NO: 144, a homolog or an ortholog of a different organism species, and the like. The hsa-miR-6769a-5p gene can be obtained by a method described in Ladewig E et al., 2012, Genome Res, Vol. 22, p. 1634-1634-1645. Also, "hsa-mir-6769a" (miRBase Accession No. MI0022614, SEQ ID NO: 336) having a hairpin-like structure is known as a precursor of "hsa-miR-6769a-5p".

The term "hsa-miR-4327 gene" or "hsa-miR-4327" used herein includes the hsa-miR-4327 gene (miRBase Accession No. MIMAT0016889) described in SEQ ID NO: 145, a homolog or an ortholog of a different organism species, and the like. The hsa-miR-4327 gene can be obtained by a method described in Goff L A et al., 2009, PLOS One, Vol. 4, e7192. Also, "hsa-mir-4327" (miRBase Accession No. MI0015867, SEQ ID NO: 337) having a hairpin-like structure is known as a precursor of "hsa-miR-4327".

The term "hsa-miR-6765-3p gene" or "hsa-miR-6765-3p" used herein includes the hsa-miR-6765-3p gene (miRBase Accession No. MIMAT0027431) described in SEQ ID NO: 146, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 338) having a hairpin-like structure is known as a precursor of "hsa-miR-6765-3p".

The term "hsa-miR-6716-5p gene" or "hsa-miR-6716-5p" used herein includes the hsa-miR-6716-5p gene (miRBase Accession No. MIMAT0025844) described in SEQ ID NO: 147, a homolog or an ortholog of a different organism species, and the like. The hsa-miR-6716-5p gene can be obtained by a method described in Li Y et al., 2012, Gene, Vol. 497, p. 330-335. Also, "hsa-mir-6716" (miRBase Accession No. MI0022550, SEQ ID NO: 339) having a hairpin-like structure is known as a precursor of "hsa-miR-6716-5p".

The term "hsa-miR-6877-5p gene" or "hsa-miR-6877-5p" used herein includes the hsa-miR-6877-5p gene (miRBase Accession No. MIMAT0027654) described in SEQ ID NO: 148, a homolog or an ortholog of a different organism species, and the like. The hsa-miR-6877-5p gene can be obtained by a method described in Ladewig E et al., 2012, Genome Res, Vol. 22, p. 1634-1634-1645. Also, "hsa-mir-6877" (miRBase Accession No. MI0022724, SEQ ID NO: 340) having a hairpin-like structure is known as a precursor of "hsa-miR-6877-5p".

The term "hsa-miR-6727-5p gene" or "hsa-miR-6727-5p" used herein includes the hsa-miR-6727-5p gene (miRBase Accession No. MIMAT0027355) described in SEQ ID NO: 149, a homolog or an ortholog of a different organism species, and the like. The hsa-miR-6727-5p gene can be obtained by a method described in Ladewig E et al., 2012, Genome Res, Vol. 22, p. 1634-1645. Also, "hsa-mir-6727" (miRBase Accession No. MI0022572, SEQ ID NO: 341) having a hairpin-like structure is known as a precursor of "hsa-miR-6727-5p".

The term "hsa-miR-4534 gene" or "hsa-miR-4534" used herein includes the hsa-miR-4534 gene (miRBase Accession No. MIMAT0019073) described in SEQ ID NO: 150, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 342) having a hairpin-like structure is known as a precursor of "hsa-miR-4534".

The term "hsa-miR-614 gene" or "hsa-miR-614" used herein includes the hsa-miR-614 gene (miRBase Accession No. MIMAT0003282) described in SEQ ID NO: 151, a homolog or an ortholog of a different organism species, and the like. The hsa-miR-614 gene can be obtained by a method described in Cummins J M et al., 2006, Proc Natl Acad Sci USA, Vol. 103, p. 3687-3692. Also, "hsa-mir-614" (miRBase Accession No. MI0003627, SEQ ID NO: 343) having a hairpin-like structure is known as a precursor of "hsa-miR-614".

The term "hsa-miR-1202 gene" or "hsa-miR-1202" used herein includes the hsa-miR-1202 gene (miRBase Accession No. MIMAT0005865) described in SEQ ID NO: 152, a homolog or an ortholog of a different organism species, and the like. The hsa-miR-1202 gene can be obtained by a method described in Marton S et al., 2008, Leukemia, Vol. 22, p. 330-338. Also, "hsa-mir-1202" (miRBase Accession No. MI0006334, SEQ ID NO: 344) having a hairpin-like structure is known as a precursor of "hsa-miR-1202".

The term "hsa-miR-575 gene" or "hsa-miR-575" used herein includes the hsa-miR-575 gene (miRBase Accession No. MIMAT0003240) described in SEQ ID NO: 153, a homolog or an ortholog of a different organism species, and the like. The hsa-miR-575 gene can be obtained by a method described in Cummins J M et al., 2006, Proc Natl Acad Sci USA, Vol. 103, p. 3687-3692. Also, "hsa-mir-575" (miRBase Accession No. MI0003582, SEQ ID NO: 345) having a hairpin-like structure is known as a precursor of "hsa-miR-575".

The term "hsa-miR-6870-5p gene" or "hsa-miR-6870-5p" used herein includes the hsa-miR-6870-5p gene (miRBase Accession No. MIMAT0027640) described in SEQ ID NO: 154, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 346) having a hairpin-like structure is known as a precursor of "hsa-miR-6870-5p".

The term "hsa-miR-6722-3p gene" or "hsa-miR-6722-3p" used herein includes the hsa-miR-6722-3p gene (miRBase Accession No. MIMAT0025854) described in SEQ ID NO: 155, a homolog or an ortholog of a different organism species, and the like. The hsa-miR-6722-3p gene can be obtained by a method described in Li Y et al., 2012, Gene, Vol. 497, p. 330-335. Also, "hsa-mir-6722" (miRBase Accession No. MI0022557, SEQ ID NO: 347) having a hairpin-like structure is known as a precursor of "hsa-miR-6722-3p".

The term "hsa-miR-7977 gene" or "hsa-miR-7977" used herein includes the hsa-miR-7977 gene (miRBase Accession No. MIMAT0031180) described in SEQ ID NO: 156, a homolog or an ortholog of a different organism species, and the like. The hsa-miR-7977 gene can be obtained by a method described in Velthut-Meikas A et al., 2013, Mol Endocrinol, online. Also, "hsa-mir-7977" (miRBase Accession No. MI0025753, SEQ ID NO: 348) having a hairpin-like structure is known as a precursor of "hsa-miR-7977".

The term "hsa-miR-4649-5p gene" or "hsa-miR-4649-5p" used herein includes the hsa-miR-4649-5p gene (miRBase Accession No. MIMAT0019711) described in SEQ ID NO: 157, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI0017276, SEQ ID NO: 349) having a hairpin-like structure is known as a precursor of "hsa-miR-4649-5p".

The term "hsa-miR-4675 gene" or "hsa-miR-4675" used herein includes the hsa-miR-4675 gene (miRBase Accession No. MIMAT0019757) described in SEQ ID NO: 158, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 350) having a hairpin-like structure is known as a precursor of "hsa-miR-4675".

The term "hsa-miR-6075 gene" or "hsa-miR-6075" used herein includes the hsa-miR-6075 gene (miRBase Accession No. MIMAT0023700) described in SEQ ID NO: 159, a homolog or an ortholog of a different organism species, and the like. The hsa-miR-6075 gene can be obtained by a method described in Voellenkle C et al., 2012, RNA, Vol. 18, p. 472-484. Also, "hsa-mir-6075" (miRBase Accession No. MI0020352, SEQ ID NO: 351) having a hairpin-like structure is known as a precursor of "hsa-miR-6075".

The term "hsa-miR-6779-5p gene" or "hsa-miR-6779-5p" used herein includes the hsa-miR-6779-5p gene (miRBase Accession No. MIMAT0027458) described in SEQ ID NO: 160, a homolog or an ortholog of a different organism species, and the like. The hsa-miR-6779-5p gene can be obtained by a method described in Ladewig E et al., 2012, Genome Res, Vol. 22, p. 1634-1634-1645. Also, "hsa-mir-6779" (miRBase Accession No. MI0022624, SEQ ID NO: 352) having a hairpin-like structure is known as a precursor of "hsa-miR-6779-5p".

The term "hsa-miR-4271 gene" or "hsa-miR-4271" used herein includes the hsa-miR-4271 gene (miRBase Accession No. MIMAT0016901) described in SEQ ID NO: 161, a homolog or an ortholog of a different organism species, and the like. The hsa-miR-4271 gene can be obtained by a method described in Goff L A et al., 2009, PLOS One, Vol.

4, e7192. Also, "hsa-mir-4271" (miRBase Accession No. MI0015879, SEQ ID NO: 353) having a hairpin-like structure is known as a precursor of "hsa-miR-4271".

The term "hsa-miR-3196 gene" or "hsa-miR-3196" used herein includes the hsa-miR-3196 gene (miRBase Accession No. MIMAT0015080) described in SEQ ID NO: 162, a homolog or an ortholog of a different organism species, and the like. The hsa-miR-3196 gene can be obtained by a method described in Stark M S et al., 2010, PLOS One, Vol. 5, e9685. Also, "hsa-mir-3196" (miRBase Accession No. MI0014241, SEQ ID NO: 354) having a hairpin-like structure is known as a precursor of "hsa-miR-3196".

The term "hsa-miR-6803-5p gene" or "hsa-miR-6803-5p" used herein includes the hsa-miR-6803-5p gene (miRBase Accession No. MIMAT0027506) described in SEQ ID NO: 163, a homolog or an ortholog of a different organism species, and the like. The hsa-miR-6803-5p gene can be obtained by a method described in Ladewig E et al., 2012, Genome Res, Vol. 22, p. 1634-1645. Also, "hsa-mir-6803" (miRBase Accession No. MI0022648, SEQ ID NO: 355) having a hairpin-like structure is known as a precursor of "hsa-miR-6803-5p".

The term "hsa-miR-6789-5p gene" or "hsa-miR-6789-5p" used herein includes the hsa-miR-6789-5p gene (miRBase Accession No. MIMAT0027478) described in SEQ ID NO: 164, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 356) having a hairpin-like structure is known as a precursor of "hsa-miR-6789-5p".

The term "hsa-miR-4648 gene" or "hsa-miR-4648" used herein includes the hsa-miR-4648 gene (miRBase Accession No. MIMAT0019710) described in SEQ ID NO: 165, a homolog or an ortholog of a different organism species, and the like. The hsa-miR-4648 gene can be obtained by a method described in Persson H et al., 2011, Cancer Res, Vol. 71, p. 78-86. Also, "hsa-mir-4648" (miRBase Accession No. MI0017275, SEQ ID NO: 357) having a hairpin-like structure is known as a precursor of "hsa-miR-4648".

The term "hsa-miR-4508 gene" or "hsa-miR-4508" used herein includes the hsa-miR-4508 gene (miRBase Accession No. MIMAT0019045) described in SEQ ID NO: 166, a homolog or an ortholog of a different organism species, and the like. The hsa-miR-4508 gene can be obtained by a method described in Jima D D et al., 2010, Blood, Vol. 116, e118-e127. Also, "hsa-mir-4508" (miRBase Accession No. MI0016872, SEQ ID NO: 358) having a hairpin-like structure is known as a precursor of "hsa-miR-4508".

The term "hsa-miR-4749-5p gene" or "hsa-miR-4749-5p" used herein includes the hsa-miR-4749-5p gene (miRBase Accession No. MIMAT0019885) described in SEQ ID NO: 167, a homolog or an ortholog of a different organism species, and the like. The hsa-miR-4749-5p gene can be obtained by a method described in Persson H et al., 2011, Cancer Res, Vol. 71, p. 78-86. Also, "hsa-mir-4749" (miRBase Accession No. MI0017388, SEQ ID NO: 359) having a hairpin-like structure is known as a precursor of "hsa-miR-4749-5p".

The term "hsa-miR-4505 gene" or "hsa-miR-4505" used herein includes the hsa-miR-4505 gene (miRBase Accession No. MIMAT0019041) described in SEQ ID NO: 168, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No.

MI0016868, SEQ ID NO: 360) having a hairpin-like structure is known as a precursor of "hsa-miR-4505".

The term "hsa-miR-5698 gene" or "hsa-miR-5698" used herein includes the hsa-miR-5698 gene (miRBase Accession No. MIMAT0022491) described in SEQ ID NO: 169, a homolog or an ortholog of a different organism species, and the like. The hsa-miR-5698 gene can be obtained by a method described in Watahiki A et al., 2011, PLOS One, Vol. 6, e24950. Also, "hsa-mir-5698" (miRBase Accession No. MI0019305, SEQ ID NO: 361) having a hairpin-like structure is known as a precursor of "hsa-miR-5698".

The term "hsa-miR-1199-5p gene" or "hsa-miR-1199-5p" used herein includes the hsa-miR-1199-5p gene (miRBase Accession No. MIMAT0031119) described in SEQ ID NO: 170, a homolog or an ortholog of a different organism species, and the like. The hsa-miR-1199-5p gene can be obtained by a method described in Salvi A et al., 2013, Int J Oncol, Vol. 42, p. 391-402. Also, "hsa-mir-1199" (miRBase Accession No. MI0020340, SEQ ID NO: 362) having a hairpin-like structure is known as a precursor of "hsa-miR-1199-5p".

The term "hsa-miR-4763-3p gene" or "hsa-miR-4763-3p" used herein includes the hsa-miR-4763-3p gene (miRBase Accession No. MIMAT0019913) described in SEQ ID NO: 171, a homolog or an ortholog of a different organism species, and the like. The hsa-miR-4763-3p gene can be obtained by a method described in Persson H et al., 2011, Cancer Res, Vol. 71, p. 78-86. Also, "hsa-mir-4763" (miRBase Accession No. MI0017404, SEQ ID NO: 363) having a hairpin-like structure is known as a precursor of "hsa-miR-4763-3p".

The term "hsa-miR-1231 gene" or "hsa-miR-1231" used herein includes the hsa-miR-1231 gene (miRBase Accession No. MIMAT0005586) described in SEQ ID NO: 172, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 364) having a hairpin-like structure is known as a precursor of "hsa-miR-1231".

The term "hsa-miR-1233-5p gene" or "hsa-miR-1233-5p" used herein includes the hsa-miR-1233-5p gene (miRBase Accession No. MIMAT0022943) described in SEQ ID NO: 173, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 365 and 366) having a hairpin-like structure are known as precursors of "hsa-miR-1233-5p".

The term "hsa-miR-150-3p gene" or "hsa-miR-150-3p" used herein includes the hsa-miR-150-3p gene (miRBase Accession No. MIMAT0004610) described in SEQ ID NO: 174, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI0000479, SEQ ID NO: 367) having a hairpin-like structure is known as a precursor of "hsa-miR-150-3p".

The term "hsa-miR-1225-3p gene" or "hsa-miR-1225-3p" used herein includes the hsa-miR-1225-3p gene (miRBase Accession No. MIMAT0005573) described in SEQ ID NO: 175, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 235) having a hairpin-like structure is known as a precursor of "hsa-miR-1225-3p".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 176, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 368) having a hairpin-like structure is known as a precursor of "hsa-miR-92a-2-5p".

The term "hsa-miR-423-5p gene" or "hsa-miR-423-5p" used herein includes the hsa-miR-423-5p gene (miRBase Accession No. MIMAT0004748) described in SEQ ID NO: 177, a homolog or an ortholog of a different organism species, and the like. The hsa-miR-423-5p gene can be obtained by a method described in Kasashima K et al., 2004, Biochem Biophys Res Commun, Vol. 322, p. 403-410. Also, "hsa-mir-423" (miRBase Accession No. MI0001445, SEQ ID NO: 369) having a hairpin-like structure is known as a precursor of "hsa-miR-423-5p".

The term "hsa-miR-1268a gene" or "hsa-miR-1268a" used herein includes the hsa-miR-1268a gene (miRBase Accession No. MIMAT0005922) described in SEQ ID NO: 178, a homolog or an ortholog of a different organism species, and the like. The hsa-miR-1268a gene can be obtained by a method described in Morin R D et al., 2008, Genome Res, Vol. 18, p. 610-621. Also, "hsa-mir-1268a" (miRBase Accession No. MI0006405, SEQ ID NO: 370) having a hairpin-like structure is known as a precursor of "hsa-miR-1268a".

The term "hsa-miR-128-2-5p gene" or "hsa-miR-128-2-5p" used herein includes the hsa-miR-128-2-5p gene (miRBase Accession No. MIMAT0031095) described in SEQ ID NO: 179, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 371) having a hairpin-like structure is known as a precursor of "hsa-miR-128-2-5p".

The term "hsa-miR-24-3p gene" or "hsa-miR-24-3p" used herein includes the hsa-miR-24-3p gene (miRBase Accession No. MIMAT0000080) described in SEQ ID NO: 180, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 372 and 373) having a hairpin-like structure are known as precursors of "hsa-miR-24-3p".

The term "hsa-miR-4697-5p gene" or "hsa-miR-4697-5p" used herein includes the hsa-miR-4697-5p gene (miRBase Accession No. MIMAT0019791) described in SEQ ID NO: 181, a homolog or an ortholog of a different organism species, and the like. The hsa-miR-4697-5p gene can be obtained by a method described in Persson H et al., 2011, Cancer Res, Vol. 71, p. 78-86. Also, "hsa-mir-4697" (miRBase Accession No. MI0017330, SEQ ID NO: 374) having a hairpin-like structure is known as a precursor of "hsa-miR-4697-5p".

The term "hsa-miR-3197 gene" or "hsa-miR-3197" used herein includes the hsa-miR-3197 gene (miRBase Accession No. MIMAT0015082) described in SEQ ID NO: 182, a homolog or an ortholog of a different organism species, and the like. The hsa-miR-3197 gene can be obtained by a method described in Stark M S et al., 2010, PLOS One, Vol. 5, e9685. Also, "hsa-mir-3197" (miRBase Accession No. MI0014245, SEQ ID NO: 375) having a hairpin-like structure is known as a precursor of "hsa-miR-3197".

The term "hsa-miR-675-5p gene" or "hsa-miR-675-5p" used herein includes the hsa-miR-675-5p gene (miRBase Accession No. MIMAT0004284) described in SEQ ID NO: 183, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 376) having a hairpin-like structure is known as a precursor of "hsa-miR-675-5p".

The term "hsa-miR-4486 gene" or "hsa-miR-4486" used herein includes the hsa-miR-4486 gene (miRBase Accession No. MIMAT0019020) described in SEQ ID NO: 184, a homolog or an ortholog of a different organism species, and the like. The hsa-miR-4486 gene can be gene can be obtained by a method described in Jima D D et al., 2010, Blood, Vol. 116, e118-e127. Also, "hsa-mir-4486" (miRBase Accession No. MI0016847, SEQ ID NO: 377) having a hairpin-like structure is known as a precursor of "hsa-miR-4486".

The term "hsa-miR-7107-5p gene" or "hsa-miR-7107-5p" used herein includes the hsa-miR-7107-5p gene (miRBase Accession No. MIMAT0028111) described in SEQ ID NO: 185, a homolog or an ortholog of a different organism species, and the like. The hsa-miR-7107-5p gene can be obtained by a method described in Ladewig E et al., 2012, Genome Res, Vol. 22, p. 1634-1645. Also, "hsa-mir-7107" (miRBase Accession No. MI0022958, SEQ ID NO: 378) having a hairpin-like structure is known as a precursor of "hsa-miR-7107-5p".

The term "hsa-miR-23a-3p gene" or "hsa-miR-23a-3p" used herein includes the hsa-miR-23a-3p gene (miRBase Accession No. MIMAT0000078) described in SEQ ID NO: 186, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 379) having a hairpin-like structure is known as a precursor of "hsa-miR-23a-3p".

The term "hsa-miR-4667-5p gene" or "hsa-miR-4667-5p" used herein includes the hsa-miR-4667-5p gene (miRBase Accession No. MIMAT0019743) described in SEQ ID NO: 187, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 380) having a hairpin-like structure is known as a precursor of "hsa-miR-4667-5p".

The term "hsa-miR-451a gene" or "hsa-miR-451a" used herein includes the hsa-miR-451a gene (miRBase Accession No. MIMAT0001631) described in SEQ ID NO: 188, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 381) having a hairpin-like structure is known as a precursor of "hsa-miR-451a".

The term "hsa-miR-3940-5p gene" or "hsa-miR-3940-5p" used herein includes the hsa-miR-3940-5p gene (miRBase Accession No. MIMAT0019229) described in SEQ ID NO: 189, a homolog or an ortholog of a different organism species, and the like. The hsa-miR-3940-5p gene can be obtained by a method described in Liao J Y et al., 2010, PLOS One, Vol. 5, e10563. Also, "hsa-mir-3940" (miRBase Accession No. MI0016597, SEQ ID NO: 382) having a hairpin-like structure is known as a precursor of "hsa-miR-3940-5p".

The term "hsa-miR-8059 gene" or "hsa-miR-8059" used herein includes the hsa-miR-8059 gene (miRBase Accession No. MIMAT0030986) described in SEQ ID NO: 190, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 383) having a hairpin-like structure is known as a precursor of "hsa-miR-8059".

The term "hsa-miR-6813-5p gene" or "hsa-miR-6813-5p" used herein includes the hsa-miR-6813-5p gene (miRBase Accession No. MIMAT0027526) described in SEQ ID NO: 191, a homolog or an ortholog of a different organism species, and the like. The hsa-miR-6813-5p gene can be obtained by a method described in Ladewig E et al., 2012, Genome Res, Vol. 22, p. 1634-1645. Also, "hsa-mir-6813" (miRBase Accession No. MI0022658, SEQ ID NO: 384) having a hairpin-like structure is known as a precursor of "hsa-miR-6813-5p".

The term "hsa-miR-4492 gene" or "hsa-miR-4492" used herein includes the hsa-miR-4492 gene (miRBase Accession No. MIMAT0019027) described in SEQ ID NO: 192, a homolog or an ortholog of a different organism species, and the like. The hsa-miR-4492 gene can be obtained by a method described in Jima D D et al., 2010, Blood, Vol. 116, e118-e127. Also, "hsa-mir-4492" (miRBase Accession No. MI0016854, SEQ ID NO: 385) having a hairpin-like structure is known as a precursor of "hsa-miR-4492".

The term "hsa-miR-4476 gene" or "hsa-miR-4476" used herein includes the hsa-miR-4476 gene (miRBase Accession No. MIMAT0019003) described in SEQ ID NO: 193, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 386) having a hairpin-like structure is known as a precursor of "hsa-miR-4476".

The term "hsa-miR-6090 gene" or "hsa-miR-6090" used herein includes the hsa-miR-6090 gene (miRBase Accession No. MIMAT0023715) described in SEQ ID NO: 194, a homolog or an ortholog of a different organism species, and the like. The hsa-miR-6090 gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 387) having a hairpin-like structure is known as a precursor of "hsa-miR-6090".

The term "hsa-miR-6836-3p gene" or "hsa-miR-6836-3p" used herein includes the hsa-miR-6836-3p gene (miRBase Accession No. MIMAT0027575) described in SEQ ID NO: 606, a homolog or an ortholog of a different organism species, and the like. The hsa-miR-6836-3p gene can be obtained by a method described in Ladewig E et al., 2012, Genome Res, Vol. 22, p. 1634-1645. Also, "hsa-mir-6836" (miRBase Accession No. MI0022682, SEQ ID NO: 615) having a hairpin-like structure is known as a precursor of "hsa-miR-6836-3p".

The term "hsa-miR-3195 gene" or "hsa-miR-3195" used herein includes the hsa-miR-3195 gene (miRBase Accession No. MIMAT0015079) described in SEQ ID NO: 607, a homolog or an ortholog of a different organism species, and the like. The hsa-miR-3195 gene can be obtained by a method described in Stark M S et al., 2010, PLOS One, Vol. 5, e9685. Also, "hsa-mir-3195" (miRBase Accession No. MI0014240, SEQ ID NO: 616) having a hairpin-like structure is known as a precursor of "hsa-miR-3195".

The term "hsa-miR-718 gene" or "hsa-miR-718" used herein includes the hsa-miR-718 gene (miRBase Accession No. MIMAT0012735) described in SEQ ID NO: 608, a homolog or an ortholog of a different organism species, and the like. The hsa-miR-718 gene can be obtained by a method described in Artzi S et al., 2008, BMC Bioinformatics, Vol. 9, p. 39. Also, "hsa-mir-718" (miRBase Accession No. MI0012489, SEQ ID NO: 617) having a hairpin-like structure is known as a precursor of "hsa-miR-718".

The term "hsa-miR-3178 gene" or "hsa-miR-3178" used herein includes the hsa-miR-3178 gene (miRBase Accession No. MIMAT0015055) described in SEQ ID NO: 609, a homolog or an ortholog of a different organism species, and the like. The hsa-miR-3178 gene can be obtained by a method described in Stark M S et al., 2010, PLOS One, Vol. 5, e9685. Also, "hsa-mir-3178" (miRBase Accession No. MI0014212, SEQ ID NO: 618) having a hairpin-like structure is known as a precursor of "hsa-miR-3178".

The term "hsa-miR-638 gene" or "hsa-miR-638" used herein includes the hsa-miR-638 gene (miRBase Accession No. MIMAT0003308) described in SEQ ID NO: 610, a homolog or an ortholog of a different organism species, and the like. The hsa-miR-638 gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 619) having a hairpin-like structure is known as a precursor of "hsa-miR-638".

The term "hsa-miR-4497 gene" or "hsa-miR-4497" used herein includes the hsa-miR-4497 gene (miRBase Accession No. MIMAT0019032) described in SEQ ID NO: 611, a homolog or an ortholog of a different organism species, and the like. The hsa-miR-4497 gene can be obtained by a method described in Jima D D et al., 2010, Blood, Vol. 116, e118-e127. Also, "hsa-mir-4497" (miRBase Accession No. MI0016859, SEQ ID NO: 620) having a hairpin-like structure is known as a precursor of "hsa-miR-4497".

The term "hsa-miR-6085 gene" or "hsa-miR-6085" used herein includes the hsa-miR-6085 gene (miRBase Accession No. MIMAT0023710) described in SEQ ID NO: 612, a homolog or an ortholog of a different organism species, and the like. The hsa-miR-6085 gene can be obtained by a method described in Voellenkle C et al., 2012, RNA, Vol. 18, p. 472-484. Also, "hsa-mir-6085" (miRBase Accession No. MI0020362, SEQ ID NO: 621) having a hairpin-like structure is known as a precursor of "hsa-miR-6085".

The term "hsa-miR-6752-5p gene" or "hsa-miR-6752-5p" used herein includes the hsa-miR-6752-5p gene (miRBase Accession No. MIMAT0027404) described in SEQ ID NO: 613, a homolog or an ortholog of a different organism species, and the like. The hsa-miR-6752-5p gene can be obtained by a method described in Ladewig E et al., 2012, Genome Res, Vol. 22, p. 1634-1645. Also, "hsa-mir-6752" (miRBase Accession No. MI0022597, SEQ ID NO: 622) having a hairpin-like structure is known as a precursor of "hsa-miR-6752-5p".

The term "hsa-miR-135a-3p gene" or "hsa-miR-135a-3p" used herein includes the hsa-miR-135a-3p gene (miRBase Accession No. MIMAT0004595) described in SEQ ID NO: 614, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a" (miRBase Accession No. MI0000452, SEQ ID NO: 623) having a hairpin-like structure is known as a precursor of "hsa-miR-135a-3p".

A mature miRNA may become a variant due to the sequence that is cleaved shorter or longer by one to several upstream or downstream nucleotides or nucleotide substitution when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 194 and 606 to 614 as well as a large number of the nucleotide sequence variants and fragments represented by SEQ ID NOs: 388 to 605 and 624 to 635, which are called isomiRs. These variants can also be obtained as miRNAs having a nucleotide sequence represented by any of SEQ ID NOs: 1 to 194 and 606 to 614. Specifically, among the variants of polynucleotides consisting of the nucleotide sequence represented by any of SEQ ID NOs: 5, 7, 8, 9, 11, 16, 19, 20, 21, 26, 27, 28, 30, 34, 37, 38, 39, 41, 43, 45, 46, 48, 50, 54, 55, 57, 58, 61, 62, 63, 64, 65, 66, 67, 69, 70, 71, 73, 74, 76, 77, 78, 80, 81, 82, 84, 85, 86, 88, 89, 94, 95, 97, 98, 99, 100, 101, 104, 107, 108, 109, 110, 111, 112, 113, 115, 116, 117, 119, 120, 123, 125, 131, 132, 133, 135, 136, 137, 140, 141, 142, 147, 151, 152, 157, 161, 162, 165, 166, 167, 168, 169, 171, 173, 174, 176, 177, 178, 179, 180, 182, 183, 184, 186, 187, 188, 189, 192, 193, 607, 608, 609, 610, 611 and 614, or a nucleotide sequence derived from the nucleotide sequence by the replacement of u with t according to the present invention, examples of the longest variants registered in the miRBase Release 20 include polynucleotides represented by SEQ ID NOs:388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 624, 626, 628, 630, 632 and 634, respectively. Also, among the variants of polynucleotides consisting of a nucleotide sequence represented by any of SEQ ID NOs: 5, 7, 8, 9, 11, 16, 19, 20, 21, 26, 27, 28, 30, 34, 37, 38, 39, 41, 43, 45, 46, 48, 50, 54, 55, 57, 58, 61, 62, 63, 64, 65, 66, 67, 69, 70, 71, 73, 74, 76, 77, 78, 80, 81, 82, 84, 85, 86, 88, 89, 94, 95, 97, 98, 99, 100, 101, 104, 107, 108, 109, 110, 111, 112, 113, 115, 116, 117, 119, 120, 123, 125, 131, 132, 133, 135, 136, 137, 140, 141, 142, 147, 151, 152, 157, 161, 162, 165, 166, 167, 168, 169, 171, 173, 174, 176, 177, 178, 179, 180, 182, 183, 184, 186, 187, 188, 189, 192, 193, 607, 608, 609, 610, 611 and 614, or a nucleotide sequence derived from the nucleotide sequence by the replacement of u with t according to the present invention, examples of the shortest variants registered in the miRBase Release 20 include polynucleotides having sequences represented by SEQ ID NOs: 389, 391, 393, 395, 397, 399, 401, 403, 405, 407, 409, 411, 413, 415, 417, 419, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 499, 501, 503, 505, 507, 509, 511, 513, 515, 517, 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 625, 627, 629, 631, 633 and 635, respectively. In addition to these variants and fragments, examples thereof include a large number of isomiR polynucleotides of SEQ ID NOs: 1 to 194 and 606 to 614 registered in miRBase. Examples of the polynucleotide comprising a nucleotide sequence represented by any of SEQ ID NOs: 1 to 194 and 606 to 614 to 494 include a polynucleotide represented by any of SEQ ID NOs: 195 to 387 and 615 to 623, which are their respective precursors.

The names and miRBase Accession Nos. (registration numbers) of the genes represented by SEQ ID NOs: 1 to 635 are shown in Table 1.

TABLE 1

| SEQ ID NO: | Gene name | miRBase registration No. |
|---|---|---|
| 1 | hsa-miR-6726-5p | MIMAT0027353 |
| 2 | hsa-miR-4257 | MIMAT0016878 |
| 3 | hsa-miR-6787-5p | MIMAT0027474 |
| 4 | hsa-miR-6780b-5p | MIMAT0027572 |
| 5 | hsa-miR-3131 | MIMAT0014996 |
| 6 | hsa-miR-7108-5p | MIMAT0028113 |
| 7 | hsa-miR-1343-3p | MIMAT0019776 |
| 8 | hsa-miR-1247-3p | MIMAT0022721 |
| 9 | hsa-miR-4651 | MIMAT0019715 |
| 10 | hsa-miR-6757-5p | MIMAT0027414 |
| 11 | hsa-miR-3679-5p | MIMAT0018104 |
| 12 | hsa-miR-7641 | MIMAT0029782 |
| 13 | hsa-miR-6746-5p | MIMAT0027392 |
| 14 | hsa-miR-8072 | MIMAT0030999 |
| 15 | hsa-miR-6741-5p | MIMAT0027383 |
| 16 | hsa-miR-1908-5p | MIMAT0007881 |
| 17 | hsa-miR-6857-5p | MIMAT0027614 |
| 18 | hsa-miR-4746-3p | MIMAT0019881 |
| 19 | hsa-miR-744-5p | MIMAT0004945 |
| 20 | hsa-miR-4792 | MIMAT0019964 |
| 21 | hsa-miR-564 | MIMAT0003228 |
| 22 | hsa-miR-6791-5p | MIMAT0027482 |
| 23 | hsa-miR-6825-5p | MIMAT0027550 |
| 24 | hsa-miR-6826-5p | MIMAT0027552 |
| 25 | hsa-miR-4665-3p | MIMAT0019740 |
| 26 | hsa-miR-4467 | MIMAT0018994 |
| 27 | hsa-miR-3188 | MIMAT0015070 |
| 28 | hsa-miR-6125 | MIMAT0024598 |
| 29 | hsa-miR-6756-5p | MIMAT0027412 |
| 30 | hsa-miR-1228-3p | MIMAT0005583 |
| 31 | hsa-miR-8063 | MIMAT0030990 |
| 32 | hsa-miR-8069 | MIMAT0030996 |
| 33 | hsa-miR-6875-5p | MIMAT0027650 |
| 34 | hsa-miR-3185 | MIMAT0015065 |
| 35 | hsa-m iR-4433b-3p | MIMAT0030414 |
| 36 | hsa-miR-6887-5p | MIMAT0027674 |
| 37 | hsa-miR-12 8-1 -5p | MIMAT0026477 |
| 38 | hsa-miR-6724-5p | MIMAT0025856 |
| 39 | hsa-miR-1914-3p | MIMAT0007890 |
| 40 | hsa-miR-1225-5p | MIMAT0005572 |
| 41 | hsa-m iR-4419b | MIMAT0019034 |
| 42 | hsa-miR-7110-5p | MIMAT0028117 |
| 43 | hsa-m iR-187-5p | MIMAT0004561 |
| 44 | hsa-miR-3184-5p | MIMAT0015064 |
| 45 | hsa-m iR-204-3p | MIMAT0022693 |
| 46 | hsa-miR-5572 | MIMAT0022260 |
| 47 | hsa-miR-6729-5p | MIMAT0027359 |
| 48 | hsa-m iR-615-5p | MIMAT0004804 |
| 49 | hsa-miR-6749-5p | MIMAT0027398 |
| 50 | hsa-miR-6515-3p | MIMAT0025487 |
| 51 | hsa-miR-3937 | MIMAT0018352 |
| 52 | hsa-miR-6840-3p | MIMAT0027583 |
| 53 | hsa-miR-6893-5p | MIMAT0027686 |
| 54 | hsa-miR-4728-5p | MIMAT0019849 |
| 55 | hsa-miR-6717-5p | MIMAT0025846 |
| 56 | hsa-miR-7113-3p | MIMAT0028124 |
| 57 | hsa-miR-4665-5p | MIMAT0019739 |

TABLE 1-continued

| SEQ ID NO: | Gene name | miRBase registration No. |
|---|---|---|
| 58 | hsa-miR-642b-3p | MIMAT0018444 |
| 59 | hsa-miR-7109-5p | MIMAT0028115 |
| 60 | hsa-miR-6842-5p | MIMAT0027586 |
| 61 | hsa-miR-4442 | MIMAT0018960 |
| 62 | hsa-miR-4433-3p | MIMAT0018949 |
| 63 | hsa-miR-4707-5p | MIMAT0019807 |
| 64 | hsa-miR-6126 | MIMAT0024599 |
| 65 | hsa-miR-4449 | MIMAT0018968 |
| 66 | hsa-miR-4706 | MIMAT0019806 |
| 67 | hsa-miR-1913 | MIMAT0007888 |
| 68 | hsa-miR-602 | MIMAT0003270 |
| 69 | hsa-miR-939-5p | MIMAT0004982 |
| 70 | hsa-miR-4695-5p | MIMAT0019788 |
| 71 | hsa-miR-711 | MIMAT0012734 |
| 72 | hsa-miR-6816-5p | MIMAT0027532 |
| 73 | hsa-miR-4632-5p | MIMAT0022977 |
| 74 | hsa-miR-6721-5p | MIMAT0025852 |
| 75 | hsa-miR-7847-3p | MIMAT0030422 |
| 76 | hsa-miR-6132 | MIMAT0024616 |
| 77 | hsa-miR-887-3p | MIMAT0004951 |
| 78 | hsa-miR-3679-3p | MIMAT0018105 |
| 79 | hsa-miR-6784-5p | MIMAT0027468 |
| 80 | hsa-miR-1249 | MIMAT0005901 |
| 81 | hsa-miR-937-5p | MIMAT0022938 |
| 82 | hsa-miR-5195-3p | MIMAT0021127 |
| 83 | hsa-miR-6732-5p | MIMAT0027365 |
| 84 | hsa-miR-4417 | MIMAT0018929 |
| 85 | hsa-miR-4281 | MIMAT0016907 |
| 86 | hsa-miR-4734 | MIMAT0019859 |
| 87 | hsa-miR-6766-3p | MIMAT0027433 |
| 88 | hsa-miR-663a | MIMAT0003326 |
| 89 | hsa-miR-4513 | MIMAT0019050 |
| 90 | hsa-miR-6781 -5p | MIMAT0027462 |
| 91 | hsa-miR-1227-5p | MIMAT0022941 |
| 92 | hsa-miR-6845-5p | MIMAT0027590 |
| 93 | hsa-miR-6798-5p | MIMAT0027496 |
| 94 | hsa-miR-3620-5p | MIMAT0022967 |
| 95 | hsa-miR-1915-5p | MIMAT0007891 |
| 96 | hsa-miR-4294 | MIMAT0016849 |
| 97 | hsa-miR-642a-3p | MIMAT0020924 |
| 98 | hsa-miR-371a-5p | MIMAT0004687 |
| 99 | hsa-miR-940 | MIMAT0004983 |
| 100 | hsa-miR-4450 | MIMAT0018971 |
| 101 | hsa-miR-4723-5p | MIMAT0019838 |
| 102 | hsa-miR-1469 | MIMAT0007347 |
| 103 | hsa-miR-6861-5p | MIMAT0027623 |
| 104 | hsa-miR-7975 | MIMAT0031178 |
| 105 | hsa-miR-6879-5p | MIMAT0027658 |
| 106 | hsa-miR-6802-5p | MIMAT0027504 |
| 107 | hsa-miR- 1268b | MIMAT0018925 |
| 108 | hsa-miR-663b | MIMAT0005867 |
| 109 | hsa-miR-125a-3p | MIMAT0004602 |
| 110 | hsa-miR-2861 | MIMAT0013802 |
| 111 | hsa-miR-6088 | MIMAT0023713 |
| 112 | hsa-miR-4758-5p | MIMAT0019903 |
| 113 | hsa-miR-296-3p | MIMAT0004679 |
| 114 | hsa-miR-6738-5p | MIMAT0027377 |
| 115 | hsa-miR-671-5p | MIMAT0003880 |
| 116 | hsa-miR-4454 | MIMAT0018976 |
| 117 | hsa-miR-4516 | MIMAT0019053 |
| 118 | hsa-miR-7845-5p | MIMAT0030420 |
| 119 | hsa-miR-4741 | MIMAT0019871 |
| 120 | hsa-miR-92b-5p | MIMAT0004792 |
| 121 | hsa-miR-6795-5p | MIMAT0027490 |
| 122 | hsa-miR-6805-3p | MIMAT0027511 |
| 123 | hsa-miR-4725-3p | MIMAT0019844 |
| 124 | hsa-miR-6782-5p | MIMAT0027464 |
| 125 | hsa-miR-4688 | MIMAT0019777 |
| 126 | hsa-miR-6850-5p | MIMAT0027600 |
| 127 | hsa-miR-6777-5p | MIMAT0027454 |
| 128 | hsa-miR-6785-5p | MIMAT0027470 |
| 129 | hsa-miR-7106-5p | MIMAT0028109 |
| 130 | hsa-miR-3663-3p | MIMAT0018085 |
| 131 | hsa-miR-6131 | MIMAT0024615 |
| 132 | hsa-miR-1915-3p | MIMAT0007892 |
| 133 | hsa-miR-4532 | MIMAT0019071 |
| 134 | hsa-miR-6820-5p | MIMAT0027540 |

TABLE 1-continued

TABLE 1-continued

| SEQ ID NO: | Gene name | miRBase registration No. |
|---|---|---|
| 135 | hsa-miR-4689 | MIMAT0019778 |
| 136 | hsa-miR-4638-5p | MIMAT0019695 |
| 137 | hsa-miR-3656 | MIMAT0018076 |
| 138 | hsa-miR-3621 | MIMAT0018002 |
| 139 | hsa-miR-6769b-5p | MIMAT0027620 |
| 140 | hsa-miR-149-3p | MIMAT0004609 |
| 141 | hsa-miR-23b-3p | MIMAT0000418 |
| 142 | hsa-miR-3135b | MIMAT0018985 |
| 143 | hsa-miR-6848-5p | MIMAT0027596 |
| 144 | hsa-miR-6769a-5p | MIMAT0027438 |
| 145 | hsa-miR-4327 | MIMAT0016889 |
| 146 | hsa-miR-6765-3p | MIMAT0027431 |
| 147 | hsa-miR-6716-5p | MIMAT0025844 |
| 148 | hsa-miR-6877-5p | MIMAT0027654 |
| 149 | hsa-miR-6727-5p | MIMAT0027355 |
| 150 | hsa-miR-4534 | MIMAT0019073 |
| 151 | hsa-miR-614 | MIMAT0003282 |
| 152 | hsa-miR-1202 | MIMAT0005865 |
| 153 | hsa-miR-575 | MIMAT0003240 |
| 154 | hsa-miR-6870-5p | MIMAT0027640 |
| 155 | hsa-miR-6722-3p | MIMAT0025854 |
| 156 | hsa-miR-7977 | MIMAT0031180 |
| 157 | hsa-miR-4649-5p | MIMAT0019711 |
| 158 | hsa-miR-4675 | MIMAT0019757 |
| 159 | hsa-miR-6075 | MIMAT0023700 |
| 160 | hsa-miR-6779-5p | MIMAT0027458 |
| 161 | hsa-miR-4271 | MIMAT0016901 |
| 162 | hsa-miR-3196 | MIMAT0015080 |
| 163 | hsa-miR-6803-5p | MIMAT0027506 |
| 164 | hsa-miR-6789-5p | MIMAT0027478 |
| 165 | hsa-miR-4648 | MIMAT0019710 |
| 166 | hsa-miR-4508 | MIMAT0019045 |
| 167 | hsa-miR-4749-5p | MIMAT0019885 |
| 168 | hsa-miR-4505 | MIMAT0019041 |
| 169 | hsa-miR-5698 | MIMAT0022491 |
| 170 | hsa-miR-1199-5p | MIMAT0031119 |
| 171 | hsa-miR-4763-3p | MIMAT0019913 |
| 172 | hsa-miR-1231 | MIMAT0005586 |
| 173 | hsa-miR-1233-5p | MIMAT0022943 |
| 174 | hsa-miR-150-3p | MIMAT0004610 |
| 175 | hsa-miR-1225-3p | MIMAT0005573 |
| 176 | hsa-miR-92a-2-5p | MIMAT0004508 |
| 177 | hsa-miR-423-5p | MIMAT0004748 |
| 178 | hsa-miR-1268a | MIMAT0005922 |
| 179 | hsa-miR-128-2-5p | MIMAT0031095 |
| 180 | hsa-miR-24-3p | MIMAT0000080 |
| 181 | hsa-miR-4697-5p | MIMAT0019791 |
| 182 | hsa-miR-3197 | MIMAT0015082 |
| 183 | hsa-miR-675-5p | MIMAT0004284 |
| 184 | hsa-miR-4486 | MIMAT0019020 |
| 185 | hsa-miR-7107-5p | MIMAT0028111 |
| 186 | hsa-miR-23a-3p | MIMAT0000078 |
| 187 | hsa-miR-4667-5p | MIMAT0019743 |
| 188 | hsa-miR-451a | MIMAT0001631 |
| 189 | hsa-miR-3940-5p | MIMAT0019229 |
| 190 | hsa-miR-8059 | MIMAT0030986 |
| 191 | hsa-miR-6813-5p | MIMAT0027526 |
| 192 | hsa-miR-4492 | MIMAT0019027 |
| 193 | hsa-miR-4476 | MIMAT0019003 |
| 194 | hsa-miR-6090 | MIMAT0023715 |
| 195 | hsa-mir-6726 | MI0022571 |
| 196 | hsa-mir-4257 | MI0015856 |
| 197 | hsa-mir-6787 | MI0022632 |
| 198 | hsa-mir-6780b | MI0022681 |
| 199 | hsa-mir-3131 | MI0014151 |
| 200 | hsa-mir-7108 | MI0022959 |
| 201 | hsa-mir-1343 | MI0017320 |
| 202 | hsa-mir-1247 | MI0006382 |
| 203 | hsa-mir-4651 | MI0017279 |
| 204 | hsa-mir-6757 | MI0022602 |
| 205 | hsa-mir-3679 | MI0016080 |
| 206 | hsa-mir-7641-1 | MI0024975 |
| 207 | hsa-mir-7641-2 | MI0024976 |
| 208 | hsa-mir-6746 | MI0022591 |
| 209 | hsa-mir-8072 | MI0025908 |
| 210 | hsa-mir-6741 | MI0022586 |
| 211 | hsa-mir-1908 | MI0008329 |

| SEQ ID NO: | Gene name | miRBase registration No. |
|---|---|---|
| 212 | hsa-mir-6857 | MI0022703 |
| 213 | hsa-mir-4746 | MI0017385 |
| 214 | hsa-mir-744 | MI0005559 |
| 215 | hsa-mir-4792 | MI0017439 |
| 216 | hsa-mir-564 | MI0003570 |
| 217 | hsa-mir-6791 | MI0022636 |
| 218 | hsa-mir-6825 | MI0022670 |
| 219 | hsa-mir-6826 | MI0022671 |
| 220 | hsa-mir-4665 | MI0017295 |
| 221 | hsa-mir-4467 | MI0016818 |
| 222 | hsa-mir-3188 | MI0014232 |
| 223 | hsa-mir-6125 | MI0021259 |
| 224 | hsa-mir-6756 | MI0022601 |
| 225 | hsa-mir-1228 | MI0006318 |
| 226 | hsa-mir-8063 | MI0025899 |
| 227 | hsa-mir-8069 | MI0025905 |
| 228 | hsa-mir-6875 | MI0022722 |
| 229 | hsa-mir-3185 | MI0014227 |
| 230 | hsa-mir-4433b | MI0025511 |
| 231 | hsa-mir-6887 | MI0022734 |
| 232 | hsa-mir-128-1 | MI0000447 |
| 233 | hsa-mir-6724 | MI0022559 |
| 234 | hsa-mir-1914 | MI0008335 |
| 235 | hsa-mir-1225 | MI0006311 |
| 236 | hsa-mir-4419b | MI0016861 |
| 237 | hsa-mir-7110 | MI0022961 |
| 238 | hsa-mir-187 | MI0000274 |
| 239 | hsa-mir-3184 | MI0014226 |
| 240 | hsa-mir-204 | MI0000284 |
| 241 | hsa-mir-5572 | MI0019117 |
| 242 | hsa-mir-6729 | MI0022574 |
| 243 | hsa-mir-615 | MI0003628 |
| 244 | hsa-mir-6749 | MI0022594 |
| 245 | hsa-mir-6515 | MI0022227 |
| 246 | hsa-mir-3937 | MI0016593 |
| 247 | hsa-mir-6840 | MI0022686 |
| 248 | hsa-mir-6893 | MI0022740 |
| 249 | hsa-mir-4728 | MI0017365 |
| 250 | hsa-mir-6717 | MI0022551 |
| 251 | hsa-mir-7113 | MI0022964 |
| 252 | hsa-mir-642b | MI0016685 |
| 253 | hsa-mir-7109 | MI0022960 |
| 254 | hsa-mir-6842 | MI0022688 |
| 255 | hsa-mir-4442 | MI0016785 |
| 256 | hsa-mir-4433 | MI0016773 |
| 257 | hsa-mir-4707 | MI0017340 |
| 258 | hsa-mir-6126 | MI0021260 |
| 259 | hsa-mir-4449 | MI0016792 |
| 260 | hsa-mir-4706 | MI0017339 |
| 261 | hsa-mir-1913 | MI0008334 |
| 262 | hsa-mir-602 | MI0003615 |
| 263 | hsa-mir-939 | MI0005761 |
| 264 | hsa-mir-4695 | MI0017328 |
| 265 | hsa-mir-711 | MI0012488 |
| 266 | hsa-mir-6816 | MI0022661 |
| 267 | hsa-mir-4632 | MI0017259 |
| 268 | hsa-mir-6721 | MI0022556 |
| 269 | hsa-mir-7847 | MI0025517 |
| 270 | hsa-mir-6132 | MI0021277 |
| 271 | hsa-mir-887 | MI0005562 |
| 272 | hsa-mir-6784 | MI0022629 |
| 273 | hsa-mir-1249 | MI0006384 |
| 274 | hsa-mir-937 | MI0005759 |
| 275 | hsa-mir-5195 | MI0018174 |
| 276 | hsa-mir-6732 | MI0022577 |
| 277 | hsa-mir-4417 | MI0016753 |
| 278 | hsa-mir-4281 | MI0015885 |
| 279 | hsa-mir-4734 | MI0017371 |
| 280 | hsa-mir-6766 | MI0022611 |
| 281 | hsa-mir-663a | MI0003672 |
| 282 | hsa-mir-4513 | MI0016879 |
| 283 | hsa-mir-6781 | MI0022626 |
| 284 | hsa-mir-1227 | MI0006316 |
| 285 | hsa-mir-6845 | MI0022691 |
| 286 | hsa-mir-6798 | MI0022643 |
| 287 | hsa-mir-3620 | MI0016011 |
| 288 | hsa-mir-1915 | MI0008336 |

TABLE 1-continued

| SEQ ID NO: | Gene name | miRBase registration No. |
|---|---|---|
| 289 | hsa-mir-4294 | MI0015 827 |
| 290 | hsa-mir-642a | MI0003657 |
| 291 | hsa-mir-371a | MI0000779 |
| 292 | hsa-mir-940 | MI0005762 |
| 293 | hsa-mir-4450 | MI0016795 |
| 294 | hsa-mir-4723 | MI0017359 |
| 295 | hsa-mir-1469 | MI0007074 |
| 296 | hsa-mir-6861 | MI0022708 |
| 297 | hsa-mir-7975 | MI0025751 |
| 298 | hsa-mir-6879 | MI0022726 |
| 299 | hsa-mir-6802 | MI0022647 |
| 300 | hsa-mir-1268b | MI0016748 |
| 301 | hsa-mir-663b | MI0006336 |
| 302 | hsa-mir-125a | MI0000469 |
| 303 | hsa-mir-2861 | MI0013006 |
| 304 | hsa-mir-6088 | MI0020365 |
| 305 | hsa-mir-4758 | MI0017399 |
| 306 | hsa-mir-296 | MI0000747 |
| 307 | hsa-mir-6738 | MI0022583 |
| 308 | hsa-mir-671 | MI0003760 |
| 309 | hsa-mir-4454 | MI0016800 |
| 310 | hsa-mir-4516 | MI0016882 |
| 311 | hsa-mir-7845 | MI0025515 |
| 312 | hsa-mir-4741 | MI0017379 |
| 313 | hsa-mir-92b | MI0003560 |
| 314 | hsa-mir-6795 | MI0022640 |
| 315 | hsa-mir-6805 | MI0022650 |
| 316 | hsa-mir-4725 | MI0017362 |
| 317 | hsa-mir-6782 | MI0022627 |
| 318 | hsa-mir-4688 | MI0017321 |
| 319 | hsa-mir-6850 | MI0022696 |
| 320 | hsa-mir-6777 | MI0022622 |
| 321 | hsa-mir-6785 | MI0022630 |
| 322 | hsa-mir-7106 | MI0022957 |
| 323 | hsa-mir-3663 | MI0016064 |
| 324 | hsa-mir-6131 | MI0021276 |
| 325 | hsa-mir-4532 | MI0016899 |
| 326 | hsa-mir-6820 | MI0022665 |
| 327 | hsa-mir-4689 | MI0017322 |
| 328 | hsa-mir-4638 | MI0017265 |
| 329 | hsa-mir-3656 | MI0016056 |
| 330 | hsa-mir-3621 | MI0016012 |
| 331 | hsa-mir-6769b | MI0022706 |
| 332 | hsa-mir-149 | MI0000478 |
| 333 | hsa-mir-23b | MI0000439 |
| 334 | hsa-mir-3135b | MI0016809 |
| 335 | hsa-mir-6848 | MI0022694 |
| 336 | hsa-mir- 6769a | MI0022614 |
| 337 | hsa-mir-4327 | MI0015867 |
| 338 | hsa-mir-6765 | MI0022610 |
| 339 | hsa-mir-6716 | MI0022550 |
| 340 | hsa-mir-6877 | MI0022724 |
| 341 | hsa-mir-6727 | MI0022572 |
| 342 | hsa-mir-4534 | MI0016901 |
| 343 | hsa-mir-614 | MI0003627 |
| 344 | hsa-mir-1202 | MI0006334 |
| 345 | hsa-mir-575 | MI0003582 |
| 346 | hsa-mir-6870 | MI0022717 |
| 347 | hsa-mir-6722 | MI0022557 |
| 348 | hsa-mir-7977 | MI0025753 |
| 349 | hsa-mir-4649 | MI0017276 |
| 350 | hsa-mir-4675 | MI0017306 |
| 351 | hsa-mir-6075 | MI0020352 |
| 352 | hsa-mir-6779 | MI0022624 |
| 353 | hsa-mir-4271 | MI0015879 |
| 354 | hsa-mir-3196 | MI0014241 |
| 355 | hsa-mir-6803 | MI0022648 |
| 356 | hsa-mir-6789 | MI0022634 |
| 357 | hsa-mir-4648 | MI0017275 |
| 358 | hsa-mir-4508 | MI0016872 |
| 359 | hsa-mir-4749 | MI0017388 |
| 360 | hsa-mir-4505 | MI0016868 |
| 361 | hsa-mir-5698 | MI0019305 |
| 362 | hsa-mir-1199 | MI0020340 |
| 363 | hsa-mir-4763 | MI0017404 |
| 364 | hsa-mir-1231 | MI0006321 |
| 365 | hsa-mir-1233-1 | MI0006323 |

TABLE 1-continued

| SEQ ID NO: | Gene name | miRBase registration No. |
|---|---|---|
| 366 | hsa-mir-1233-2 | MI0015973 |
| 367 | hsa-mir-150 | MI0000479 |
| 368 | hsa-mir-92a-2 | MI0000094 |
| 369 | hsa-mir-423 | MI0001445 |
| 370 | hsa-mir-1268a | MI0006405 |
| 371 | hsa-mir-128-2 | MI0000727 |
| 372 | hsa-mir-24-1 | MI0000080 |
| 373 | hsa-mir-24-2 | MI0000081 |
| 374 | hsa-mir-4697 | MI0017330 |
| 375 | hsa-mir-3197 | MI0014245 |
| 376 | hsa-mir-675 | MI0005416 |
| 377 | hsa-mir-4486 | MI0016847 |
| 378 | hsa-mir-7107 | MI0022958 |
| 379 | hsa-mir-23a | MI0000079 |
| 380 | hsa-mir-4667 | MI0017297 |
| 381 | hsa-mir-45la | MI0001729 |
| 382 | hsa-mir-3940 | MI0016597 |
| 383 | hsa-mir-8059 | MI0025895 |
| 384 | hsa-mir-6813 | MI0022658 |
| 385 | hsa-mir-4492 | MI0016854 |
| 386 | hsa-mir-4476 | MI0016828 |
| 387 | hsa-mir-6090 | MI0020367 |
| 388 | isomiR example 1 of SEQ ID NO: 5 | — |
| 389 | isomiR example 2 of SEQ ID NO: 5 | — |
| 390 | isomiR example 1 of SEQ ID NO: 7 | — |
| 391 | isomiR example 2 of SEQ ID NO: 7 | — |
| 392 | isomiR example 1 of SEQ ID NO: 8 | — |
| 393 | isomiR example 2 of SEQ ID NO: 8 | — |
| 394 | isomiR example 1 of SEQ ID NO: 9 | — |
| 395 | isomiR example 2 of SEQ ID NO: 9 | — |
| 396 | isomiR example 1 of SEQ ID NO: 11 | — |
| 397 | isomiR example 2 of SEQ ID NO: 11 | — |
| 398 | isomiR example 1 of SEQ ID NO: 16 | — |
| 399 | isomiR example 2 of SEQ ID NO: 16 | — |
| 400 | isomiR example 1 of SEQ ID NO: 19 | — |
| 401 | isomiR example 2 of SEQ ID NO: 19 | — |
| 402 | isomiR example 1 of SEQ ID NO: 20 | — |
| 403 | isomiR example 2 of SEQ ID NO: 20 | — |
| 404 | isomiR example 1 of SEQ ID NO: 21 | — |
| 405 | isomiR example 2 of SEQ ID NO: 21 | — |
| 406 | isomiR example 1 of SEQ ID NO: 26 | — |
| 407 | isomiR example 2 of SEQ ID NO: 26 | — |
| 408 | isomiR example 1 of SEQ ID NO: 27 | — |
| 409 | isomiR example 2 of SEQ ID NO: 27 | — |
| 410 | isomiR example 1 of SEQ ID NO: 28 | — |
| 411 | isomiR example 2 of SEQ ID NO: 28 | — |
| 412 | isomiR example 1 of SEQ ID NO: 30 | — |
| 413 | isomiR example 2 of SEQ ID NO: 30 | — |
| 414 | isomiR example 1 of SEQ ID NO: 34 | — |
| 415 | isomiR example 2 of SEQ ID NO: 34 | — |
| 416 | isomiR example 1 of SEQ ID NO: 37 | — |
| 417 | isomiR example 2 of SEQ ID NO: 37 | — |
| 418 | isomiR example 1 of SEQ ID NO: 38 | — |
| 419 | isomiR example 2 of SEQ ID NO: 38 | — |
| 420 | isomiR example 1 of SEQ ID NO: 39 | — |
| 421 | isomiR example 2 of SEQ ID NO: 39 | — |
| 422 | isomiR example 1 of SEQ ID NO: 41 | — |
| 423 | isomiR example 2 of SEQ ID NO: 41 | — |
| 424 | isomiR example 1 of SEQ ID NO: 43 | — |
| 425 | isomiR example 2 of SEQ ID NO: 43 | — |
| 426 | isomiR example 1 of SEQ ID NO: 45 | — |
| 427 | isomiR example 2 of SEQ ID NO: 45 | — |
| 428 | isomiR example 1 of SEQ ID NO: 46 | — |
| 429 | isomiR example 2 of SEQ ID NO: 46 | — |
| 430 | isomiR example 1 of SEQ ID NO: 48 | — |
| 431 | isomiR example 2 of SEQ ID NO: 48 | — |
| 432 | isomiR example 1 of SEQ ID NO: 50 | — |
| 433 | isomiR example 2 of SEQ ID NO: 50 | — |
| 434 | isomiR example 1 of SEQ ID NO: 54 | — |
| 435 | isomiR example 2 of SEQ ID NO: 54 | — |
| 436 | isomiR example 1 of SEQ ID NO: 55 | — |
| 437 | isomiR example 2 of SEQ ID NO: 55 | — |
| 438 | isomiR example 1 of SEQ ID NO: 57 | — |
| 439 | isomiR example 2 of SEQ ID NO: 57 | — |
| 440 | isomiR example 1 of SEQ ID NO: 58 | — |
| 441 | isomiR example 2 of SEQ ID NO: 58 | — |
| 442 | isomiR example 1 of SEQ ID NO: 61 | — |

TABLE 1-continued

| SEQ ID NO: | Gene name | miRBase registration No. |
|---|---|---|
| 443 | isomiR example 2 of SEQ ID NO: 61 | — |
| 444 | isomiR example 1 of SEQ ID NO: 62 | — |
| 445 | isomiR example 2 of SEQ ID NO: 62 | — |
| 446 | isomiR example 1 of SEQ ID NO: 63 | — |
| 447 | isomiR example 2 of SEQ ID NO: 63 | — |
| 448 | isomiR example 1 of SEQ ID NO: 64 | — |
| 449 | isomiR example 2 of SEQ ID NO: 64 | — |
| 450 | isomiR example 1 of SEQ ID NO: 65 | — |
| 451 | isomiR example 2 of SEQ ID NO: 65 | — |
| 452 | isomiR example 1 of SEQ ID NO: 66 | — |
| 453 | isomiR example 2 of SEQ ID NO: 66 | — |
| 454 | isomiR example 1 of SEQ ID NO: 67 | — |
| 455 | isomiR example 2 of SEQ ID NO: 67 | — |
| 456 | isomiR example 1 of SEQ ID NO: 69 | — |
| 457 | isomiR example 2 of SEQ ID NO: 69 | — |
| 458 | isomiR example 1 of SEQ ID NO: 70 | — |
| 459 | isomiR example 2 of SEQ ID NO: 70 | — |
| 460 | isomiR example 1 of SEQ ID NO: 71 | — |
| 461 | isomiR example 2 of SEQ ID NO: 71 | — |
| 462 | isomiR example 1 of SEQ ID NO: 73 | — |
| 463 | isomiR example 2 of SEQ ID NO: 73 | — |
| 464 | isomiR example 1 of SEQ ID NO: 74 | — |
| 465 | isomiR example 2 of SEQ ID NO: 74 | — |
| 466 | isomiR example 1 of SEQ ID NO: 76 | — |
| 467 | isomiR example 2 of SEQ ID NO: 76 | — |
| 468 | isomiR example 1 of SEQ ID NO: 77 | — |
| 469 | isomiR example 2 of SEQ ID NO: 77 | — |
| 470 | isomiR example 1 of SEQ ID NO: 78 | — |
| 471 | isomiR example 2 of SEQ ID NO: 78 | — |
| 472 | isomiR example 1 of SEQ ID NO: 80 | — |
| 473 | isomiR example 2 of SEQ ID NO: 80 | — |
| 474 | isomiR example 1 of SEQ ID NO: 81 | — |
| 475 | isomiR example 2 of SEQ ID NO: 81 | — |
| 476 | isomiR example 1 of SEQ ID NO: 82 | — |
| 477 | isomiR example 2 of SEQ ID NO: 82 | — |
| 478 | isomiR example 1 of SEQ ID NO: 84 | — |
| 479 | isomiR example 2 of SEQ ID NO: 84 | — |
| 480 | isomiR example 1 of SEQ ID NO: 85 | — |
| 481 | isomiR example 2 of SEQ ID NO: 85 | — |
| 482 | isomiR example 1 of SEQ ID NO: 86 | — |
| 483 | isomiR example 2 of SEQ ID NO: 86 | — |
| 484 | isomiR example 1 of SEQ ID NO: 88 | — |
| 485 | isomiR example 2 of SEQ ID NO: 88 | — |
| 486 | isomiR example 1 of SEQ ID NO: 89 | — |
| 487 | isomiR example 2 of SEQ ID NO: 89 | — |
| 488 | isomiR example 1 of SEQ ID NO: 94 | — |
| 489 | isomiR example 2 of SEQ ID NO: 94 | — |
| 490 | isomiR example 1 of SEQ ID NO: 95 | — |
| 491 | isomiR example 2 of SEQ ID NO: 95 | — |
| 492 | isomiR example 1 of SEQ ID NO: 97 | — |
| 493 | isomiR example 2 of SEQ ID NO: 97 | — |
| 494 | isomiR example 1 of SEQ ID NO: 98 | — |
| 495 | isomiR example 2 of SEQ ID NO: 98 | — |
| 496 | isomiR example 1 of SEQ ID NO: 99 | — |
| 497 | isomiR example 2 of SEQ ID NO: 99 | — |
| 498 | isomiR example 1 of SEQ ID NO: 100 | — |
| 499 | isomiR example 2 of SEQ ID NO: 100 | — |
| 500 | isomiR example 1 of SEQ ID NO: 101 | — |
| 501 | isomiR example 2 of SEQ ID NO: 101 | — |
| 502 | isomiR example 1 of SEQ ID NO: 104 | — |
| 503 | isomiR example 2 of SEQ ID NO: 104 | — |
| 504 | isomiR example 1 of SEQ ID NO: 107 | — |
| 505 | isomiR example 2 of SEQ ID NO: 107 | — |
| 506 | isomiR example 1 of SEQ ID NO: 108 | — |
| 507 | isomiR example 2 of SEQ ID NO: 108 | — |
| 508 | isomiR example 1 of SEQ ID NO: 109 | — |
| 509 | isomiR example 2 of SEQ ID NO: 109 | — |
| 510 | isomiR example 1 of SEQ ID NO: 110 | — |
| 511 | isomiR example 2 of SEQ ID NO: 110 | — |
| 512 | isomiR example 1 of SEQ ID NO: 111 | — |
| 513 | isomiR example 2 of SEQ ID NO: 111 | — |
| 514 | isomiR example 1 of SEQ ID NO: 112 | — |
| 515 | isomiR example 2 of SEQ ID NO: 112 | — |
| 516 | isomiR example 1 of SEQ ID NO: 113 | — |
| 517 | isomiR example 2 of SEQ ID NO: 113 | — |
| 518 | isomiR example 1 of SEQ ID NO: 115 | — |
| 519 | isomiR example 2 of SEQ ID NO: 115 | — |

TABLE 1-continued

| SEQ ID NO: | Gene name | miRBase registration No. |
|---|---|---|
| 520 | isomiR example 1 of SEQ ID NO: 116 | — |
| 521 | isomiR example 2 of SEQ ID NO: 116 | — |
| 522 | isomiR example 1 of SEQ ID NO: 117 | — |
| 523 | isomiR example 2 of SEQ ID NO: 117 | — |
| 524 | isomiR example 1 of SEQ ID NO: 119 | — |
| 525 | isomiR example 2 of SEQ ID NO: 119 | — |
| 526 | isomiR example 1 of SEQ ID NO: 120 | — |
| 527 | isomiR example 2 of SEQ ID NO: 120 | — |
| 528 | isomiR example 1 of SEQ ID NO: 123 | — |
| 529 | isomiR example 2 of SEQ ID NO: 123 | — |
| 530 | isomiR example 1 of SEQ ID NO: 125 | — |
| 531 | isomiR example 2 of SEQ ID NO: 125 | — |
| 532 | isomiR example 1 of SEQ ID NO: 131 | — |
| 533 | isomiR example 2 of SEQ ID NO: 131 | — |
| 534 | isomiR example 1 of SEQ ID NO: 132 | — |
| 535 | isomiR example 2 of SEQ ID NO: 132 | — |
| 536 | isomiR example 1 of SEQ ID NO: 133 | — |
| 537 | isomiR example 2 of SEQ ID NO: 133 | — |
| 538 | isomiR example 1 of SEQ ID NO: 135 | — |
| 539 | isomiR example 2 of SEQ ID NO: 135 | — |
| 540 | isomiR example 1 of SEQ ID NO: 136 | — |
| 541 | isomiR example 2 of SEQ ID NO: 136 | — |
| 542 | isomiR example 1 of SEQ ID NO: 137 | — |
| 543 | isomiR example 2 of SEQ ID NO: 137 | — |
| 544 | isomiR example 1 of SEQ ID NO: 140 | — |
| 545 | isomiR example 2 of SEQ ID NO: 140 | — |
| 546 | isomiR example 1 of SEQ ID NO: 141 | — |
| 547 | isomiR example 2 of SEQ ID NO: 141 | — |
| 548 | isomiR example 1 of SEQ ID NO: 142 | — |
| 549 | isomiR example 2 of SEQ ID NO: 142 | — |
| 550 | isomiR example 1 of SEQ ID NO: 147 | — |
| 551 | isomiR example 2 of SEQ ID NO: 147 | — |
| 552 | isomiR example 1 of SEQ ID NO: 151 | — |
| 553 | isomiR example 2 of SEQ ID NO: 151 | — |
| 554 | isomiR example 1 of SEQ ID NO: 152 | — |
| 555 | isomiR example 2 of SEQ ID NO: 152 | — |
| 556 | isomiR example 1 of SEQ ID NO: 157 | — |
| 557 | isomiR example 2 of SEQ ID NO: 157 | — |
| 558 | isomiR example 1 of SEQ ID NO: 161 | — |
| 559 | isomiR example 2 of SEQ ID NO: 161 | — |
| 560 | isomiR example 1 of SEQ ID NO: 162 | — |
| 561 | isomiR example 2 of SEQ ID NO: 162 | — |
| 562 | isomiR example 1 of SEQ ID NO: 165 | — |
| 563 | isomiR example 2 of SEQ ID NO: 165 | — |
| 564 | isomiR example 1 of SEQ ID NO: 166 | — |
| 565 | isomiR example 2 of SEQ ID NO: 166 | — |
| 566 | isomiR example 1 of SEQ ID NO: 167 | — |
| 567 | isomiR example 2 of SEQ ID NO: 167 | — |
| 568 | isomiR example 1 of SEQ ID NO: 168 | — |
| 569 | isomiR example 2 of SEQ ID NO: 168 | — |
| 570 | isomiR example 1 of SEQ ID NO: 169 | — |
| 571 | isomiR example 2 of SEQ ID NO: 169 | — |
| 572 | isomiR example 1 of SEQ ID NO: 171 | — |
| 573 | isomiR example 2 of SEQ ID NO: 171 | — |
| 574 | isomiR example 1 of SEQ ID NO: 173 | — |
| 575 | isomiR example 2 of SEQ ID NO: 173 | — |
| 576 | isomiR example 1 of SEQ ID NO: 174 | — |
| 577 | isomiR example 2 of SEQ ID NO: 174 | — |
| 578 | isomiR example 1 of SEQ ID NO: 176 | — |
| 579 | isomiR example 2 of SEQ ID NO: 176 | — |
| 580 | isomiR example 1 of SEQ ID NO: 177 | — |
| 581 | isomiR example 2 of SEQ ID NO: 177 | — |
| 582 | isomiR example 1 of SEQ ID NO: 178 | — |
| 583 | isomiR example 2 of SEQ ID NO: 178 | — |
| 584 | isomiR example 1 of SEQ ID NO: 179 | — |
| 585 | isomiR example 2 of SEQ ID NO: 179 | — |
| 586 | isomiR example 1 of SEQ ID NO: 180 | — |
| 587 | isomiR example 2 of SEQ ID NO: 180 | — |
| 588 | isomiR example 1 of SEQ ID NO: 182 | — |
| 589 | isomiR example 2 of SEQ ID NO: 182 | — |
| 590 | isomiR example 1 of SEQ ID NO: 183 | — |
| 591 | isomiR example 2 of SEQ ID NO: 183 | — |
| 592 | isomiR example 1 of SEQ ID NO: 184 | — |
| 593 | isomiR example 2 of SEQ ID NO: 184 | — |
| 594 | isomiR example 1 of SEQ ID NO: 186 | — |
| 595 | isomiR example 2 of SEQ ID NO: 186 | — |
| 596 | isomiR example 1 of SEQ ID NO: 187 | — |

TABLE 1-continued

| SEQ ID NO: | Gene name | miRBase registration No. |
|---|---|---|
| 597 | isomiR example 2 of SEQ ID NO: 187 | — |
| 598 | isomiR example 1 of SEQ ID NO: 188 | — |
| 599 | isomiR example 2 of SEQ ID NO: 188 | — |
| 600 | isomiR example 1 of SEQ ID NO: 189 | — |
| 601 | isomiR example 2 of SEQ ID NO: 189 | — |
| 602 | isomiR example 1 of SEQ ID NO: 192 | — |
| 603 | isomiR example 2 of SEQ ID NO: 192 | — |
| 604 | isomiR example 1 of SEQ ID NO: 193 | — |
| 605 | isomiR example 2 of SEQ ID NO: 193 | — |
| 606 | hsa-miR-6836-3p | MIMAT0027575 |
| 607 | hsa-miR-3195 | MIMAT0015079 |
| 608 | hsa-miR-718 | MIMAT0012735 |
| 609 | hsa-miR-3178 | MIMAT0015055 |
| 610 | hsa-miR-638 | MIMAT0003308 |
| 611 | hsa-miR-4497 | MIMAT0019032 |
| 612 | hsa-miR-6085 | MIMAT0023710 |
| 613 | hsa-miR-6752-5p | MIMAT0027404 |
| 614 | hsa-miR-135a-3p | MIMAT0004595 |
| 615 | hsa-mir-6836 | MI0022682 |
| 616 | hsa-mir-3195 | MI0014240 |
| 617 | hsa-mir-718 | MI0012489 |
| 618 | hsa-mir-3178 | MI0014212 |
| 619 | hsa-mir-638 | MI0003653 |
| 620 | hsa-mir-4497 | MI0016859 |
| 621 | hsa-mir-6085 | MI0020362 |
| 622 | hsa-mir-6752 | MI0022597 |
| 623 | hsa-mir-135a | MI0000452 |
| 624 | isomiR example 1 of SEQ ID NO: 607 | — |
| 625 | isomiR example 2 of SEQ ID NO: 607 | — |
| 626 | isomiR example 1 of SEQ ID NO: 608 | — |
| 627 | isomiR example 2 of SEQ ID NO: 608 | — |
| 628 | isomiR example 1 of SEQ ID NO: 609 | — |
| 629 | isomiR example 2 of SEQ ID NO: 609 | — |
| 630 | isomiR example 1 of SEQ ID NO: 610 | — |
| 631 | isomiR example 2 of SEQ ID NO: 610 | — |
| 632 | isomiR example 1 of SEQ ID NO: 611 | — |
| 633 | isomiR example 2 of SEQ ID NO: 611 | — |
| 634 | isomiR example 1 of SEQ ID NO: 614 | — |
| 635 | isomiR example 2 of SEQ ID NO: 614 | — |

The present specification encompasses the contents described in the specifications and/or drawings of Japanese Patent Application No. 2014-122686 and Japanese Patent Application No. 2015-070182 on which the priority of the present application is based.

Advantageous Effects of Invention

According to the present invention, colorectal cancer can be detected easily and highly accurately.

For example, the presence or absence of colorectal cancer in a patient can be easily detected by using, as an index, the expression level measurement values of several miRNAs in blood, serum, and/or plasma of the patient, which can be collected with limited invasiveness.

DESCRIPTION OF EMBODIMENTS

Figure 1:
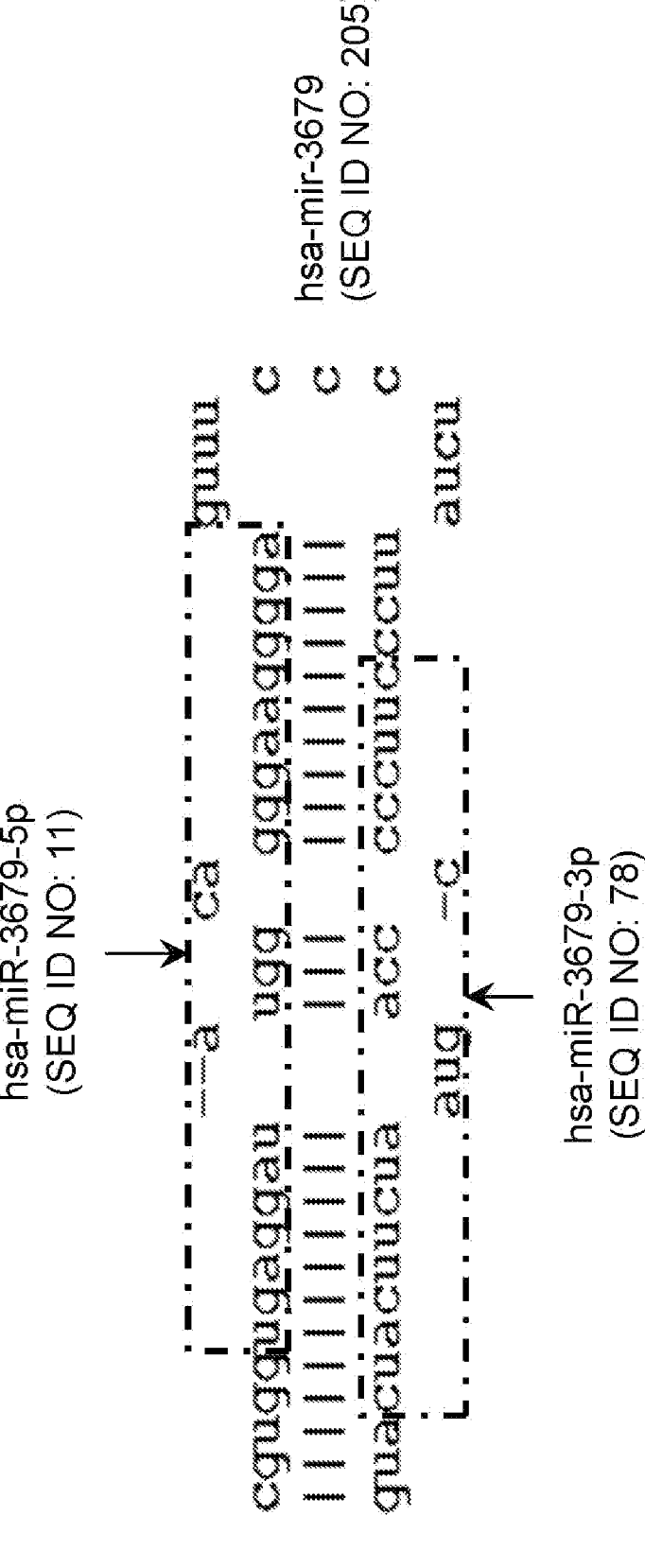
FIG. 1 This figure shows the relationship between the nucleotide sequences of hsa-miR-3679-5p represented by SEQ ID NO: 11 and hsa-miR-3679-3p represented by SEQ ID NO: 78, which are produced from a precursor hsa-mir-3679 represented by SEQ ID NO: 205.

Hereinafter, the present invention will be described further specifically.

1. Target Nucleic Acid for Colorectal Cancer

A primary target nucleic acid as a colorectal cancer marker for detecting the presence and/or absence of colorectal cancer or colorectal cancer cells using the nucleic acid probe or the primer for the detection of colorectal cancer defined above according to the present invention can use at least one or more miRNA(s) selected from the group consisting of hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p. Furthermore, at least one or more miRNA(s) selected from the group consisting of other colorectal cancer markers that can be combined with these miRNAs, i.e., hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p and hsa-miR-24-3p can also be preferably used as a target nucleic acid. Moreover, at least one or more miRNA(s) selected from the group consisting of other colorectal cancer markers that can be combined with these miRNAs, i.e., hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476 and hsa-miR-6090 can also be preferably used as a target nucleic acid.

These miRNAs include, for example, a human gene comprising a nucleotide sequence represented by any of SEQ ID NOs: 1 to 194 and 606 to 614 (i.e., hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p, hsa-miR-24-3p, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR- 4492, hsa-miR-4476, hsa-miR-6090, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p, respectively), a congener thereof, a transcript thereof, and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 635 or a transcript thereof, more preferably the transcript, i.e., a miRNA or its precursor RNA (pri-miRNA or pre-miRNA).

The first target gene is the hsa-miR-6726-5p gene, a congener thereof, a transcript thereof, or a variant or a derivative thereof. None of the previously known reports show that change in the expression of the gene or the transcript thereof can serve as a marker for colorectal cancer.

The second target gene is the hsa-miR-4257 gene, a congener thereof, a transcript thereof, or a variant or a derivative thereof. None of the previously known reports show that change in the expression of the gene or the transcript thereof can serve as a marker for colorectal cancer.

The third target gene is the hsa-miR-6787-5p gene, a congener thereof, a transcript thereof, or a variant or a derivative thereof. None of the previously known reports show that change in the expression of the gene or the transcript thereof can serve as a marker for colorectal cancer.

The fourth target gene is the hsa-miR-6780b-5p gene, a congener thereof, a transcript thereof, or a variant or a derivative thereof. None of the previously known reports show that change in the expression of the gene or the transcript thereof can serve as a marker for colorectal cancer.

The fifth target gene is the hsa-miR-3131 gene, a congener thereof, a transcript thereof, or a variant or a derivative thereof. None of the previously known reports show that change in the expression of the gene or the transcript thereof can serve as a marker for colorectal cancer.

The sixth target gene is the hsa-miR-7108-5p gene, a congener thereof, a transcript thereof, or a variant or a derivative thereof. None of the previously known reports show that change in the expression of the gene or the transcript thereof can serve as a marker for colorectal cancer.

The seventh target gene is the hsa-miR-1343-3p gene, a congener thereof, a transcript thereof, or a variant or a derivative thereof. None of the previously known reports show that change in the expression of the gene or the transcript thereof can serve as a marker for colorectal cancer.

The eighth target gene is the hsa-miR-1247-3p gene, a congener thereof, a transcript thereof, or a variant or a derivative thereof. None of the previously known reports show that change in the expression of the gene or the transcript thereof can serve as a marker for colorectal cancer.

The ninth target gene is the hsa-miR-4651 gene, a congener thereof, a transcript thereof, or a variant or a derivative thereof. None of the previously known reports show that change in the expression of the gene or the transcript thereof can serve as a marker for colorectal cancer.

The 10th target gene is the hsa-miR-6757-5p gene, a congener thereof, a transcript thereof, or a variant or a derivative thereof. None of the previously known reports show that change in the expression of the gene or the transcript thereof can serve as a marker for colorectal cancer.

The 11th target gene is the hsa-miR-3679-5p gene, a congener thereof, a transcript thereof, or a variant or a derivative thereof. None of the previously known reports show that change in the expression of the gene or the transcript thereof can serve as a marker for colorectal cancer.

The 12th target gene is the hsa-miR-7641 gene, a congener thereof, a transcript thereof, or a variant or a derivative thereof. None of the previously known reports show that change in the expression of the gene or the transcript thereof can serve as a marker for colorectal cancer.

The 13th target gene is the hsa-miR-6746-5p gene, a congener thereof, a transcript thereof, or a variant or a derivative thereof. None of the previously known reports show that change in the expression of the gene or the transcript thereof can serve as a marker for colorectal cancer.

The 14th target gene is the hsa-miR-8072 gene, a congener thereof, a transcript thereof, or a variant or a derivative thereof. None of the previously known reports show that change in the expression of the gene or the transcript thereof can serve as a marker for colorectal cancer.

The 15th target gene is the hsa-miR-6741-5p gene, a congener thereof, a transcript thereof, or a variant or a derivative thereof. None of the previously known reports show that change in the expression of the gene or the transcript thereof can serve as a marker for colorectal cancer.

The 16th target gene is the hsa-miR-1908-5p gene, a congener thereof, a transcript thereof, or a variant or a derivative thereof. None of the previously known reports show that change in the expression of the gene or the transcript thereof can serve as a marker for colorectal cancer.

The 17th target gene is the hsa-miR-6857-5p gene, a congener thereof, a transcript thereof, or a variant or a derivative thereof. None of the previously known reports show that change in the expression of the gene or the transcript thereof can serve as a marker for colorectal cancer.

The 18th target gene is the hsa-miR-4746-3p gene, a congener thereof, a transcript thereof, or a variant or a derivative thereof. None of the previously known reports show that change in the expression of the gene or the transcript thereof can serve as a marker for colorectal cancer.

The 19th target gene is the hsa-miR-744-5p gene, a congener thereof, a transcript thereof, or a variant or a derivative thereof. None of the previously known reports show that change in the expression of the gene or the transcript thereof can serve as a marker for colorectal cancer.

The 20th target gene is the hsa-miR-4792 gene, a congener thereof, a transcript thereof, or a variant or a derivative thereof. None of the previously known reports show that change in the expression of the gene or the transcript thereof can serve as a marker for colorectal cancer.

The 21st target gene is the hsa-miR-564 gene, a congener thereof, a transcript thereof, or a variant or a derivative thereof. None of the previously known reports show that change in the expression of the gene or the transcript thereof can serve as a marker for colorectal cancer.

The 22nd target gene is the hsa-miR-6791-5p gene, a congener thereof, a transcript thereof, or a variant or a derivative thereof. None of the previously known reports show that change in the expression of the gene or the transcript thereof can serve as a marker for colorectal cancer.

The 23rd target gene is the hsa-miR-6825-5p gene, a congener thereof, a transcript thereof, or a variant or a derivative thereof. None of the previously known reports show that change in the expression of the gene or the transcript thereof can serve as a marker for colorectal cancer.

The 24th target gene is the hsa-miR-6826-5p gene, a congener thereof, a transcript thereof, or a variant or a derivative thereof. None of the previously known reports show that change in the expression of the gene or the transcript thereof can serve as a marker for colorectal cancer.

The 25th target gene is the hsa-miR-4665-3p gene, a congener thereof, a transcript thereof, or a variant or a derivative thereof. None of the previously known reports show that change in the expression of the gene or the transcript thereof can serve as a marker for colorectal cancer.

The 26th target gene is the hsa-miR-4467 gene, a congener thereof, a transcript thereof, or a variant or a derivative thereof. None of the previously known reports show that change in the expression of the gene or the transcript thereof can serve as a marker for colorectal cancer.

The 27th target gene is the hsa-miR-3188 gene, a congener thereof, a transcript thereof, or a variant or a derivative thereof. None of the previously known reports show that change in the expression of the gene or the transcript thereof can serve as a marker for colorectal cancer.

The 28th target gene is the hsa-miR-6125 gene, a congener thereof, a transcript thereof, or a variant or a derivative thereof. None of the previously known reports show that change in the expression of the gene or the transcript thereof can serve as a marker for colorectal cancer.

The 29th target gene is the hsa-miR-6756-5p gene, a congener thereof, a transcript thereof, or a variant or a derivative thereof. None of the previously known reports show that change in the expression of the gene or the transcript thereof can serve as a marker for colorectal cancer.

The 30th target gene is the hsa-miR-1228-3p gene, a congener thereof, a transcript thereof, or a variant or a derivative thereof. None of the previously known reports show that change in the expression of the gene or the transcript thereof can serve as a marker for colorectal cancer.

The 31st target gene is the hsa-miR-8063 gene, a congener thereof, a transcript thereof, or a variant or a derivative thereof. None of the previously known reports show that change in the expression of the gene or the transcript thereof can serve as a marker for colorectal cancer.

The 32nd target gene is the hsa-miR-8069 gene, a congener thereof, a transcript thereof, or a variant or a derivative thereof. None of the previously known reports show that change in the expression of the gene or the transcript thereof can serve as a marker for colorectal cancer.

The 33rd target gene is the hsa-miR-6875-5p gene, a congener thereof, a transcript thereof, or a variant or a derivative thereof. None of the previously known reports show that change in the expression of the gene or the transcript thereof can serve as a marker for colorectal cancer.

The 34th target gene is the hsa-miR-3185 gene, a congener thereof, a transcript thereof, or a variant or a derivative thereof. None of the previously known reports show that change in the expression of the gene or the transcript thereof can serve as a marker for colorectal cancer.

The 35th target gene is the hsa-miR-4433b-3p gene, a congener thereof, a transcript thereof, or a variant or a derivative thereof. None of the previously known reports show that change in the expression of the gene or the transcript thereof can serve as a marker for colorectal cancer.

The 36th target gene is the hsa-miR-6887-5p gene, a congener thereof, a transcript thereof, or a variant or a derivative thereof. None of the previously known reports show that change in the expression of the gene or the transcript thereof can serve as a marker for colorectal cancer.

The 37th target gene is the hsa-miR-128-1-5p gene, a congener thereof, a transcript thereof, or a variant or a derivative thereof. None of the previously known reports show that change in the expression of the gene or the transcript thereof can serve as a marker for colorectal cancer.

The 38th target gene is the hsa-miR-6724-5p gene, a congener thereof, a transcript thereof, or a variant or a derivative thereof. None of the previously known reports show that change in the expression of the gene or the transcript thereof can serve as a marker for colorectal cancer.

The 39th target gene is the hsa-miR-1914-3p gene, a congener thereof, a transcript thereof, or a variant or a derivative thereof. None of the previously known reports show that change in the expression of the gene or the transcript thereof can serve as a marker for colorectal cancer.

The 40th target gene is the hsa-miR-1225-5p gene, a congener thereof, a transcript thereof, or a variant or a derivative thereof. None of the previously known reports show that change in the expression of the gene or the transcript thereof can serve as a marker for colorectal cancer.

The 41st target gene is the hsa-miR-4419b gene, a congener thereof, a transcript thereof, or a variant or a derivative thereof. None of the previously known reports show that change in the expression of the gene or the transcript thereof can serve as a marker for colorectal cancer.

The 42nd target gene is the hsa-miR-7110-5p gene, a congener thereof, a transcript thereof, or a variant or a derivative thereof. None of the previously known reports show that change in the expression of the gene or the transcript thereof can serve as a marker for colorectal cancer.

The 43rd target gene is the hsa-miR-187-5p gene, a congener thereof, a transcript thereof, or a variant or a derivative thereof. None of the previously known reports show that change in the expression of the gene or the transcript thereof can serve as a marker for colorectal cancer.

The 44th target gene is the hsa-miR-3184-5p gene, a congener thereof, a transcript thereof, or a variant or a derivative thereof. None of the previously known reports show that change in the expression of the gene or the transcript thereof can serve as a marker for colorectal cancer.

The 45th target gene is the hsa-miR-204-3p gene, a congener thereof, a transcript thereof, or a variant or a derivative thereof. None of the previously known reports show that change in the expression of the gene or the transcript thereof can serve as a marker for colorectal cancer.

The 46th target gene is the hsa-miR-5572 gene, a congener thereof, a transcript thereof, or a variant or a derivative thereof. None of the previously known reports show that change in the expression of the gene or the transcript thereof can serve as a marker for colorectal cancer.

The 47th target gene is the hsa-miR-6729-5p gene, a congener thereof, a transcript thereof, or a variant or a derivative thereof. None of the previously known reports show that change in the expression of the gene or the transcript thereof can serve as a marker for colorectal cancer.

The 48th target gene is the hsa-miR-615-5p gene, a congener thereof, a transcript thereof, or a variant or a derivative thereof. None of the previously known reports show that change in the expression of the gene or the transcript thereof can serve as a marker for colorectal cancer.

The 49th target gene is the hsa-miR-6749-5p gene, a congener thereof, a transcript thereof, or a variant or a derivative thereof. None of the previously known reports show that change in the expression of the gene or the transcript thereof can serve as a marker for colorectal cancer.

The 50th target gene is the hsa-miR-6515-3p gene, a congener thereof, a transcript thereof, or a variant or a derivative thereof. None of the previously known reports show that change in the expression of the gene or the transcript thereof can serve as a marker for colorectal cancer.

The 51st target gene is the hsa-miR-3937 gene, a congener thereof, a transcript thereof, or a variant or a derivative thereof. None of the previously known reports show that change in the expression of the gene or the transcript thereof can serve as a marker for colorectal cancer.

The 52nd target gene is the hsa-miR-6840-3p gene, a congener thereof, a transcript thereof, or a variant or a derivative thereof. None of the previously known reports show that change in the expression of the gene or the transcript thereof can serve as a marker for colorectal cancer.

The 53rd target gene is the hsa-miR-6893-5p gene, a congener thereof, a transcript thereof, or a variant or a derivative thereof. None of the previously known reports show that change in the expression of the gene or the transcript thereof can serve as a marker for colorectal cancer.

The 54th target gene is the hsa-miR-4728-5p gene, a congener thereof, a transcript thereof, or a variant or a derivative thereof. None of the previously known reports show that change in the expression of the gene or the transcript thereof can serve as a marker for colorectal cancer.

The 55th target gene is the hsa-miR-6717-5p gene, a congener thereof, a transcript thereof, or a variant or a derivative thereof. None of the previously known reports show that change in the expression of the gene or the transcript thereof can serve as a marker for colorectal cancer.

The 56th target gene is the hsa-miR-7113-3p gene, a congener thereof, a transcript thereof, or a variant or a derivative thereof. None of the previously known reports show that change in the expression of the gene or the transcript thereof can serve as a marker for colorectal cancer.

The 57th target gene is the hsa-miR-4665-5p gene, a congener thereof, a transcript thereof, or a variant or a derivative thereof. None of the previously known reports show that change in the expression of the gene or the transcript thereof can serve as a marker for colorectal cancer.

The 58th target gene is the hsa-miR-642b-3p gene, a congener thereof, a transcript thereof, or a variant or a derivative thereof. None of the previously known reports show that change in the expression of the gene or the transcript thereof can serve as a marker for colorectal cancer.

The 59th target gene is the hsa-miR-7109-5p gene, a congener thereof, a transcript thereof, or a variant or a derivative thereof. None of the previously known reports show that change in the expression of the gene or the transcript thereof can serve as a marker for colorectal cancer.

The 60th target gene is the hsa-miR-6842-5p gene, a congener thereof, a transcript thereof, or a variant or a derivative thereof. None of the previously known reports show that change in the expression of the gene or the transcript thereof can serve as a marker for colorectal cancer.

The 61st target gene is the hsa-miR-4442 gene, a congener thereof, a transcript thereof, or a variant or a derivative thereof. None of the previously known reports show that change in the expression of the gene or the transcript thereof can serve as a marker for colorectal cancer.

The 62nd target gene is the hsa-miR-4433-3p gene, a congener thereof, a transcript thereof, or a variant or a derivative thereof. None of the previously known reports show that change in the expression of the gene or the transcript thereof can serve as a marker for colorectal cancer.

The 63rd target gene is the hsa-miR-4707-5p gene, a congener thereof, a transcript thereof, or a variant or a derivative thereof. None of the previously known reports show that change in the expression of the gene or the transcript thereof can serve as a marker for colorectal cancer.

The 64th target gene is the hsa-miR-6126 gene, a congener thereof, a transcript thereof, or a variant or a derivative thereof. None of the previously known reports show that change in the expression of the gene or the transcript thereof can serve as a marker for colorectal cancer.

The 65th target gene is the hsa-miR-4449 gene, a congener thereof, a transcript thereof, or a variant or a derivative thereof. None of the previously known reports show that change in the expression of the gene or the transcript thereof can serve as a marker for colorectal cancer.

The 66th target gene is the hsa-miR-4706 gene, a congener thereof, a transcript thereof, or a variant or a derivative thereof. None of the previously known reports show that change in the expression of the gene or the transcript thereof can serve as a marker for colorectal cancer.

The 67th target gene is the hsa-miR-1913 gene, a congener thereof, a transcript thereof, or a variant or a derivative thereof. None of the previously known reports show that change in the expression of the gene or the transcript thereof can serve as a marker for colorectal cancer.

The 68th target gene is the hsa-miR-602 gene, a congener thereof, a transcript thereof, or a variant or a derivative thereof. None of the previously known reports show that change in the expression of the gene or the transcript thereof can serve as a marker for colorectal cancer.

The 69th target gene is the hsa-miR-939-5p gene, a congener thereof, a transcript thereof, or a variant or a derivative thereof. None of the previously known reports show that change in the expression of the gene or the transcript thereof can serve as a marker for colorectal cancer.

The 70th target gene is the hsa-miR-4695-5p gene, a congener thereof, a transcript thereof, or a variant or a derivative thereof. None of the previously known reports show that change in the expression of the gene or the transcript thereof can serve as a marker for colorectal cancer.

The 71st target gene is the hsa-miR-711 gene, a congener thereof, a transcript thereof, or a variant or a derivative thereof. None of the previously known reports show that change in the expression of the gene or the transcript thereof can serve as a marker for colorectal cancer.

The 72nd target gene is the hsa-miR-6816-5p gene, a congener thereof, a transcript thereof, or a variant or a derivative thereof. None of the previously known reports show that change in the expression of the gene or the transcript thereof can serve as a marker for colorectal cancer.

The 73rd target gene is the hsa-miR-4632-5p gene, a congener thereof, a transcript thereof, or a variant or a derivative thereof. None of the previously known reports show that change in the expression of the gene or the transcript thereof can serve as a marker for colorectal cancer.

The 74th target gene is the hsa-miR-6721-5p gene, a congener thereof, a transcript thereof, or a variant or a derivative thereof. None of the previously known reports show that change in the expression of the gene or the transcript thereof can serve as a marker for colorectal cancer.

The 75th target gene is the hsa-miR-7847-3p gene, a congener thereof, a transcript thereof, or a variant or a derivative thereof. None of the previously known reports show that change in the expression of the gene or the transcript thereof can serve as a marker for colorectal cancer.

The 76th target gene is the hsa-miR-6132 gene, a congener thereof, a transcript thereof, or a variant or a derivative thereof. None of the previously known reports show that change in the expression of the gene or the transcript thereof can serve as a marker for colorectal cancer.

The 77th target gene is the hsa-miR-887-3p gene, a congener thereof, a transcript thereof, or a variant or a derivative thereof. None of the previously known reports show that change in the expression of the gene or the transcript thereof can serve as a marker for colorectal cancer.

The 78th target gene is the hsa-miR-3679-3p gene, a congener thereof, a transcript thereof, or a variant or a derivative thereof. None of the previously known reports show that change in the expression of the gene or the transcript thereof can serve as a marker for colorectal cancer.

The 79th target gene is the hsa-miR-6784-5p gene, a congener thereof, a transcript thereof, or a variant or a derivative thereof. None of the previously known reports show that change in the expression of the gene or the transcript thereof can serve as a marker for colorectal cancer.

The 80th target gene is the hsa-miR-1249 gene, a congener thereof, a transcript thereof, or a variant or a derivative thereof. None of the previously known reports show that change in the expression of the gene or the transcript thereof can serve as a marker for colorectal cancer.

The 81st target gene is the hsa-miR-937-5p gene, a congener thereof, a transcript thereof, or a variant or a derivative thereof. None of the previously known reports show that change in the expression of the gene or the transcript thereof can serve as a marker for colorectal cancer.

The 82nd target gene is the hsa-miR-5195-3p gene, a congener thereof, a transcript thereof, or a variant or a derivative thereof. None of the previously known reports show that change in the expression of the gene or the transcript thereof can serve as a marker for colorectal cancer.

The 83rd target gene is the hsa-miR-6732-5p gene, a congener thereof, a transcript thereof, or a variant or a derivative thereof. None of the previously known reports show that change in the expression of the gene or the transcript thereof can serve as a marker for colorectal cancer.

The 84th target gene is the hsa-miR-4417 gene, a congener thereof, a transcript thereof, or a variant or a derivative thereof. None of the previously known reports show that change in the expression of the gene or the transcript thereof can serve as a marker for colorectal cancer.

The 85th target gene is the hsa-miR-4281 gene, a congener thereof, a transcript thereof, or a variant or a derivative thereof. None of the previously known reports show that change in the expression of the gene or the transcript thereof can serve as a marker for colorectal cancer.

The 86th target gene is the hsa-miR-4734 gene, a congener thereof, a transcript thereof, or a variant or a derivative thereof. None of the previously known reports show that change in the expression of the gene or the transcript thereof can serve as a marker for colorectal cancer.

The 87th target gene is the hsa-miR-6766-3p gene, a congener thereof, a transcript thereof, or a variant or a derivative thereof. None of the previously known reports show that change in the expression of the gene or the transcript thereof can serve as a marker for colorectal cancer.

The 88th target gene is the hsa-miR-663a gene, a congener thereof, a transcript thereof, or a variant or a derivative thereof. None of the previously known reports show that change in the expression of the gene or the transcript thereof can serve as a marker for colorectal cancer.

The 89th target gene is the hsa-miR-4513 gene, a congener thereof, a transcript thereof, or a variant or a derivative thereof. None of the previously known reports show that change in the expression of the gene or the transcript thereof can serve as a marker for colorectal cancer.

The 90th target gene is the hsa-miR-6781-5p gene, a congener thereof, a transcript thereof, or a variant or a derivative thereof. None of the previously known reports show that change in the expression of the gene or the transcript thereof can serve as a marker for colorectal cancer.

The 91 st target gene is the hsa-miR-1227-5p gene, a congener thereof, a transcript thereof, or a variant or a derivative thereof. None of the previously known reports show that change in the expression of the gene or the transcript thereof can serve as a marker for colorectal cancer.

The 92nd target gene is the hsa-miR-6845-5p gene, a congener thereof, a transcript thereof, or a variant or a derivative thereof. None of the previously known reports show that change in the expression of the gene or the transcript thereof can serve as a marker for colorectal cancer.

The 93rd target gene is the hsa-miR-6798-5p gene, a congener thereof, a transcript thereof, or a variant or a derivative thereof. None of the previously known reports show that change in the expression of the gene or the transcript thereof can serve as a marker for colorectal cancer.

The 94th target gene is the hsa-miR-3620-5p gene, a congener thereof, a transcript thereof, or a variant or a derivative thereof. None of the previously known reports show that change in the expression of the gene or the transcript thereof can serve as a marker for colorectal cancer.

The 95th target gene is the hsa-miR-1915-5p gene, a congener thereof, a transcript thereof, or a variant or a derivative thereof. None of the previously known reports show that change in the expression of the gene or the transcript thereof can serve as a marker for colorectal cancer.

The 96th target gene is the hsa-miR-4294 gene, a congener thereof, a transcript thereof, or a variant or a derivative thereof. None of the previously known reports show that change in the expression of the gene or the transcript thereof can serve as a marker for colorectal cancer.

The 97th target gene is the hsa-miR-642a-3p gene, a congener thereof, a transcript thereof, or a variant or a derivative thereof. None of the previously known reports show that change in the expression of the gene or the transcript thereof can serve as a marker for colorectal cancer.

The 98th target gene is the hsa-miR-371a-5p gene, a congener thereof, a transcript thereof, or a variant or a derivative thereof. None of the previously known reports show that change in the expression of the gene or the transcript thereof can serve as a marker for colorectal cancer.

The 99th target gene is the hsa-miR-940 gene, a congener thereof, a transcript thereof, or a variant or a derivative thereof. None of the previously known reports show that change in the expression of the gene or the transcript thereof can serve as a marker for colorectal cancer.

The 100th target gene is the hsa-miR-4450 gene, a congener thereof, a transcript thereof, or a variant or a derivative thereof. None of the previously known reports show that change in the expression of the gene or the transcript thereof can serve as a marker for colorectal cancer.

The 101st target gene is the hsa-miR-4723-5p gene, a congener thereof, a transcript thereof, or a variant or a derivative thereof. None of the previously known reports show that change in the expression of the gene or the transcript thereof can serve as a marker for colorectal cancer.

The 102nd target gene is the hsa-miR-1469 gene, a congener thereof, a transcript thereof, or a variant or a derivative thereof. None of the previously known reports show that change in the expression of the gene or the transcript thereof can serve as a marker for colorectal cancer.

The 103rd target gene is the hsa-miR-6861-5p gene, a congener thereof, a transcript thereof, or a variant or a derivative thereof. None of the previously known reports show that change in the expression of the gene or the transcript thereof can serve as a marker for colorectal cancer.

The 104th target gene is the hsa-miR-7975 gene, a congener thereof, a transcript thereof, or a variant or a derivative thereof. None of the previously known reports show that change in the expression of the gene or the transcript thereof can serve as a marker for colorectal cancer.

The 105th target gene is the hsa-miR-6879-5p gene, a congener thereof, a transcript thereof, or a variant or a derivative thereof. None of the previously known reports show that change in the expression of the gene or the transcript thereof can serve as a marker for colorectal cancer.

The 106th target gene is the hsa-miR-6802-5p gene, a congener thereof, a transcript thereof, or a variant or a derivative thereof. None of the previously known reports show that change in the expression of the gene or the transcript thereof can serve as a marker for colorectal cancer.

The 107th target gene is the hsa-miR-1268b gene, a congener thereof, a transcript thereof, or a variant or a derivative thereof. None of the previously known reports show that change in the expression of the gene or the transcript thereof can serve as a marker for colorectal cancer.

The 108th target gene is the hsa-miR-663b gene, a congener thereof, a transcript thereof, or a variant or a derivative thereof. None of the previously known reports show that change in the expression of the gene or the transcript thereof can serve as a marker for colorectal cancer.

The 109th target gene is the hsa-miR-125a-3p gene, a congener thereof, a transcript thereof, or a variant or a derivative thereof. None of the previously known reports show that change in the expression of the gene or the transcript thereof can serve as a marker for colorectal cancer.

The 110th target gene is the hsa-miR-2861 gene, a congener thereof, a transcript thereof, or a variant or a derivative thereof. None of the previously known reports show that change in the expression of the gene or the transcript thereof can serve as a marker for colorectal cancer.

The 111th target gene is the hsa-miR-6088 gene, a congener thereof, a transcript thereof, or a variant or a derivative thereof. None of the previously known reports show that change in the expression of the gene or the transcript thereof can serve as a marker for colorectal cancer.

The 112th target gene is the hsa-miR-4758-5p gene, a congener thereof, a transcript thereof, or a variant or a derivative thereof. None of the previously known reports show that change in the expression of the gene or the transcript thereof can serve as a marker for colorectal cancer.

The 113th target gene is the hsa-miR-296-3p gene, a congener thereof, a transcript thereof, or a variant or a derivative thereof. None of the previously known reports show that change in the expression of the gene or the transcript thereof can serve as a marker for colorectal cancer.

The 114th target gene is the hsa-miR-6738-5p gene, a congener thereof, a transcript thereof, or a variant or a derivative thereof. None of the previously known reports show that change in the expression of the gene or the transcript thereof can serve as a marker for colorectal cancer.

The 115th target gene is the hsa-miR-671-5p gene, a congener thereof, a transcript thereof, or a variant or a derivative thereof. None of the previously known reports show that change in the expression of the gene or the transcript thereof can serve as a marker for colorectal cancer.

The 116th target gene is the hsa-miR-4454 gene, a congener thereof, a transcript thereof, or a variant or a derivative thereof. None of the previously known reports show that change in the expression of the gene or the transcript thereof can serve as a marker for colorectal cancer.

The 117th target gene is the hsa-miR-4516 gene, a congener thereof, a transcript thereof, or a variant or a derivative thereof. None of the previously known reports show that change in the expression of the gene or the transcript thereof can serve as a marker for colorectal cancer.

The 118th target gene is the hsa-miR-7845-5p gene, a congener thereof, a transcript thereof, or a variant or a derivative thereof. None of the previously known reports show that change in the expression of the gene or the transcript thereof can serve as a marker for colorectal cancer.

The 119th target gene is the hsa-miR-4741 gene, a congener thereof, a transcript thereof, or a variant or a derivative thereof. None of the previously known reports show that change in the expression of the gene or the transcript thereof can serve as a marker for colorectal cancer.

The 120th target gene is the hsa-miR-92b-5p gene, a congener thereof, a transcript thereof, or a variant or a derivative thereof. None of the previously known reports show that change in the expression of the gene or the transcript thereof can serve as a marker for colorectal cancer.

The 121st target gene is the hsa-miR-6795-5p gene, a congener thereof, a transcript thereof, or a variant or a derivative thereof. None of the previously known reports show that change in the expression of the gene or the transcript thereof can serve as a marker for colorectal cancer.

The 122nd target gene is the hsa-miR-6805-3p gene, a congener thereof, a transcript thereof, or a variant or a derivative thereof. None of the previously known reports show that change in the expression of the gene or the transcript thereof can serve as a marker for colorectal cancer.

The 123rd target gene is the hsa-miR-4725-3p gene, a congener thereof, a transcript thereof, or a variant or a derivative thereof. None of the previously known reports show that change in the expression of the gene or the transcript thereof can serve as a marker for colorectal cancer.

The 124th target gene is the hsa-miR-6782-5p gene, a congener thereof, a transcript thereof, or a variant or a derivative thereof. None of the previously known reports show that change in the expression of the gene or the transcript thereof can serve as a marker for colorectal cancer.

The 125th target gene is the hsa-miR-4688 gene, a congener thereof, a transcript thereof, or a variant or a derivative thereof. None of the previously known reports show that change in the expression of the gene or the transcript thereof can serve as a marker for colorectal cancer.

The 126th target gene is the hsa-miR-6850-5p gene, a congener thereof, a transcript thereof, or a variant or a derivative thereof. None of the previously known reports show that change in the expression of the gene or the transcript thereof can serve as a marker for colorectal cancer.

The 127th target gene is the hsa-miR-6777-5p gene, a congener thereof, a transcript thereof, or a variant or a derivative thereof. None of the previously known reports show that change in the expression of the gene or the transcript thereof can serve as a marker for colorectal cancer.

The 128th target gene is the hsa-miR-6785-5p gene, a congener thereof, a transcript thereof, or a variant or a derivative thereof. None of the previously known reports show that change in the expression of the gene or the transcript thereof can serve as a marker for colorectal cancer.

The 129th target gene is the hsa-miR-7106-5p gene, a congener thereof, a transcript thereof, or a variant or a derivative thereof. None of the previously known reports show that change in the expression of the gene or the transcript thereof can serve as a marker for colorectal cancer.

The 130th target gene is the hsa-miR-3663-3p gene, a congener thereof, a transcript thereof, or a variant or a derivative thereof. None of the previously known reports show that change in the expression of the gene or the transcript thereof can serve as a marker for colorectal cancer.

The 131st target gene is the hsa-miR-6131 gene, a congener thereof, a transcript thereof, or a variant or a derivative thereof. None of the previously known reports show that change in the expression of the gene or the transcript thereof can serve as a marker for colorectal cancer.

The 132nd target gene is the hsa-miR-1915-3p gene, a congener thereof, a transcript thereof, or a variant or a derivative thereof. None of the previously known reports show that change in the expression of the gene or the transcript thereof can serve as a marker for colorectal cancer.

The 133rd target gene is the hsa-miR-4532 gene, a congener thereof, a transcript thereof, or a variant or a derivative thereof. None of the previously known reports show that change in the expression of the gene or the transcript thereof can serve as a marker for colorectal cancer.

The 134th target gene is the hsa-miR-6820-5p gene, a congener thereof, a transcript thereof, or a variant or a derivative thereof. None of the previously known reports show that change in the expression of the gene or the transcript thereof can serve as a marker for colorectal cancer.

The 135th target gene is the hsa-miR-4689 gene, a congener thereof, a transcript thereof, or a variant or a derivative thereof. None of the previously known reports show that change in the expression of the gene or the transcript thereof can serve as a marker for colorectal cancer.

The 136th target gene is the hsa-miR-4638-5p gene, a congener thereof, a transcript thereof, or a variant or a derivative thereof. None of the previously known reports show that change in the expression of the gene or the transcript thereof can serve as a marker for colorectal cancer.

The 137th target gene is the hsa-miR-3656 gene, a congener thereof, a transcript thereof, or a variant or a derivative thereof. None of the previously known reports show that change in the expression of the gene or the transcript thereof can serve as a marker for colorectal cancer.

The 138th target gene is the hsa-miR-3621 gene, a congener thereof, a transcript thereof, or a variant or a derivative thereof. None of the previously known reports show that change in the expression of the gene or the transcript thereof can serve as a marker for colorectal cancer.

The 139th target gene is the hsa-miR-6769b-5p gene, a congener thereof, a transcript thereof, or a variant or a derivative thereof. None of the previously known reports show that change in the expression of the gene or the transcript thereof can serve as a marker for colorectal cancer.

The 140th target gene is the hsa-miR-149-3p gene, a congener thereof, a transcript thereof, or a variant or a derivative thereof. None of the previously known reports show that change in the expression of the gene or the transcript thereof can serve as a marker for colorectal cancer.

The 141st target gene is the hsa-miR-23b-3p gene, a congener thereof, a transcript thereof, or a variant or a derivative thereof. None of the previously known reports show that change in the expression of the gene or the transcript thereof can serve as a marker for colorectal cancer.

The 142nd target gene is the hsa-miR-3135b gene, a congener thereof, a transcript thereof, or a variant or a derivative thereof. None of the previously known reports show that change in the expression of the gene or the transcript thereof can serve as a marker for colorectal cancer.

The 143rd target gene is the hsa-miR-6848-5p gene, a congener thereof, a transcript thereof, or a variant or a derivative thereof. None of the previously known reports show that change in the expression of the gene or the transcript thereof can serve as a marker for colorectal cancer.

The 144th target gene is the hsa-miR-6769a-5p gene, a congener thereof, a transcript thereof, or a variant or a derivative thereof. None of the previously known reports show that change in the expression of the gene or the transcript thereof can serve as a marker for colorectal cancer.

The 145th target gene is the hsa-miR-4327 gene, a congener thereof, a transcript thereof, or a variant or a derivative thereof. None of the previously known reports show that change in the expression of the gene or the transcript thereof can serve as a marker for colorectal cancer.

The 146th target gene is the hsa-miR-6765-3p gene, a congener thereof, a transcript thereof, or a variant or a derivative thereof. None of the previously known reports show that change in the expression of the gene or the transcript thereof can serve as a marker for colorectal cancer.

The 147th target gene is the hsa-miR-6716-5p gene, a congener thereof, a transcript thereof, or a variant or a derivative thereof. None of the previously known reports show that change in the expression of the gene or the transcript thereof can serve as a marker for colorectal cancer.

The 148th target gene is the hsa-miR-6877-5p gene, a congener thereof, a transcript thereof, or a variant or a derivative thereof. None of the previously known reports show that change in the expression of the gene or the transcript thereof can serve as a marker for colorectal cancer.

The 149th target gene is the hsa-miR-6727-5p gene, a congener thereof, a transcript thereof, or a variant or a derivative thereof. None of the previously known reports show that change in the expression of the gene or the transcript thereof can serve as a marker for colorectal cancer.

The 150th target gene is the hsa-miR-4534 gene, a congener thereof, a transcript thereof, or a variant or a derivative thereof. None of the previously known reports show that change in the expression of the gene or the transcript thereof can serve as a marker for colorectal cancer.

The 151st target gene is the hsa-miR-614 gene, a congener thereof, a transcript thereof, or a variant or a derivative thereof. None of the previously known reports show that change in the expression of the gene or the transcript thereof can serve as a marker for colorectal cancer.

The 152nd target gene is the hsa-miR-1202 gene, a congener thereof, a transcript thereof, or a variant or a derivative thereof. None of the previously known reports show that change in the expression of the gene or the transcript thereof can serve as a marker for colorectal cancer.

The 153rd target gene is the hsa-miR-575 gene, a congener thereof, a transcript thereof, or a variant or a derivative thereof. None of the previously known reports show that change in the expression of the gene or the transcript thereof can serve as a marker for colorectal cancer.

The 154th target gene is the hsa-miR-6870-5p gene, a congener thereof, a transcript thereof, or a variant or a derivative thereof. None of the previously known reports show that change in the expression of the gene or the transcript thereof can serve as a marker for colorectal cancer.

The 155th target gene is the hsa-miR-6722-3p gene, a congener thereof, a transcript thereof, or a variant or a derivative thereof. None of the previously known reports show that change in the expression of the gene or the transcript thereof can serve as a marker for colorectal cancer.

The 156th target gene is the hsa-miR-7977 gene, a congener thereof, a transcript thereof, or a variant or a derivative thereof. None of the previously known reports show that change in the expression of the gene or the transcript thereof can serve as a marker for colorectal cancer.

The 157th target gene is the hsa-miR-4649-5p gene, a congener thereof, a transcript thereof, or a variant or a derivative thereof. None of the previously known reports show that change in the expression of the gene or the transcript thereof can serve as a marker for colorectal cancer.

The 158th target gene is the hsa-miR-4675 gene, a congener thereof, a transcript thereof, or a variant or a derivative thereof. None of the previously known reports show that change in the expression of the gene or the transcript thereof can serve as a marker for colorectal cancer.

The 159th target gene is the hsa-miR-6075 gene, a congener thereof, a transcript thereof, or a variant or a derivative thereof. None of the previously known reports show that change in the expression of the gene or the transcript thereof can serve as a marker for colorectal cancer.

The 160th target gene is the hsa-miR-6779-5p gene, a congener thereof, a transcript thereof, or a variant or a derivative thereof. None of the previously known reports show that change in the expression of the gene or the transcript thereof can serve as a marker for colorectal cancer.

The 161st target gene is the hsa-miR-4271 gene, a congener thereof, a transcript thereof, or a variant or a derivative thereof. None of the previously known reports show that change in the expression of the gene or the transcript thereof can serve as a marker for colorectal cancer.

The 162nd target gene is the hsa-miR-3196 gene, a congener thereof, a transcript thereof, or a variant or a derivative thereof. None of the previously known reports show that change in the expression of the gene or the transcript thereof can serve as a marker for colorectal cancer.

The 163rd target gene is the hsa-miR-6803-5p gene, a congener thereof, a transcript thereof, or a variant or a derivative thereof. None of the previously known reports show that change in the expression of the gene or the transcript thereof can serve as a marker for colorectal cancer.

The 164th target gene is the hsa-miR-6789-5p gene, a congener thereof, a transcript thereof, or a variant or a derivative thereof. None of the previously known reports show that change in the expression of the gene or the transcript thereof can serve as a marker for colorectal cancer.

The 165th target gene is the hsa-miR-4648 gene, a congener thereof, a transcript thereof, or a variant or a derivative thereof. None of the previously known reports show that change in the expression of the gene or the transcript thereof can serve as a marker for colorectal cancer.

The 166th target gene is the hsa-miR-4508 gene, a congener thereof, a transcript thereof, or a variant or a derivative thereof. None of the previously known reports show that change in the expression of the gene or the transcript thereof can serve as a marker for colorectal cancer.

The 167th target gene is the hsa-miR-4749-5p gene, a congener thereof, a transcript thereof, or a variant or a derivative thereof. None of the previously known reports show that change in the expression of the gene or the transcript thereof can serve as a marker for colorectal cancer.

The 168th target gene is the hsa-miR-4505 gene, a congener thereof, a transcript thereof, or a variant or a derivative thereof. None of the previously known reports show that change in the expression of the gene or the transcript thereof can serve as a marker for colorectal cancer.

The 169th target gene is the hsa-miR-5698 gene, a congener thereof, a transcript thereof, or a variant or a derivative thereof. None of the previously known reports show that change in the expression of the gene or the transcript thereof can serve as a marker for colorectal cancer.

The 170th target gene is the hsa-miR-1199-5p gene, a congener thereof, a transcript thereof, or a variant or a derivative thereof. None of the previously known reports show that change in the expression of the gene or the transcript thereof can serve as a marker for colorectal cancer.

The 171st target gene is the hsa-miR-4763-3p gene, a congener thereof, a transcript thereof, or a variant or a derivative thereof. None of the previously known reports show that change in the expression of the gene or the transcript thereof can serve as a marker for colorectal cancer.

The 172nd target gene is the hsa-miR-1231 gene, a congener thereof, a transcript thereof, or a variant or a derivative thereof. The previously known report shows that change in the expression of the gene or the transcript thereof can serve as a marker for colorectal cancer (Patent Literature 3).

The 173rd target gene is the hsa-miR-1233-5p gene, a congener thereof, a transcript thereof, or a variant or a derivative thereof. The previously known report shows that change in the expression of the gene or the transcript thereof can serve as a marker for colorectal cancer (Patent Literature 2).

The 174th target gene is the hsa-miR-150-3p gene, a congener thereof, a transcript thereof, or a variant or a derivative thereof. The previously known report shows that change in the expression of the gene or the transcript thereof can serve as a marker for colorectal cancer (Patent Literature 4).

The 175th target gene is the hsa-miR-1225-3p gene, a congener thereof, a transcript thereof, or a variant or a derivative thereof. The previously known report shows that change in the expression of the gene or the transcript thereof can serve as a marker for colorectal cancer (Patent Literature 2).

The 176th target gene is the hsa-miR-92a-2-5p gene, a congener thereof, a transcript thereof, or a variant or a derivative thereof. The previously known report shows that change in the expression of the gene or the transcript thereof can serve as a marker for colorectal cancer (Patent Literatures 1 and 4).

The 177th target gene is the hsa-miR-423-5p gene, a congener thereof, a transcript thereof, or a variant or a derivative thereof. The previously known report shows that change in the expression of the gene or the transcript thereof can serve as a marker for colorectal cancer (Patent Literature 3).

The 178th target gene is the hsa-miR-1268a gene, a congener thereof, a transcript thereof, or a variant or a derivative thereof. The previously known report shows that change in the expression of the gene or the transcript thereof can serve as a marker for colorectal cancer (Patent Literature 3).

The 179th target gene is the hsa-miR-128-2-5p gene, a congener thereof, a transcript thereof, or a variant or a derivative thereof. The previously known report shows that change in the expression of the gene or the transcript thereof can serve as a marker for colorectal cancer (Patent Literature 1).

The 180th target gene is the hsa-miR-24-3p gene, a congener thereof, a transcript thereof, or a variant or a derivative thereof. The previously known report shows that change in the expression of the gene or the transcript thereof can serve as a marker for colorectal cancer (Patent Literature 1).

The 181st target gene is the hsa-miR-4697-5p gene, a congener thereof, a transcript thereof, or a variant or a derivative thereof. None of the previously known reports show that change in the expression of the gene or the transcript thereof can serve as a marker for colorectal cancer.

The 182nd target gene is the hsa-miR-3197 gene, a congener thereof, a transcript thereof, or a variant or a derivative thereof. None of the previously known reports show that change in the expression of the gene or the transcript thereof can serve as a marker for colorectal cancer.

The 183rd target gene is the hsa-miR-675-5p gene, a congener thereof, a transcript thereof, or a variant or a derivative thereof. None of the previously known reports show that change in the expression of the gene or the transcript thereof can serve as a marker for colorectal cancer.

The 184th target gene is the hsa-miR-4486 gene, a congener thereof, a transcript thereof, or a variant or a derivative thereof. None of the previously known reports show that change in the expression of the gene or the transcript thereof can serve as a marker for colorectal cancer.

The 185th target gene is the hsa-miR-7107-5p gene, a congener thereof, a transcript thereof, or a variant or a derivative thereof. None of the previously known reports show that change in the expression of the gene or the transcript thereof can serve as a marker for colorectal cancer.

The 186th target gene is the hsa-miR-23a-3p gene, a congener thereof, a transcript thereof, or a variant or a derivative thereof. The previously known report shows that change in the expression of the gene or the transcript thereof can serve as a marker for colorectal cancer (Patent Literature 2).

The 187th target gene is the hsa-miR-4667-5p gene, a congener thereof, a transcript thereof, or a variant or a derivative thereof. None of the previously known reports show that change in the expression of the gene or the transcript thereof can serve as a marker for colorectal cancer.

The 188th target gene is the hsa-miR-451a gene, a congener thereof, a transcript thereof, or a variant or a derivative thereof. None of the previously known reports show that change in the expression of the gene or the transcript thereof can serve as a marker for colorectal cancer.

The 189th target gene is the hsa-miR-3940-5p gene, a congener thereof, a transcript thereof, or a variant or a derivative thereof. None of the previously known reports show that change in the expression of the gene or the transcript thereof can serve as a marker for colorectal cancer.

The 190th target gene is the hsa-miR-8059 gene, a congener thereof, a transcript thereof, or a variant or a derivative thereof. None of the previously known reports show that change in the expression of the gene or the transcript thereof can serve as a marker for colorectal cancer.

The 191st target gene is the hsa-miR-6813-5p gene, a congener thereof, a transcript thereof, or a variant or a derivative thereof. None of the previously known reports show that change in the expression of the gene or the transcript thereof can serve as a marker for colorectal cancer.

The 192nd target gene is the hsa-miR-4492 gene, a congener thereof, a transcript thereof, or a variant or a derivative thereof. None of the previously known reports show that change in the expression of the gene or the transcript thereof can serve as a marker for colorectal cancer.

The 193rd target gene is the hsa-miR-4476 gene, a congener thereof, a transcript thereof, or a variant or a derivative thereof. None of the previously known reports show that change in the expression of the gene or the transcript thereof can serve as a marker for colorectal cancer.

The 194th target gene is the hsa-miR-6090 gene, a congener thereof, a transcript thereof, or a variant or a derivative thereof. None of the previously known reports show that change in the expression of the gene or the transcript thereof can serve as a marker for colorectal cancer.

The 195th target gene is the hsa-miR-6836-3p gene, a congener thereof, a transcript thereof, or a variant or a derivative thereof. None of the previously known reports show that change in the expression of the gene or the transcript thereof can serve as a marker for colorectal cancer.

The 196th target gene is the hsa-miR-3195 gene, a congener thereof, a transcript thereof, or a variant or a derivative thereof. None of the previously known reports show that change in the expression of the gene or the transcript thereof can serve as a marker for colorectal cancer.

The 197th target gene is the hsa-miR-718 gene, a congener thereof, a transcript thereof, or a variant or a derivative thereof. None of the previously known reports show that change in the expression of the gene or the transcript thereof can serve as a marker for colorectal cancer.

The 198th target gene is the hsa-miR-3178 gene, a congener thereof, a transcript thereof, or a variant or a derivative thereof. None of the previously known reports show that change in the expression of the gene or the transcript thereof can serve as a marker for colorectal cancer.

The 199th target gene is the hsa-miR-638 gene, a congener thereof, a transcript thereof, or a variant or a derivative thereof. None of the previously known reports show that change in the expression of the gene or the transcript thereof can serve as a marker for colorectal cancer.

The 200th target gene is the hsa-miR-4497 gene, a congener thereof, a transcript thereof, or a variant or a derivative thereof. None of the previously known reports show that change in the expression of the gene or the transcript thereof can serve as a marker for colorectal cancer.

The 201st target gene is the hsa-miR-6085 gene, a congener thereof, a transcript thereof, or a variant or a derivative thereof. None of the previously known reports show that change in the expression of the gene or the transcript thereof can serve as a marker for colorectal cancer.

The 202nd target gene is the hsa-miR-6752-5p gene, a congener thereof, a transcript thereof, or a variant or a derivative thereof. None of the previously known reports show that change in the expression of the gene or the transcript thereof can serve as a marker for colorectal cancer.

The 203rd target gene is the hsa-miR-135a-3p gene, a congener thereof, a transcript thereof, or a variant or a derivative thereof. None of the previously known reports show that change in the expression of the gene or the transcript thereof can serve as a marker for colorectal cancer.

2. Nucleic Acid Probe or Primer for Detection of Colorectal Cancer

In the present invention, a nucleic acid capable of specifically binding to any of the target nucleic acids as the colorectal cancer markers described above can be used as a nucleic acid, for example, a nucleic acid probe or a primer, for the detection or diagnosis of colorectal cancer.

In the present invention, the nucleic acid probe or the primer that can be used for detecting colorectal cancer or for diagnosing colorectal cancer permits qualitative and/or quantitative measurement of the presence, expression level, or abundance of any of the target nucleic acids as the colorectal cancer markers described above, for example, human-derived hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR- 6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p, or a combination thereof, congeners thereof, transcripts thereof, or variants or derivatives thereof; and, optionally in combination therewith, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p and hsa-miR-24-3p or a combination thereof, congeners thereof, transcripts thereof, or variants or derivatives thereof; and, optionally in combination therewith, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476 and hsa-miR-6090 or a combination thereof, congeners thereof, transcripts thereof, or variants or derivatives thereof.

The expression level of each target nucleic acid described above is increased or decreased (hereinafter, referred to as "increased/decreased") according to the type of the target nucleic acid in a subject who has colorectal cancer as compared with a healthy subject. Hence, the nucleic acid of the present invention can be effectively used for measuring the expression level of the target nucleic acid described above in a body fluid derived from a subject (e.g., a human) suspected of having colorectal cancer and a body fluid derived from a healthy subject and detecting colorectal cancer by the comparison thereof.

The nucleic acid probe or the primer that can be used in the present invention is a nucleic acid probe capable of specifically binding to a polynucleotide that consists of a nucleotide sequence represented by at least one of SEQ ID NOs: 1 to 171 and 606 to 614, or a primer for amplifying a polynucleotide that consists of a nucleotide sequence represented by at least one of SEQ ID NOs: 1 to 171 and 606 to 614.

The nucleic acid probe or the primer that can be further used in the present invention can comprise a nucleic acid probe capable of specifically binding to a polynucleotide consisting of a nucleotide sequence represented by at least one of SEQ ID NOs: 172 to 180, or a primer for amplifying a polynucleotide consisting of a nucleotide sequence represented by at least one of SEQ ID NOs: 172 to 180.

The nucleic acid probe or the primer that can be further used in the present invention can comprise a nucleic acid probe capable of specifically binding to a polynucleotide consisting of a nucleotide sequence represented by at least one of SEQ ID NOs: 181 to 194, or a primer for amplifying a polynucleotide consisting of a nucleotide sequence represented by at least one of SEQ ID NOs: 181 to 194.

Specifically, these nucleic acid probes or primers comprise a combination of one or more polynucleotides selected from a polynucleotide group comprising nucleotide sequences represented by any of SEQ ID NOs: 1 to 635 or nucleotide sequences derived from the nucleotide sequences by the replacement of u with t, and a complementary polynucleotide group thereof, a polynucleotide group respectively hybridizing under stringent conditions (mentioned later) to DNAs consisting of nucleotide sequences complementary to these nucleotide sequences, and a complementary polynucleotide group thereof, and a polynucleotide group comprising 15 or more, preferably 17 or more consecutive nucleotides in the nucleotide sequences of these polynucleotide groups. These polynucleotides can be used as nucleic acid probes and primers for detecting the colorectal cancer markers as target nucleic acids.

More specifically, examples of the nucleic acid probe or the primer that can be used in the present invention include one or more polynucleotide(s) selected from the group consisting of the following polynucleotides (a) to (e):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

In addition to at least one or more polynucleotide(s) selected from the polynucleotides (a) to (e), the nucleic acid probe or the primer that can be further used in the present invention can comprise polynucleotides selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180, (h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

In addition to at least one or more polynucleotide(s) selected from the polynucleotides (a) to (j), the nucleic acid probe or the primer that can be further used in the present invention can comprise polynucleotides selected from the group consisting of the following polynucleotides (k) to (o):

(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 181 to 194, (m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 181 to 194 or a nucleotide sequence derived from the nucleotide sequence by the replacement of u with t, and (o) a polynucleotide hybridizing under stringent conditions to any of the polynucleotides (k) to (n).

For these polynucleotides, the "fragment thereof comprising 15 or more consecutive nucleotides" can contain the number of nucleotides in the range of, for example, from 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide, though the fragment is not limited thereto.

These polynucleotides or the fragments thereof used in the present invention may each be DNA or may each be RNA.

The polynucleotides that can be used in the present invention can each be prepared by use of a general technique such as a DNA recombination technique, PCR, or a method using an automatic DNA/RNA synthesizer.

The DNA recombination technique and the PCR can employ a technique described in, for example, Ausubel et al., Current Protocols in Molecular Biology, John Willey &

Sons, US (1993); and Sambrook et al., Molecular Cloning—A Laboratory Manual, Cold Spring Harbor Laboratory Press, US (1989).

The human-derived hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsa-miR-5698, hsa-miR-1199-5p, hsa-miR-4763-3p, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p, hsa-miR-24-3p, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476, hsa-miR-6090, hsa-miR-6836-3p, hsa-miR-3195, hsa-miR-718, hsa-miR-3178, hsa-miR-638, hsa-miR-4497, hsa-miR-6085, hsa-miR-6752-5p and hsa-miR-135a-3p represented by SEQ ID NOs: 1 to 194 and 606 to 614 are known in the art, and their acquisition methods are also known as mentioned above.

Therefore, each polynucleotide that can be used as a nucleic acid probe or a primer in the present invention can be prepared by cloning the gene.

Such a nucleic acid probe or a primer can be chemically synthesized using an automatic DNA synthesis apparatus. In general, a phosphoramidite method is used in this synthesis, and single-stranded DNA up to approximately 100 nucleotides can be automatically synthesized by this method. The automatic DNA synthesis apparatus is commercially available from, for example, Polygen GmbH, ABI, or Applied Biosystems, Inc.

Alternatively, the polynucleotide of the present invention can also be prepared by a cDNA cloning method. The cDNA cloning technique can employ, for example, microRNA Cloning Kit Wako.

In this context, the sequences of the nucleic acid probe and the primer for detecting the polynucleotide consisting of a nucleotide sequence represented by any of SEQ ID NOs: 1 to 194 and 606 to 614 do not exist as miRNAs or precursors thereof in vivo. For example, the nucleotide sequences represented by SEQ ID NO: 11 and SEQ ID NO: 78 are produced from the precursor represented by SEQ ID NO: 205. This precursor has a hairpin-like structure as shown in FIG. 1, and the nucleotide sequences represented by SEQ ID NO: 11 and SEQ ID NO: 78 have mismatch sequences with each other. Likewise, a nucleotide sequence completely complementary to the nucleotide sequence represented by SEQ ID NO: 11 or SEQ ID NO: 78 is not naturally produced in vivo. Therefore, the nucleic acid probe and the primer for detecting the nucleotide sequence represented by any of SEQ ID NOs: 1 to 194 and 606 to 614 each have an artificial nucleotide sequence that does not exist in vivo.

3. Kit or Device for Detection of Colorectal Cancer

The present invention also provides a kit or a device for the detection of colorectal cancer, comprising one or more polynucleotide(s) (which can include a variant, a fragment, and a derivative; hereinafter, also referred to as a polynucleotide for detection) that can be used as a nucleic acid probe or a primer in the present invention for measuring a target nucleic acid as a colorectal cancer marker.

The target nucleic acid as a colorectal cancer marker according to the present invention is preferably selected from the following group 1:

miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR- 6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p.

An additional target nucleic acid that can be optionally used in the measurement is selected from the following group 2: miR-1231, miR-1233-5p, miR-150-3p, miR-1225-3p, miR-92a-2-5p, miR-423-5p, miR-1268a, miR-128-2-5p and miR-24-3p.

An additional target nucleic acid that can be optionally further used in the measurement is selected from the following group 3: miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090.

The kit or the device of the present invention comprises one or more nucleic acid(s) capable of specifically binding to any of the target nucleic acids as the colorectal cancer markers described above, preferably one or more polynucleotide(s) selected from the nucleic acid probes or the primers described in the preceding Section 2, specifically, the polynucleotides described in the preceding Section 2, or variant (s) thereof.

Specifically, the kit or the device of the present invention can comprise at least one or more polynucleotide(s) comprising (or consisting of) a nucleotide sequence represented by any of SEQ ID NOs: 1 to 171 and 606 to 614 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, or variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 172 to 180 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The kit or the device of the present invention can further comprise one or more polynucleotide(s) comprising (or consisting of) a nucleotide sequence represented by any of SEQ ID NOs: 181 to 194 or a nucleotide sequence derived from the nucleotide sequence by the replacement of u with t, polynucleotide(s) comprising (or consisting of) a complementary sequence thereof, polynucleotide(s) hybridizing under stringent conditions to any of these polynucleotides, variant(s) or fragment(s) comprising 15 or more consecutive nucleotides of any of these polynucleotide sequences.

The fragment that can be contained in the kit or the device of the present invention is, for example, one or more, preferably two or more polynucleotides selected from the group consisting of the following polynucleotides (1) to (3):

(1) a polynucleotide comprising 15 or more consecutive nucleotides in a nucleotide sequence derived from a nucleotide sequence represented by any of SEQ ID NOs: 1 to 171 and 606 to 614 by the replacement of u with t, or a complementary sequence thereof;

(2) a polynucleotide comprising 15 or more consecutive nucleotides in a nucleotide sequence derived from a nucleotide sequence represented by any of SEQ ID NOs: 172 to 180 by the replacement of u with t, or a complementary sequence thereof; and (3) a polynucleotide comprising 15 or more consecutive nucleotides in a nucleotide sequence derived from a nucleotide sequence represented by any of SEQ ID NOs: 181 to 194 by the replacement of u with t, or a complementary sequence thereof.

In a preferred embodiment, the polynucleotide is a polynucleotide consisting of a nucleotide sequence represented by any of SEQ ID NOs: 1 to 171 and 606 to 614 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 172 to 180 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 181 to 194 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of bases in the range of, for example, from 15 consecutive nucleotides to less than the total number of bases of the sequence, from 17 consecutive nucleotides to less than the total number of bases of the sequence, or from 19 consecutive nucleotides to less than the total number of nucleotides of the sequence, in the nucleotide sequence of each polynucleotide.

Specific examples of the aforementioned polynucleotide combination constituting the kit or the device of the present invention can include combinations of 1, 2, 3, 4, 5, 6, 7, 8, 9, 10 or more of the polynucleotides consisting of nucleotide sequences represented by SEQ ID NOS shown in Table 1 (SEQ ID NOs: 1 to 194 and 606 to 614 corresponding to the miRNA markers in the table). However, these are given merely for illustrative purposes, and various other possible combinations are included in the present invention.

The combination constituting the kit or the device for discriminating a colorectal cancer patient from a healthy subject according to the present invention is desirably, for example, a combination of two or more of the polynucleotides consisting of nucleotide sequences represented by SEQ ID NOs shown in Table 1. Usually, a combination of two of these polynucleotides can produce adequate performance.

The specific combination of two polynucleotides consisting of the nucleotide sequences or the complementary sequences thereof for discriminating a colorectal cancer patient from a healthy subject is preferably a combination comprising at least one or more of newly found polynucleotides consisting of the nucleotide sequences represented by SEQ ID NOs: 1 to 171, among the combinations constituted by two of the aforementioned polynucleotides consisting of the nucleotide sequences represented by SEQ ID NOs: 1 to 194 and 606 to 614. More specifically, a combination comprising at least one of polynucleotides consisting of the nucleotide sequences represented by SEQ ID NOs: 5, 15, 24, 32, 38, 45, 55, 64, 96, 97, and 162, among the combinations of the polynucleotides consisting of the nucleotide sequences represented by SEQ ID NOs: 1 to 194 and 606 to 614, is more preferred.

The combination of polynucleotides with cancer type specificity capable of discriminating a colorectal cancer patient not only from a healthy subject but also from other cancer patients is preferably, for example, a combination of multiple polynucleotides comprising at least one polynucleotide selected from the group consisting of polynucleotides of SEQ ID NOs: 5, 13, 15, 24, 32, 38, 41, 45, 55, 57, 64, 72, 75, 77, 96, 97, 115, 162, 163, 173, 189, 606, 607, 608, 609, 610, 611, 612, 613 and 614 (hereinafter, this group is referred to as "cancer type-specific polynucleotide group 1"), with any of the polynucleotides of the other SEQ ID NOs.

The combination of polynucleotides with cancer type specificity capable of discriminating a colorectal cancer patient not only from a healthy subject but also from other cancer patients is more preferably a combination of multiple polynucleotides selected from the cancer type-specific polynucleotide group 1.

The combination of polynucleotides with cancer type specificity capable of discriminating a colorectal cancer patient not only from a healthy subject but also from other cancer patients is more preferably a combination comprising at least one or more polynucleotide(s) selected from the group consisting of polynucleotides of SEQ ID NOs: 5, 45, 57, 96, and 606 (hereinafter, this group is referred to as "cancer type-specific polynucleotide group 2") included in the cancer type-specific polynucleotide group 1, among the combinations of multiple polynucleotides selected from the cancer type-specific polynucleotide group 1.

The number of the aforementioned polynucleotides with cancer type specificity in the combination can be 1, 2, 3, 4, 5, 6, 7, 8, 9, 10 or more for the combination and is more preferably 6 or more for the combination. Usually, the combination of 5 or 6 of these polynucleotides can produce adequate performance.

Non-limiting examples of the combination of the polynucleotide consisting of the nucleotide sequence represented by SEQ ID NO: 5 or a complementary sequence thereof with polynucleotides consisting of nucleotide sequences represented by SEQ ID NOs of four or five polynucleotides selected from the cancer type-specific polynucleotide group 1 or complementary sequences thereof will be listed.

(1) a combination of SEQ ID NOs: 5, 45, 57, 75, and 607 (markers: hsa-miR-3131, hsa-miR-204-3p, hsa-miR-4665-5p, hsa-miR-7847-3p, and hsa-miR-3195);

(2) a combination of SEQ ID NOs: 5, 45, 96, 606, and 607 (markers: hsa-miR-3131, hsa-miR-204-3p, hsa-miR-4294, hsa-miR-6836-3p, and hsa-miR-3195);

(3) a combination of SEQ ID NOs: 5, 45, 57, 97, 115, and 607 (markers: hsa-miR-3131, hsa-miR-204-3p, hsa-miR-4665-5p, hsa-miR-642a-3p, hsa-miR-671-5p, and hsa-miR-3195);

(4) a combination of SEQ ID NOs: 5, 45, 57, 97, 162, and 607 (markers: hsa-miR-3131, hsa-miR-204-3p, hsa-miR-4665-5p, hsa-miR-642a-3p, hsa-miR-3196, and hsa-miR-3195);

(5) a combination of SEQ ID NOs: 5, 45, 57, 162, 607, and 613 (markers: hsa-miR-3131, hsa-miR-204-3p, hsa-miR-4665-5p, hsa-miR-3196, hsa-miR-3195, and hsa-miR-6752-5p);

(6) a combination of SEQ ID NOs: 5, 45, 57, 97, 607, and 612 (markers: hsa-miR-3131, hsa-miR-204-3p, hsa-miR-4665-5p, hsa-miR-642a-3p, hsa-miR-3195, and hsa-miR-6085);

(7) a combination of SEQ ID NOs: 5, 13, 45, 57, 606, and 607 (markers: hsa-miR-3131, hsa-miR-6746-5p, hsa-miR-204-3p, hsa-miR-4665-5p, hsa-miR-6836-3p, and hsa-miR-3195);

(8) a combination of SEQ ID NOs: 5, 45, 96, 189, 606, and 608 (markers: hsa-miR-3131, hsa-miR-204-3p, hsa-miR-4294, hsa-miR-3940-5p, hsa-miR-6836-3p, and hsa-miR-718);

(9) a combination of SEQ ID NOs: 5, 45, 57, 96, 189, and 606 (markers: hsa-miR-3131, hsa-miR-204-3p, hsa-miR-4665-5p, hsa-miR-4294, hsa-miR-3940-5p, and hsa-miR-6836-3p);

(10) a combination of SEQ ID NOs: 5, 24, 45, 57, 96, and 608 (markers: hsa-miR-3131, hsa-miR-6826-5p, hsa-miR-204-3p, hsa-miR-4665-5p, hsa-miR-4294, and hsa-miR-718);

(11) a combination of SEQ ID NOs: 5, 45, 57, 162, 607, and 610 (markers: hsa-miR-3131, hsa-miR-204-3p, hsa-miR-4665-5p, hsa-miR-3196, hsa-miR-3195, and hsa-miR-638); and

(12) a combination of SEQ ID NOs: 5, 45, 57, 189, 606, and 607 (markers: hsa-miR-3131, hsa-miR-204-3p, hsa-miR-4665-5p, hsa-miR-3940-5p, hsa-miR-6836-3p, and hsa-miR-3195).

Non-limiting examples of the combination of the polynucleotide consisting of the nucleotide sequence represented by SEQ ID NO: 45 or a complementary sequence thereof with polynucleotides consisting of nucleotide sequences represented by SEQ ID NOs of four or five polynucleotides selected from the cancer type-specific polynucleotide group 1 or complementary sequences thereof will be further listed.

(1) a combination of SEQ ID NOs: 5, 45, 96, 606, and 607 (markers: hsa-miR-3131, hsa-miR-204-3p, hsa-miR-4294, hsa-miR-6836-3p, and hsa-miR-3195);

(2) a combination of SEQ ID NOs: 5, 45, 57, 75, and 607 (markers: hsa-miR-3131, hsa-miR-204-3p, hsa-miR-4665-5p, hsa-miR-7847-3p, and hsa-miR-3195);

(3) a combination of SEQ ID NOs: 5, 45, 57, 75, 606, and 607 (markers: hsa-miR-3131, hsa-miR-204-3p, hsa-miR-4665-5p, hsa-miR-7847-3p, hsa-miR-6836-3p, and hsa-miR-3195);

(4) a combination of SEQ ID NOs: 5, 45, 57, 77, 607, and 613 (markers: hsa-miR-3131, hsa-miR-204-3p, hsa-miR-4665-5p, hsa-miR-887-3p, hsa-miR-3195, and hsa-miR-6752-5p);

(5) a combination of SEQ ID NOs: 5, 45, 57, 97, 606, and 607 (markers: hsa-miR-3131, hsa-miR-204-3p, hsa-miR-4665-5p, hsa-miR-642a-3p, hsa-miR-6836-3p, and hsa-miR-3195);

(6) a combination of SEQ ID NOs: 5, 45, 57, 75, 77, and 607 (markers: hsa-miR-3131, hsa-miR-204-3p, hsa-miR-4665-5p, hsa-miR-7847-3p, hsa-miR-887-3p, and hsa-miR-3195);

(7) a combination of SEQ ID NOs: 5, 32, 45, 57, 96, and 606 (markers: hsa-miR-3131, hsa-miR-8069, hsa-miR-204-3p, hsa-miR-4665-5p, hsa-miR-4294, and hsa-miR-6836-3p);

(8) a combination of SEQ ID NOs: 5, 24, 45, 57, 96, and 606 (markers: hsa-miR-3131, hsa-miR-6826-5p, hsa-miR-204-3p, hsa-miR-4665-5p, hsa-miR-4294, and hsa-miR-6836-3p);

(9) a combination of SEQ ID NOs: 5, 45, 57, 96, 162, and 606 (markers: hsa-miR-3131, hsa-miR-204-3p, hsa-miR-4665-5p, hsa-miR-4294, hsa-miR-3196, and hsa-miR-6836-3p);

(10) a combination of SEQ ID NOs: 5, 15, 45, 75, 96, and 606 (markers: hsa-miR-3131, hsa-miR-6741-5p, hsa-miR-204-3p, hsa-miR-7847-3p, hsa-miR-4294, and hsa-miR-6836-3p);

(11) a combination of SEQ ID NOs: 5, 32, 45, 57, 162, and 607 (markers: hsa-miR-3131, hsa-miR-8069, hsa-miR-204-3p, hsa-miR-4665-5p, hsa-miR-3196, and hsa-miR-3195); and

(12) a combination of SEQ ID NOs: 38, 45, 96, 606, 608, and 611 (markers: hsa-miR-6724-5p, hsa-miR-204-3p, hsa-miR-4294, hsa-miR-6836-3p, hsa-miR-718, and hsa-miR-4497).

Non-limiting examples of the combination of the polynucleotide consisting of the nucleotide sequence represented by SEQ ID NO: 57 or a complementary sequence thereof with polynucleotides consisting of nucleotide sequences represented by SEQ ID NOs of four or five polynucleotides selected from the cancer type-specific polynucleotide group 1 or complementary sequences thereof will be further listed.

(1) a combination of SEQ ID NOs: 24, 41, 57, 45, and 96 (markers: hsa-miR-6826-5p, hsa-miR-4419b, hsa-miR-4665-5p, hsa-miR-204-3p, and hsa-miR-4294);

(2) a combination of SEQ ID NOs: 5, 45, 57, 607, and 612 (markers: hsa-miR-3131, hsa-miR-204-3p, hsa-miR-4665-5p, hsa-miR-3195, and hsa-miR-6085);

(3) a combination of SEQ ID NOs: 5, 45, 57, 606, 607, and 608 (markers: hsa-miR-3131, hsa-miR-204-3p, hsa-miR-4665-5p, hsa-miR-6836-3p, hsa-miR-3195, and hsa-miR-718);

(4) a combination of SEQ ID NOs: 5, 13, 45, 57, 75, and 607 (markers: hsa-miR-3131, hsa-miR-6746-5p, hsa-miR-204-3p, hsa-miR-4665-5p, hsa-miR-7847-3p, and hsa-miR-3195);

(5) a combination of SEQ ID NOs: 5, 45, 57, 64, 75, and 607 (markers: hsa-miR-3131, hsa-miR-204-3p, hsa-miR-4665-5p, hsa-miR-6126, hsa-miR-7847-3p, and hsa-miR-3195);

(6) a combination of SEQ ID NOs: 5, 45, 55, 57, 607, and 613 (markers: hsa-miR-3131, hsa-miR-204-3p, hsa-miR-6717-5p, hsa-miR-4665-5p, hsa-miR-3195, and hsa-miR-6752-5p);

(7) a combination of SEQ ID NOs: 5, 45, 55, 57, 75, and 607 (markers: hsa-miR-3131, hsa-miR-204-3p, hsa-miR-6717-5p, hsa-miR-4665-5p, hsa-miR-7847-3p, and hsa-miR-3195);

(8) a combination of SEQ ID NOs: 5, 38, 45, 57, 96, and 607 (markers: hsa-miR-3131, hsa-miR-6724-5p, hsa-miR-204-3p, hsa-miR-4665-5p, hsa-miR-4294, and hsa-miR-3195);

(9) a combination of SEQ ID NOs: 5, 45, 57, 75, 162, and 607 (markers: hsa-miR-3131, hsa-miR-204-3p, hsa-miR-4665-5p, hsa-miR-7847-3p, hsa-miR-3196, and hsa-miR-3195);

(10) a combination of SEQ ID NOs: 5, 45, 57, 75, 162, and 609 (markers: hsa-miR-3131, hsa-miR-204-3p, hsa-miR-4665-5p, hsa-miR-7847-3p, hsa-miR-3196, and hsa-miR-3178);

(11) a combination of SEQ ID NOs: 5, 45, 57, 64, 96, and 607 (markers: hsa-miR-3131, hsa-miR-204-3p, hsa-miR-4665-5p, hsa-miR-6126, hsa-miR-4294, and hsa-miR-3195); and

(12) a combination of SEQ ID NOs: 57, 64, 96, 606, 608, and 611 (markers: hsa-miR-4665-5p, hsa-miR-6126, hsa-miR-4294, hsa-miR-6836-3p, hsa-miR-718, and hsa-miR-4497).

Non-limiting examples of the combination of the poly-nucleotide consisting of the nucleotide sequence represented by SEQ ID NO: 96 or a complementary sequence thereof with polynucleotides consisting of nucleotide sequences represented by SEQ ID NOs of four or five polynucleotides selected from the cancer type-specific polynucleotide group 1 or complementary sequences thereof will be further listed below.

(1) a combination of SEQ ID NOs: 38, 96, 606, 608, and 611 (markers: hsa-miR-6724-5p, hsa-miR-4294, hsa-miR-6836-3p, hsa-miR-718, and hsa-miR-4497);

(2) a combination of SEQ ID NOs: 5, 45, 57, 96, and 607 (markers: hsa-miR-3131, hsa-miR-204-3p, hsa-miR-4665-5p, hsa-miR-4294, and hsa-miR-3195);

(3) a combination of SEQ ID NOs: 38, 72, 96, 606, 608, and 611 (markers: hsa-miR-6724-5p, hsa-miR-6816-5p, hsa-miR-4294, hsa-miR-6836-3p, hsa-miR-718, and hsa-miR-4497);

(4) a combination of SEQ ID NOs: 32, 38, 96, 606, 608, and 611 (markers: hsa-miR-8069, hsa-miR-6724-5p, hsa-miR-4294, hsa-miR-6836-3p, hsa-miR-718, and hsa-miR-4497);

(5) a combination of SEQ ID NOs: 38, 96, 163, 606, 608, and 611 (markers: hsa-miR-6724-5p, hsa-miR-4294, hsa-miR-6803-5p, hsa-miR-6836-3p, hsa-miR-718, and hsa-miR-4497);

(6) a combination of SEQ ID NOs: 64, 72, 96, 162, 609, and 611 (markers: hsa-miR-6126, hsa-miR-6816-5p, hsa-miR-4294, hsa-miR-3196, hsa-miR-3178, and hsa-miR-4497);

(7) a combination of SEQ ID NOs: 38, 64, 96, 163, 606, and 608 (markers: hsa-miR-6724-5p, hsa-miR-6126, hsa-miR-4294, hsa-miR-6803-5p, hsa-miR-6836-3p, and hsa-miR-718);

(8) a combination of SEQ ID NOs: 5, 45, 57, 75, 96, and 606 (markers: hsa-miR-3131, hsa-miR-204-3p, hsa-miR-4665-5p, hsa-miR-7847-3p, hsa-miR-4294, and hsa-miR-6836-3p);

(9) a combination of SEQ ID NOs: 5, 15, 45, 57, 96, and 606 (markers: hsa-miR-3131, hsa-miR-6741-5p, hsa-miR-204-3p, hsa-miR-4665-5p, hsa-miR-4294, and hsa-miR-6836-3p);

(10) a combination of SEQ ID NOs: 5, 41, 45, 57, 96, and 606 (markers: hsa-miR-3131, hsa-miR-4419b, hsa-miR-204-3p, hsa-miR-4665-5p, hsa-miR-4294, and hsa-miR-6836-3p);

(11) a combination of SEQ ID NOs: 5, 41, 45, 96, 189, and 606 (markers: hsa-miR-3131, hsa-miR-4419b, hsa-miR-204-3p, hsa-miR-4294, hsa-miR-3940-5p, and hsa-miR-6836-3p); and

(12) a combination of SEQ ID NOs: 5, 45, 75, 96, 189, and 606 (markers: hsa-miR-3131, hsa-miR-204-3p, hsa-miR-7847-3p, hsa-miR-4294, hsa-miR-3940-5p, and hsa-miR-6836-3p).

Non-limiting examples of the combination of the poly-nucleotide consisting of the nucleotide sequence represented by SEQ ID NO: 606 or a complementary sequence thereof with polynucleotides consisting of nucleotide sequences represented by SEQ ID NOs of three polynucleotides selected from the cancer type-specific polynucleotide group 1 or complementary sequences thereof will be further listed.

(1) a combination of SEQ ID NOs: 5, 24, 45, 96, 189, and 606 (markers: hsa-miR-3131, hsa-miR-6826-5p, hsa-miR-204-3p, hsa-miR-4294, hsa-miR-3940-5p, and hsa-miR-6836-3p);

(2) a combination of SEQ ID NOs: 5, 15, 45, 96, 189, and 606 (markers: hsa-miR-3131, hsa-miR-6741-5p, hsa-miR-204-3p, hsa-miR-4294, hsa-miR-3940-5p, and hsa-miR-6836-3p);

(3) a combination of SEQ ID NOs: 5, 45, 96, 189, 606, and 613 (markers: hsa-miR-3131, hsa-miR-204-3p, hsa-miR-4294, hsa-miR-3940-5p, hsa-miR-6836-3p, and hsa-miR-6752-5p);

(4) a combination of SEQ ID NOs: 5, 45, 72, 96, 189, and 606 (markers: hsa-miR-3131, hsa-miR-204-3p, hsa-miR-6816-5p, hsa-miR-4294, hsa-miR-3940-5p, and hsa-miR-6836-3p); and (5) a combination of SEQ ID NOs: 5, 15, 32, 45, 96, and 606 (markers: hsa-miR-3131, hsa-miR-6741-5p, hsa-miR-8069, hsa-miR-204-3p, hsa-miR-4294, and hsa-miR-6836-3p).

The kit or the device of the present invention can also contain a polynucleotide that is already known or that will be found in the future, to enable detection of colorectal cancer, in addition to the polynucleotide(s) (which can include a variant, a fragment, and a derivative) according to the present invention described above.

The kit of the present invention can also contain an antibody for measuring a marker for colorectal cancer examination known in the art, such as CEA or CA19-9, in addition to the polynucleotide(s) according to the present invention described above.

These polynucleotides contained in the kit of the present invention can be packaged in different containers either individually or in any combination.

The kit of the present invention can contain a kit for extracting a nucleic acid (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above are bonded or attached to, for example, a solid phase. Examples of the material for the solid phase include plastics, paper, glass, and silicon. The material for the solid phase is preferably a plastic from the viewpoint of easy processabil-ity. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves binding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezo-electric element or the like from a nozzle, or a method of sequentially synthesizing nucleotides on the solid phase] to prepare an array such as a chip and measuring a target nucleic acid through the use of hybridization using this array.

The kit or the device of the present invention comprises nucleic acids capable of specifically binding to the poly-nucleotides of at least one or more, preferably at least two or more, more preferably at least three or more, most preferably at least five or more to all of the colorectal cancer marker miRNAs, respectively, of group 1 described above. The kit or the device of the present invention can optionally further comprise nucleic acids capable of specifically binding to the polynucleotides of at least one or more, preferably at least two or more, more preferably at least three or more, most preferably at least five or more to all of the colorectal cancer marker miRNAs, respectively, of group 2 described above. The kit or the device of the present invention can optionally further comprise nucleic acids capable of specifically binding to the polynucleotides of at least one or more, preferably at least two or more, more preferably at least three or more, most preferably at least five or more to all of the colorectal cancer marker miRNAs, respectively, of group 3 described above.

The kit or the device of the present invention can be used for detecting colorectal cancer as described in the Section 4 below.

4. Method for Detecting Colorectal Cancer

The present invention further provides a method for detecting colorectal cancer, comprising using the kit or the device of the present invention (including the nucleic acid(s) that can be used in the present invention) described in the preceding Section 3 above to measure an expression level of one or more colorectal cancer-derived gene(s) represented by an expression level of colorectal cancer-derived gene(s) selected from the following group: miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-

5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p, optionally an expression level of colorectal cancer-derived gene(s) selected from the following group: miR-1231, miR-1233-5p, miR-150-3p, miR-1225-3p, miR-92a-2-5p, miR-423-5p, miR-1268a, miR-128-2-5p and miR-24-3p, and optionally an expression level of colorectal cancer-derived gene(s) selected from the following group: miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090 in a sample in vitro, further comparing, for example, the expression level of the aforementioned gene in the sample (e.g., blood, serum, or plasma) collected from a subject suspected of having colorectal cancer with a control expression level in the sample collected from a healthy subject (including a non-colorectal cancer patient), and evaluating the subject as having colorectal cancer when the expression level of the target nucleic acid is statistically significantly different between the samples.

This method of the present invention permits lowly-invasive early diagnosis of cancer with high sensitivity and specificity and thereby brings about early treatment and improved prognosis. In addition, exacerbation of the disease or the effectiveness of surgical, radiotherapeutic, and chemotherapeutic treatments can be monitored.

The method for extracting the colorectal cancer-derived gene from the sample such as blood, serum, or plasma according to the present invention is particularly preferably prepared by the addition of a reagent for RNA extraction in 3D-Gene™ RNA extraction reagent from liquid sample kit (Toray Industries, Inc.). A general acidic phenol method (acid guanidinium-phenol-chloroform (AGPC)) may be used, or Trizol™ (Life Technologies Corp.) may be used. The colorectal cancer-derived gene may be prepared by the addition of a reagent for RNA extraction containing acidic phenol, such as Trizol (Life Technologies Corp.) or Isogen (Nippon Gene Co., Ltd.). Alternatively, a kit such as miRNeasy™ Mini Kit (Qiagen N.V.) can be used, though the method is not limited thereto.

The present invention also provides use of the kit or the device of the present invention for detecting in vitro an expression product of a colorectal cancer-derived miRNA gene in a sample derived from a subject.

In the method of the present invention, a kit or a device comprising, each alone or in every possible composition, the polynucleotides that can be used in the present invention as described above is used as the kit or the device.

In the detection or (genetic) diagnosis of colorectal cancer according to the present invention, each polynucleotide contained in the kit or the device of the present invention can be used as a probe or a primer. In the case of using the polynucleotide as a primer, TaqMan™ MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting the particular gene, for example, a hybridization technique such as Northern blot, Southern blot, in situ hybridization, Northern hybridization, or Southern hybridization, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The kit or the device of the present invention is useful for the diagnosis of colorectal cancer or the detection of the presence or absence of colorectal cancer. Specifically, the detection of colorectal cancer using the kit or the device can be performed by detecting in vitro an expression level of a gene using the nucleic acid probe or the primer contained in the kit or the device in a sample such as blood, serum, plasma, or urine from a subject suspected of having colorectal cancer. The subject suspected of having colorectal cancer can be evaluated as having colorectal cancer when the expression level of a target miRNA marker measured using polynucleotide(s) (including a variant, a fragment, and a derivative thereof) consisting of a nucleotide sequence represented by at least one or more of SEQ ID NOs: 1 to 171 and 606 to 614 or a complementary sequence thereof, optionally a nucleotide sequence represented by one or more of SEQ ID NOs: 172 to 180 or a complementary sequence thereof, and optionally a nucleotide sequence represented by one or more of SEQ ID NOs: 181 to 194 or a complementary sequence thereof in the sample such as blood, serum, plasma, or urine of the subject is statistically significantly different from the expression level thereof in the sample such as blood, serum, or plasma, or urine of a healthy subject.

The method of the present invention can be combined with fecal occult blood, rectal examination, and colonoscopy as well as a diagnostic imaging method such as barium enema, CT, MRI, or bone scintigraphy. The method of the present invention is capable of specifically detecting colorectal cancer and can substantially discriminate colorectal cancer from other cancers.

The method for detecting the absence of an expression product of a colorectal cancer-derived gene or the presence of the expression product of a colorectal cancer-derived gene in a sample using the kit or the device of the present invention comprises; collecting a body fluid such as blood, serum, plasma, or urine from a subject, measuring the expression level of the target gene that contains therein using one or more polynucleotide(s) (including a variant, a fragment, and a derivative) selected from the polynucleotide group of the present invention, and evaluating the presence or absence of colorectal cancer or detecting colorectal cancer. Using the method for detecting colorectal cancer according to the present invention, for example, the presence or absence of amelioration of the disease or the degree of amelioration thereof in a colorectal cancer patient given a therapeutic drug for the amelioration of the disease can be also evaluated or diagnosed.

The method of the present invention can comprise, for example, the following steps (a), (b), and (c):

(a) a step of contacting a sample derived from a subject with a polynucleotide in the kit or the device of the present invention in vitro;

(b) a step of measuring an expression level of the target nucleic acid in the sample using the polynucleotide as a nucleic acid probe or a primer; and (c) a step of evaluating the presence or absence of colorectal cancer (cells) in the subject on the basis of the step (b).

Specifically, the present invention provides a method for detecting colorectal cancer, comprising measuring an expression level of a target nucleic acid in a sample of a subject using a nucleic acid capable of specifically binding to at least one or more (preferably at least two or more) polynucleotide(s) selected from the group consisting of miR-6726-5p, miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-3937, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-887-3p, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p and miR-4763-3p, miR-6836-3p, miR-3195, miR-718, miR-3178, miR-638, miR-4497, miR-6085, miR-6752-5p and miR-135a-3p and evaluating in vitro whether or not the subject has colorectal cancer using the measured expression level and a control expression level of a healthy subject measured in the same way as above.

As used herein, the term "evaluation" is evaluation support based on results of in vitro examination, not physician's judgment.

As described above, as for the target nucleic acids in a preferred embodiment of the method of the present invention, specifically, miR-6726-5p is hsa-miR-6726-5p, miR-4257 is hsa-miR-4257, miR-6787-5p is hsa-miR-6787-5p, miR-6780b-5p is hsa-miR-6780b-5p, miR-3131 is hsa-miR-3131, miR-7108-5p is hsa-miR-7108-5p, miR-1343-3p is hsa-miR-1343-3p, miR-1247-3p is hsa-miR-1247-3p, miR-4651 is hsa-miR-4651, miR-6757-5p is hsa-miR-6757-5p, miR-3679-5p is hsa-miR-3679-5p, miR-7641 is hsa-miR-7641, miR-6746-5p is hsa-miR-6746-5p, miR-8072 is hsa-miR-8072, miR-6741-5p is hsa-miR-6741-5p, miR-1908-5p is hsa-miR-1908-5p, miR-6857-5p is hsa-miR-6857-5p, miR-4746-3p is hsa-miR-4746-3p, miR-744-5p is hsa-miR-744-5p, miR-4792 is hsa-miR-4792, miR-564 is hsa-miR-564, miR-6791-5p is hsa-miR-6791-5p, miR-6825-5p is hsa-miR-6825-5p, miR-6826-5p is hsa-miR-6826-5p, miR-4665-3p is hsa-miR-4665-3p, miR-4467 is hsa-miR-4467, miR-3188 is hsa-miR-3188, miR-6125 is hsa-miR-6125, miR-6756-5p is hsa-miR-6756-5p, miR-1228-3p is hsa-miR-1228-3p, miR-8063 is hsa-miR-8063, miR-8069 is hsa-miR-8069, miR-6875-5p is hsa-miR-6875-5p, miR-3185 is hsa-miR-3185, miR-4433b-3p is hsa-miR-4433b-3p, miR-6887-5p is hsa-miR-6887-5p, miR-128-1-5p is hsa-miR-128-1-5p, miR-6724-5p is hsa-miR-6724-5p, miR-1914-3p is hsa-miR-1914-3p, miR-1225-5p is hsa-miR-1225-5p, miR-4419b is hsa-miR-4419b, miR-7110-5p is hsa-miR-7110-5p, miR-187-5p is hsa-miR-187-5p, miR-3184-5p is hsa-miR-3184-5p, miR-204-3p is hsa-miR-204-3p, miR-5572 is hsa-miR-5572, miR-6729-5p is hsa-miR-6729-5p, miR-615-5p is hsa-miR-615-5p, miR-6749-5p is hsa-miR-6749-5p, miR-6515-3p is hsa-miR-6515-3p, miR-3937 is hsa-miR-3937, miR-6840-3p is hsa-miR-6840-3p, miR-6893-5p is hsa-miR-6893-5p, miR-4728-5p is hsa-miR-4728-5p, miR-6717-5p is hsa-miR-6717-5p, miR-7113-3p is hsa-miR-7113-3p, miR-4665-5p is hsa-miR-4665-5p, miR-642b-3p is hsa-miR-642b-3p, miR-7109-5p is hsa-miR-7109-5p, miR-6842-5p is hsa-miR-6842-5p, miR-4442 is hsa-miR-4442, miR-4433-3p is hsa-miR-4433-3p, miR-4707-5p is hsa-miR-4707-5p, miR-6126 is hsa-miR-6126, miR-4449 is hsa-miR-4449, miR-4706 is hsa-miR-4706, miR-1913 is hsa-miR-1913, miR-602 is hsa-miR-602, miR-939-5p is hsa-miR-939-5p, miR-4695-5p is hsa-miR-4695-5p, miR-711 is hsa-miR-711, miR-6816-5p is hsa-miR-6816-5p, miR-4632-5p is hsa-miR-4632-5p, miR-6721-5p is hsa-miR-6721-5p, miR-7847-3p is hsa-miR-7847-3p, miR-6132 is hsa-miR-6132, miR-887-3p is hsa-miR-887-3p, miR-3679-3p is hsa-miR-3679-3p, miR-6784-5p is hsa-miR-6784-5p, miR-1249 is hsa-miR-1249, miR-937-5p is hsa-miR-937-5p, miR-5195-3p is hsa-miR-5195-3p, miR-6732-5p is hsa-miR-6732-5p, miR-4417 is hsa-miR-4417, miR-4281 is hsa-miR-4281, miR-4734 is hsa-miR-4734, miR-6766-3p is hsa-miR-6766-3p, miR-663a is hsa-miR-663a, miR-4513 is hsa-miR-4513, miR-6781-5p is hsa-miR-6781-5p, miR-1227-5p is hsa-miR-1227-5p, miR-6845-5p is hsa-miR-6845-5p, miR-6798-5p is hsa-miR-6798-5p, miR-3620-5p is hsa-miR-3620-5p, miR-1915-5p is hsa-miR-1915-5p, miR-4294 is hsa-miR-4294, miR-642a-3p is hsa-miR-642a-3p, miR-371a-5p is hsa-miR-371a-5p, miR-940 is hsa-miR-940, miR-4450 is hsa-miR-4450, miR-4723-5p is hsa-miR-4723-5p, miR-1469 is hsa-miR-1469, miR-6861-5p is hsa-miR-6861-5p, miR-7975 is hsa-miR-7975, miR-6879-5p is hsa-miR-6879-5p, miR-6802-5p is hsa-miR-6802-5p, miR-1268b is hsa-miR-1268b, miR-663b is hsa-miR-663b, miR-125a-3p is hsa-miR-125a-3p, miR- 2861 is hsa-miR-2861, miR-6088 is hsa-miR-6088, miR-4758-5p is hsa-miR-4758-5p, miR-296-3p is hsa-miR-296-3p, miR-6738-5p is hsa-miR-6738-5p, miR-671-5p is hsa-miR-671-5p, miR-4454 is hsa-miR-4454, miR-4516 is hsa-miR-4516, miR-7845-5p is hsa-miR-7845-5p, miR-4741 is hsa-miR-4741, miR-92b-5p is hsa-miR-92b-5p, miR-6795-5p is hsa-miR-6795-5p, miR-6805-3p is hsa-miR-6805-3p, miR-4725-3p is hsa-miR-4725-3p, miR-6782-5p is hsa-miR-6782-5p, miR-4688 is hsa-miR-4688, miR-6850-5p is hsa-miR-6850-5p, miR-6777-5p is hsa-miR-6777-5p, miR-6785-5p is hsa-miR-6785-5p, miR-7106-5p is hsa-miR-7106-5p, miR-3663-3p is hsa-miR-3663-3p, miR-6131 is hsa-miR-6131, miR-1915-3p is hsa-miR-1915-3p, miR-4532 is hsa-miR-4532, miR-6820-5p is hsa-miR-6820-5p, miR-4689 is hsa-miR-4689, miR-4638-5p is hsa-miR-4638-5p, miR-3656 is hsa-miR-3656, miR-3621 is hsa-miR-3621, miR-6769b-5p is hsa-miR-6769b-5p, miR-149-3p is hsa-miR-149-3p, miR-23b-3p is hsa-miR-23b-3p, miR-3135b is hsa-miR-3135b, miR-6848-5p is hsa-miR-6848-5p, miR-6769a-5p is hsa-miR-6769a-5p, miR-4327 is hsa-miR-4327, miR-6765-3p is hsa-miR-6765-3p, miR-6716-5p is hsa-miR-6716-5p, miR-6877-5p is hsa-miR-6877-5p, miR-6727-5p is hsa-miR-6727-5p, miR-4534 is hsa-miR-4534, miR-614 is hsa-miR-614, miR-1202 is hsa-miR-1202, miR-575 is hsa-miR-575, miR-6870-5p is hsa-miR-6870-5p, miR-6722-3p is hsa-miR-6722-3p, miR-7977 is hsa-miR-7977, miR-4649-5p is hsa-miR-4649-5p, miR-4675 is hsa-miR-4675, miR-6075 is hsa-miR-6075, miR-6779-5p is hsa-miR-6779-5p, miR-4271 is hsa-miR-4271, miR-3196 is hsa-miR-3196, miR-6803-5p is hsa-miR-6803-5p, miR-6789-5p is hsa-miR-6789-5p, miR-4648 is hsa-miR-4648, miR-4508 is hsa-miR-4508, miR-4749-5p is hsa-miR-4749-5p, miR-4505 is hsa-miR-4505, miR-5698 is hsa-miR-5698, miR-1199-5p is hsa-miR-1199-5p, miR-4763-3p is hsa-miR-4763-3p, miR-6836-3p is hsa-miR-6836-3p, miR-3195 is hsa-miR-3195, miR-718 is hsa-miR-718, miR-3178 is hsa-miR-3178, miR-638 is hsa-miR-638, miR-4497 is hsa-miR-4497, miR-6085 is hsa-miR-6085, miR-6752-5p is hsa-miR-6752-5p, and miR-135a-3p is hsa-miR-135a-3p.

In a preferred embodiment of the method of the present invention, specifically, the nucleic acid (specifically, probe or primer) is selected from the group consisting of the following polynucleotides (a) to (e):

(a) a polynucleotide consisting of a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (b) a polynucleotide comprising a nucleotide sequence represented by any of SEQ ID NOs: 1 to 171 and 606 to 614, (c) a polynucleotide consisting of a nucleotide sequence complementary to a nucleotide sequence represented by any of SEQ ID NOs: 1 to 171 and 606 to 614 or a nucleotide sequence derived from the nucleotide sequence by the replacement of u with t, a variant thereof, a derivative thereof, or a fragment thereof comprising 15 or more consecutive nucleotides, (d) a polynucleotide comprising a nucleotide sequence complementary to a nucleotide sequence represented by any of SEQ ID NOs: 1 to 171 and 606 to 614 or a nucleotide sequence derived from the nucleotide sequence by the replacement of u with t, and (e) a polynucleotide hybridizing under stringent conditions to any of the polynucleotides (a) to (d).

The method of the present invention can further employ a nucleic acid capable of specifically binding to at least one or more polynucleotide(s) selected from the group consisting of miR-1231, miR-1233-5p, miR-150-3p, miR-1225-3p, miR-92a-2-5p, miR-423-5p, miR-1268a, miR-128-2-5p and miR-24-3p.

As for such a nucleic acid, specifically, miR-1231 is hsa-miR-1231, miR-1233-5p is hsa-miR-1233-5p, miR-150-3p is hsa-miR-150-3p, miR-1225-3p is hsa-miR-1225-3p, miR-92a-2-5p is hsa-miR-92a-2-5p, miR-423-5p is hsa-miR-423-5p, miR-1268a is hsa-miR-1268a, miR-128-2-5p is hsa-miR-128-2-5p, and miR-24-3p is hsa-miR-24-3p.

In a preferred embodiment, such a nucleic acid is specifically selected from the group consisting of the following polynucleotides (f) to (j):

(f) a polynucleotide consisting of a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (g) a polynucleotide comprising a nucleotide sequence represented by any of SEQ ID NOs: 172 to 180, (h) a polynucleotide consisting of a nucleotide sequence complementary to a nucleotide sequence represented by any of SEQ ID NOs: 172 to 180 or a nucleotide sequence derived from the nucleotide sequence by the replacement of u with t, a variant thereof, a derivative thereof, or a fragment thereof comprising 15 or more consecutive nucleotides, (i) a polynucleotide comprising a nucleotide sequence complementary to a nucleotide sequence represented by any of SEQ ID NOs: 172 to 180 or a nucleotide sequence derived from the nucleotide sequence by the replacement of u with t, and (j) a polynucleotide hybridizing under stringent conditions to any of the polynucleotides (f) to (i).

The nucleic acid further used in the method of the present invention can comprise a nucleic acid capable of specifically binding to at least one or more polynucleotide(s) selected from the group consisting of miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476 and miR-6090.

As for such a nucleic acid, specifically, miR-4697-5p is hsa-miR-4697-5p, miR-3197 is hsa-miR-3197, miR-675-5p is hsa-miR-675-5p, miR-4486 is hsa-miR-4486, miR-7107-5p is hsa-miR-7107-5p, miR-23a-3p is hsa-miR-23a-3p, miR-4667-5p is hsa-miR-4667-5p, miR-451a is hsa-miR-451a, miR-3940-5p is hsa-miR-3940-5p, miR-8059 is hsa-miR-8059, miR-6813-5p is hsa-miR-6813-5p, miR-4492 is hsa-miR-4492, miR-4476 is hsa-miR-4476, and miR-6090 is hsa-miR-6090.

In a preferred embodiment, such a nucleic acid is specifically a polynucleotide selected from the group consisting of the following polynucleotides (k) to (o):

(k) a polynucleotide consisting of a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (l) a polynucleotide comprising a nucleotide sequence represented by any of SEQ ID NOs: 181 to 194, (m) a polynucleotide consisting of a nucleotide sequence complementary to a nucleotide sequence represented by any of SEQ ID NOs: 181 to 194 or a nucleotide sequence derived from the nucleotide sequence by the replacement of u with t, a variant thereof, a derivative thereof, or a fragment thereof comprising 15 or more consecutive nucleotides, (n) a polynucleotide comprising a nucleotide sequence complementary to a nucleotide sequence represented by any of SEQ ID NOs: 181 to 194 or a nucleotide sequence derived from the nucleotide sequence by the replacement of u with t, and (o) a polynucleotide hybridizing under stringent conditions to any of the polynucleotides (k) to (n).

Examples of the sample used in the method of the present invention can include samples prepared from a living tissue (preferably a colorectal tissue) or a body fluid such as blood, serum, plasma, or urine from the subject. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse and a rat without any limitation, and is preferably a human.

The steps of the method of the present invention can be changed according to the type of the sample to be assayed.

In the case of using RNA as an analyte, the detection of colorectal cancer (cells) can comprise, for example, the following steps (a), (b), and (c):

(a) a step of binding RNA prepared from the sample of the subject or a complementary polynucleotide (cDNA) transcribed therefrom to a polynucleotide in the kit or the device of the present invention;

(b) a step of measuring the sample-derived RNA or the cDNA synthesized from the RNA, bound with the polynucleotide by hybridization using the polynucleotide as a nucleic acid probe or by quantitative RT-PCR using the polynucleotide as a primer; and (c) a step of evaluating the presence or absence of colorectal cancer (or colorectal cancer-derived gene expression) on the basis of the measurement results of the step (b).

For example, various hybridization methods can be used for detecting, examining, evaluating, or diagnosing colorectal cancer (or colorectal cancer-derived gene expression) in vitro according to the present invention. For example, Northern blot, Southern blot, RT-PCR, DNA chip analysis, in situ hybridization, Northern hybridization, or Southern hybridization can be used as such a hybridization method.

In the case of using the Northern blot, the presence or absence of expression of each gene or the expression level thereof in the RNA can be detected or measured by use of the nucleic acid probe that can be used in the present invention. Specific examples thereof can include a method which involves labeling the nucleic acid probe (or its complementary strand) with a radioisotope ($^{32}$P, $^{33}$P, $^{35}$S, etc.), a fluorescent material, or the like, that hybridizes the labeled product with the living tissue-derived RNA from a subject transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which involves; preparing cDNA from the living tissue-derived RNA of a subject according to a routine method, hybridizing a pair of primers (consisting of a plus strand and a reverse strand binding to the cDNA) of the present invention with the cDNA such that the region of each target gene can be amplified with the cDNA as a template, and performing PCR according to a routine method to detect the obtained double-stranded DNA. The method for detecting the double-stranded DNA can include a method of performing the PCR using the primers labeled in advance with a radioisotope or a fluorescent material, a method of electrophoresis the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the nucleic acid array analysis, an RNA chip or a DNA chip in which the nucleic acid probes (single-stranded or double-stranded) of the present invention is attached to a substrate (solid phase) is used. Regions that have the attached nucleic acid probes are referred to as probe spots, and regions that have no attached nucleic acid probe are referred to as blank spots. A gene group immobilized on a solid-phase substrate is generally called a nucleic acid chip, a nucleic acid array, a microarray, or the like. The DNA or RNA array includes a DNA or RNA macroarray and a DNA or RNA microarray. The term "chip" used herein includes all of these arrays. 3D-Gene™ Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label on the nucleic acid probes using an image detector (examples thereof can include Typhoon 9410 (GE Healthcare Japan Corp.) and 3D-Gene™ scanner (Toray Industries, Inc.)).

The "stringent conditions" used herein are, as mentioned above, conditions under which a nucleic acid probe hybridizes to its target sequence to a larger extent (e.g., a measurement value equal to or larger than a mean of background measurement values+a standard deviation of the background measurement values×2) than that for other sequences.

The stringent conditions are defined by hybridization and subsequent washing conditions. The hybridization conditions involve, for example, but not limited to, 30° C. to 60° C. for 1 to 24 hours in a solution containing SSC, a surfactant, formamide, dextran sulfate, a blocking agent, etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably involve 3 to 10×SSC and 0.1 to 1% SDS. Examples of the conditions of the washing, following the hybridization, which is another condition to define the stringent conditions, can include conditions involving continuous washing at 30° C. in a solution containing 0.5×SSC and 0.1% SDS, at 30° C. in a solution containing 0.2×SSC and 0.1% SDS, and at 30° ° C. in a 0.05×SSC solution. It is desirable that the complementary strand should maintain its hybridized state with a target plus strand even by the washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using a polynucleotide fragment in the kit of the present invention as a primer include treatment for approximately 15 seconds to 1 minute at 5 to 10° C. plus a Tm value calculated from the sequence of the primer, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.); LNA™-based MicroRNA PCR (Exiqon); or Ncode™ miRNA qRT-PCT kit (Invitrogen Corp.) may be used.

For the calculation of gene expression levels, statistical analysis described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of 26, preferably 28, more preferably 210 or larger, in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method comprising measuring a target gene or gene expression level in a sample derived from a subject using the polynucleotide, the kit, or the device (e.g., chip) for detection of the present invention, or a combination thereof, preparing a discriminant (discriminant function) with gene expression levels in a sample derived from a colorectal cancer patient and a sample derived from a healthy subject as supervising samples, and determining or evaluating the presence and/or absence of the colorectal cancer-derived gene in the sample.

Specifically, the present invention further provides the method comprising: a first step of measuring in vitro an expression level of a target gene (target nucleic acid) in multiple samples known to determine or evaluate the presence and/or absence of the colorectal cancer-derived gene in the samples, using the polynucleotide, the kit, or the device (e.g., chip) for detection of the present invention, or a combination thereof; a second step of preparing a discriminant with the measurement values of the expression level of the target gene obtained in the first step as supervising samples; a third step of measuring in vitro an expression level of the target gene in a sample derived from a subject in the same way as in the first step; and a fourth step of assigning the measurement value of the expression level of the target gene obtained in the third step into the discriminant obtained in the second step, and determining or evaluating the presence or absence of the colorectal cancer-derived gene in the sample on the basis of the results obtained from the discriminant, wherein the target gene can be detected using the polynucleotide or using a polynucleotide for detection contained in the kit or the device (e.g., chip). In this context, the discriminant can be prepared by use of Fisher's discriminant analysis, nonlinear discriminant analysis based on Mahalanobis' distance, neural network, Support Vector Machine (SVM), or the like, though the method is not limited thereto.

When a clustering boundary is a straight line or a hyperplane, the linear discriminant analysis is a method for determining the association of a cluster using Formula 1 as a discriminant. In Formula 1, x represents an explanatory variable, w represents a coefficient of the explanatory variable, and w0 represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, one type of linear discriminant analysis, is a dimensionality reduction method for selecting a dimension suitable for discriminating classes, and constructs synthetic variable with highly discriminant performance by focusing on the variance of synthetic variables and minimizing the variance of data having the same label (Venables, W. N. et al., Modern Applied Statistics with S. Fourth edition. Springer., 2002). In the Fisher's discriminant analysis, direction w of projection is determined so as to maximize Formula 2. In this Formula, μ represents an average input, ng represents the number of data associated to class g, and μg represents an average input of the data associated to class g. The numerator and the denominator are the inter-classe variance and the intra-classe variance, respectively, when each data is projected in the direction of the vector w. Discriminant coefficient wi is determined by maximizing this ratio (Takafumi Kanamori et al., "Pattern Recognition", Kyoritsu Shuppan Co., Ltd. (2009); and Richard O. et al., Pattern Classification Second Edition., Wiley-Interscience, 2000).

$$\text{Formula 2}$$

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \quad \text{subject to } \mu = \sum_{i=1}^{n} \frac{x_i}{n},$$

$$\mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining a cluster having a closer Mahalanobis' distance from each cluster as an associated cluster. In this Formula 3, μ represents a central vector of each cluster, and S-1 represents an inverse matrix of the variance-covariance matrix of the cluster. The central vector is calculated from explanatory variable x, and an average vector, a median value vector, or the like can be used.

$$D(x, \mu) = \left\{ (x - \mu)^t S^{-1} (x - \mu) \right\}^{\frac{1}{2}} \qquad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (2004); Nello Cristianini et al., Introduction to SVM, Kyoritsu Shuppan Co., Ltd. (2008)).

C-support vector classification (C-SVC), one type of SVM, involves preparing a hyperplane by supervising with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a colorectal cancer patient group and a healthy subject group. For example, colorectal tissue examination can be used for each subject to be confirmed either as a colorectal cancer patient or as a healthy subject.

Next, a data set consisting of comprehensive gene expression levels of serum-derived samples of the two divided groups (hereinafter, this data set is referred to as a training cohort) is prepared, and a C-SVC discriminant is determined by using explanatory variables that are genes found to differ clearly in their gene expression levels between the two groups, and objective variables (e.g., −1 and +1) that are the grouping. An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2}a^T Q a - e^T a \text{ subject to } y^T a = 0, 0 \le a_i \le C, i = 1, \ldots, l, \quad \text{Formula 4}$$

Formula 5 is a finally obtained discriminant, and an associated group can be determined on the basis of the sign of a value obtained according to the discriminant. In this Formula, x represents a support vector, y represents a label indicating the association of a group, a represents the corresponding coefficient, b represents a constant term, and K represents a kernel function.

$$f(x) = \text{sgn}\left(\sum_{i=1}^{l} y_i a_i K(x_i, x) + b\right) \quad \text{Formula 5}$$

For example, a RBF kernel defined by Formula 6 can be used as the kernel function. In this Formula, x represents a support vector, and y represents a kernel parameter for adjusting the complexity of the hyperplane.

$$K(x_i, x_j) = \exp\left(-r\|x_i - x_j\|^2\right), r < 0 \quad \text{Formula 6}$$

In addition, an approach such as neural network, k-nearest neighbor algorithms, decision trees, or logistic regression analysis can be selected as a method for determining or evaluating the presence and/or absence of expression of a colorectal cancer-derived target gene in a sample derived from a subject, or for evaluating the expression level thereof by comparison with a control derived from a healthy subject.

The method of the present invention can comprise, for example, the following steps (a), (b), and (c):

(a) a step of measuring an expression level of a target gene in tissues containing colorectal cancer-derived genes derived from colorectal cancer patients and/or samples already known to be tissues containing no colorectal cancer-derived gene derived from healthy subjects, using the polynucleotide, the kit, or the device (e.g., DNA chip) for detection according to the present invention;

(b) a step of preparing the discriminants of Formulas 1 to 3, 5, and 6 described above from the measurement values of the expression level measured in the step (a); and (c) measuring an expression level of the target gene in a sample derived from a subject using the polynucleotide, the kit, or the device (e.g., DNA chip) for detection according to the present invention, assigning the obtained measurement value to the discriminants prepared in the step (b), and determining or evaluating the presence and/or absence of the colorectal cancer-derived target gene in the sample, or evaluating the expression level thereof by comparison with a healthy subject-derived control, on the basis of the obtained results. In this context, in the discriminants of Formulas 1 to 3, 5, and 6, x represents an explanatory variable and includes a value obtained by measuring a polynucleotide selected from the polynucleotides described in Section 2 above, or a fragment thereof, etc. Specifically, the explanatory variable for discriminating a colorectal cancer patient from a healthy subject according to the present invention is a gene expression level selected from, for example, the following expression levels (1) to (3):

(1) a gene expression level in the serum of a colorectal cancer patient or a healthy subject measured by any DNA comprising 15 or more consecutive nucleotides in a nucleotide sequence represented by any of SEQ ID NOs: 1 to 171 and 606 to 614 or a complementary sequence thereof, (2) a gene expression level in the serum of a colorectal cancer patient or a healthy subject measured by any DNA comprising 15 or more consecutive nucleotides in a nucleotide sequence represented by any of SEQ ID NOs: 172 to 180 or a complementary sequence thereof, and (3) a gene expression level in the serum of a colorectal cancer patient or a healthy subject measured by any DNA comprising 15 or more consecutive nucleotides in a nucleotide sequence represented by any of SEQ ID NOs: 181 to 194 or a complementary sequence thereof.

As described above, for the method for determining or evaluating the presence and/or absence of a colorectal cancer-derived gene in a sample derived from a subject, the preparation of a discriminant requires a discriminant constructed from a training cohort. For enhancing the discriminant accuracy of the discriminant, it is necessary for the discriminant to use genes that show clear difference between two groups in the training cohort.

Each gene that is used for an explanatory variable in a discriminant is preferably determined as follows. First, comprehensive gene expression levels of a colorectal cancer patient group and comprehensive gene expression levels of a healthy subject group in a training cohort are used as a data set, the degree of difference in the expression level of each gene between the two groups is determined through the use of, for example, the P value of t test, which is parametric analysis, or the P value of Mann-Whitney's U test or Wilcoxon test, which is nonparametric analysis.

The gene can be regarded as being statistically significant when the critical rate (significance level) of the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the statistical test, the absolute value (fold change) of an expression ratio of a median value of each gene expression level between gene expression levels of a colorectal cancer patient group and gene expression levels of a healthy subject group may be calculated to select a gene that is used for an explanatory variable in a discriminant. Alternatively, ROC curves may be prepared using gene expression levels of a colorectal cancer patient group and a healthy subject group, and a gene that is used for an explanatory variable in a discriminant can be selected on the basis of an AUROC value.

Next, a discriminant that can be calculated by various methods described above is constructed using any number of genes that show large difference in their gene expression levels determined here. Examples of the method for constructing a discriminant that produces the largest discriminant accuracy include a method of constructing a discriminant in every combination of genes that satisfy the significance level of P value, and a method of repetitively evaluating the genes for use in the construction of a discriminant while increasing the number of genes one by one in a descending order of the difference in gene expression level (Furey T S. et al., 2000, Bioinformatics, Vol. 16, p. 906-14). A gene expression level of another independent colorectal cancer patient or healthy subject is assigned as an explanatory variable to this discriminant, and a result of the discriminant analysis regarding the group to which this independent colorectal cancer patient or healthy subject associated, is calculated. Specifically, the found gene set for diagnosis and the discriminant constructed using the gene set for diagnosis can be evaluated in an independent sample group to find a more universal gene set for diagnosis capable of detecting colorectal cancer and a more universal method for discriminating colorectal cancer.

Split-sample method is preferably used for evaluating the discriminant performance (generality) of the discriminant. Specifically, a data set is divided into a training cohort and a validation cohort, and gene selection by a statistical test and discriminant construction are performed in the training cohort. Accuracy, sensitivity, and specificity are calculated using results of discriminating a validation cohort according to the discriminant and a true group to which the validation cohort associated, to evaluate the discriminant performance. On the other hand, instead of dividing a data set, gene selection by a statistical test and discriminant preparation may be performed using all of samples, and accuracy, sensitivity, and specificity can be calculated by the discriminant of newly prepared samples according to the discriminant to evaluate the discriminant performance.

The present invention provides a polynucleotide for detection or for disease diagnosis useful in the diagnosis and treatment of colorectal cancer, a method for detecting colorectal cancer using the polynucleotide, and a kit and a device for the detection of colorectal cancer, comprising the polynucleotide. Particularly, in order to select a gene for diagnosis and prepare a discriminant so as to exhibit accuracy beyond a colorectal cancer diagnosis method using existing tumor markers CEA, a gene set for diagnosis and a discriminant for the method of the present invention can be constructed, which exhibit accuracy beyond CEA, for example, by comparing genes expressed in serum derived from a patient confirmed to be negative using CEA but finally found to have colorectal cancer by detailed examination such as computed tomography using a contrast medium, with genes expressed in serum derived from a patient who has no colorectal cancer.

For example, the gene set for diagnosis is set to any combination selected from one or two or more of the polynucleotides based on a nucleotide sequence represented by any of SEQ ID NOs: 1 to 171 and 606 to 614 or a complementary sequence thereof as described above, optionally one or two or more of the polynucleotides based on a nucleotide sequence represented by any of SEQ ID NOs: 172 to 180 or a complementary sequence thereof, and optionally one or two or more of the polynucleotides based on a nucleotide sequence represented by any of SEQ ID NOs: 181 to 194 or a complementary sequence thereof. Further, a discriminant is constructed using expression levels of the gene set for diagnosis in samples derived from class I colorectal cancer patients and samples derived from class II healthy subjects as a result of tissue diagnosis. As a result, the presence or absence of colorectal cancer-derived genes in an unknown sample can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples from Colorectal Cancer Patients and Healthy Subjects>

Serum was collected using VENOJECT II vacuum blood collecting tube VP-AS109K60 (Terumo Corp.) from each of 100 healthy subjects and 34 colorectal cancer patients (15 cases with stage I, 6 cases with stage IIA, 4 cases with stage IIIA, 6 cases with stage IIIB, 2 cases with stage IIIC, and 1 case with stage IV) who were confirmed to have no primary cancer other than colorectal cancer after acquisition of informed consent, and used as a training cohort. Likewise, serum was collected using VENOJECT II vacuum blood collecting tube VP-AS109K60 (Terumo Corp.) from each of 50 healthy subjects and 16 colorectal cancer patients (3 cases with stage I, 4 cases with stage IIA, 1 case with stage IIB, 2 cases with stage IIIB, 2 cases with stage IIIC, and 4 cases with stage IV) who were confirmed to have no primary cancer other than colorectal cancer after acquisition of informed consent, and used as a validation cohort.

<Extraction of Total RNA>

Total RNA was obtained from 300 μL of the serum sample obtained from each of 200 persons in total of 150 healthy subjects and 50 colorectal cancer patients included in the training cohort and the validation cohort, using a reagent for RNA extraction in 3D-Gene™ RNA extraction reagent from liquid sample kit (Toray Industries, Inc.) according to the protocol provided by the manufacturer.

<Measurement of Gene Expression Level> miRNAs in the total RNA obtained from the serum sample of each of 200 persons in total of 150 healthy subjects and 50 colorectal cancer patients included in the training cohort and the validation cohort were fluorescently labeled using 3D-Gene™ miRNA Labeling kit (Toray Industries, Inc.) according to the protocol (ver 2.20) provided by the manufacturer. The oligo DNA chip used was 3D-Gene™ Human miRNA Oligo chip (Toray Industries, Inc.) with attached probes having sequences complementary to 2,555 miRNAs among the miRNAs registered in miR-Base Release 20. Hybridization between the miRNAs in the total RNA and the probes on the DNA chip under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value with a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the serum were obtained for the 50 colorectal cancer patients and the 150 healthy subjects. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples from Patients with Cancer Other than Colorectal Cancer>

Serum was collected using VENOJECT II vacuum blood collecting tube VP-AS109K60 (Terumo Corp.) from each of 69 pancreatic cancer patients, 66 biliary tract cancer patients, 30 stomach cancer patients, 33 esophageal cancer patients, 32 liver cancer patients, and 15 benign pancreaticobiliary disease patients who were confirmed to have no cancer in other organs after acquisition of informed consent, and used as a training cohort together with the samples of 34 colorectal cancer patients and 103 healthy subjects of Reference Example 1. Likewise, serum was collected using VENOJECT II vacuum blood collecting tube VP-AS109K60 (Terumo Corp.) from each of 30 pancreatic cancer patients, 33 bile duct cancer patients, 20 stomach cancer patients, 17 esophageal cancer patients, 20 liver cancer patients, and 6 benign pancreaticobiliary disease patients who were confirmed to have no cancer in other organs after acquisition of informed consent, and used as a validation cohort together with the samples of 16 colorectal cancer patients confirmed to have no cancer in organs other than the large intestine and 47 healthy subjects of Reference Example 1. Subsequent operations were conducted in the same way as in Reference Example 1.

Example 1

<Selection of Gene Marker Using Samples in the Training Cohort, and Method for Evaluating Colorectal Cancer Discriminant Performance of Single Gene Marker Using Samples of in the Validation Cohort>

In this Example, a gene marker for discriminating a colorectal cancer patient from a healthy subject was selected in the training cohort and studied in samples in the validation cohort independent of the training cohort, for a method for evaluating the colorectal cancer discriminant performance of each selected gene marker alone.

Specifically, first, the miRNA expression levels of the training cohort and the validation cohort obtained in the preceding Reference Examples were combined and normalized by quantile normalization.

Next, genes for diagnosis were selected using the training cohort. Here, in order to acquire diagnostic markers with higher reliability, only genes that show a gene expression level of 26 or higher in 50% or more of the samples in either of the colorectal cancer patient group in the training cohort or the healthy subject group in the training cohort were selected. In order to further acquire statistically significant genes for discriminating a colorectal cancer patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant. The obtained genes are described in Table 2.

In this way, hsa-miR-6726-5p, hsa-miR-4257, hsa-miR-6787-5p, hsa-miR-6780b-5p, hsa-miR-3131, hsa-miR-7108-5p, hsa-miR-1343-3p, hsa-miR-1247-3p, hsa-miR-4651, hsa-miR-6757-5p, hsa-miR-3679-5p, hsa-miR-7641, hsa-miR-6746-5p, hsa-miR-8072, hsa-miR-6741-5p, hsa-miR-1908-5p, hsa-miR-6857-5p, hsa-miR-4746-3p, hsa-miR-744-5p, hsa-miR-4792, hsa-miR-564, hsa-miR-6791-5p, hsa-miR-6825-5p, hsa-miR-6826-5p, hsa-miR-4665-3p, hsa-miR-4467, hsa-miR-3188, hsa-miR-6125, hsa-miR-6756-5p, hsa-miR-1228-3p, hsa-miR-8063, hsa-miR-8069, hsa-miR-6875-5p, hsa-miR-3185, hsa-miR-4433b-3p, hsa-miR-6887-5p, hsa-miR-128-1-5p, hsa-miR-6724-5p, hsa-miR-1914-3p, hsa-miR-1225-5p, hsa-miR-4419b, hsa-miR-7110-5p, hsa-miR-187-5p, hsa-miR-3184-5p, hsa-miR-204-3p, hsa-miR-5572, hsa-miR-6729-5p, hsa-miR-615-5p, hsa-miR-6749-5p, hsa-miR-6515-3p, hsa-miR-3937, hsa-miR-6840-3p, hsa-miR-6893-5p, hsa-miR-4728-5p, hsa-miR-6717-5p, hsa-miR-7113-3p, hsa-miR-4665-5p, hsa-miR-642b-3p, hsa-miR-7109-5p, hsa-miR-6842-5p, hsa-miR-4442, hsa-miR-4433-3p, hsa-miR-4707-5p, hsa-miR-6126, hsa-miR-4449, hsa-miR-4706, hsa-miR-1913, hsa-miR-602, hsa-miR-939-5p, hsa-miR-4695-5p, hsa-miR-711, hsa-miR-6816-5p, hsa-miR-4632-5p, hsa-miR-6721-5p, hsa-miR-7847-3p, hsa-miR-6132, hsa-miR-887-3p, hsa-miR-3679-3p, hsa-miR-6784-5p, hsa-miR-1249, hsa-miR-937-5p, hsa-miR-5195-3p, hsa-miR-6732-5p, hsa-miR-4417, hsa-miR-4281, hsa-miR-4734, hsa-miR-6766-3p, hsa-miR-663a, hsa-miR-4513, hsa-miR-6781-5p, hsa-miR-1227-5p, hsa-miR-6845-5p, hsa-miR-6798-5p, hsa-miR-3620-5p, hsa-miR-1915-5p, hsa-miR-4294, hsa-miR-642a-3p, hsa-miR-371a-5p, hsa-miR-940, hsa-miR-4450, hsa-miR-4723-5p, hsa-miR-1469, hsa-miR-6861-5p, hsa-miR-7975, hsa-miR-6879-5p, hsa-miR-6802-5p, hsa-miR-1268b, hsa-miR-663b, hsa-miR-125a-3p, hsa-miR-2861, hsa-miR-6088, hsa-miR-4758-5p, hsa-miR-296-3p, hsa-miR-6738-5p, hsa-miR-671-5p, hsa-miR-4454, hsa-miR-4516, hsa-miR-7845-5p, hsa-miR-4741, hsa-miR-92b-5p, hsa-miR-6795-5p, hsa-miR-6805-3p, hsa-miR-4725-3p, hsa-miR-6782-5p, hsa-miR-4688, hsa-miR-6850-5p, hsa-miR-6777-5p, hsa-miR-6785-5p, hsa-miR-7106-5p, hsa-miR-3663-3p, hsa-miR-6131, hsa-miR-1915-3p, hsa-miR-4532, hsa-miR-6820-5p, hsa-miR-4689, hsa-miR-4638-5p, hsa-miR-3656, hsa-miR-3621, hsa-miR-6769b-5p, hsa-miR-149-3p, hsa-miR-23b-3p, hsa-miR-3135b, hsa-miR-6848-5p, hsa-miR-6769a-5p, hsa-miR-4327, hsa-miR-6765-3p, hsa-miR-6716-5p, hsa-miR-6877-5p, hsa-miR-6727-5p, hsa-miR-4534, hsa-miR-614, hsa-miR-1202, hsa-miR-575, hsa-miR-6870-5p, hsa-miR-6722-3p, hsa-miR-7977, hsa-miR-4649-5p, hsa-miR-4675, hsa-miR-6075, hsa-miR-6779-5p, hsa-miR-4271, hsa-miR-3196, hsa-miR-6803-5p, hsa-miR-6789-5p, hsa-miR-4648, hsa-miR-4508, hsa-miR-4749-5p, hsa-miR-4505, hsamiR-5698, hsa-miR-1199-5p and hsa-miR-4763-3p, hsa-miR-1231, hsa-miR-1233-5p, hsa-miR-150-3p, hsa-miR-1225-3p, hsa-miR-92a-2-5p, hsa-miR-423-5p, hsa-miR-1268a, hsa-miR-128-2-5p and hsa-miR-24-3p genes, and polynucleotides consisting of the nucleotide sequences of SEQ ID NOs: 1 to 180 related thereto were found.

Among them, genes newly found as markers for examining the presence or absence of colorectal cancer are polynucleotides consisting of the nucleotide sequences represented by SEQ ID NOs: 1 to 171.

A discriminant for determining the presence or absence of colorectal cancer was further prepared by Fisher's discriminant analysis with the expression levels of these genes as an index. Specifically, any polynucleotide consisting of a nucleotide sequence represented by any of SEQ ID NOs: 1 to 180 found in the training cohort was applied to Formula 2 above to construct a discriminant. Calculated accuracy, sensitivity, and specificity are shown in Table 3. In this respect, a discriminant coefficient and a constant term are shown in Table 4.

Figure 2:
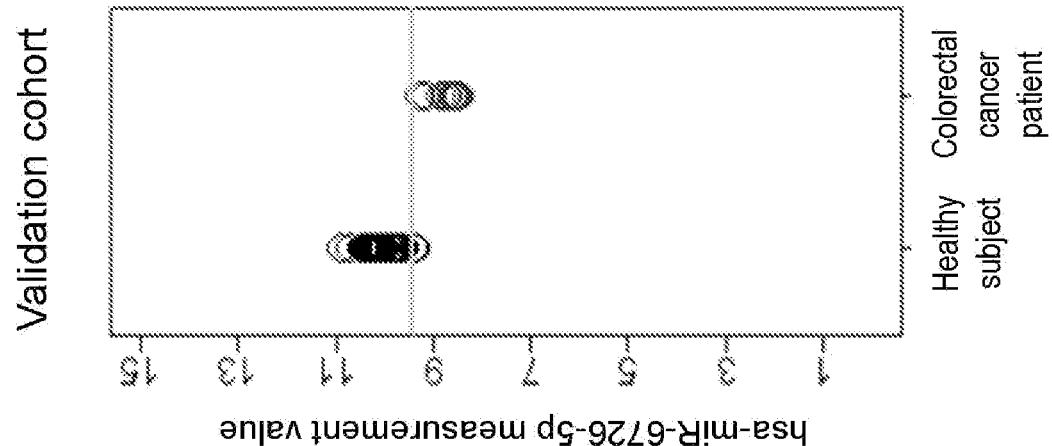
FIG. 2 Left diagram: the expression level measurement values of hsa-miR-6726-5p (SEQ ID NO: 1) in healthy subjects (100 persons) and colorectal cancer patients (34 persons) selected as a training cohort were each plotted on the ordinate. The horizontal line in the diagram depicts a threshold (9.43) that was optimized by Fisher's discriminant analysis and discriminated between the two groups. Right diagram: the expression level measurement values of hsa-miR-6726-5p (SEQ ID NO: 1) in healthy subjects (50 persons) and colorectal cancer patients (16 persons) selected as validation cohort were each plotted on the ordinate. The horizontal line in the diagram depicts the threshold (9.43) that was set for the training cohort and discriminated between the two groups.
Figure 2:
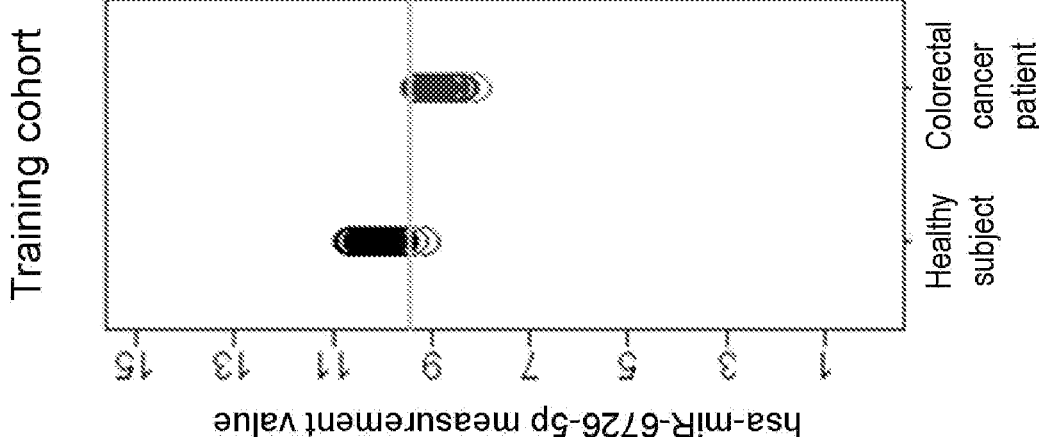

Accuracy, sensitivity, and specificity in the validation cohort were calculated using the discriminant thus prepared, and the discriminant performance of the selected polynucleotides was validated using independent samples (Table 3). For example, the expression level measurement value of the nucleotide sequence represented by SEQ ID NO: 1 was compared between the healthy subjects (100 persons) and the colorectal cancer patients (34 persons) in the training cohort. As a result, the gene expression level measurement values were found to be significantly lower in the colorectal cancer patient group than in the healthy subject group (see the left diagram of FIG. 2). These results were also reproducible for the healthy subjects (50 persons) and the colorectal cancer patients (16 persons) in the validation cohort (see the right diagram of FIG. 2). Likewise, the results obtained about the other polynucleotides shown in SEQ ID NOs: 2 to 180 showed that the gene expression level measurement values were significantly lower (−) or higher (+) in the colorectal cancer patient group than in the healthy subject group (Table 2). These results were able to be validated in the validation cohort. For example, as for this nucleotide sequence represented by SEQ ID NO: 1, the number of samples that correctly identified in the detection of colorectal cancer in the validation cohort was calculated using the threshold (9.43) that was set in the training cohort and discriminated between the two groups. As a result, 16 true positives, 50 true negatives, 0 false positives, and 0 false negatives were obtained. From these values, 100% accuracy, 100% sensitivity, and 100% specificity were obtained as detection performance. In this way, the detection performance was calculated as to all of the polynucleotides shown in SEQ ID NOs: 1 to 180, and described in Table 3.

For example, 110 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 55, 56, 57, 58, 59, 60, 61, 62, 63, 65, 66, 67, 68, 69, 71, 72, 73, 74, 76, 77, 78, 79, 80, 81, 83, 84, 86, 87, 88, 90, 92, 93, 95, 96, 97, 99, 100, 101, 102, 107, 109, 110, 111, 113, 114, 115, 118, 120, 122, 124, 126, 134, 136, 142, 153, 172, 173 and 175 exhibited sensitivity of 100%, 100%, 100%, 75%, 93.8%, 75%, 87.5%, 75%, 93.8%, 68.8%, 81.2%, 100%, 75%, 50%, 75%, 75%, 68.8%, 75%, 81.2%, 81.2%, 75%, 62.5%, 75%, 56.2%, 75%, 68.8%, 56.2%, 62.5%, 68.8%, 75%, 68.8%, 68.8%, 56.2%, 68.8%, 62.5%, 68.8%, 62.5%, 50%, 56.2%, 56.2%, 56.2%, 75%, 50%, 68.8%, 68.8%, 68.8%, 50%, 56.2%, 62.5%, 62.5%, 50%, 62.5%, 68.8%, 56.2%, 56.2%, 43.8%, 75%, 62.5%, 62.5%, 56.2%, 62.5%, 62.5%, 56.2%, 62.5%, 56.2%, 56.2%, 56.2%, 56.2%, 43.8%, 43.8%, 50%, 68.8%, 56.2%, 62.5%, 62.5%, 43.8%, 62.5%, 56.2%, 62.5%, 62.5%, 50%, 56.2%, 43.8%, 50%, 43.8%, 50%, 43.8%, 56.2%, 43.8%, 50%, 50%, 50%, 50%, 50%, 50%, 43.8%, 50%, 43.8%, 50%, 50%, 50%, 43.8%, 43.8%, 50%, 43.8%, 43.8%, 50%, 81.2%, 68.8% and 56.2%, respectively in the validation cohort (Table 3). As seen from Comparative Example mentioned later, the existing markers CEA had sensitivity of 43.75% in the validation cohort (Tables 5-1 and 5-2), demonstrating that the 110 polynucleotides consisting of the nucleotide sequences represented by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 49, 50, 51, 52, 53, 55, 56, 57, 58, 59, 60, 61, 62, 63, 65, 66, 67, 68, 69, 71, 72, 73, 74, 76, 77, 78, 79, 80, 81, 83, 84, 86, 87, 88, 90, 92, 93, 95, 96, 97, 99, 100, 101, 102, 107, 109, 110, 111, 113, 114, 115, 118, 120, 122, 124, 126, 134, 136, 142, 153, 172, 173 and 175 can discriminate, each alone, colorectal cancer in the validation cohort with sensitivity beyond CEA.

For example, 14 polynucleotides consisting of the nucleotide sequences represented by SEQ ID NOs: 1, 2, 3, 10, 14, 17, 21, 23, 32, 36, 47, 59, 65, and 101 were able to correctly determine colorectal cancer as to all of three stage 1 colorectal cancer samples that were contained in the validation cohort. Thus, these polynucleotides can detect even early colorectal cancer and contribute to the early diagnosis of colorectal cancer.

For example, 12 polynucleotides consisting of the nucleotide sequences represented by SEQ ID NOs: 1, 2, 3, 5, 7, 10, 14, 39, 46, 73, 81, and 148 were able to correctly determine colorectal cancer as to all of one cecal cancer case and 3 ascending colon cancer cases, which were cancer cases in the upper large intestine that are reportedly difficult to detect by the fecal occult blood test, in the validation cohort. Thus, these polynucleotides can detect colorectal cancer regardless of where colorectal cancer develops.

Example 2

<Method for Evaluating Colorectal Cancer Discriminant Performance by Combination of Multiple Gene Markers Using Samples in the Validation Cohort>

In this Example, a method for evaluating colorectal cancer discriminant performance by a combination of the gene markers selected in Example 1 was studied. Specifically, Fisher's discriminant analysis was conducted as to 16,074 combinations of two polynucleotides comprising at least one or more of the expression level measurement values of the newly found polynucleotides consisting of the nucleotide sequences represented by SEQ ID NOs: 1 to 171 among the polynucleotides consisting of the nucleotide sequences represented by SEQ ID NOs: 1 to 180 selected in Example 1, to construct a discriminant for determining the presence or absence of colorectal cancer. Next, accuracy, sensitivity, and specificity in the validation cohort were calculated using the discriminant thus prepared, and the discriminant performance of the selected polynucleotides was validated using independent samples.

Figure 3:
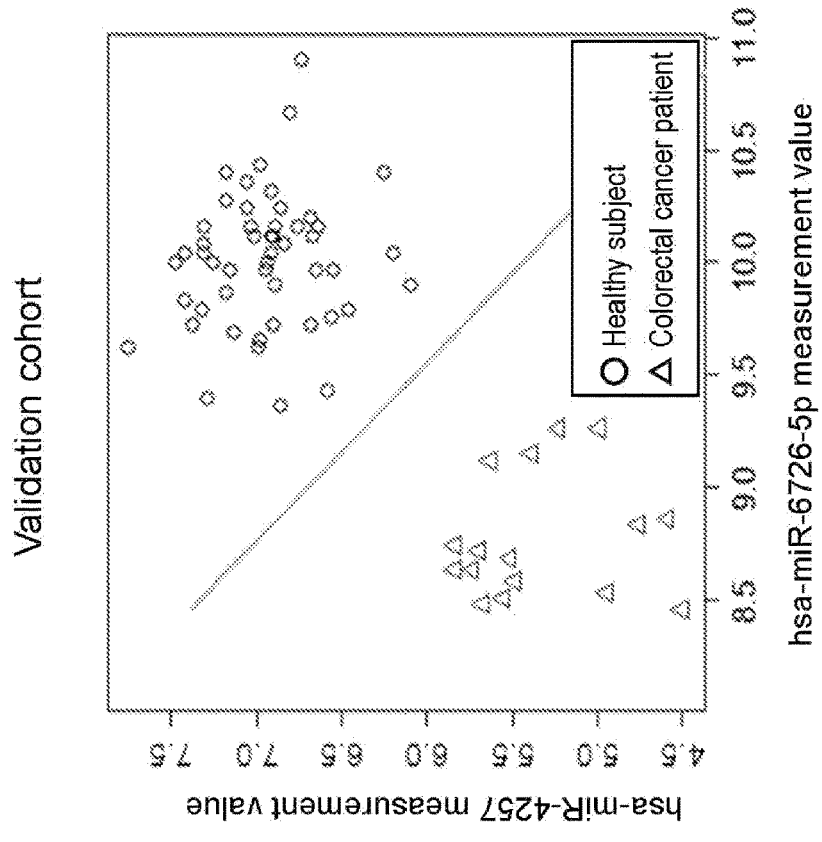
FIG. 3 Left diagram: the expression level measurement values of hsa-miR-6726-5p (SEQ ID NO: 1) in healthy subjects (100 persons, circles) and colorectal cancer patients (34 persons, triangles) selected as a training cohort were each plotted on the abscissa against their expression level measurement values of hsa-miR-4257 (SEQ ID NO: 2) on the ordinate. The line in the diagram depicts a discriminant function ($0=1.26x+y-18.06$) that was optimized by Fisher's discriminant analysis and discriminated between the two groups. Right diagram: the expression level measurement values of hsa-miR-6726-5p (SEQ ID NO: 1) in healthy subjects (50 persons, circles) and colorectal cancer patients (16 persons, triangles) selected as a validation cohort were each plotted on the abscissa against their expression level measurement values of hsa-miR-4257 (SEQ ID NO: 2) on the ordinate. The line in the diagram depicts the threshold ($0=1.26x+y-18.06$) that was set in the training cohort and discriminated between the two groups.
Figure 3:
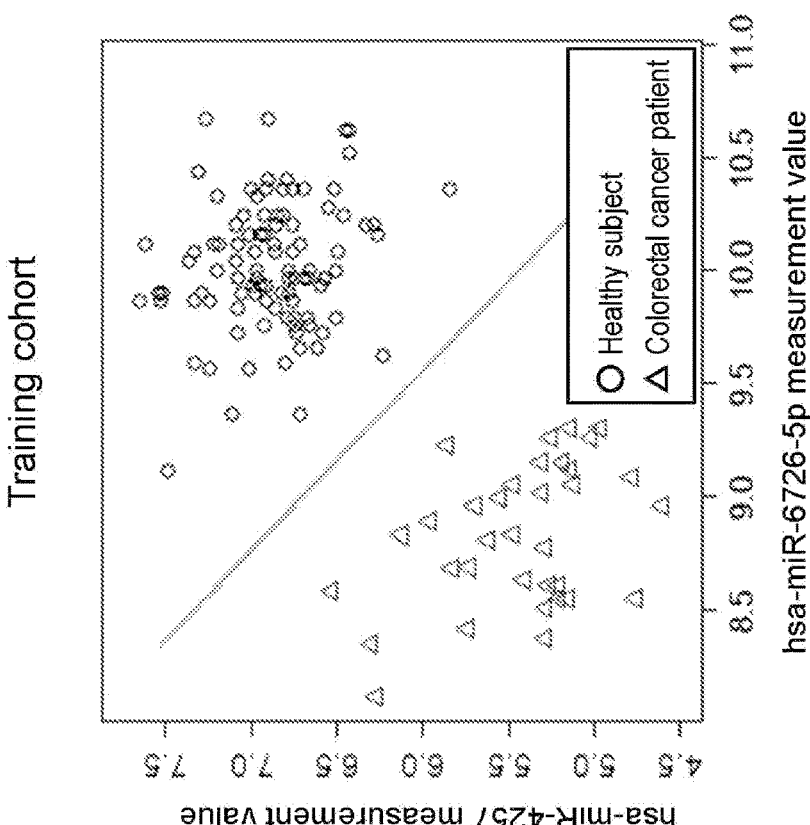

For example, the expression level measurement values of the nucleotide sequences represented by SEQ ID NO: 1 and SEQ ID NO: 2 were compared between the healthy subjects (100 persons) and the colorectal cancer patients (34 persons) in the training cohort. As a result, a scatter diagram that significantly separated the gene expression level measurement values of the colorectal cancer patient group from those of the healthy subject group was obtained (see the left diagram of FIG. 3). These results were also reproducible for the healthy subjects (50 persons) and the colorectal cancer patients (16 persons) in the validation cohort (see the right diagram of FIG. 3). Likewise, a scatter diagram that significantly separated the gene expression level measurement values of the colorectal cancer patient group from those of the healthy subject group was also obtained as to the other combinations of two expression level measurement values comprising at least one or more of the expression level measurement values of the newly found polynucleotides consisting of the nucleotide sequences represented by SEQ ID NOs: 1 to 171 among the polynucleotides consisting of the nucleotide sequences represented by SEQ ID NOS: 1 to 180. These results were able to be validated in the validation cohort. For example, as for these nucleotide sequences represented by SEQ ID NO: 1 and SEQ ID NO: 2, the number of samples that correctly identified in the detection of colorectal cancer was calculated using the function (0=1.26x+y−18.06) that was set in the training cohort and discriminated between the two groups. As a result, 16 true positives, 50 true negatives, 0 false positives, and 0 false negatives were obtained. From these values, 100% accuracy, 100% sensitivity, and 100% specificity were obtained as detection performance. In this way, the detection performance was calculated as to all of the combinations of two expression level measurement values comprising at least one or more of the expression level measurement values of the newly found polynucleotides consisting of the nucleotide sequences represented by SEQ ID NOs: 1 to 171 among the polynucleotides consisting of the nucleotide sequences represented by SEQ ID NOS: 1 to 180. Among them, 179 combinations comprising the expression level measurement value of the polynucleotide consisting of the nucleotide sequence represented by SEQ ID NO: 1 and the detection performance thereof were described in Table 6 as an example. For example, all of combinations of the expression level measurement values of the polynucleotides consisting of the nucleotide sequences represented by SEQ ID NOs: 1 and 2, SEQ ID NOs: 1 and 3, SEQ ID NOs: 1 and 4, and SEQ ID NOs: 1 and 5 exhibited sensitivity of 100% in the validation cohort (Table 6). Further, combinations of two polynucleotides consisting of nucleotide sequences other than SEQ ID NO: 1 were described in Table 7 as an example. As specific combinations of two polynucleotides, for example, combinations represented by SEQ ID NOs: 5 and 6, SEQ ID NOS: 5 and 11, SEQ ID NOs: 5 and 38, SEQ ID NOs: 15 and 16, SEQ ID NOs: 15 and 21, SEQ ID NOs: 15 and 64, SEQ ID NOs: 24 and 25, SEQ ID NOs: 24 and 30, SEQ ID NOs: 24 and 32, SEQ ID NOs: 2 and 32, SEQ ID NOs: 32 and 36, SEQ ID NOs: 15 and 32, SEQ ID NOs: 3 and 38, SEQ ID NOs: 38 and 39, SEQ ID NOs: 38 and 64, SEQ ID NOs: 3 and 45, SEQ ID NOs: 45 and 58, SEQ ID NOs: 45 and 64, SEQ ID NOs: 2 and 55, SEQ ID NOs: 6 and 55, SEQ ID NOS: 55 and 64, SEQ ID NOs: 2 and 64, SEQ ID NOs: 4 and 64, SEQ ID NOs: 2 and 96, SEQ ID NOs: 7 and 96, SEQ ID NOs: 96 and 97, SEQ ID NOs: 2 and 97, SEQ ID NOs: 3 and 97, SEQ ID NOs: 5 and 97, SEQ ID NOs: 2 and 162, SEQ ID NOs: 3 and 162, and SEQ ID NOs: 5 and 162, exhibited accuracy of 75% or higher for discriminating the colorectal cancer patients from the healthy subjects in both of the training cohort and the validation cohort. In this way, 14,598 combinations of the expression level measurement values of two polynucleotides that have sensitivity beyond the existing marker CEA (43.8% in Table 5-2) were obtained in the validation cohort. All of the nucleotide sequences 1 to 180 described in Table 2 obtained in Example 1 were employed at least once in these combinations. These results demonstrated that the combined use of two of the polynucleotides consisting of the nucleotide sequences represented by SEQ ID NOs: 1 to 180 can also discriminate colorectal cancer with excellent performance beyond the existing marker.

Markers for the detection of colorectal cancer with better sensitivity are obtained by combining 3, 4, 5, 6, 7, 8, 9, 10 or more of the expression level measurement values of the polynucleotides consisting of the nucleotide sequences represented by SEQ ID NOs: 1 to 180. For example, the newly found polynucleotides consisting of the nucleotide sequences represented by SEQ ID NOs: 1 to 171 among the polynucleotides consisting of the nucleotide sequences represented by SEQ ID NOs: 1 to 180 selected in Example 1 were measured to obtain their expression levels between the healthy subject group and the colorectal cancer group in the validation cohort. All of the polynucleotides were ranked in the descending order of their P values obtained by the Student's t-test, which indicates statistical significance of difference between groups (i.e., one having the lowest P value was ranked in the first place), and colorectal cancer detection sensitivity was evaluated using combinations of one or more polynucleotides to which the polynucleotides were added to the combination one by one from the top to the bottom according to the rank. In short, the order in which the polynucleotides were combined in this evaluation is in reverse in terms of SEQ ID NOs, from SEQ ID NO: 171 to SEQ ID NOs: 170, 169, . . . as shown in Table 2. As a result, the sensitivity in the validation cohort was 12.5% for 1 polynucleotide (SEQ ID NO: 171), 18.8% for 2 polynucleotides (SEQ ID NOs: 170 and 171), 25.0% for 4 polynucleotides (SEQ ID NOs: 168 to 171), 31.2% for 5 polynucleotides (SEQ ID NOs: 167 to 171), 37.5% for 7 polynucleotides (SEQ ID NOs: 165 to 171), 87.5% for 10 polynucleotides (SEQ ID NOs: 162 to 171), 100% for 20 polynucleotides (SEQ ID NOs: 152 to 171), 100% for 30 polynucleotides (SEQ ID NOs: 142 to 171), 100% for 80 polynucleotides (SEQ ID NOs: 92 to 171), 100% for 170 polynucleotides (SEQ ID NOs: 2 to 171), and 100% for 171 polynucleotides (SEQ ID NOs: 1 to 171).

These results demonstrated that a combination of multiple polynucleotides can produce higher colorectal cancer discriminant performance than that of each polynucleotide alone or a combination of a fewer number of polynucleotides. In this context, the combinations of multiple polynucleotides are not limited to the combinations of the polynucleotides added in the order of statistically significant difference as described above, and any combination of multiple polynucleotides can be used in the detection of colorectal cancer.

From these results, it can be concluded that all of the polynucleotides consisting of the nucleotide sequences represented by SEQ ID NOs: 1 to 180 serve as excellent markers for the detection of colorectal cancer.

TABLE 2

| SEQ ID NO: | Gene name | P value after Bonferroni correction | Expression level in colorectal cancer patient with respect to healthy subject |
|---|---|---|---|
| 1 | hsa-miR-6726-5p | 5.20.E−41 | − |
| 2 | hsa-miR-4257 | 7.54.E−40 | − |

TABLE 2-continued

| SEQ ID NO: | Gene name | P value after Bonferroni correction | Expression level in colorectal cancer patient with respect to healthy subject |
|---|---|---|---|
| 3 | hsa-miR-6787-5p | 1.72.E−30 | − |
| 4 | hsa-miR-6780b-5p | 3.42.E−30 | + |
| 5 | hsa-miR-3131 | 1.62.E−27 | − |
| 6 | hsa-miR-7108-5p | 5.42.E−27 | + |
| 7 | hsa-miR-1343-3p | 2.12.E−26 | − |
| 8 | hsa-miR-1247-3p | 9.98.E−26 | + |
| 9 | hsa-miR-4651 | 3.90.E−24 | − |
| 10 | hsa-miR-6757-5p | 2.25.E−23 | − |
| 11 | hsa-miR-3679-5p | 2.55.E−23 | + |
| 12 | hsa-miR-7641 | 971.E−22 | − |
| 13 | hsa-miR-6746-5p | 1.64.E−21 | − |
| 14 | hsa-miR-8072 | 4.09.E−21 | + |
| 15 | hsa-miR-6741-5p | 7.23.E−21 | − |
| 16 | hsa-miR-1908-5p | 2.12.E−20 | + |
| 17 | hsa-miR-6857-5p | 2.70.E−20 | + |
| 18 | hsa-miR-4746-3p | 3.58.E−20 | + |
| 19 | hsa-miR-744-5p | 4.23.E−20 | + |
| 20 | hsa-miR-4792 | 8.25.E−20 | + |
| 21 | hsa-miR-564 | 1.78.E−19 | − |
| 22 | hsa-miR-6791-5p | 3.80.E−19 | + |
| 23 | hsa-miR-6825-5p | 5.93.E−19 | + |
| 24 | hsa-miR-6826-5p | 8.67.E−19 | − |
| 25 | hsa-miR-4665-3p | 1.92.E−18 | + |
| 26 | hsa-miR-4467 | 5.55.E−18 | + |
| 27 | hsa-miR-3188 | 8.48.E−18 | + |
| 28 | hsa-miR-6125 | 1.09.E−17 | + |
| 29 | hsa-miR-6756-5p | 1.24.E−17 | − |
| 30 | hsa-miR-1228-3p | 1.68.E−17 | + |
| 31 | hsa-miR-8063 | 2.70.E−17 | − |
| 32 | hsa-miR-8069 | 3.58.E−17 | + |
| 33 | hsa-miR-6875-5p | 6.07.E−17 | + |
| 34 | hsa-miR-3185 | 5.07.E−16 | + |
| 35 | hsa-miR-4433b-3p | 1.22.E−15 | + |
| 36 | hsa-miR-6887-5p | 1.30.E−15 | − |
| 37 | hsa-miR-128-1-5p | 3.61.E−15 | + |
| 38 | hsa-miR-6724-5p | 3.81.E−15 | + |
| 39 | hsa-miR-1914-3p | 1.05.E−14 | − |
| 40 | hsa-miR-1225-5p | 3.93.E−14 | + |
| 41 | hsa-miR-4419b | 5.90.E−14 | − |
| 42 | hsa-miR-7110-5p | 6.01.E−14 | + |
| 43 | hsa-miR-187-5p | 8.57.E−14 | − |
| 44 | hsa-miR-3184-5p | 1.40.E−13 | + |
| 45 | hsa-miR-204-3p | 2.23.E−13 | − |
| 46 | hsa-miR-5572 | 2.34.E−13 | + |
| 47 | hsa-miR-6729-5p | 3.33.E−13 | + |
| 48 | hsa-miR-615-5p | 4.27.E−13 | − |
| 49 | hsa-miR-6749-5p | 5.30.E−13 | − |
| 50 | hsa-miR-6515-3p | 7.31.E−13 | + |
| 51 | hsa-miR-3937 | 8.10.E−13 | + |
| 52 | hsa-miR-6840-3p | 1.15.E−12 | − |
| 53 | hsa-miR-6893-5p | 1.34.E−12 | − |
| 54 | hsa-miR-4728-5p | 2.48.E−12 | − |
| 55 | hsa-miR-6717-5p | 4.45.E−12 | − |
| 56 | hsa-miR-7113-3p | 5.11.E−12 | + |
| 57 | hsa-miR-4665-5p | 5.33.E−12 | − |
| 58 | hsa-miR-642b-3p | 6.74.E−12 | − |
| 59 | hsa-miR-7109-5p | 6.88.E−12 | − |
| 60 | hsa-miR-6842-5p | 6.91.E−12 | + |
| 61 | hsa-miR-4442 | 8.87.E−12 | − |
| 62 | hsa-miR-4433-3p | 9.88.E−12 | + |
| 63 | hsa-miR-4707-5p | 1.19.E−11 | + |
| 64 | hsa-miR-6126 | 1.27.E−11 | + |
| 65 | hsa-miR-4449 | 1.32.E−11 | + |
| 66 | hsa-miR-4706 | 2.85.E−11 | − |
| 67 | hsa-miR-1913 | 3.15.E−11 | + |
| 68 | hsa-miR-602 | 4.98.E−11 | + |
| 69 | hsa-miR-939-5p | 6.08.E−11 | + |
| 70 | hsa-miR-4695-5p | 8.15.E−11 | + |
| 71 | hsa-miR-711 | 1.23 E−10 | + |
| 72 | hsa-miR-6816-5p | 1.29.E−10 | + |
| 73 | hsa-miR-4632-5p | 1.50.E−10 | + |
| 74 | hsa-miR-6721-5p | 1.98.E−10 | + |
| 75 | hsa-miR-7847-3p | 2.14.E−10 | − |
| 76 | hsa-miR-6132 | 2.68.E−10 | + |
| 77 | hsa-miR-887-3p | 2.81.E−10 | + |
| 78 | hsa-miR-3679-3p | 3.07.E−10 | + |
| 79 | hsa-miR-6784-5p | 3.20.E−10 | + |
| 80 | hsa-miR-1249 | 3.40.E−10 | + |
| 81 | hsa-miR-937-5p | 5.57.E−10 | − |
| 82 | hsa-miR-5195-3p | 6.88.E−10 | − |
| 83 | hsa-miR-6732-5p | 7.27.E−10 | + |
| 84 | hsa-miR-4417 | 7.95.E−10 | + |
| 85 | hsa-miR-4281 | 9.35.E−10 | − |
| 86 | hsa-miR-4734 | 1.04.E−09 | + |
| 87 | hsa-miR-6766-3p | 1.07.E−09 | + |
| 88 | hsa-miR-663a | 2.19.E−09 | + |
| 89 | hsa-miR-4513 | 3.03.E−09 | − |
| 90 | hsa-miR-6781-5p | 5.11.E−09 | + |
| 91 | hsa-miR-1227-5p | 6.16.E−09 | + |
| 92 | hsa-miR-6845-5p | 6.49.E−09 | + |
| 93 | hsa-miR-6798-5p | 8.99.E−09 | + |
| 94 | hsa-miR-3620-5p | 1.09.E−08 | + |
| 95 | hsa-miR-1915-5p | 1.78.E−08 | − |
| 96 | hsa-miR-4294 | 2.30.E−08 | − |
| 97 | hsa-miR-642a-3p | 2.61.E−08 | − |
| 98 | hsa-miR-371a-5p | 3.15.E−08 | − |
| 99 | hsa-miR-940 | 3.18.E−08 | + |
| 100 | hsa-miR-4450 | 3.25.E−08 | − |
| 101 | hsa-miR-4723-5p | 4.21.E−08 | − |
| 102 | hsa-miR-1469 | 4.26.E−08 | + |
| 103 | hsa-miR-6861-5p | 4.71.E−08 | − |
| 104 | hsa-miR-7975 | 7.28.E−08 | − |
| 105 | hsa-miR-6879-5p | 7.64.E−08 | + |
| 106 | hsa-miR-6802-5p | 9.22.E−08 | − |
| 107 | hsa-miR-1268b | 1.08.E−07 | + |
| 108 | hsa-miR-663b | 1.12.E−07 | − |
| 109 | hsa-miR-125a-3p | 1.16.E−07 | − |
| 110 | hsa-miR-2861 | 1.87.E−07 | − |
| 111 | hsa-miR-6088 | 2.97.E−07 | − |
| 112 | hsa-miR-4758-5p | 3.12.E−07 | − |
| 113 | hsa-miR-296-3p | 3.43.E−07 | − |
| 114 | hsa-miR-6738-5p | 4.05.E−07 | − |
| 115 | hsa-miR-671-5p | 5.76.E−07 | − |
| 116 | hsa-miR-4454 | 6.68.E−07 | − |
| 117 | hsa-miR-4516 | 1.04.E−06 | − |
| 118 | hsa-miR-7845-5p | 1.10.E−06 | + |
| 119 | hsa-miR-4741 | 1.52.E−06 | + |
| 120 | hsa-miR-92b-5p | 1.63.E−06 | + |
| 121 | hsa-miR-6795-5p | 2.31.E−06 | − |
| 122 | hsa-miR-6805-3p | 3.95.E−06 | + |
| 123 | hsa-miR-4725-3p | 5.35.E−06 | + |
| 124 | hsa-miR-6782-5p | 5.69.E−06 | + |
| 125 | hsa-miR-4688 | 8.95.E−06 | − |
| 126 | hsa-miR-6850-5p | 1.66.E−05 | + |
| 127 | hsa-miR-6777-5p | 1.74.E−05 | − |
| 128 | hsa-miR-6785-5p | 1.89.E−05 | − |
| 129 | hsa-miR-7106-5p | 1.94.E−05 | − |
| 130 | hsa-miR-3663-3p | 2.08.E−05 | − |
| 131 | hsa-miR-6131 | 2.29.E−05 | − |
| 132 | hsa-miR-1915-3p | 3.16.E−05 | + |
| 133 | hsa-miR-4532 | 3.46.E−05 | − |
| 134 | hsa-miR-6820-5p | 3.81.E−05 | − |
| 135 | hsa-miR-4689 | 4.54.E−05 | − |
| 136 | hsa-miR-4638-5p | 4.70.E−05 | − |
| 137 | hsa-miR-3656 | 5.75.E−05 | + |
| 138 | hsa-miR-3621 | 6.34.E−05 | − |
| 139 | hsa-miR-6769b-5p | 6.63.E−05 | − |
| 140 | hsa-miR-149-3p | 1.01.E−04 | − |
| 141 | hsa-miR-23b-3p | 1.11.E−04 | − |
| 142 | hsa-miR-3135b | 1.16.E−04 | − |
| 143 | hsa-miR-6848-5p | 1.17.E−04 | + |
| 144 | hsa-miR-6769a-5p | 1.23.E−04 | − |
| 145 | hsa-miR-4327 | 1.40.E−04 | + |
| 146 | hsa-miR-6765-3p | 1.50.E−04 | − |
| 147 | hsa-miR-6716-5p | 1.51.E−04 | + |
| 148 | hsa-miR-6877-5p | 1.52.E−04 | − |
| 149 | hsa-miR-6727-5p | 2.04.E−04 | − |
| 150 | hsa-miR-4534 | 2.10.E−04 | − |
| 151 | hsa-miR-614 | 3.18.E−04 | − |
| 152 | hsa-miR-1202 | 4.86.E−04 | − |

TABLE 2-continued

| SEQ ID NO: | Gene name | P value after Bonferroni correction | Expression level in colorectal cancer patient with respect to healthy subject |
|---|---|---|---|
| 153 | hsa-miR-575 | 4.92.E–04 | – |
| 154 | hsa-miR-6870-5p | 5.55.E–04 | + |
| 155 | hsa-miR-6722-3p | 7.07.E–04 | + |
| 156 | hsa-miR-7977 | 7.17.E–04 | – |
| 157 | hsa-miR-4649-5p | 7.70.E–04 | – |
| 158 | hsa-miR-4675 | 9.21.E–04 | – |
| 159 | hsa-miR-6075 | 1.03.E–03 | + |
| 160 | hsa-miR-6779-5p | 1.04.E–03 | – |
| 161 | hsa-miR-4271 | 1.43.E–03 | – |
| 162 | hsa-miR-3196 | 1.45.E–03 | + |
| 163 | hsa-miR-6803-5p | 1.46.E–03 | + |
| 164 | hsa-miR-6789-5p | 1.71.E–03 | + |
| 165 | hsa-miR-4648 | 1.90.E–03 | + |
| 166 | hsa-miR-4508 | 3.41.E–03 | + |
| 167 | hsa-miR-4749-5p | 3.52.E–03 | + |

TABLE 2-continued

| SEQ ID NO: | Gene name | P value after Bonferroni correction | Expression level in colorectal cancer patient with respect to healthy subject |
|---|---|---|---|
| 168 | hsa-miR-4505 | 4.01.E–03 | + |
| 169 | hsa-miR-5698 | 4.99.E–03 | – |
| 170 | hsa-miR-1199-5p | 5.88.E–03 | – |
| 171 | hsa-miR-4763-3p | 8.40.E–03 | + |
| 172 | hsa-miR-1231 | 7.36.E–25 | + |
| 173 | hsa-miR-1233-5p | 1.21.E–22 | – |
| 174 | hsa-miR-150-3p | 5.76.E–07 | – |
| 175 | hsa-miR-1225-3p | 1.44.E–06 | + |
| 176 | hsa-miR-92a-2-5p | 2.36.E–05 | + |
| 177 | hsa-miR-423-5p | 4.62.E–05 | – |
| 178 | hsa-miR-1268a | 4.30.E–04 | + |
| 179 | hsa-miR-128-2-5p | 6.64.E–04 | – |
| 180 | hsa-miR-24-3p | 1.31.E–03 | – |

TABLE 3

| SEQ ID NO: | Training cohort | | | Validation cohort | | |
|---|---|---|---|---|---|---|
| | Accuracy (9) | Sensitivity (%) | Specificity (%) | Accuracy (%) | Sensitivity (%) | Specificity (%) |
| 1 | 99.3 | 100 | 99 | 100 | 100 | 100 |
| 2 | 96.3 | 88.2 | 99 | 100 | 100 | 100 |
| 3 | 96.3 | 91.2 | 98 | 98.5 | 100 | 98 |
| 4 | 93.3 | 85.3 | 96 | 93.9 | 75 | 100 |
| 5 | 97 | 91.2 | 99 | 97 | 93.8 | 98 |
| 6 | 94 | 82.4 | 98 | 90.9 | 75 | 96 |
| 7 | 96.3 | 88.2 | 99 | 95.5 | 87.5 | 98 |
| 8 | 92.5 | 82.4 | 96 | 89.4 | 75 | 94 |
| 9 | 93.3 | 85.3 | 96 | 97 | 93.8 | 98 |
| 10 | 91.8 | 79.4 | 96 | 92.4 | 68.8 | 100 |
| 11 | 94.8 | 91.2 | 96 | 95.5 | 81.2 | 100 |
| 12 | 90.3 | 82.4 | 93 | 97 | 100 | 96 |
| 13 | 89.6 | 79.4 | 93 | 90.9 | 75 | 96 |
| 14 | 91 | 73.5 | 97 | 80.3 | 50 | 90 |
| 15 | 94 | 79.4 | 99 | 89.4 | 75 | 94 |
| 16 | 88.1 | 73.5 | 93 | 89.4 | 75 | 94 |
| 17 | 91 | 85.3 | 93 | 87.9 | 68.8 | 94 |
| 18 | 91 | 79.4 | 95 | 92.4 | 75 | 98 |
| 19 | 90.3 | 76.5 | 95 | 93.9 | 81.2 | 98 |
| 20 | 91.8 | 88.2 | 93 | 92.4 | 81.2 | 96 |
| 21 | 87.3 | 58.8 | 97 | 92.4 | 75 | 98 |
| 22 | 88.1 | 73.5 | 93 | 89.4 | 62.5 | 98 |
| 23 | 87.3 | 79.4 | 90 | 87.9 | 75 | 92 |
| 24 | 90.3 | 67.6 | 98 | 89.4 | 56.2 | 100 |
| 25 | 89.6 | 67.6 | 97 | 84.8 | 75 | 88 |
| 26 | 83.6 | 70.6 | 88 | 89.4 | 68.8 | 96 |
| 27 | 91.8 | 76.5 | 97 | 87.9 | 56.2 | 98 |
| 28 | 91 | 82.4 | 94 | 87.9 | 62.5 | 96 |
| 29 | 88.8 | 67.6 | 96 | 83.3 | 68.8 | 88 |
| 30 | 91.8 | 85.3 | 94 | 86.4 | 75 | 90 |
| 31 | 87.3 | 79.4 | 90 | 87.9 | 68.8 | 94 |
| 32 | 87.3 | 64.7 | 95 | 89.4 | 68.8 | 96 |
| 33 | 91 | 79.4 | 95 | 80.3 | 56.2 | 88 |
| 34 | 89.6 | 76.5 | 94 | 89.4 | 68.8 | 96 |
| 35 | 89.6 | 79.4 | 93 | 78.8 | 62.5 | 84 |
| 36 | 88.1 | 55.9 | 99 | 92.4 | 68.8 | 100 |
| 37 | 85.1 | 61.8 | 93 | 80.3 | 62.5 | 86 |
| 38 | 86.6 | 70.6 | 92 | 78.8 | 50 | 88 |
| 39 | 88.1 | 70.6 | 94 | 81.8 | 56.2 | 90 |
| 40 | 91 | 76.5 | 96 | 84.8 | 56.2 | 94 |
| 41 | 86.6 | 58.8 | 96 | 87.9 | 56.2 | 98 |
| 42 | 84.3 | 64.7 | 91 | 86.4 | 75 | 90 |
| 43 | 84.3 | 52.9 | 95 | 86.4 | 50 | 98 |
| 44 | 87.3 | 70.6 | 93 | 87.9 | 68.8 | 94 |
| 45 | 87.3 | 61.8 | 96 | 77.3 | 68.8 | 80 |
| 46 | 83.6 | 70.6 | 88 | 84.8 | 68.8 | 90 |
| 47 | 86.6 | 52.9 | 98 | 86.4 | 50 | 98 |
| 48 | 88.8 | 58.8 | 99 | 81.8 | 31.2 | 98 |
| 49 | 87.3 | 61.8 | 96 | 87.9 | 56.2 | 98 |
| 50 | 86.6 | 73.5 | 91 | 77.3 | 62.5 | 82 |

TABLE 3-continued

| SEQ ID NO: | Training cohort | | | Validation cohort | | |
|---|---|---|---|---|---|---|
| | Accuracy (9) | Sensitivity (%) | Specificity (%) | Accuracy (%) | Sensitivity (%) | Specificity (%) |
| 51 | 86.6 | 64.7 | 94 | 87.9 | 62.5 | 96 |
| 52 | 84.3 | 52.9 | 95 | 84.8 | 50 | 96 |
| 53 | 88.8 | 64.7 | 97 | 87.9 | 62.5 | 96 |
| 54 | 81.3 | 50 | 92 | 77.3 | 31.2 | 92 |
| 55 | 88.8 | 58.8 | 99 | 90.9 | 68.8 | 98 |
| 56 | 84.2 | 66.7 | 90 | 83.3 | 56.2 | 92 |
| 57 | 84.3 | 58.8 | 93 | 80.3 | 56.2 | 88 |
| 58 | 85.1 | 50 | 97 | 86.4 | 43.8 | 100 |
| 59 | 82.8 | 55.9 | 92 | 89.4 | 75 | 94 |
| 60 | 87.3 | 64.7 | 95 | 87.9 | 62.5 | 96 |
| 61 | 81.3 | 52.9 | 91 | 84.8 | 62.5 | 92 |
| 62 | 82.8 | 67.6 | 88 | 80.3 | 56.2 | 88 |
| 63 | 82.1 | 55.9 | 91 | 84.8 | 62.5 | 92 |
| 64 | 78.4 | 38.2 | 92 | 83.3 | 37.5 | 98 |
| 65 | 86.6 | 61.8 | 95 | 87.9 | 62.5 | 96 |
| 66 | 85.1 | 58.8 | 94 | 84.8 | 56.2 | 94 |
| 67 | 83.6 | 61.8 | 91 | 80 | 62.5 | 85.7 |
| 68 | 85.1 | 61.8 | 93 | 84.8 | 56.2 | 94 |
| 69 | 80.6 | 64.7 | 86 | 80.3 | 56.2 | 88 |
| 70 | 81.3 | 52.9 | 91 | 78.8 | 31.2 | 94 |
| 71 | 85.1 | 58.8 | 94 | 87.9 | 56.2 | 98 |
| 72 | 83.6 | 64.7 | 90 | 83.3 | 56.2 | 92 |
| 73 | 87.3 | 55.9 | 98 | 84.8 | 43.8 | 98 |
| 74 | 83.6 | 64.7 | 90 | 77.3 | 43.8 | 88 |
| 75 | 82.7 | 33.3 | 99 | 84.8 | 37.5 | 100 |
| 76 | 83.6 | 44.1 | 97 | 86.4 | 50 | 98 |
| 77 | 85.8 | 73.5 | 90 | 83.3 | 68.8 | 88 |
| 78 | 83.6 | 52.9 | 94 | 81.8 | 56.2 | 90 |
| 79 | 83.6 | 67.6 | 89 | 81.8 | 62.5 | 88 |
| 80 | 85 | 58.8 | 93.9 | 83.3 | 62.5 | 90 |
| 81 | 84.3 | 50 | 96 | 83.3 | 43.8 | 96 |
| 82 | 81.3 | 44.1 | 94 | 81.8 | 37.5 | 96 |
| 83 | 82.1 | 61.8 | 89 | 78.8 | 62.5 | 84 |
| 84 | 90.3 | 70.6 | 97 | 84.8 | 56.2 | 94 |
| 85 | 83.6 | 55.9 | 93 | 80.3 | 31.2 | 96 |
| 86 | 80.6 | 41.2 | 94 | 86.4 | 62.5 | 94 |
| 87 | 83.6 | 50 | 95 | 83.3 | 62.5 | 90 |
| 88 | 84.3 | 52.9 | 95 | 83.3 | 50 | 94 |
| 89 | 84.3 | 44.1 | 98 | 77.3 | 12.5 | 98 |
| 90 | 82.8 | 50 | 94 | 81.8 | 56.2 | 90 |
| 91 | 79.9 | 38.2 | 94 | 75.8 | 31.2 | 90 |
| 92 | 84.3 | 50 | 96 | 78.8 | 43.8 | 90 |
| 93 | 82.8 | 61.8 | 90 | 75.8 | 50 | 84 |
| 94 | 84.3 | 55.9 | 94 | 77.3 | 31.2 | 92 |
| 95 | 82.1 | 41.2 | 96 | 83.3 | 43.8 | 96 |
| 96 | 85.1 | 55.9 | 95 | 81.8 | 50 | 92 |
| 97 | 78.4 | 38.2 | 92 | 78.8 | 43.8 | 90 |
| 98 | 82.8 | 50 | 94 | 75.8 | 37.5 | 88 |
| 99 | 81.3 | 47.1 | 93 | 86.4 | 56.2 | 96 |
| 100 | 85.1 | 47.1 | 98 | 83.3 | 43.8 | 96 |
| 101 | 87.3 | 58.8 | 97 | 83.3 | 50 | 94 |
| 102 | 80.6 | 38.2 | 95 | 80.3 | 50 | 90 |
| 103 | 83.6 | 47.1 | 96 | 80.3 | 37.5 | 94 |
| 104 | 79.1 | 35.3 | 94 | 78.8 | 37.5 | 92 |
| 105 | 82.8 | 38.2 | 98 | 84.8 | 37.5 | 100 |
| 106 | 82.8 | 44.1 | 96 | 81.8 | 37.5 | 96 |
| 107 | 74.6 | 32.4 | 89 | 75.8 | 50 | 84 |
| 108 | 83.6 | 47.1 | 96 | 83.3 | 31.2 | 100 |
| 109 | 85.1 | 44.1 | 99 | 87.9 | 50 | 100 |
| 110 | 82.8 | 52.9 | 93 | 84.8 | 50 | 96 |
| 111 | 78.4 | 44.1 | 90 | 81.8 | 50 | 92 |
| 112 | 84.3 | 44.1 | 98 | 80.3 | 25 | 98 |
| 113 | 82.8 | 50 | 94 | 80.3 | 43.8 | 92 |
| 114 | 82.8 | 52.9 | 93 | 83.3 | 50 | 94 |
| 115 | 82.1 | 44.1 | 95 | 84.8 | 43.8 | 98 |
| 116 | 79.9 | 41.2 | 93 | 77.3 | 31.2 | 92 |
| 117 | 87.3 | 50 | 100 | 84.8 | 37.5 | 100 |
| 118 | 88.1 | 58.8 | 98 | 81.8 | 50 | 92 |
| 119 | 78.4 | 29.4 | 95 | 77.3 | 25 | 94 |
| 120 | 78.4 | 41.2 | 91 | 84.8 | 50 | 96 |
| 121 | 80.6 | 26.5 | 99 | 80.3 | 18.8 | 100 |
| 122 | 77.6 | 38.2 | 91 | 83.3 | 50 | 94 |
| 123 | 76.1 | 26.5 | 93 | 74.2 | 12.5 | 94 |
| 124 | 83.6 | 44.1 | 97 | 83.3 | 43.8 | 96 |
| 125 | 77.6 | 35.3 | 92 | 74.2 | 18.8 | 92 |

TABLE 3-continued

| SEQ ID NO: | Training cohort | | | Validation cohort | | |
|---|---|---|---|---|---|---|
| | Accuracy (9) | Sensitivity (%) | Specificity (%) | Accuracy (%) | Sensitivity (%) | Specificity (%) |
| 126 | 80.6 | 41.2 | 94 | 78.8 | 43.8 | 90 |
| 127 | 79.1 | 23.5 | 98 | 83.3 | 31.2 | 100 |
| 128 | 80.6 | 38.2 | 95 | 80.3 | 31.2 | 96 |
| 129 | 78.4 | 23.5 | 97 | 80.3 | 25 | 98 |
| 130 | 78.4 | 29.4 | 95 | 80.3 | 31.2 | 96 |
| 131 | 81.3 | 35.3 | 97 | 83.3 | 37.5 | 98 |
| 132 | 80.6 | 35.3 | 96 | 80.3 | 25 | 98 |
| 133 | 82.8 | 44.1 | 96 | 80.3 | 37.5 | 94 |
| 134 | 83.6 | 41.2 | 98 | 83.3 | 50 | 94 |
| 135 | 79.9 | 29.4 | 97 | 81.8 | 25 | 100 |
| 136 | 83.6 | 41.2 | 98 | 86.4 | 43.8 | 100 |
| 137 | 79.9 | 38.2 | 94 | 77.3 | 12.5 | 98 |
| 138 | 76.1 | 26.5 | 93 | 77.3 | 25 | 94 |
| 139 | 79.1 | 26.5 | 97 | 78.8 | 18.8 | 98 |
| 140 | 76.9 | 23.5 | 95 | 77.3 | 25 | 94 |
| 141 | 79.1 | 26.5 | 97 | 75.8 | 18.8 | 94 |
| 142 | 83.6 | 38.2 | 99 | 86.4 | 43.8 | 100 |
| 143 | 77.6 | 26.5 | 95 | 78.8 | 25 | 96 |
| 144 | 74.6 | 17.6 | 94 | 80.3 | 31.2 | 96 |
| 145 | 79.1 | 41.2 | 92 | 75.8 | 25 | 92 |
| 146 | 78.4 | 32.4 | 94 | 80.3 | 31.2 | 96 |
| 147 | 79.1 | 29.4 | 96 | 77.3 | 31.2 | 92 |
| 148 | 73.9 | 20.6 | 92 | 71.2 | 6.2 | 92 |
| 149 | 79.1 | 38.2 | 93 | 81.8 | 31.2 | 98 |
| 150 | 78.4 | 23.5 | 97 | 74.2 | 25 | 90 |
| 151 | 76.1 | 32.4 | 91 | 77.3 | 25 | 94 |
| 152 | 81.3 | 29.4 | 99 | 81.8 | 25 | 100 |
| 153 | 82.1 | 29.4 | 100 | 87.9 | 50 | 100 |
| 154 | 81.3 | 35.3 | 97 | 84.8 | 37.5 | 100 |
| 155 | 79.1 | 29.4 | 96 | 78.8 | 31.2 | 94 |
| 156 | 78.9 | 24.2 | 97 | 77.3 | 25 | 94 |
| 157 | 79.9 | 29.4 | 97 | 83.3 | 31.2 | 100 |
| 158 | 80.6 | 35.3 | 96 | 84.8 | 37.5 | 100 |
| 159 | 82.1 | 35.3 | 98 | 81.8 | 31.2 | 98 |
| 160 | 78.4 | 20.6 | 98 | 81.8 | 31.2 | 98 |
| 161 | 78.4 | 26.5 | 96 | 81.8 | 25 | 100 |
| 162 | 79.1 | 29.4 | 96 | 77.3 | 18.8 | 96 |
| 163 | 74.6 | 26.5 | 91 | 63.6 | 0 | 84 |
| 164 | 76.1 | 20.6 | 95 | 71.2 | 12.5 | 90 |
| 165 | 77.6 | 23.5 | 96 | 81.8 | 25 | 100 |
| 166 | 78.4 | 29.4 | 95 | 69.7 | 6.2 | 90 |
| 167 | 78.4 | 14.7 | 100 | 75.8 | 0 | 100 |
| 168 | 78.2 | 21.2 | 97 | 78.8 | 12.5 | 100 |
| 169 | 78.4 | 23.5 | 97 | 77.3 | 6.2 | 100 |
| 170 | 73.9 | 2.9 | 98 | 77.3 | 6.2 | 100 |
| 171 | 80.6 | 26.5 | 99 | 78.8 | 12.5 | 100 |
| 172 | 93.3 | 85.3 | 96 | 90.9 | 81.2 | 94 |
| 173 | 91 | 76.5 | 96 | 90.9 | 68.8 | 98 |
| 174 | 82.1 | 35.3 | 98 | 77.3 | 31.2 | 92 |
| 175 | 87.3 | 52.9 | 99 | 89.4 | 56.2 | 100 |
| 176 | 74.6 | 29.4 | 90 | 78.8 | 37.5 | 92 |
| 177 | 79.9 | 35.3 | 95 | 69.7 | 12.5 | 88 |
| 178 | 73.9 | 17.6 | 93 | 71.2 | 6.2 | 92 |
| 179 | 81.3 | 32.4 | 98 | 84.8 | 37.5 | 100 |
| 180 | 76.9 | 11.8 | 99 | 81.8 | 25 | 100 |

TABLE 4

| SEQ ID NO: | Discriminant coefficient | Constant term |
|---|---|---|
| 1 | 3.451 | 32.537 |
| 2 | 2.778 | 17.111 |
| 3 | 3.893 | 32.032 |
| 4 | 3.208 | 29.340 |
| 5 | 2.408 | 15.716 |
| 6 | 4.760 | 44.132 |
| 7 | 1.872 | 13.040 |
| 8 | 4.189 | 26.554 |
| 9 | 5.692 | 61.192 |
| 10 | 2.915 | 20.140 |
| 11 | 2.801 | 19.585 |

TABLE 4-continued

| SEQ ID NO: | Discriminant coefficient | Constant term |
|---|---|---|
| 12 | 1.247 | 8.323 |
| 13 | 3.434 | 21.316 |
| 14 | 5.315 | 65.956 |
| 15 | 3.971 | 26.352 |
| 16 | 4.335 | 50.272 |
| 17 | 1.843 | 9.956 |
| 18 | 2.796 | 18.550 |
| 19 | 2.726 | 19.273 |
| 20 | 2.151 | 14.586 |
| 21 | 1.432 | 7.567 |
| 22 | 4.810 | 44.500 |

TABLE 4-continued

| SEQ ID NO: | Discriminant coefficient | Constant term |
|---|---|---|
| 23 | 2.202 | 14.554 |
| 24 | 1.787 | 9.999 |
| 25 | 4.048 | 23.773 |
| 26 | 2.353 | 23.473 |
| 27 | 3.139 | 19.203 |
| 28 | 5.364 | 64.417 |
| 29 | 5.274 | 42.891 |
| 30 | 4.406 | 27.813 |
| 31 | 2.590 | 20.814 |
| 32 | 6.586 | 84.911 |
| 33 | 3.426 | 31.099 |
| 34 | 2.365 | 16.821 |
| 35 | 3.810 | 30.817 |
| 36 | 2.245 | 13.547 |
| 37 | 2.667 | 20.060 |
| 38 | 4.817 | 48.162 |
| 39 | 4.582 | 33.609 |
| 40 | 3.409 | 25.092 |
| 41 | 2.180 | 12.620 |
| 42 | 1.846 | 14.493 |
| 43 | 2.092 | 20.352 |
| 44 | 2.237 | 18.151 |
| 45 | 1.808 | 22.979 |
| 46 | 2.361 | 15.747 |
| 47 | 8.658 | 108.735 |
| 48 | 1.910 | 11.860 |
| 49 | 4.384 | 43.382 |
| 50 | 4.476 | 30.075 |
| 51 | 4.069 | 35.285 |
| 52 | 2.888 | 24.905 |
| 53 | 2.016 | 16.544 |
| 54 | 4.690 | 32.139 |
| 55 | 2.207 | 13.044 |
| 56 | 3.152 | 18.319 |
| 57 | 3.384 | 31.679 |
| 58 | 2.167 | 19.956 |
| 59 | 5.078 | 36.907 |
| 60 | 3.628 | 21.525 |
| 61 | 3.373 | 31.520 |
| 62 | 3.836 | 28.118 |
| 63 | 4.332 | 31.744 |
| 64 | 2.949 | 32.215 |
| 65 | 3.709 | 24.031 |
| 66 | 3.738 | 28.272 |
| 67 | 3.638 | 22.448 |
| 68 | 3.013 | 19.232 |
| 69 | 2.461 | 18.582 |
| 70 | 4.311 | 32.255 |
| 71 | 3.548 | 29.298 |
| 72 | 4.499 | 45.352 |
| 73 | 4.079 | 32.445 |
| 74 | 3.995 | 30.128 |
| 75 | 2.483 | 15.148 |
| 76 | 3.479 | 27.463 |
| 77 | 2.342 | 16.975 |
| 78 | 3.352 | 20.098 |
| 79 | 3.684 | 46.309 |
| 80 | 3.835 | 22.808 |
| 81 | 3.983 | 32.779 |
| 82 | 2.904 | 19.401 |
| 83 | 3.426 | 29.138 |
| 84 | 5.296 | 43.216 |
| 85 | 3.793 | 43.429 |
| 86 | 5.582 | 66.478 |
| 87 | 3.815 | 22.562 |
| 88 | 4.509 | 45.905 |
| 89 | 2.269 | 12.804 |
| 90 | 5.547 | 57.838 |
| 91 | 6.325 | 60.270 |
| 92 | 3.946 | 37.787 |
| 93 | 2.967 | 30.962 |
| 94 | 3.865 | 30.606 |
| 95 | 1.266 | 7.550 |
| 96 | 2.410 | 24.206 |
| 97 | 2.733 | 20.281 |
| 98 | 3.561 | 25.772 |
| 99 | 3.064 | 19.551 |

TABLE 4-continued

| SEQ ID NO: | Discriminant coefficient | Constant term |
|---|---|---|
| 100 | 1.188 | 6.373 |
| 101 | 2.565 | 22.283 |
| 102 | 5.084 | 51.748 |
| 103 | 3.700 | 26.315 |
| 104 | 2.224 | 21.832 |
| 105 | 3.135 | 25.894 |
| 106 | 4.526 | 37.574 |
| 107 | 3.166 | 31.384 |
| 108 | 2.839 | 24.460 |
| 109 | 1.007 | 6.029 |
| 110 | 5.545 | 68.155 |
| 111 | 3.299 | 33.145 |
| 112 | 6.271 | 53.263 |
| 113 | 2.148 | 12.402 |
| 114 | 3.608 | 25.322 |
| 115 | 2.758 | 17.059 |
| 116 | 2.175 | 25.025 |
| 117 | 3.823 | 49.903 |
| 118 | 2.725 | 18.024 |
| 119 | 3.890 | 38.378 |
| 120 | 3.506 | 27.825 |
| 121 | 2.582 | 15.075 |
| 122 | 2.476 | 18.382 |
| 123 | 4.084 | 39.823 |
| 124 | 2.978 | 18.190 |
| 125 | 3.980 | 27.914 |
| 126 | 5.916 | 67.040 |
| 127 | 2.075 | 13.104 |
| 128 | 2.317 | 20.667 |
| 129 | 2.093 | 12.035 |
| 130 | 4.219 | 50.899 |
| 131 | 1.841 | 19.246 |
| 132 | 3.960 | 43.646 |
| 133 | 3.277 | 38.660 |
| 134 | 2.733 | 19.515 |
| 135 | 3.239 | 30.244 |
| 136 | 1.482 | 8.655 |
| 137 | 4.554 | 52.325 |
| 138 | 5.175 | 61.317 |
| 139 | 3.430 | 21.115 |
| 140 | 5.430 | 50.527 |
| 141 | 1.168 | 6.718 |
| 142 | 2.311 | 17.824 |
| 143 | 4.599 | 33.779 |
| 144 | 3.921 | 24.668 |
| 145 | 4.968 | 43.118 |
| 146 | 1.700 | 14.753 |
| 147 | 3.593 | 23.332 |
| 148 | 4.307 | 30.486 |
| 149 | 6.087 | 77.329 |
| 150 | 2.704 | 17.759 |
| 151 | 1.757 | 11.661 |
| 152 | 2.635 | 16.886 |
| 153 | 1.214 | 6.968 |
| 154 | 3.201 | 23.463 |
| 155 | 6.593 | 55.857 |
| 156 | 2.177 | 21.212 |
| 157 | 2.411 | 24.700 |
| 158 | 2.636 | 19.709 |
| 159 | 3.045 | 25.772 |
| 160 | 5.593 | 39.283 |
| 161 | 3.606 | 29.381 |
| 162 | 6.360 | 76.890 |
| 163 | 6.727 | 74.567 |
| 164 | 4.350 | 42.883 |
| 165 | 1.256 | 7.389 |
| 166 | 6.503 | 84.138 |
| 167 | 3.665 | 29.142 |
| 168 | 4.233 | 35.592 |
| 169 | 1.766 | 10.169 |
| 170 | 1.955 | 12.693 |
| 171 | 3.328 | 27.665 |
| 172 | 3.674 | 24.498 |
| 173 | 2.869 | 31.161 |
| 174 | 1.758 | 11.388 |
| 175 | 2.132 | 11.850 |
| 176 | 2.148 | 20.104 |

TABLE 4-continued

| SEQ ID NO: | Discriminant coefficient | Constant term |
|---|---|---|
| 177 | 2.169 | 15.443 |
| 178 | 3.124 | 34.907 |
| 179 | 2.552 | 27.422 |
| 180 | 1.417 | 8.536 |

TABLE 5-1

| Training cohort | | | |
|---|---|---|---|
| Sample name | Cancer stage | CEA(ng/mL) | CA19-9(U/mL) |
| CC03 | I | 1.6 | 13.5 |
| CC04 | I | 2 | 30.6 |
| CC05 | I | 1.3 | 3.2 |
| CC06 | I | 1.7 | 13.5 |
| CC07 | IIIA | 4.4 | 0.1 |
| CC09 | IIIB | 0.9 | 4.4 |
| CC10 | I | 1.5 | 13.2 |
| CC12 | I | 0.9 | 13.2 |
| CC13 | I | 0.8 | 3.1 |
| CC15 | I | 1.6 | 5.6 |
| CC17 | IIIA | 2.7 | 21.7 |
| CC18 | I | 3.2 | 16.4 |
| CC19 | IVL | 6.2 | 45.9 |
| CC20 | IIIC | 9.4 | 5.4 |
| CC23 | I | 2.3 | 7.9 |
| CC24 | IIA | 8.8 | 106.7 |
| CC25 | IIA | 6.2 | 29.6 |
| CC26 | I | 4.5 | 18.6 |
| CC27 | IIIC | 17.3 | 14.4 |
| CC29 | IIA | 2.1 | 6.9 |
| CC30 | IIIA | 3.2 | 13.2 |
| CC31 | IIIB | 6 | 5.7 |
| CC32 | IIIA | 2.4 | 26.7 |
| CC34 | I | 0.6 | 9.3 |
| CC36 | I | 6.7 | 0.1 |

TABLE 5-1-continued

| Training cohort | | | |
|---|---|---|---|
| Sample name | Cancer stage | CEA(ng/mL) | CA19-9(U/mL) |
| CC38 | IIA | 1.2 | 6.1 |
| CC40 | IIIB | 2.1 | 7.6 |
| CC41 | I | 2.8 | 10.6 |
| CC42 | IIIB | 46.7 | 3524 |
| CC45 | I | 2.2 | 38.4 |
| CC47 | IIIB | 1.7 | 7.1 |
| CC48 | IIA | 2 | 19.1 |
| CC49 | IIIB | 0.9 | 8.1 |
| CC50 | IIA | 7.6 | 12.2 |
| Sensitivity | 26.5% | | 12% |

TABLE 5-2

| Validation cohort | | | |
|---|---|---|---|
| Sample name | Cancer stage | CEA(ng/mL) | CA19-9(U/mL) |
| CC0l | I | 2.2 | 13.9 |
| CC02 | I | 3.9 | 16 |
| CC08 | IVH | 15.4 | 9.5 |
| CC11 | IIIC | 7.2 | 8 |
| CC14 | I | 0.6 | 14 |
| CC16 | IVL | 10.1 | 106.7 |
| CC21 | IIIB | 6.7 | 23.6 |
| CC22 | IIIC | 2.9 | 42.4 |
| CC28 | IIIB | 35.5 | 71 |
| CC33 | IIB | 5 | — |
| CC35 | IVH | 20.3 | 552 |
| CC37 | IIA | 0.1 | 8.1 |
| CC39 | IVHLu | 267.7 | 269.6 |
| CC43 | IIA | 2 | 10.3 |
| CC44 | IIA | 3.7 | 14 |
| CC46 | IIA | 1.7 | 4.2 |
| Sensitivity | 43.8% | | 31% |

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 100 | 100 | 100 | 100 | 100 | 100 |
| 1_3 | 99.3 | 97.1 | 100 | 100 | 100 | 100 |
| 1_4 | 100 | 100 | 100 | 100 | 100 | 100 |
| 1_5 | 100 | 100 | 100 | 100 | 100 | 100 |
| 1_6 | 100 | 100 | 100 | 100 | 100 | 100 |
| 1_7 | 100 | 100 | 100 | 100 | 100 | 100 |
| 1_8 | 100 | 100 | 100 | 100 | 100 | 100 |
| 1_9 | 98.5 | 100 | 98 | 98.5 | 100 | 98 |
| 1_10 | 100 | 100 | 100 | 100 | 100 | 100 |
| 1_11 | 99.3 | 100 | 99 | 100 | 100 | 100 |
| 1_12 | 99.3 | 100 | 99 | 98.5 | 100 | 98 |
| 1_13 | 99.3 | 100 | 99 | 100 | 100 | 100 |
| 1_14 | 100 | 100 | 100 | 98.5 | 100 | 98 |
| 1_15 | 99.3 | 97.1 | 100 | 97 | 100 | 96 |
| 1_16 | 100 | 100 | 100 | 100 | 100 | 100 |
| 1_17 | 97.8 | 94.1 | 99 | 100 | 100 | 100 |
| 1_18 | 99.3 | 100 | 99 | 100 | 100 | 100 |
| 1_19 | 98.5 | 100 | 98 | 100 | 100 | 100 |
| 1_20 | 100 | 100 | 100 | 100 | 100 | 100 |
| 1_21 | 99.3 | 100 | 99 | 100 | 100 | 100 |
| 1_22 | 98.5 | 97.1 | 99 | 100 | 100 | 100 |
| 1_23 | 99.3 | 100 | 99 | 100 | 100 | 100 |
| 1_24 | 98.5 | 94.1 | 100 | 100 | 100 | 100 |
| 1_25 | 99.3 | 100 | 99 | 98.5 | 100 | 98 |
| 1_26 | 99.3 | 100 | 99 | 100 | 100 | 100 |
| 1_27 | 98.5 | 94.1 | 100 | 100 | 100 | 100 |
| 1_28 | 100 | 100 | 100 | 98.5 | 100 | 98 |
| 1_29 | 98.5 | 97.1 | 99 | 100 | 100 | 100 |
| 1_30 | 100 | 100 | 100 | 100 | 100 | 100 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_31 | 98.5 | 97.1 | 99 | 100 | 100 | 100 |
| 1_32 | 99.3 | 100 | 99 | 98.5 | 100 | 98 |
| 1_33 | 98.5 | 97.1 | 99 | 100 | 100 | 100 |
| 1_34 | 97.8 | 97.1 | 98 | 100 | 100 | 100 |
| 1_35 | 98.5 | 97.1 | 99 | 98.5 | 100 | 98 |
| 1_36 | 100 | 100 | 100 | 100 | 100 | 100 |
| 1_37 | 97.8 | 97.1 | 98 | 98.5 | 100 | 98 |
| 1_38 | 98.5 | 97.1 | 99 | 100 | 100 | 100 |
| 1_39 | 99.3 | 97.1 | 100 | 100 | 100 | 100 |
| 1_40 | 97.8 | 97.1 | 98 | 100 | 100 | 100 |
| 1_41 | 99.3 | 100 | 99 | 100 | 100 | 100 |
| 1_42 | 98.5 | 100 | 98 | 98.5 | 100 | 98 |
| 1_43 | 100 | 100 | 100 | 100 | 100 | 100 |
| 1_44 | 97.8 | 97.1 | 98 | 100 | 100 | 100 |
| 1_45 | 98.5 | 100 | 98 | 100 | 100 | 100 |
| 1_46 | 98.5 | 100 | 98 | 100 | 100 | 100 |
| 1_47 | 100 | 100 | 100 | 98.5 | 100 | 98 |
| 1_48 | 99.3 | 100 | 99 | 100 | 100 | 100 |
| 1_49 | 97.8 | 97.1 | 98 | 98.5 | 100 | 98 |
| 1_50 | 100 | 100 | 100 | 98.5 | 100 | 98 |
| 1_51 | 98.5 | 97.1 | 99 | 100 | 100 | 100 |
| 1_52 | 97.8 | 94.1 | 99 | 98.5 | 100 | 98 |
| 1_53 | 98.5 | 100 | 98 | 100 | 100 | 100 |
| 1_54 | 100 | 100 | 100 | 98.5 | 93.8 | 100 |
| 1_55 | 99.3 | 97.1 | 100 | 100 | 100 | 100 |
| 1_56 | 100 | 100 | 100 | 98.5 | 100 | 98 |
| 1_57 | 99.3 | 100 | 99 | 100 | 100 | 100 |
| 1_58 | 98.5 | 97.1 | 99 | 100 | 100 | 100 |
| 1_59 | 99.3 | 100 | 99 | 100 | 100 | 100 |
| 1_60 | 99.3 | 100 | 99 | 100 | 100 | 100 |
| 1_61 | 99.3 | 100 | 99 | 98.5 | 100 | 98 |
| 1_62 | 99.3 | 100 | 99 | 100 | 100 | 100 |
| 1_63 | 99.3 | 100 | 99 | 100 | 100 | 100 |
| 1_64 | 100 | 100 | 100 | 98.5 | 100 | 98 |
| 1_65 | 99.3 | 100 | 99 | 98.5 | 100 | 98 |
| 1_66 | 99.3 | 97.1 | 100 | 100 | 100 | 100 |
| 1_67 | 99.3 | 100 | 99 | 98.5 | 100 | 98 |
| 1_68 | 100 | 100 | 100 | 98.5 | 100 | 98 |
| 1_69 | 98.5 | 100 | 98 | 98.5 | 100 | 98 |
| 1_70 | 99.3 | 100 | 99 | 100 | 100 | 100 |
| 1_71 | 99.3 | 100 | 99 | 100 | 100 | 100 |
| 1_72 | 99.3 | 100 | 99 | 100 | 100 | 100 |
| 1_73 | 97.8 | 97.1 | 98 | 100 | 100 | 100 |
| 1_74 | 98.5 | 97.1 | 99 | 98.5 | 100 | 98 |
| 1_75 | 99.2 | 100 | 99 | 98.5 | 100 | 98 |
| 1_76 | 98.5 | 100 | 98 | 100 | 100 | 100 |
| 1_77 | 99.3 | 100 | 99 | 98.5 | 100 | 98 |
| 1_78 | 99.3 | 100 | 99 | 98.5 | 100 | 98 |
| 1_79 | 99.3 | 100 | 99 | 98.5 | 100 | 98 |
| 1_80 | 98.5 | 100 | 98 | 98.5 | 100 | 98 |
| 1_81 | 98.5 | 97.1 | 99 | 98.5 | 100 | 98 |
| 1_82 | 99.3 | 100 | 99 | 100 | 100 | 100 |
| 1_83 | 99.3 | 100 | 99 | 98.5 | 100 | 98 |
| 1_84 | 98.5 | 97.1 | 99 | 100 | 100 | 100 |
| 1_85 | 98.5 | 97.1 | 99 | 100 | 100 | 100 |
| 1_86 | 99.3 | 100 | 99 | 100 | 100 | 100 |
| 1_87 | 99.3 | 97.1 | 100 | 100 | 100 | 100 |
| 1_88 | 98.5 | 100 | 98 | 100 | 100 | 100 |
| 1_89 | 99.3 | 100 | 99 | 100 | 100 | 100 |
| 1_90 | 100 | 100 | 100 | 100 | 100 | 100 |
| 1_91 | 99.3 | 100 | 99 | 100 | 100 | 100 |
| 1_92 | 99.3 | 100 | 99 | 100 | 100 | 100 |
| 1_93 | 99.3 | 100 | 99 | 98.5 | 100 | 98 |
| 1_94 | 98.5 | 97.1 | 99 | 100 | 100 | 100 |
| 1_95 | 99.3 | 100 | 99 | 100 | 100 | 100 |
| 1_96 | 99.3 | 100 | 99 | 100 | 100 | 100 |
| 1_97 | 99.3 | 100 | 99 | 98.5 | 100 | 98 |
| 1_98 | 99.3 | 100 | 99 | 98.5 | 100 | 98 |
| 1_99 | 98.5 | 100 | 98 | 100 | 100 | 100 |
| 1_100 | 97 | 97.1 | 97 | 100 | 100 | 100 |
| 1_101 | 98.5 | 97.1 | 99 | 100 | 100 | 100 |
| 1_102 | 99.3 | 100 | 99 | 98.5 | 100 | 98 |
| 1_103 | 97.8 | 97.1 | 98 | 98.5 | 100 | 98 |
| 1_104 | 100 | 100 | 100 | 100 | 100 | 100 |
| 1_105 | 98.5 | 100 | 98 | 100 | 100 | 100 |

US 12,644,157 B2

123
124

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_106 | 98.5 | 97.1 | 99 | 98.5 | 100 | 98 |
| 1_107 | 99.3 | 100 | 99 | 100 | 100 | 100 |
| 1_108 | 97.8 | 97.1 | 98 | 100 | 100 | 100 |
| 1_109 | 98.5 | 97.1 | 99 | 100 | 100 | 100 |
| 1_110 | 98.5 | 97.1 | 99 | 100 | 100 | 100 |
| 1_111 | 98.5 | 100 | 98 | 100 | 100 | 100 |
| 1_112 | 98.5 | 97.1 | 99 | 100 | 100 | 100 |
| 1_113 | 99.3 | 97.1 | 100 | 98.5 | 93.8 | 100 |
| 1_114 | 97.8 | 97.1 | 98 | 98.5 | 100 | 98 |
| 1_115 | 99.3 | 100 | 99 | 100 | 100 | 100 |
| 1_116 | 100 | 100 | 100 | 100 | 100 | 100 |
| 1_117 | 97.8 | 94.1 | 99 | 98.5 | 100 | 98 |
| 1_118 | 99.3 | 100 | 99 | 98.5 | 100 | 98 |
| 1_119 | 99.3 | 100 | 99 | 100 | 100 | 100 |
| 1_120 | 98.5 | 100 | 98 | 97 | 93.8 | 98 |
| 1_121 | 99.3 | 97.1 | 100 | 100 | 100 | 100 |
| 1_122 | 98.5 | 100 | 98 | 98.5 | 100 | 98 |
| 1_123 | 97.8 | 97.1 | 98 | 100 | 100 | 100 |
| 1_124 | 98.5 | 100 | 98 | 100 | 100 | 100 |
| 1_125 | 98.5 | 97.1 | 99 | 98.5 | 93.8 | 100 |
| 1_126 | 99.3 | 100 | 99 | 100 | 100 | 100 |
| 1_127 | 99.3 | 100 | 99 | 100 | 100 | 100 |
| 1_128 | 99.3 | 100 | 99 | 98.5 | 100 | 98 |
| 1_129 | 99.3 | 100 | 99 | 100 | 100 | 100 |
| 1_130 | 97.8 | 97.1 | 98 | 100 | 100 | 100 |
| 1_131 | 97 | 94.1 | 98 | 100 | 100 | 100 |
| 1_132 | 97.8 | 97.1 | 98 | 98.5 | 100 | 98 |
| 1_133 | 99.3 | 100 | 99 | 100 | 100 | 100 |
| 1_134 | 99.3 | 100 | 99 | 100 | 100 | 100 |
| 1_135 | 98.5 | 97.1 | 99 | 100 | 100 | 100 |
| 1_136 | 97.8 | 100 | 97 | 100 | 100 | 100 |
| 1_137 | 99.3 | 100 | 99 | 100 | 100 | 100 |
| 1_138 | 99.3 | 100 | 99 | 100 | 100 | 100 |
| 1_139 | 98.5 | 97.1 | 99 | 97 | 100 | 96 |
| 1_140 | 98.5 | 94.1 | 100 | 100 | 100 | 100 |
| 1_141 | 99.3 | 100 | 99 | 100 | 100 | 100 |
| 1_142 | 98.5 | 100 | 98 | 100 | 100 | 100 |
| 1_143 | 98.5 | 97.1 | 99 | 100 | 100 | 100 |
| 1_144 | 99.3 | 100 | 99 | 100 | 100 | 100 |
| 1_145 | 97.8 | 97.1 | 98 | 100 | 100 | 100 |
| 1_146 | 100 | 100 | 100 | 100 | 100 | 100 |
| 1_147 | 99.3 | 100 | 99 | 100 | 100 | 100 |
| 1_148 | 99.3 | 100 | 99 | 100 | 100 | 100 |
| 1_149 | 98.5 | 97.1 | 99 | 98.5 | 100 | 98 |
| 1_150 | 99.3 | 100 | 99 | 100 | 100 | 100 |
| 1_151 | 99.3 | 100 | 99 | 100 | 100 | 100 |
| 1_152 | 98.5 | 97.1 | 99 | 100 | 100 | 100 |
| 1_153 | 99.3 | 100 | 99 | 100 | 100 | 100 |
| 1_154 | 99.3 | 100 | 99 | 100 | 100 | 100 |
| 1_155 | 98.5 | 100 | 98 | 100 | 100 | 100 |
| 1_156 | 100 | 100 | 100 | 100 | 100 | 100 |
| 1_157 | 97.8 | 97.1 | 98 | 98.5 | 100 | 98 |
| 1_158 | 98.5 | 97.1 | 99 | 100 | 100 | 100 |
| 1_159 | 97.8 | 97.1 | 98 | 100 | 100 | 100 |
| 1_160 | 99.3 | 100 | 99 | 98.5 | 100 | 98 |
| 1_161 | 98.5 | 100 | 98 | 100 | 100 | 100 |
| 1_162 | 99.3 | 100 | 99 | 100 | 100 | 100 |
| 1_163 | 97.8 | 100 | 97 | 100 | 100 | 100 |
| 1_164 | 99.3 | 100 | 99 | 100 | 100 | 100 |
| 1_165 | 98.5 | 97.1 | 99 | 100 | 100 | 100 |
| 1_166 | 99.3 | 100 | 99 | 98.5 | 100 | 98 |
| 1_167 | 99.3 | 100 | 99 | 100 | 100 | 100 |
| 1_168 | 99.2 | 100 | 99 | 100 | 100 | 100 |
| 1_169 | 99.3 | 100 | 99 | 100 | 100 | 100 |
| 1_170 | 99.3 | 100 | 99 | 100 | 100 | 100 |
| 1_171 | 97.8 | 100 | 97 | 100 | 100 | 100 |
| 1_172 | 98.5 | 97.1 | 99 | 98.5 | 100 | 98 |
| 1_173 | 99.3 | 100 | 99 | 100 | 100 | 100 |
| 1_174 | 99.3 | 100 | 99 | 100 | 100 | 100 |
| 1_175 | 98.5 | 97.1 | 99 | 100 | 100 | 100 |
| 1_176 | 100 | 100 | 100 | 98.5 | 100 | 98 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_177 | 98.5 | 97.1 | 99 | 100 | 100 | 100 |
| 1_178 | 99.3 | 100 | 99 | 98.5 | 93.8 | 100 |
| 1_179 | 99.3 | 100 | 99 | 98.5 | 100 | 98 |
| 1_180 | 99.3 | 100 | 99 | 100 | 100 | 100 |

TABLE 7

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 5_6 | 98.5 | 97.1 | 99.0 | 93.9 | 87.5 | 96.0 |
| 5_11 | 98.5 | 97.1 | 99.0 | 97.0 | 87.5 | 100 |
| 5_38 | 97.0 | 97.1 | 97.0 | 95.5 | 87.5 | 98.0 |
| 15_16 | 93.3 | 82.4 | 97.0 | 92.4 | 75.0 | 98.0 |
| 15_21 | 97.8 | 97.1 | 98.0 | 95.5 | 93.8 | 96.0 |
| 15_64 | 91.0 | 70.6 | 98.0 | 90.9 | 68.8 | 98.0 |
| 24_25 | 97.8 | 94.1 | 99.0 | 95.5 | 81.2 | 100 |
| 24_30 | 96.3 | 91.2 | 98.0 | 89.4 | 75.0 | 94.0 |
| 24_32 | 90.3 | 70.6 | 97.0 | 90.9 | 68.8 | 98.0 |
| 2_32 | 97.0 | 88.2 | 100 | 100 | 100 | 100 |
| 32_36 | 94.8 | 82.4 | 99.0 | 89.4 | 68.8 | 96.0 |
| 15_32 | 92.5 | 76.5 | 98.0 | 95.5 | 87.5 | 98.0 |
| 3_38 | 97.0 | 97.1 | 97.0 | 97.0 | 100 | 96.0 |
| 38_39 | 93.3 | 82.4 | 97.0 | 87.9 | 75.0 | 92.0 |
| 38_64 | 87.3 | 61.8 | 96.0 | 87.9 | 62.5 | 96.0 |
| 3_45 | 96.3 | 85.3 | 100 | 97.0 | 100 | 96.0 |
| 45_58 | 96.3 | 91.2 | 98.0 | 83.3 | 75.0 | 86.0 |
| 45_64 | 95.5 | 94.1 | 96.0 | 95.5 | 87.5 | 98.0 |
| 2_55 | 96.3 | 88.2 | 99.0 | 100 | 100 | 100 |
| 6_55 | 95.5 | 85.3 | 99.0 | 90.9 | 81.2 | 94.0 |
| 55_64 | 88.1 | 61.8 | 97.0 | 84.8 | 56.2 | 94.0 |
| 2_64 | 97.0 | 91.2 | 99.0 | 100 | 100 | 100 |
| 4_64 | 94.8 | 85.3 | 98.0 | 97.0 | 87.5 | 100 |
| 2_96 | 97.8 | 94.1 | 99.0 | 98.5 | 100 | 98.0 |
| 7_96 | 98.5 | 100 | 98.0 | 93.9 | 93.8 | 94.0 |
| 96_97 | 85.1 | 61.8 | 93.0 | 77.3 | 31.2 | 92.0 |
| 2_97 | 96.3 | 88.2 | 99.0 | 100 | 100 | 100 |
| 3_97 | 98.5 | 97.1 | 99.0 | 98.5 | 100 | 98.0 |
| 5_97 | 96.3 | 91.2 | 98.0 | 97.0 | 93.8 | 98.0 |
| 2_162 | 96.3 | 88.2 | 99.0 | 98.5 | 100 | 98.0 |
| 3_162 | 97.8 | 94.1 | 99.0 | 100 | 100 | 100 |
| 5_162 | 97.8 | 94.1 | 99.0 | 98.5 | 93.8 | 100 |

Example 3

<Selection of Gene Marker Using all Samples and Method for Evaluating Colorectal Cancer Discriminant Performance of Acquired Gene Marker>

In this Example, the samples in the training cohort and the validation cohort used in Examples 1 and 2 were integrated, and selection of a gene marker and evaluation of its colorectal cancer discriminant performance were conducted using all of the samples.

Specifically, the miRNA expression levels in the serum of the 50 colorectal cancer patients and the 150 healthy subjects obtained in the preceding Reference Examples were normalized by quantile normalization. In order to acquire diagnostic markers with higher reliability, only genes having a gene expression level of 26 or higher in 50% or more of the samples in either of the colorectal cancer patient group or the healthy subject group were selected in the gene marker selection. In order to further acquire statistical significance for discriminating a colorectal cancer patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant, and the obtained genes are described in Table 8. In this way, hsa-miR-4697-5p, hsa-miR-3197, hsa-miR-675-5p, hsa-miR-4486, hsa-miR-7107-5p, hsa-miR-23a-3p, hsa-miR-4667-5p, hsa-miR-451a, hsa-miR-3940-5p, hsa-miR-8059, hsa-miR-6813-5p, hsa-miR-4492, hsa-miR-4476 and hsa-miR-6090 genes, and the nucleotide sequences of SEQ ID NOs: 181 to 194 related thereto were found in addition to the genes described in Table 2. As with the nucleotide sequences of SEQ ID NOs: 1 to 180, the results obtained about the polynucleotides shown in SEQ ID NOs: 181 to 194 also showed that the gene measurement values were significantly lower (−) or higher (+) in the colorectal cancer patient group than in the healthy subject group (Table 8). These results were able to be validated in the validation cohort. Thus, the presence or absence of colorectal cancer in the newly obtained samples can be determined by the methods described in Examples 1 and 2 by using the gene expression level measurement values described in Table 8 either alone or in combination with the gene expression level measurement values described in Table 2.

TABLE 8

| SEQ ID NO: | Gene name | P value after Bonferroni correction | Expression level in colorectal cancer patient with respect to healthy subject |
|---|---|---|---|
| 1 | hsa-miR-6726-5p | 5.31.E−62 | − |
| 2 | hsa-miR-4257 | 1.09.E−61 | − |
| 3 | hsa-miR-6787-5p | 2.44.E−47 | − |
| 4 | hsa-miR-6780b-5p | 2.11.E−42 | + |
| 5 | hsa-miR-3131 | 4.30.E−42 | − |
| 6 | hsa-miR-7108-5p | 3.00.E−35 | + |
| 7 | hsa-miR-1343-3p | 4.27.E−43 | − |
| 8 | hsa-miR-1247-3p | 9.79.E−35 | + |
| 9 | hsa-miR-4651 | 9.99.E−39 | − |
| 10 | hsa-miR-6757-5p | 2.24.E−34 | − |
| 11 | hsa-miR-3679-5p | 3.50.E−37 | + |
| 12 | hsa-miR-7641 | 5.56.E−34 | − |
| 13 | hsa-miR-6746-5p | 1.02.E−31 | − |
| 14 | hsa-miR-8072 | 1.54.E−27 | + |
| 15 | hsa-miR-6741-5p | 2.21.E−31 | − |
| 16 | hsa-miR-1908-5p | 4.52.E−29 | + |
| 17 | hsa-miR-6857-5p | 3.92.E−22 | + |
| 18 | hsa-miR-4746-3p | 3.57.E−31 | + |
| 19 | hsa-miR-744-5p | 7.34.E−32 | + |
| 20 | hsa-miR-4792 | 1.24.E−27 | + |
| 21 | hsa-miR-564 | 2.13.E−30 | − |
| 22 | hsa-miR-6791-5p | 2.90.E−27 | + |
| 23 | hsa-miR-6825-5p | 4.61.E−29 | + |
| 24 | hsa-miR-6826-5p | 2.05.E−29 | − |
| 25 | hsa-miR-4665-3p | 7.74.E−29 | + |
| 26 | hsa-miR-4467 | 5.07.E−27 | + |
| 27 | hsa-miR-3188 | 5.96.E−29 | + |
| 28 | hsa-miR-6125 | 2.14.E−23 | + |
| 29 | hsa-miR-6756-5p | 2.14.E−22 | − |
| 30 | hsa-miR-1228-3p | 7.24.E−25 | + |
| 31 | hsa-miR-8063 | 1.63.E−24 | − |
| 32 | hsa-miR-8069 | 9.97.E−22 | + |
| 33 | hsa-miR-6875-5p | 6.41.E−21 | + |
| 34 | hsa-miR-3185 | 1.30.E−24 | + |
| 35 | hsa-miR-4433b-3p | 2.47.E−20 | + |
| 36 | hsa-miR-6887-5p | 5.17.E−26 | − |
| 37 | hsa-miR-128-1-5p | 3.06.E−18 | + |
| 38 | hsa-miR-6724-5p | 4.44.E−21 | + |
| 39 | hsa-miR-1914-3p | 2.19.E−16 | − |
| 40 | hsa-miR-1225-5p | 9.96.E−22 | + |
| 41 | hsa-miR-4419b | 2.99.E−22 | − |
| 42 | hsa-miR-7110-5p | 1.00.E−22 | + |
| 43 | hsa-miR-187-5p | 1.62.E−19 | − |
| 44 | hsa-miR-3184-5p | 2.98.E−20 | + |
| 45 | hsa-miR-204-3p | 1.12.E−17 | − |
| 46 | hsa-miR-5572 | 5.88.E−21 | + |
| 47 | hsa-miR-6729-5p | 6.07.E−18 | + |
| 48 | hsa-miR-615-5p | 3.71.E−19 | − |
| 49 | hsa-miR-6749-5p | 1.52.E−19 | − |
| 50 | hsa-miR-6515-3p | 1.14.E−15 | + |
| 51 | hsa-miR-3937 | 1.06.E−20 | + |
| 52 | hsa-miR-6840-3p | 3.27.E−16 | − |
| 53 | hsa-miR-6893-5p | 3.70.E−20 | − |
| 54 | hsa-miR-4728-5p | 1.49.E−16 | − |
| 55 | hsa-miR-6717-5p | 5.86.E−21 | − |
| 56 | hsa-miR-7113-3p | 1.99.E−19 | + |
| 57 | hsa-miR-4665-5p | 4.71.E−16 | − |
| 58 | hsa-miR-642b-3p | 1.28.E−15 | − |
| 59 | hsa-miR-7109-5p | 6.89.E−19 | − |
| 60 | hsa-miR-6842-5p | 5.06.E−19 | + |
| 61 | hsa-miR-4442 | 9.22.E−16 | − |
| 62 | hsa-miR-4433-3p | 2.94.E−16 | + |
| 63 | hsa-miR-4707-5p | 1.21.E−7 | + |
| 64 | hsa-miR-6126 | 3.89.E−16 | + |
| 65 | hsa-miR-4449 | 3.16.E−20 | + |
| 66 | hsa-miR-4706 | 1.73.E−16 | − |
| 67 | hsa-miR-1913 | 3.48.E−16 | + |
| 68 | hsa-miR-602 | 1.60.E−16 | + |
| 69 | hsa-miR-939-5p | 4.02.E−16 | + |
| 70 | hsa-miR-4695-5p | 2.61.E−14 | + |

TABLE 8-continued

| SEQ ID NO: | Gene name | P value after Bonferroni correction | Expression level in colorectal cancer patient with respect to healthy subject |
|---|---|---|---|
| 71 | hsa-miR-711 | 1.79.E−16 | + |
| 72 | hsa-miR-6816-5p | 5.98.E−14 | + |
| 73 | hsa-miR-4632-5p | 4.56.E−14 | + |
| 74 | hsa-miR-6721-5p | 5.64.E−13 | + |
| 75 | hsa-miR-7847-3p | 7.52.E−17 | − |
| 76 | hsa-miR-6132 | 6.77.E−16 | + |
| 77 | hsa-miR-887-3p | 3.26.E−14 | + |
| 78 | hsa-miR-3679-3p | 5.22.E−14 | + |
| 79 | hsa-miR-6784-5p | 6.38.E−13 | + |
| 80 | hsa-miR-1249 | 1.62.E−14 | + |
| 81 | hsa-miR-937-5p | 8.71.E−13 | − |
| 82 | hsa-miR-5195-3p | 2.51.E−14 | − |
| 83 | hsa-miR-6732-5p | 2.71.E−13 | + |
| 84 | hsa-miR-4417 | 4.13.E−15 | + |
| 85 | hsa-miR-4281 | 1.09.E−13 | − |
| 86 | hsa-miR-4734 | 7.65.E−15 | + |
| 87 | hsa-miR-6766-3p | 1.32.E−13 | + |
| 88 | hsa-miR-663a | 1.12.E−14 | + |
| 90 | hsa-miR-6781-5p | 1.88.E−11 | + |
| 91 | hsa-miR-1227-5p | 6.26.E−12 | + |
| 92 | hsa-miR-6845-5p | 1.06.E−14 | + |
| 93 | hsa-miR-6798-5p | 2.72.E−08 | + |
| 94 | hsa-miR-3620-5p | 7.80.E−10 | + |
| 95 | hsa-miR-1915-5p | 1.02.E−11 | − |
| 96 | hsa-miR-4294 | 1.22.E−12 | − |
| 97 | hsa-miR-642a-3p | 5.69.E−12 | − |
| 98 | hsa-miR-371a-5p | 2.55.E−09 | − |
| 99 | hsa-miR-940 | 2.85.E−14 | + |
| 100 | hsa-miR-4450 | 2.15.E−13 | − |
| 101 | hsa-miR-4723-5p | 8.73.E−13 | − |
| 102 | hsa-miR-1469 | 5.67.E−12 | + |
| 103 | hsa-miR-6861-5p | 2.03.E−12 | − |
| 104 | hsa-miR-7975 | 1.02.E−09 | − |
| 105 | hsa-miR-6879-5p | 6.99.E−11 | + |
| 106 | hsa-miR-6802-5p | 1.21.E−10 | − |
| 107 | hsa-miR-1268b | 8.63.E−11 | + |
| 108 | hsa-miR-663b | 1.02.E−10 | − |
| 109 | hsa-miR-125a-3p | 1.21.E−12 | − |
| 110 | hsa-miR-2861 | 4.18.E−13 | − |
| 111 | hsa-miR-6088 | 6.31.E−12 | − |
| 112 | hsa-miR-4758-5p | 1.17.E−10 | − |
| 113 | hsa-miR-296-3p | 1.20.E−08 | − |
| 114 | hsa-miR-6738-5p | 1.29.E−09 | − |
| 115 | hsa-miR-671-5 p | 8.62.E−11 | − |
| 116 | hsa-miR-4454 | 4.34.E−10 | − |
| 117 | hsa-miR-4516 | 3.61.E−10 | − |
| 118 | hsa-miR-7845-5p | 7.69.E−09 | + |
| 119 | hsa-miR-4741 | 2.27.E−09 | + |
| 120 | hsa-miR-92b-5p | 2.68.E−09 | + |
| 121 | hsa-miR-6795-5p | 1.14.E−09 | - |
| 122 | hsa-miR-6805-3p | 1.59.E−11 | + |
| 123 | hsa-miR-4725-3p | 6.13.E−07 | + |
| 124 | hsa-miR-6782-5p | 1.59.E−08 | + |
| 125 | hsa-miR-4688 | 5.22.E−07 | − |
| 126 | hsa-miR-6850-5p | 7.32.E−08 | + |
| 127 | hsa-miR-6777-5p | 7.19.E−11 | − |
| 128 | hsa-miR-6785-5p | 1.41.E−07 | − |
| 129 | hsa-miR-7106-5p | 6.63.E−09 | − |
| 130 | hsa-miR-3663-3p | 3.69.E−09 | − |
| 131 | hsa-miR-6131 | 1.40.E−09 | − |
| 132 | hsa-miR-1915-3p | 6.80.E−08 | + |
| 133 | hsa-miR-4532 | 2.71.E−07 | − |
| 134 | hsa-miR-6820-5p | 1.32.E−07 | − |
| 135 | hsa-miR-4689 | 3.51.E−09 | − |
| 136 | hsa-miR-4638-5p | 2.60.E−07 | − |
| 137 | hsa-miR-3656 | 1.23.E−07 | + |
| 138 | hsa-miR-3621 | 6.72.E−07 | − |
| 139 | hsa-miR-6769b-5p | 7.12.E−08 | − |
| 140 | hsa-miR-149-3p | 1.99.E−07 | − |
| 141 | hsa-miR-23b-3p | 1.65.E−07 | − |
| 142 | hsa-miR-3135b | 1.27.E−07 | − |
| 143 | hsa-miR-6848-5p | 3.54.E−06 | + |
| 144 | hsa-miR-6769a-5p | 5.27.E−08 | − |
| 145 | hsa-miR-4327 | 4.27.E−06 | + |
| 146 | hsa-miR-6765-3p | 2.60.E−07 | − |

TABLE 8-continued

| SEQ ID NO: | Gene name | P value after Bonferroni correction | Expression level in colorectal cancer patient with respect to healthy subject |
|---|---|---|---|
| 147 | hsa-miR-6716-5p | 1.00.E−06 | + |
| 148 | hsa-miR-6877-5p | 1.64.E−06 | − |
| 149 | hsa-miR-6727-5p | 3.79.E−06 | − |
| 150 | hsa-miR-4534 | 4.38.E−06 | − |
| 151 | hsa-miR-614 | 2.94.E−06 | − |
| 152 | hsa-miR-1202 | 3.36.E−07 | − |
| 153 | hsa-miR-575 | 5.28.E−08 | − |
| 154 | hsa-miR-6870-5p | 3.19.E−08 | + |
| 155 | hsa-miR-6722-3p | 8.34.E−06 | + |
| 156 | hsa-miR-7977 | 6.56.E−05 | − |
| 157 | hsa-miR-4649-5p | 1.23.E−05 | − |
| 158 | hsa-miR-4675 | 3.15.E−07 | − |
| 159 | hsa-miR-6075 | 6.53.E−05 | + |
| 160 | hsa-miR-6779-5p | 5.68.E−07 | − |
| 161 | hsa-miR-4271 | 1.02.E−05 | − |
| 162 | hsa-miR-3196 | 2.40.E−06 | + |
| 163 | hsa-miR-6803-5p | 3.32.E−03 | + |
| 164 | hsa-miR-6789-5p | 1.02.E−06 | + |
| 165 | hsa-miR-4648 | 7.63.E−08 | + |
| 167 | hsa-miR-4749-5p | 3.78.E−05 | + |
| 168 | hsa-miR-4505 | 7.82.E−05 | + |
| 169 | hsa-miR-5698 | 2.28.E−04 | − |
| 170 | hsa-miR-1199-5p | 2.58.E−04 | − |
| 171 | hsa-miR-4763-3p | 1.20.E−03 | + |
| 172 | hsa-miR-1231 | 2.42.E−35 | + |
| 173 | hsa-miR-1233-5p | 4.01.E−32 | − |
| 174 | hsa-miR-150-3p | 4.05.E−09 | − |
| 175 | hsa-miR-1225-3p | 3.42.E−13 | + |
| 176 | hsa-miR-92a-2-5p | 3.89.E−08 | + |
| 177 | hsa-miR-423-5p | 1.73.E−06 | − |
| 178 | hsa-miR-1268a | 2.52.E−05 | + |
| 179 | hsa-miR-128-2-5p | 5.33.E−06 | − |
| 180 | hsa-miR-24-3p | 1.01.E−07 | − |
| 181 | hsa-miR-4697-5p | 4.79.E−05 | − |
| 182 | hsa-miR-3197 | 1.62.E−04 | + |
| 183 | hsa-miR-675-5p | 2.19.E−04 | − |
| 184 | hsa-miR-4486 | 4.27.E−04 | + |
| 185 | hsa-miR-7107-5p | 4.72.E−04 | − |
| 186 | hsa-miR-23a-3p | 1.53.E−03 | − |
| 187 | hsa-miR-4667-5p | 2.51.E−03 | + |
| 188 | hsa-miR-451a | 3.74.E−03 | − |
| 189 | hsa-miR-3940-5p | 4.95.E−03 | + |
| 190 | hsa-miR-8059 | 5.22.E−03 | − |
| 191 | hsa-miR-6813-5p | 5.33.E−03 | + |
| 192 | hsa-miR-4492 | 9.03.E−03 | + |
| 193 | hsa-miR-4476 | 9.04.E−03 | − |
| 194 | hsa-miR-6090 | 9.46.E−03 | + |

Example 4

<Method for Evaluating Colorectal Cancer-Specific Discriminant Performance by Combination of Multiple Gene Markers Using Samples in the Validation Cohort>

In this Example, a gene for diagnosis is selected by comparing gene expression levels of miRNAs in serum between colorectal cancer patients and a control group that consist of healthy subjects, pancreatic cancer patients, bile duct cancer patients, stomach cancer patients, esophageal cancer patients, liver cancer patients, and benign pancreaticobiliary disease patients in the same way as the method described in Example 1, using the gene markers selected in Example 1, and targeting the training cohort as the sample group described in Reference Example 2. The polynucleotides consisting of the nucleotide sequences represented by SEQ ID NOs: 606 to 614 thus selected were further combined therewith to study a method for evaluating colorectal cancer-specific discriminant performance.

Specifically, first, the miRNA expression levels in the training cohort and the validation cohort obtained in Reference Example 2 were combined and normalized by quantile normalization. Next, Fisher's discriminant analysis was conducted as to combinations of 1 to 6 expression level measurement values comprising at least one or more of the expression level measurement values of the polynucleotides consisting of the nucleotide sequences represented by SEQ ID NOs: 1 to 171 and 606 to 614, to construct a discriminant for determining the presence or absence of colorectal cancer. Next, accuracy, sensitivity, and specificity in the validation cohort were calculated using the discriminant thus prepared, with the colorectal cancer patient group as a positive sample group and, on the other hand, the healthy subject group, the pancreatic cancer patient group, the bile duct cancer patient group, the stomach cancer patient group, the esophageal cancer patient group, the liver cancer patient group, and the benign pancreaticobiliary disease patient group as a negative sample group. The discriminant performance of the selected polynucleotides was validated using independent samples.

Most of polynucleotides consisting of the nucleotide sequences represented by these SEQ ID NOS (SEQ ID NOs: 1 to 194 and 606 to 614 corresponding to the miRNA markers of Table 1) or complementary sequences thereof were able to provide relatively high accuracy, sensitivity, and specificity in the determination of the presence or absence of colorectal cancer, and furthermore, were able to specifically discriminate colorectal cancer from the other cancers. For example, among the combinations of multiple polynucleotides selected from the group consisting of polynucleotides consisting of the nucleotide sequences represented by SEQ ID NOs: 5, 13, 15, 24, 32, 38, 41, 45, 55, 57, 64, 72, 75, 77, 96, 97, 115, 162, 163, 173, 189, 606, 607, 608, 609, 610, 611, 612, 613 and 614, or complementary sequences thereof (the cancer type-specific polynucleotide group 1) as polynucleotides capable of specifically binding to target markers, combinations comprising at least one or more polynucleotide(s) selected from the group consisting of polynucleotides consisting of the nucleotide sequences represented by SEQ ID NOs: 5, 45, 57, 96, and 606, or complementary sequences thereof (the cancer type-specific polynucleotide group 2) included in the cancer type-specific polynucleotide group 1 were able to specifically discriminate colorectal cancer from the other cancers with high accuracy.

The number of the aforementioned polynucleotides with cancer type specificity in the combination can be 1, 2, 3, 4, 5, 6, 7, 8, 9, 10 or more for the combination. The combinations of 6 or more of these polynucleotides were able to exhibit discriminant accuracy of 90% or higher.

Specifically, the discriminant accuracy of the measurement using the polynucleotide that consists of the nucleotide sequence represented by SEQ ID NO: 5 or a complementary sequence thereof is shown in Table 9-1. The measurement using the combination of one polynucleotide comprising at least one polynucleotide consisting of the nucleotide sequence represented by SEQ ID NO: 5 or a complementary sequence thereof exhibited the highest accuracy of 90.1% in the training cohort and accuracy of 87.6% in the validation cohort. Also, for example, the measurement using the combinations of two polynucleotides comprising at least one polynucleotide consisting of the nucleotide sequence represented by SEQ ID NO: 5 or a complementary sequence thereof exhibited the highest accuracy of 91.7% in the training cohort and accuracy of 88.8% in the validation cohort. Furthermore, for example, the measurement using the combinations of three polynucleotides comprising at least one polynucleotide consisting of the nucleotide sequence represented by SEQ ID NO: 5 or a complementary sequence thereof exhibited the highest accuracy of 94.0% in the training cohort and accuracy of 91.2% in the validation cohort. Furthermore, for example, the measurement using the combinations of four polynucleotides comprising at least one polynucleotide consisting of the nucleotide sequence represented by SEQ ID NO: 5 or a complementary sequence thereof exhibited the highest accuracy of 95.6% in the training cohort and accuracy of 93.6% in the validation cohort. Furthermore, for example, the measurement using the combinations of five polynucleotides comprising at least one polynucleotide consisting of the nucleotide sequence represented by SEQ ID NO: 5 or a complementary sequence thereof exhibited the highest accuracy of 96.4% in the training cohort and accuracy of 94.8% in the validation cohort. Furthermore, for example, the measurement using the combinations of six polynucleotides comprising at least one polynucleotide consisting of the nucleotide sequence represented by SEQ ID NO: 5 or a complementary sequence thereof exhibited the highest accuracy of 96.9% in the training cohort and accuracy of 94.7% in the validation cohort.

The discriminant accuracy of the measurement using the polynucleotide consisting of the nucleotide sequence represented by SEQ ID NO: 45 or a complementary sequence thereof is shown in Table 9-2. The measurement using the combination of one polynucleotide comprising at least one polynucleotide consisting of the nucleotide sequence represented by SEQ ID NO: 45 or a complementary sequence thereof exhibited the highest accuracy of 56.7% in the training cohort and accuracy of 55.4% in the validation cohort. Also, for example, the measurement using the combinations of two polynucleotides comprising at least one polynucleotide consisting of the nucleotide sequence represented by SEQ ID NO: 45 or a complementary sequence thereof exhibited the highest accuracy of 90.7% in the training cohort and accuracy of 88.4% in the validation cohort. Furthermore, for example, the measurement using the combinations of three polynucleotides comprising at least one polynucleotide consisting of the nucleotide sequence represented by SEQ ID NO: 45 or a complementary sequence thereof exhibited the highest accuracy of 94.0% in the training cohort and accuracy of 89.6% in the validation cohort. Furthermore, for example, the measurement using the combinations of four polynucleotides comprising at least one polynucleotide consisting of the nucleotide sequence represented by SEQ ID NO: 45 or a complementary sequence thereof exhibited the highest accuracy of 95.2% in the training cohort and accuracy of 91.6% in the validation cohort. Furthermore, for example, the measurement using the combinations of five polynucleotides comprising at least one polynucleotide consisting of the nucleotide sequence represented by SEQ ID NO: 45 or a complementary sequence thereof exhibited the highest accuracy of 96.4% in the training cohort and accuracy of 94.4% in the validation cohort. Furthermore, for example, the measurement using the combinations of six polynucleotides comprising at least one polynucleotide consisting of the nucleotide sequence represented by SEQ ID NO: 45 or a complementary sequence thereof exhibited the highest accuracy of 97.6% in the training cohort and accuracy of 92.6% in the validation cohort.

The discriminant accuracy of the measurement using the polynucleotide consisting of the nucleotide sequence represented by SEQ ID NO: 57 or a complementary sequence thereof is shown in Table 9-3. The measurement using the combination of one polynucleotide comprising at least one polynucleotide consisting of the nucleotide sequence represented by SEQ ID NO: 57 or a complementary sequence thereof exhibited the highest accuracy of 60.2% in the training cohort and accuracy of 60.6% in the validation cohort. Also, for example, the measurement using the combinations of two polynucleotides comprising at least one polynucleotide consisting of the nucleotide sequence represented by SEQ ID NO: 57 or a complementary sequence thereof exhibited the highest accuracy of 86.7% in the training cohort and accuracy of 83.7% in the validation cohort. Furthermore, for example, the measurement using the combinations of three polynucleotides comprising at least one polynucleotide consisting of the nucleotide sequence represented by SEQ ID NO: 57 or a complementary sequence thereof exhibited the highest accuracy of 92.4% in the training cohort and accuracy of 90.0% in the validation cohort. Furthermore, for example, the measurement using the combinations of four polynucleotides comprising at least one polynucleotide consisting of the nucleotide sequence represented by SEQ ID NO: 57 or a complementary sequence thereof exhibited the highest accuracy of 95.2% in the training cohort and accuracy of 91.2% in the validation cohort. Furthermore, for example, the measurement using the combinations of five polynucleotides comprising at least one polynucleotide consisting of the nucleotide sequence represented by SEQ ID NO: 57 or a complementary sequence thereof exhibited the highest accuracy of 96.2% in the training cohort and accuracy of 94.8% in the validation cohort. Furthermore, for example, the measurement using the combinations of six polynucleotides comprising at least one polynucleotide consisting of the nucleotide sequence represented by SEQ ID NO: 57 or a complementary sequence thereof exhibited the highest accuracy of 96.9% in the training cohort and accuracy of 93.6% in the validation cohort.

The discriminant accuracy of the measurement using the polynucleotide consisting of the nucleotide sequence represented by SEQ ID NO: 96 or a complementary sequence thereof is shown in Table 9-4. The measurement using the combination of one polynucleotide comprising at least one polynucleotide consisting of the nucleotide sequence represented by SEQ ID NO: 96 or a complementary sequence thereof exhibited the highest accuracy of 57.9% in the training cohort and accuracy of 59.4% in the validation cohort. Also, for example, the measurement using the combinations of two polynucleotides comprising at least one polynucleotide consisting of the nucleotide sequence represented by SEQ ID NO: 96 or a complementary sequence thereof exhibited the highest accuracy of 85.9% in the training cohort and accuracy of 83.7% in the validation cohort. Furthermore, for example, the measurement using the combinations of three polynucleotides comprising at least one polynucleotide consisting of the nucleotide sequence represented by SEQ ID NO: 96 or a complementary sequence thereof exhibited the highest accuracy of 92.6% in the training cohort and accuracy of 90.4% in the validation cohort. Furthermore, for example, the measurement using the combinations of four polynucleotides comprising at least one polynucleotide consisting of the nucleotide sequence represented by SEQ ID NO: 96 or a complementary sequence thereof exhibited the highest accuracy of 94.4% in the training cohort and accuracy of 91.2% in the validation cohort. Furthermore, for example, the measurement using the combinations of five polynucleotides comprising at least one polynucleotide consisting of the nucleotide sequence represented by SEQ ID NO: 96 or a complementary sequence thereof exhibited the highest accuracy of 96.0% in the training cohort and accuracy of 94.0% in the validation cohort. Furthermore, for example, the measurement using the combinations of six polynucleotides comprising at least one polynucleotide consisting of the nucleotide sequence represented by SEQ ID NO: 96 or a complementary sequence thereof exhibited the highest accuracy of 96.3% in the training cohort and accuracy of 93.6% in the validation cohort.

The discriminant accuracy of the measurement using the polynucleotide consisting of the nucleotide sequence represented by SEQ ID NO: 606 or a complementary sequence thereof is shown in Table 9-5. The measurement using the combination of one polynucleotide comprising at least one polynucleotide consisting of the nucleotide sequence represented by SEQ ID NO: 606 or a complementary sequence thereof exhibited the highest accuracy of 59.4% in the training cohort and accuracy of 58.6% in the validation cohort. Also, for example, the measurement using the combinations of two polynucleotides comprising at least one polynucleotide consisting of the nucleotide sequence represented by SEQ ID NO: 606 or a complementary sequence thereof exhibited the highest accuracy of 86.6% in the training cohort and accuracy of 82.9% in the validation cohort. Furthermore, for example, the measurement using the combinations of three polynucleotides comprising at least one polynucleotide consisting of the nucleotide sequence represented by SEQ ID NO: 606 or a complementary sequence thereof exhibited the highest accuracy of 92.6% in the training cohort and accuracy of 91.2% in the validation cohort. Furthermore, for example, the measurement using the combinations of four polynucleotides comprising at least one polynucleotide consisting of the nucleotide sequence represented by SEQ ID NO: 606 or a complementary sequence thereof exhibited the highest accuracy of 94.8% in the training cohort and accuracy of 90.0% in the validation cohort. Furthermore, for example, the measurement using the combinations of five polynucleotides comprising at least one polynucleotide consisting of the nucleotide sequence represented by SEQ ID NO: 606 or a complementary sequence thereof exhibited the highest accuracy of 96.0% in the training cohort and accuracy of 93.6% in the validation cohort. Furthermore, for example, the measurement using the combinations of six polynucleotides comprising at least one polynucleotide consisting of the nucleotide sequence represented by SEQ ID NO: 606 or a complementary sequence thereof exhibited the highest accuracy of 95.3% in the training cohort and accuracy of 93.6% in the validation cohort.

Figure 4:
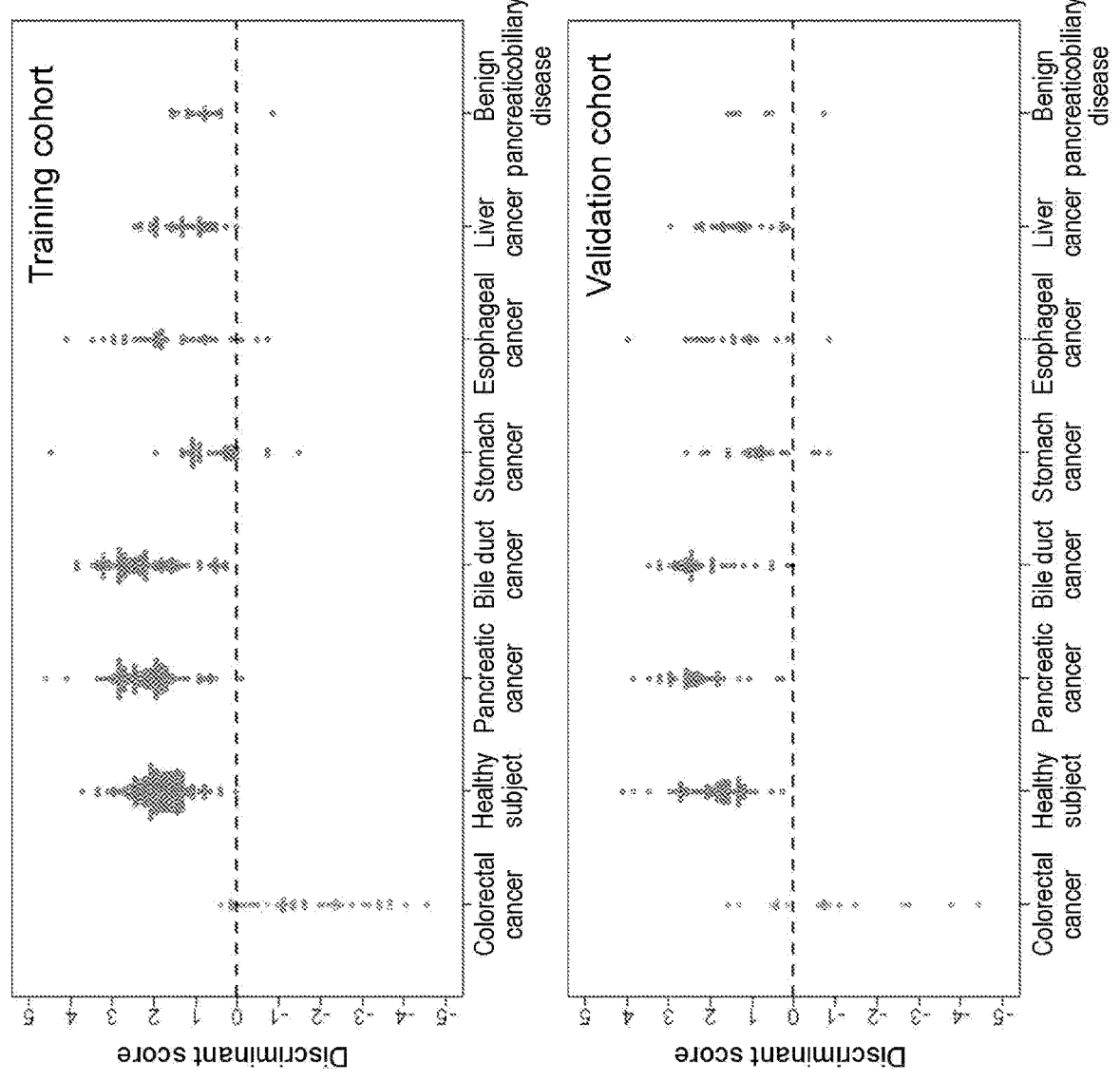
FIG. 4 Upper diagram: a discriminant ($1.49\times$hsa-miR-3131$-0.23\times$hsa-miR-7847-3p$-1.13\times$hsa-miR-3196$+1.11\times$hsa-miR-3195$+2.25\times$hsa-miR-4665-5p$-1.00\times$hsa-miR-204-3p$-11.16$) was prepared by use of Fisher's discriminant analysis from the expression level measurement values of hsa-miR-3131 (SEQ ID NO: 5), hsa-miR-204-3p (SEQ ID NO: 45), hsa-miR-4665-5p (SEQ ID NO: 57), hsa-miR-7847-3p (SEQ ID NO: 75), hsa-miR-3196 (SEQ ID NO: 162), and hsa-miR-3195 (SEQ ID NO: 607) in 34 colorectal cancer patients, 103 healthy subjects, 69 pancreatic cancer patients, 66 bile duct cancer patients, 30 stomach cancer patients, 33 esophageal cancer patients, 32 liver cancer patients, and 15 benign pancreaticobiliary disease patients selected as a training cohort, and discriminant scores obtained from the discriminant were plotted on the ordinate against the sample groups on the abscissa. The dotted line in the diagram depicts a discriminant boundary that offered a discriminant score of 0 and discriminated between the groups. Lower diagram: discriminant scores obtained from the discriminant prepared in the training cohort as to the expression level measurement values of hsa-miR-3131 (SEQ ID NO: 5), hsa-miR-204-3p (SEQ ID NO: 45), hsa-miR-4665-5p (SEQ ID NO: 57), hsa-miR-7847-3p (SEQ ID NO: 75), hsa-miR-3196 (SEQ ID NO: 162), and hsa-miR-3195 (SEQ ID NO: 607) in 16 colorectal cancer patients, 47 healthy subjects, 30 pancreatic cancer patients, 33 bile duct cancer patients, 20 stomach cancer patients, 17 esophageal cancer patients, 20 liver cancer patients, and 6 benign pancreaticobiliary disease patients selected as a validation cohort were plotted on the ordinate against the sample groups on the abscissa. The dotted line in the diagram depicts the discriminant boundary that offered a discriminant score of 0 and discriminated between the two groups.

The expression level measurement values of the nucleotide sequences represented by SEQ ID NOs: 5, 45, 57, 75, 162, and 607 were compared among 34 colorectal cancer patients, 103 healthy subject, 69 pancreatic cancer patients, 66 bile duct cancer patients, 30 stomach cancer patients, 33 esophageal cancer patients, 32 liver cancer patients, and 15 benign pancreaticobiliary disease patients in the training cohort. As a result, a scatter diagram that significantly separated the discriminant score of the colorectal cancer patient group from the discriminant scores of the other groups was obtained in the training cohort (see the upper diagram of FIG. 4). These results were also reproducible in the validation cohort (see the lower diagram of FIG. 4).

TABLE 9-1

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 5 | 90.1 | 100 | 89.3 | 87.6 | 87.5 | 87.7 |
| 5_608 | 91.7 | 91.2 | 91.7 | 88.8 | 62.5 | 90.6 |
| 5_45_607 | 94 | 91.2 | 94.2 | 91.2 | 75 | 92.3 |
| 5_45_57_607 | 95.6 | 88.2 | 96.2 | 93.6 | 62.5 | 95.7 |
| 5_45_57_75_607 | 96.3 | 84.8 | 97.4 | 93.1 | 62.5 | 95.9 |
| 5_45_96_606_607 | 96.4 | 97.1 | 96.4 | 94.8 | 87.5 | 95.3 |
| 5_45_57_97_115_607 | 96.9 | 88.2 | 97.7 | 94.7 | 75.0 | 96.5 |
| 5_45_57_97_162_607 | 96.9 | 88.2 | 97.7 | 94.1 | 68.8 | 96.5 |
| 5_45_57_162_607_613 | 96.9 | 88.2 | 97.7 | 94.1 | 62.5 | 97.1 |
| 5_45_57_97_607_612 | 96.9 | 94.1 | 97.1 | 94.1 | 81.2 | 95.3 |
| 5_13_45_57_606_607 | 96.9 | 91.2 | 97.4 | 93.6 | 68.8 | 95.9 |
| 5_45_96_189_606_608 | 95.3 | 94.1 | 95.4 | 94.7 | 75 | 96.5 |
| 5_45_57_96_189_606 | 96.3 | 97.1 | 96.3 | 93.6 | 75 | 95.3 |
| 5_24_45_57_96_608 | 95.3 | 94.1 | 95.4 | 92.6 | 56.2 | 95.9 |
| 5_45_57_162_607_610 | 95.8 | 85.3 | 96.8 | 93.6 | 62.5 | 96.5 |
| 5_45_57_189_606_607 | 96.1 | 91.2 | 96.6 | 93.6 | 75 | 95.3 |

TABLE 9-2

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 45 | 56.7 | 61.8 | 56.3 | 55.4 | 56.2 | 55.3 |
| 5_45 | 90.7 | 100 | 90 | 88.4 | 87.5 | 88.5 |
| 5_45_57 | 94 | 94.1 | 94 | 89.6 | 81.2 | 90.2 |
| 5_45_57_97 | 95.2 | 94.1 | 95.3 | 91.6 | 81.2 | 92.3 |
| 5_45_96_606_607 | 95.5 | 91.2 | 96.0 | 95.2 | 87.5 | 95.9 |
| 5_45_57_75_607 | 96.4 | 87.9 | 97 | 94.4 | 62.5 | 96.6 |
| 5_45_57_75_606_607 | 97.6 | 87.9 | 98.6 | 92.6 | 62.5 | 95.3 |
| 5_45_57_77_607_613 | 97.4 | 94.1 | 97.7 | 94.1 | 75.0 | 95.9 |
| 5_45_57_97_606_607 | 97.1 | 94.1 | 97.4 | 94.1 | 81.2 | 95.3 |
| 5_45_57_75_77_607 | 97.1 | 90.9 | 97.7 | 93.1 | 68.8 | 95.3 |

TABLE 9-2-continued

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 5_32_45_57_96_606 | 96.3 | 97.1 | 96.3 | 93.6 | 68.8 | 95.9 |
| 5_24_45_57_96_606 | 96.1 | 97.1 | 96 | 93.1 | 68.8 | 95.3 |
| 5_45_57_96_162_606 | 95.5 | 91.2 | 96 | 94.7 | 81.2 | 95.9 |
| 5_15_45_75_96_606 | 95.5 | 100 | 95.1 | 93.6 | 81.2 | 94.8 |
| 5_32_45_57_162_607 | 95.8 | 85.3 | 96.8 | 93.6 | 62.5 | 96.5 |
| 38_45_96_606_608_611 | 87.1 | 88.2 | 87.0 | 86.2 | 68.8 | 87.8 |

TABLE 9-3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 57 | 60.2 | 70.6 | 59.5 | 60.6 | 56.2 | 60.9 |
| 24_57 | 86.7 | 91.2 | 86.4 | 83.7 | 62.5 | 85.1 |
| 5_57_608 | 92.4 | 88.2 | 92.8 | 90 | 68.8 | 91.5 |
| 5_45_57_608 | 95.2 | 91.2 | 95.5 | 91.2 | 62.5 | 93.2 |
| 24_41_57_45_96 | 94.5 | 94.1 | 94.5 | 88.8 | 56.2 | 91.9 |
| 5_45_57_607_612 | 96.2 | 94.1 | 96.4 | 94.8 | 68.8 | 96.6 |
| 5_45_57_606_607_608 | 96.9 | 91.2 | 97.4 | 93.6 | 68.8 | 95.9 |
| 5_13_45_57_75_607 | 96.9 | 90.9 | 97.4 | 93.1 | 68.8 | 95.3 |
| 5_45_57_64_75_607 | 96.9 | 90.9 | 97.4 | 92.6 | 68.8 | 94.8 |
| 5_45_55_57_607_613 | 96.9 | 91.2 | 97.4 | 92.6 | 68.8 | 94.8 |
| 5_45_55_57_75_607 | 96.6 | 87.9 | 97.4 | 92.6 | 68.8 | 94.8 |
| 5_38_45_57_96_607 | 96.3 | 88.2 | 97.1 | 94.1 | 68.8 | 96.5 |
| 5_45_57_75_162_607 | 96.6 | 87.9 | 97.4 | 94.1 | 62.5 | 97.1 |
| 5_45_57_75_162_609 | 94.2 | 97 | 94 | 91.5 | 62.5 | 94.2 |
| 5_45_57_64_96_607 | 95.5 | 88.2 | 96.3 | 94.7 | 75 | 96.5 |
| 57_64_96_606_608_611 | 90.6 | 91.2 | 90.5 | 88.3 | 75.0 | 89.5 |

TABLE 9-4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 96 | 57.9 | 58.8 | 57.8 | 59.4 | 62.5 | 59.1 |
| 41_96 | 85.9 | 88.2 | 85.7 | 83.7 | 62.5 | 85.1 |
| 5_96_606 | 92.6 | 100 | 92.1 | 90.4 | 87.5 | 90.6 |
| 5_45_57_96 | 94.4 | 91.2 | 94.7 | 91.2 | 75 | 92.3 |
| 38_96_606_608_611 | 86.4 | 91.2 | 85.9 | 85.6 | 75 | 86.6 |
| 5_45_57_96_607 | 96 | 91.2 | 96.4 | 94 | 68.8 | 95.7 |
| 38_72_96_606_608_611 | 89.0 | 88.2 | 89.0 | 87.7 | 75.0 | 88.9 |
| 32_38_96_606_608_611 | 89.8 | 88.2 | 89.9 | 86.7 | 68.8 | 88.4 |
| 38_96_163_606_608_611 | 87.4 | 85.3 | 87.6 | 85.1 | 68.8 | 86.6 |
| 64_72_96_162_609_611 | 81.9 | 85.3 | 81.6 | 81.8 | 81.2 | 81.9 |
| 38_64_96_163_606_608 | 87.4 | 91.2 | 87.1 | 86.7 | 68.8 | 88.4 |
| 5_45_57_75_96_606 | 96.3 | 93.9 | 96.6 | 93.6 | 81.2 | 94.8 |
| 5_15_45_57_96_606 | 95.5 | 91.2 | 96 | 94.1 | 87.5 | 94.8 |
| 5_41_45_57_96_606 | 94.8 | 91.2 | 95.1 | 94.1 | 87.5 | 94.8 |
| 5_41_45_96_189_606 | 94.5 | 100 | 94 | 93.1 | 75 | 94.8 |
| 5_45_75_96_189_606 | 94.8 | 97 | 94.5 | 94.7 | 75 | 96.5 |

TABLE 9-5

| 606 | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 606 | 59.4 | 61.8 | 59.3 | 58.6 | 50 | 59.1 |
| 75_606 | 86.6 | 84.8 | 86.8 | 82.9 | 62.5 | 84.3 |
| 5_606_610 | 92.6 | 97.1 | 92.3 | 91.2 | 81.2 | 91.9 |
| 5_45_96_606 | 94.8 | 100 | 94.5 | 90 | 87.5 | 90.2 |
| 64_96_606_608_611 | 86.4 | 91.2 | 85.9 | 85.6 | 75.0 | 86.6 |
| 5_45_57_606_610 | 96 | 94.1 | 96.2 | 93.6 | 68.8 | 95.3 |
| 64_96_162_609_610_611 | 81.9 | 85.3 | 81.6 | 81.4 | 81.2 | 81.4 |
| 38_64_96_606_608_611 | 88.7 | 88.2 | 88.8 | 87.8 | 75.0 | 89.0 |
| 64_72_96_606_608_611 | 89.0 | 88.2 | 89.0 | 88.2 | 75.0 | 89.5 |
| 64_96_97_606_608_611 | 89.7 | 88.2 | 89.9 | 89.4 | 75.0 | 90.7 |
| 45_64_96_606_608_611 | 89.8 | 88.2 | 89.9 | 88.8 | 75.0 | 90.1 |
| 5_24_45_96_189_606 | 95.3 | 100 | 94.8 | 93.6 | 62.5 | 96.5 |
| 5_15_45_96_189_606 | 94 | 94.1 | 94 | 94.1 | 75 | 95.9 |
| 5_45_96_189_606_613 | 95 | 97.1 | 94.8 | 94.7 | 81.2 | 95.9 |
| 5_45_72_96_189_606 | 95 | 97.1 | 94.8 | 94.7 | 81.2 | 95.9 |
| 5_15_32_45_96_606 | 95.3 | 97.1 | 95.1 | 93.6 | 68.8 | 95.9 |

Comparative Example 1

<Colorectal Cancer Discriminant Performance of an Existing Tumor Marker in Blood>

The concentration of the existing tumor marker CEA in blood was measured in the training cohort and the validation cohort obtained in the preceding Reference Examples. When the concentration of the tumor marker in blood is higher than the reference value described in Non Patent Literature 4 (CEA: 5 ng/ml), subjects are generally suspected of having cancer. Thus, whether or not the concentration of CEA in blood exceeded its reference value was confirmed for each sample, and the results were assessed for the ability of the tumor marker to detect cancer in colorectal cancer patients. The sensitivity of the existing marker in the training cohort and the validation cohort was calculated. The results are shown in Tables 5-1 and 5-2. The sensitivity of CEA was as low as 26.5% in the training cohort and was as low as 43.8% in the validation cohort, demonstrating that the marker is not useful in the detection of colorectal cancer (Tables 5-1 and 5-2).

On the other hand, as shown above in Tables 3 and 6 of Examples 1 and 2, it can be concluded that in all of the polynucleotides consisting of the nucleotide sequences represented by SEQ ID NOs: 1 to 180, combinations of 1 or 2 polynucleotides exhibiting sensitivity beyond the existing colorectal cancer marker are present, and thus such polynucleotides serve as excellent diagnosis markers.

As shown in these Examples and Comparative Example, the kit, etc., and the method of the present invention can detect colorectal cancer more sensitively than the existing tumor marker and therefore permit early detection and treatment of colorectal cancer. As a result, improvement in survival rate and a therapeutic option of endoscopic operation, which places less burden on patients, can also be provided.

INDUSTRIAL APPLICABILITY

According to the present invention, colorectal cancer can be effectively detected by a simple and inexpensive method. This enables early detection, diagnosis and treatment of colorectal cancer. The method of the present invention can detect colorectal cancer with limited invasiveness using the blood of a patient and therefore allows colorectal cancer to be detected conveniently and rapidly.

All publications, patents, and patent applications cited herein are incorporated herein by reference in their entirety.

The invention claimed is:

1. A method for detecting colorectal cancer in a human subject, comprising:

measuring an expression level of hsa-miR-887-3p in a blood, serum, or plasma sample from the subject, comparing the measured expression level of hsa-miR-887-3p to a control expression level for a healthy subject;

detecting an increased level of hsa-miR-887-3p in the sample from the subject as compared to the control expression level from the sample from the healthy subject;

wherein the increased level of hsa-miR-887-3p indicates that the subject has colorectal cancer; and wherein the method further comprises treating the subject for the colorectal cancer or performing a diagnostic procedure on the subject with the colorectal cancer;

wherein the treatment comprises surgery, radiotherapy, chemotherapy or a combination thereof; and wherein the diagnostic procedure comprises fecal occult blood, rectal examination, colonoscopy, barium enema, CT, MRI, bone scintigraphy, or a combination thereof.

2. The method according to claim 1, wherein the expression level of hsa-miR-887-3p in the sample is measured by using a kit comprising a nucleic acid(s) that specifically binds to hsa-miR-887-3p.

3. The method according to claim 2, wherein the kit further comprises at least one nucleic acid capable of specifically binding to at least one polynucleotide selected from the group consisting of other colorectal cancer markers: miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR- 638, miR-4497, miR-6085, miR-6752-5p and miR-135a-3p, miR-1231, miR-1233-5p, miR-150-3p, miR-1225-3p, miR-92a-2-5p, miR-423-5p, miR-1268a, miR-128-2-5p, miR-24-3p, miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090.

4. The method according to claim 1, comprising performing the diagnostic procedure on the subject.

5. The method according to claim 1, wherein the expression level of hsa-miR-887-3p in the sample is measured by using a device comprising a nucleic acid(s) that specifically binds to hsa-miR-887-3p.

6. The method according to claim 5, wherein the device further comprises at least one nucleic acid capable of specifically binding to at least one polynucleotide selected from the group consisting of other colorectal cancer markers: miR-4257, miR-6787-5p, miR-6780b-5p, miR-3131, miR-7108-5p, miR-1343-3p, miR-1247-3p, miR-4651, miR-6757-5p, miR-3679-5p, miR-7641, miR-6746-5p, miR-8072, miR-6741-5p, miR-1908-5p, miR-6857-5p, miR-4746-3p, miR-744-5p, miR-4792, miR-564, miR-6791-5p, miR-6825-5p, miR-6826-5p, miR-4665-3p, miR-4467, miR-3188, miR-6125, miR-6756-5p, miR-1228-3p, miR-8063, miR-8069, miR-6875-5p, miR-3185, miR-4433b-3p, miR-6887-5p, miR-128-1-5p, miR-6724-5p, miR-1914-3p, miR-1225-5p, miR-4419b, miR-7110-5p, miR-187-5p, miR-3184-5p, miR-204-3p, miR-5572, miR-6729-5p, miR-615-5p, miR-6749-5p, miR-6515-3p, miR-6840-3p, miR-6893-5p, miR-4728-5p, miR-6717-5p, miR-7113-3p, miR-4665-5p, miR-642b-3p, miR-7109-5p, miR-6842-5p, miR-4442, miR-4433-3p, miR-4707-5p, miR-6126, miR-4449, miR-4706, miR-1913, miR-602, miR-939-5p, miR-4695-5p, miR-711, miR-6816-5p, miR-4632-5p, miR-6721-5p, miR-7847-3p, miR-6132, miR-3679-3p, miR-6784-5p, miR-1249, miR-937-5p, miR-5195-3p, miR-6732-5p, miR-4417, miR-4281, miR-4734, miR-6766-3p, miR-663a, miR-4513, miR-6781-5p, miR-1227-5p, miR-6845-5p, miR-6798-5p, miR-3620-5p, miR-1915-5p, miR-4294, miR-642a-3p, miR-371a-5p, miR-940, miR-4450, miR-4723-5p, miR-1469, miR-6861-5p, miR-7975, miR-6879-5p, miR-6802-5p, miR-1268b, miR-663b, miR-125a-3p, miR-2861, miR-6088, miR-4758-5p, miR-296-3p, miR-6738-5p, miR-671-5p, miR-4454, miR-4516, miR-7845-5p, miR-4741, miR-92b-5p, miR-6795-5p, miR-6805-3p, miR-4725-3p, miR-6782-5p, miR-4688, miR-6850-5p, miR-6777-5p, miR-6785-5p, miR-7106-5p, miR-3663-3p, miR-6131, miR-1915-3p, miR-4532, miR-6820-5p, miR-4689, miR-4638-5p, miR-3656, miR-3621, miR-6769b-5p, miR-149-3p, miR-23b-3p, miR-3135b, miR-6848-5p, miR-6769a-5p, miR-4327, miR-6765-3p, miR-6716-5p, miR-6877-5p, miR-6727-5p, miR-4534, miR-614, miR-1202, miR-575, miR-6870-5p, miR-6722-3p, miR-7977, miR-4649-5p, miR-4675, miR-6075, miR-6779-5p, miR-4271, miR-3196, miR-6803-5p, miR-6789-5p, miR-4648, miR-4508, miR-4749-5p, miR-4505, miR-5698, miR-1199-5p, miR-4763-3p, miR-6836-3p, miR-3195, miR-718, miR-3178, miR-638, miR-4497, miR-6085, miR-6752-5p and miR-135a-3p, miR-1231, miR-1233-5p, miR-150-3p, miR-1225-3p, miR-92a-2-5p, miR-423-5p, miR-1268a, miR-128-2-5p, miR-24-3p, miR-4697-5p, miR-3197, miR-675-5p, miR-4486, miR-7107-5p, miR-23a-3p, miR-4667-5p, miR-451a, miR-3940-5p, miR-8059, miR-6813-5p, miR-4492, miR-4476, and miR-6090.

* * * * *